United States Patent
Fuchs et al.

(10) Patent No.: US 7,501,535 B2
(45) Date of Patent: Mar. 10, 2009

(54) CHEMICAL SYNTHONS AND INTERMEDIATES

(75) Inventors: Philip L. Fuchs, West Lafayette, IN (US); David J. Meyers, Brookline, MA (US); Eduardo Torres, West Lafayette, IN (US); Taesik Park, West Lafayette, IN (US); In C. Kim, New Haven, CT (US); Yuzhong Chen, Newark, DE (US); Douglas Lantrip, Lafayette, IN (US); Jerry B. Evarts, Jr., San Mateo, CA (US)

(73) Assignee: Purdue Research Foundation, West Lafayette, IN (US)

( * ) Notice: Subject to any disclaimer, the term of this patent is extended or adjusted under 35 U.S.C. 154(b) by 782 days.

(21) Appl. No.: 10/662,781

(22) Filed: Sep. 15, 2003

(65) Prior Publication Data

US 2004/0138485 A1    Jul. 15, 2004

Related U.S. Application Data

(60) Provisional application No. 60/410,421, filed on Sep. 13, 2002.

(51) Int. Cl.
C07F 556/482 (2006.01)
C07C 315/00 (2006.01)
C07D 303/00 (2006.01)

(52) U.S. Cl. .................. 556/482; 549/546; 568/27; 568/29

(58) Field of Classification Search .................. 549/512, 549/546; 556/482; 568/27, 29
See application file for complete search history.

(56) References Cited

OTHER PUBLICATIONS

Evarts et al., J. Am. Chem. Soc., 2002, 124, 11094.*
Brittain, Polymorphism in Pharmaceutical Solids, 1999, pp. 5-8.*
Arjona et al., J. Org. Chem., 1994, 59(14), pp. 3906-3916.*
Hentemann et al., Tetrahedron Letters, 38(32), p. 5615-5618.*
Wanlong et al., Organic Letters, 2000, 2(15), 2181-2184.*
Guo, C. et al. "An Efficient Protocol for the Synthesis of Unsymmetrical Pyrazines. Total Synthesis of Dihydrocephalostatin 1" J. Am. Chem. Soc. 1996, 118:10672-10673.
Jeong, J.U. et al. "Biomimetic Total Syntheses of (+)-Cephalostatin 7, (+)-Cephalostatin 12, and (+)-Ritterazine K" J. Am. Chem. Soc. 1995, 117:10157-10158.
Li, W. et al. "An Efficient Synthesis of the C-23 Deoxy, 17alpha-Hydroxy South 1 Hemisphere and Its Cephalostatin 1 Analog" Org. Lett. 2003, 5:2849-2852.
Liu, Z. et al. "Intermolecular C—N Addition of Amides and S—N Addition of Sulfinamides to Arynes" J. Am. Chem. Soc. 2005, 127:13112-13113.
Jeong, J.U. et al. "Synthesis of the South Unit of Cephalostatin. 7. Total Syntheses of (+)-Cephalostatin 7, (+)-Cephalostatin 12, and (+)-Ritterazine K" J. Am. Chem. Soc 1999, 121:2071-2084.

(Continued)

*Primary Examiner*—Taylor Victor Oh
(74) *Attorney, Agent, or Firm*—Henry D. Coleman; R. Neil Sudol; William J. Sapone

(57) ABSTRACT

The invention provides novel six and seven-carbon termini-differentiated polypropionate stereotetrads and stereopentads useful in syntheses of natural products. The invention also provides a novel alkylative sulfenylation-desulfonylation process that efficiently transforms enantipure epoxyvinyl sulfones to syn and anti dienylsulfides in two operations.

20 Claims, 106 Drawing Sheets

Scheme 1. Preparation of acyclic arrays

Scheme 2. Initial sulfenylation attempts.

OTHER PUBLICATIONS

Kim, S. et al. "Synthesis of the North 1 Unit of the Cephalostatin Family from Hecogenin Acetate" J. Am. Chem. Soc. 1999, 121:2056-2070.

LaCour, T.G. et al. "Interphylal Product Splicing: The First Total Syntheses of Cephalostatin 1, the North Hemisphere of Ritterazine G, and the Highly Active Hybrid Analogue, Ritterostatin $G_N1_N$" J. Am. Chem. Soc. 1999, 120:692-707.

Evarts, J. et al. "Syntheses of Highly Substituted Enantiopure C6 and C7 Enones" J. Am. Chem. Soc. 2002, 124:11093-11101.

Hentenmann et al., Tetrahedron Lett. 40,2699-2702 (1999).
Evarts et al., Tetrahedron Lett., 40, 2703-2706 (1999).
Hentenmann et al., Organic Lett., 1, 355-357 (1999).
Jiang et al., Organic Lett., 2, 2181-2184 (2000).
Tong, et al., Tetrahedron Leett. 41, 7795-7799 (2000).
Evarts et al., Tetrahedron Lett., 42, 3673-3675 (2001).
Myers et al., J. Org. Chem., 67, 200-204 (2002).
Torres et al., Angew. Chem. Int. Ed., 42, 3124-3131 (2003).

* cited by examiner

Figure 1
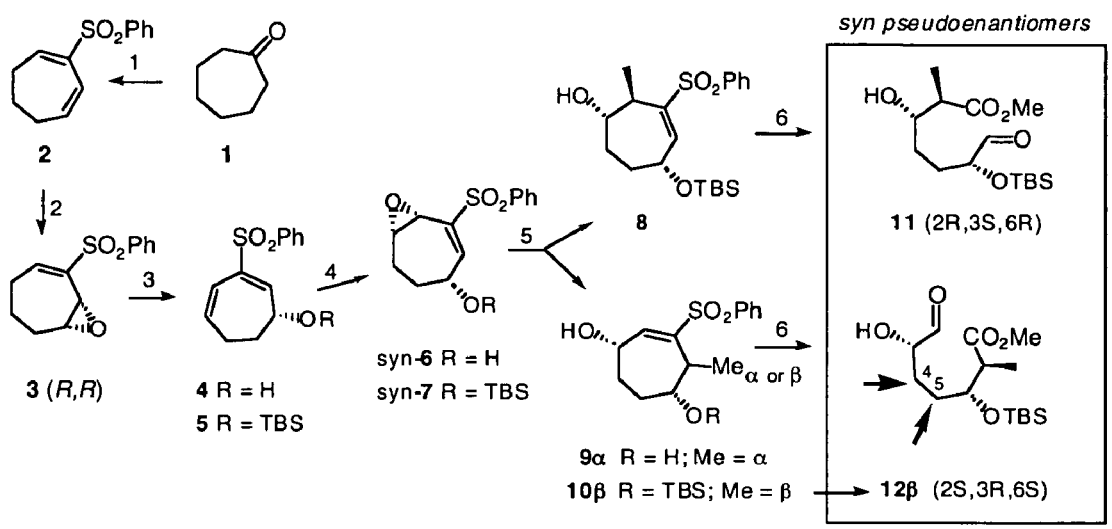
Scheme 1. Preparation of acyclic arrays
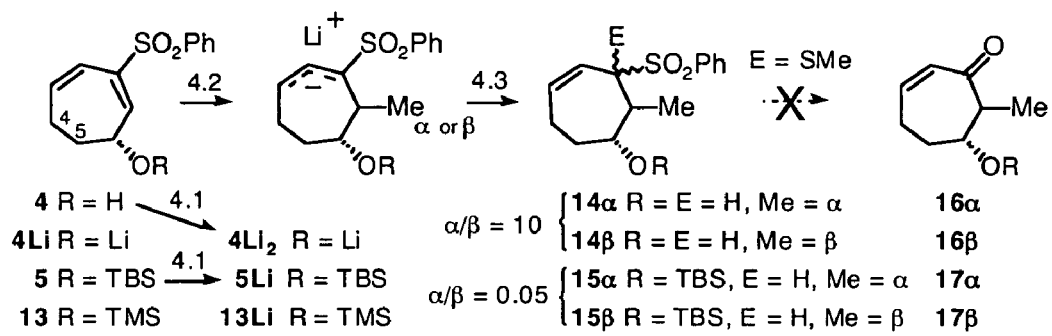
Scheme 2. Initial sulfenylation attempts.

FIGURE 2
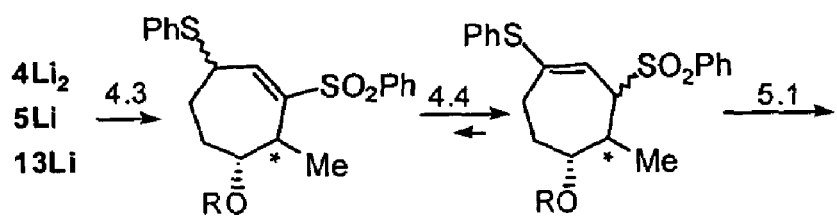
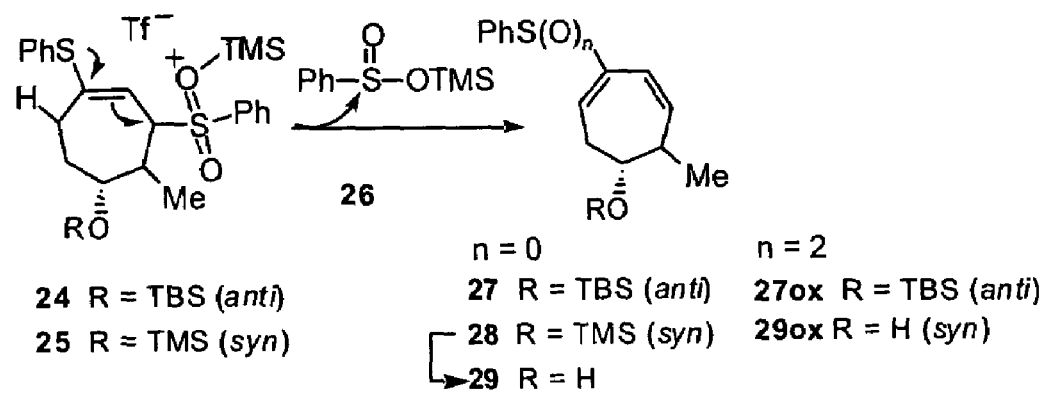
Scheme 3. Novel gamma sulfenylation and diene transposition.

Scheme 4. Prepartion of stereopentad progenitors. 1.1 n-BuLi (2.2 eq), THF, -78°C to -7°C, 1.2 MeI (5 eq), -90°C to -50°C; 2 m-CPBA (2.2 eq); $CH_2Cl_2$, 25°C, 30 min; 3 TBSOTf (1.2 eq), Lutidine (2 eq). $CH_2Cl_2$, 25°C, 2h; 4.1 n-BuLi (2.2eq), THF, -78°C to -5°C, 90 min; 4.2 Eschenmoser's salt (2.5 eq), THF, -70°C to 0°C, 1.5 h; 5 m-CPBA (4 eq); $CH_2Cl_2$, 25°C, 1h; 6 TBHP + 5% $Mo(CO)_6$, 88% >15:1 α/β; 7 10% (R,R)-Mn(salen)Cl, $H_2O_2$, 1eq $NH_4OAc$, 83% 1:>20 α/β, 8 $OsO_4$ cat. >80%, single diastereomer

FIGURE 4

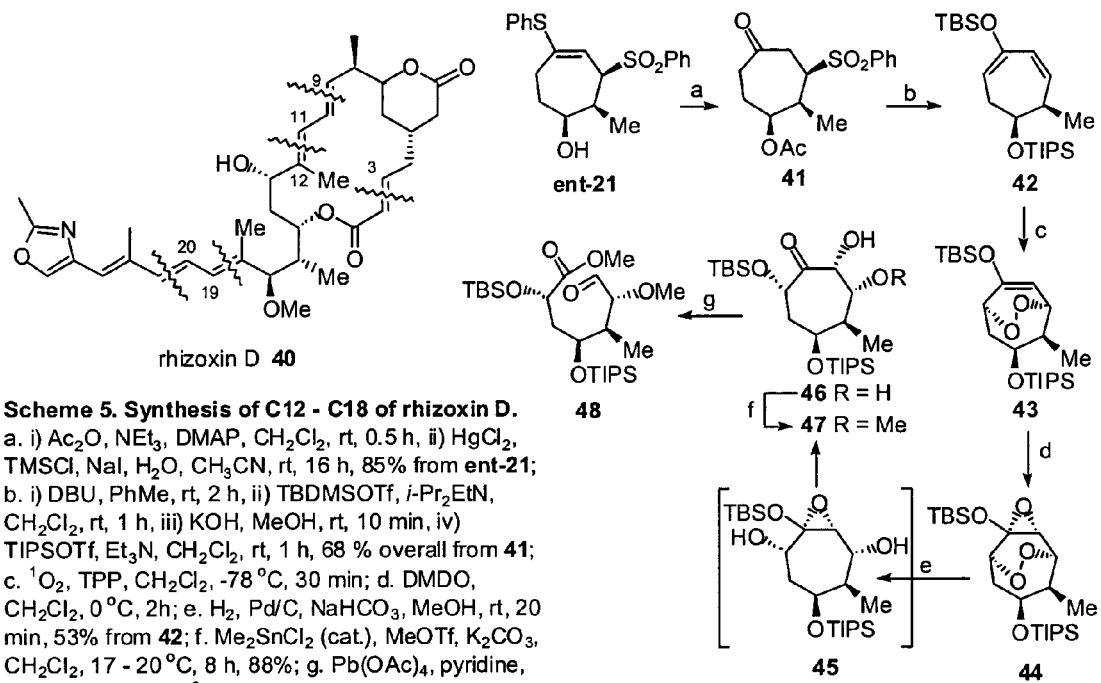

Scheme 5. Synthesis of C12 - C18 of rhizoxin D.
a. i) Ac$_2$O, NEt$_3$, DMAP, CH$_2$Cl$_2$, rt, 0.5 h, ii) HgCl$_2$, TMSCl, NaI, H$_2$O, CH$_3$CN, rt, 16 h, 85% from ent-21;
b. i) DBU, PhMe, rt, 2 h, ii) TBDMSOTf, i-Pr$_2$EtN, CH$_2$Cl$_2$, rt, 1 h, iii) KOH, MeOH, rt, 10 min, iv) TIPSOTf, Et$_3$N, CH$_2$Cl$_2$, rt, 1 h, 68 % overall from 41;
c. $^1$O$_2$, TPP, CH$_2$Cl$_2$, -78 °C, 30 min; d. DMDO, CH$_2$Cl$_2$, 0 °C, 2h; e. H$_2$, Pd/C, NaHCO$_3$, MeOH, rt, 20 min, 53% from 42; f. Me$_2$SnCl$_2$ (cat.), MeOTf, K$_2$CO$_3$, CH$_2$Cl$_2$, 17 - 20 °C, 8 h, 88%; g. Pb(OAc)$_4$, pyridine, MeOH-benzene, 0°C, 1.5 h, 85%

FIGURE 5
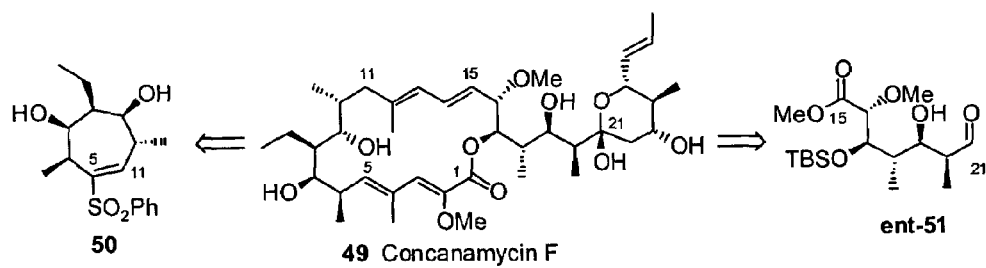
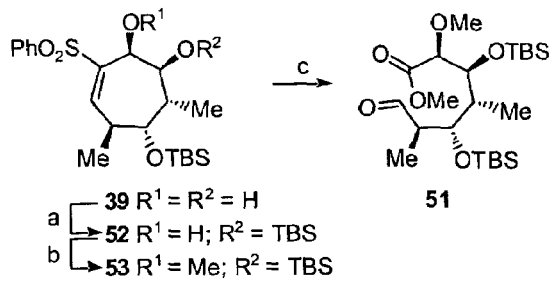
Scheme 6. Synthesis of the ent-C15-C21 fragment of Concanamycin F.
a TBSOTf, 2,6-Lutidine, $CH_2Cl_2$, -78°C, 24h, 99% ; b KOH/MeI/DMSO, 25°C, 5 min; 94%; c $O_3$, $CH_2Cl_2$, MeOH (1:2), $NaHCO_3$, -78°C, 5 min, then $PPh_3$, 92%

FIGURE 6
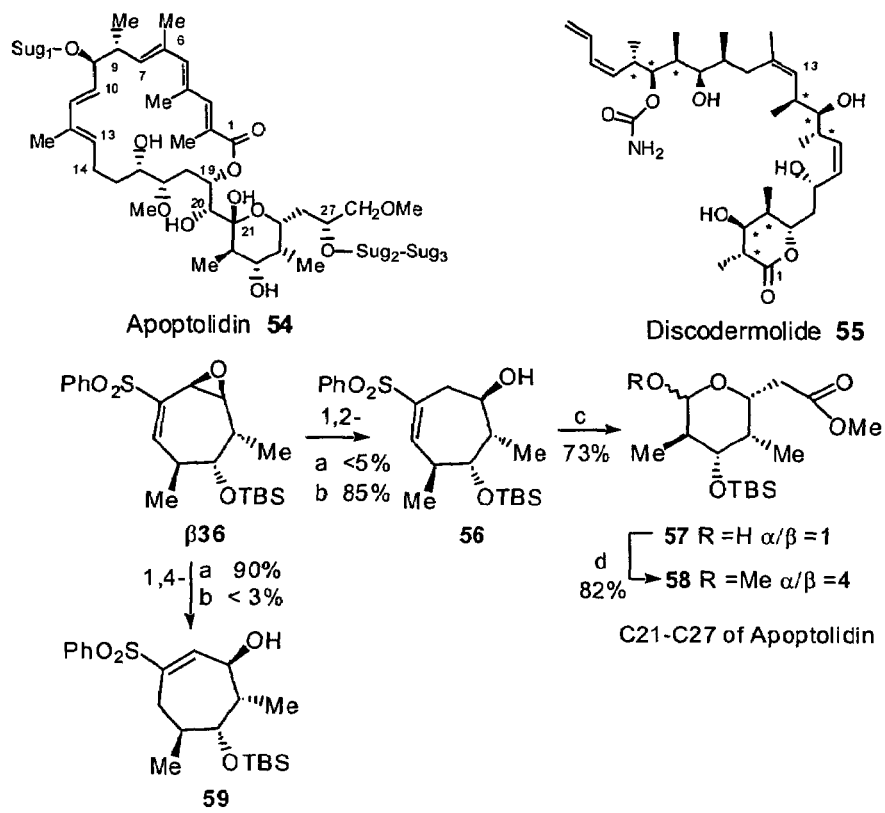
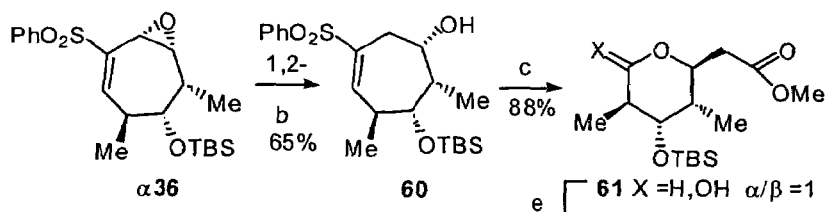
Scheme 7. Preparation of C21-C27 of Apoptolidin and C1-C7 of Discodermolide.
a BH$_3$·THF (1.6 eq), THF, 0°C, warm to 25°C, 12 h;
b 1.5 eq DIBAL-H, -78°C; c O$_3$, CH$_2$Cl$_2$/MeOH
(1:2), NaHCO$_3$, -78°C, 5 min; d Ag$_2$O, MeI, CH$_3$CN,
reflux, 3h; e PDC (5 eq), CH$_2$Cl$_2$, 25°C, 10 h Figure 1. Evaluation and impotance of the sulfur atom for this synthesis.

FIGURE 8 (99 Spectra)
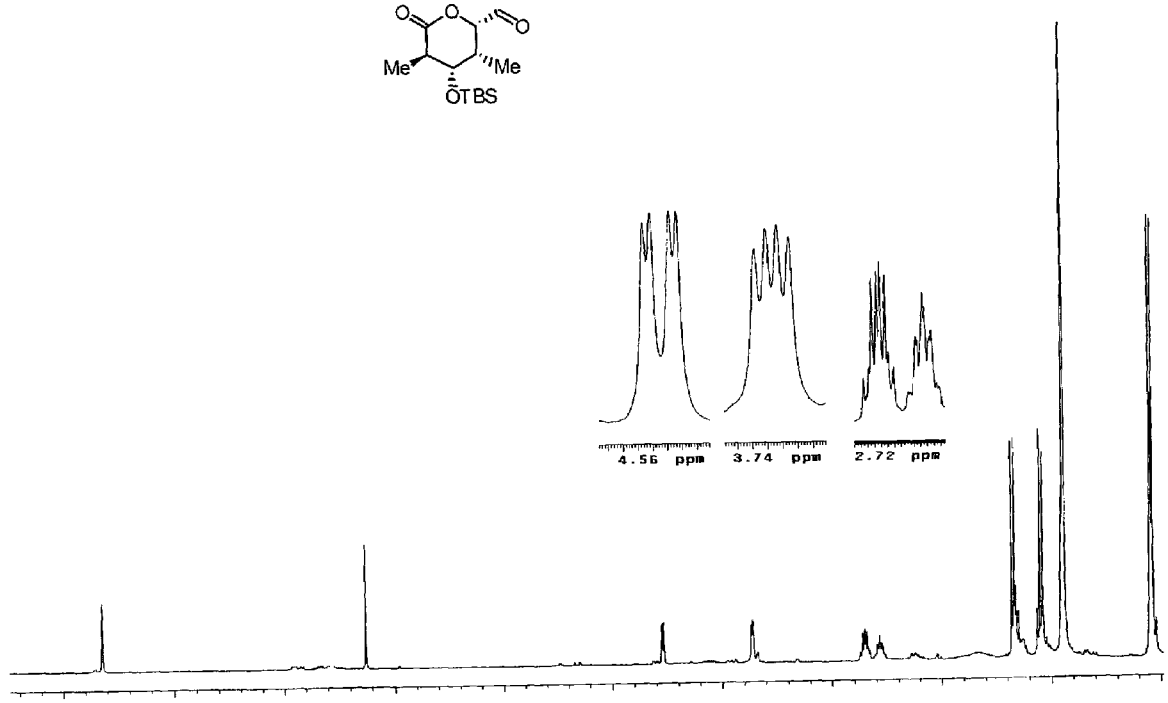
300MHz $^1$H NMR of compound 22 in CDCl$_3$

FIGURE 8 (Cont'd)
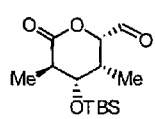
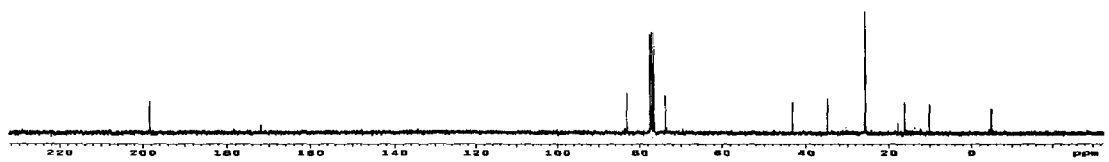
75MHz $^{13}$C NMR of compound 22 in CDCl$_3$

FIGURE 8 (Cont'd)
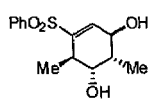
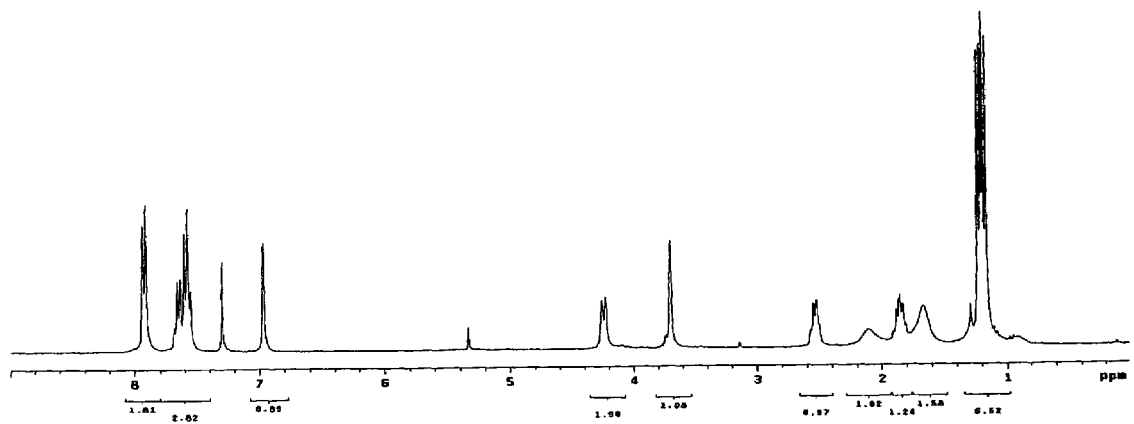
300MHz $^1$H NMR of compound 23 in CDCl$_3$ FIGURE 8 (Cont'd)
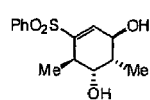
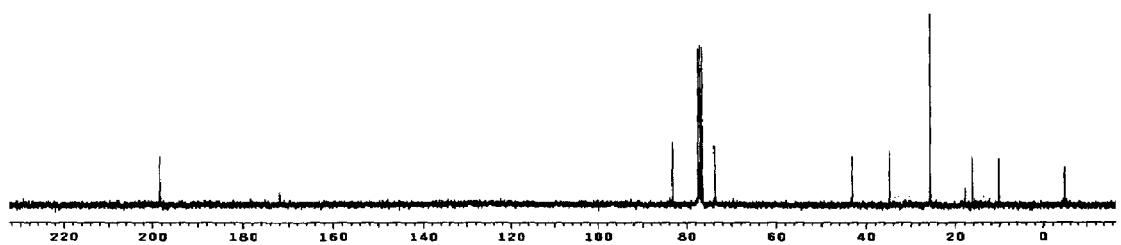
75MHz $^{13}$C NMR of compound 23 in CDCl$_3$ 300MHz $^1$H NMR of compound 24 in CDCl$_3$

FIGURE 8 (Cont'd)
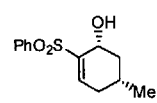
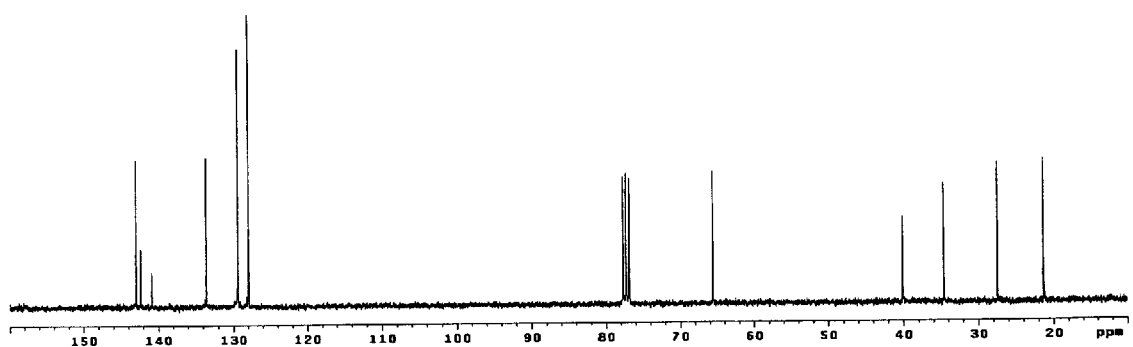
75MHz $^{13}$C NMR of compound 24 in CDCl$_3$ 300MHz $^1$H NMR of compound 28 in CDCl$_3$ FIGURE 8 (Cont'd)
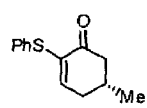
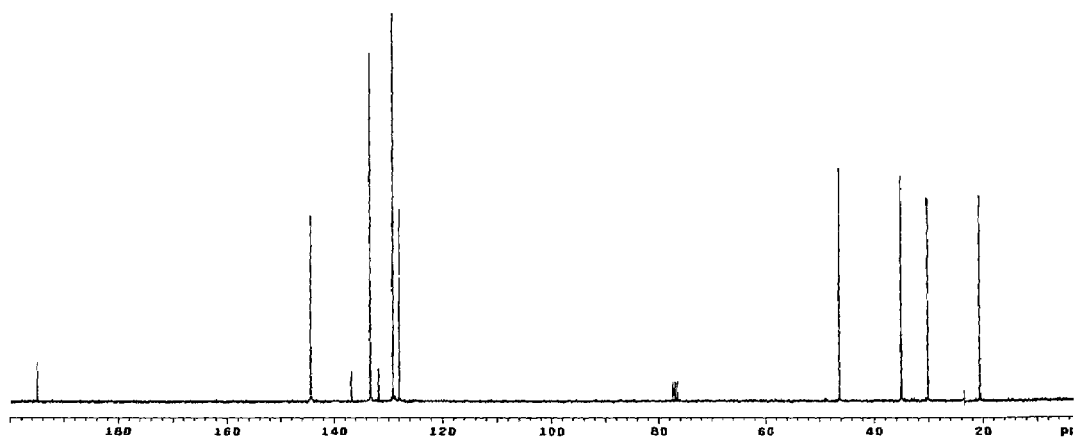
75MHz $^{13}$C NMR of compound 28 in CDCl$_3$

FIGURE 8 (Cont'd)
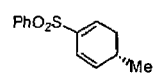
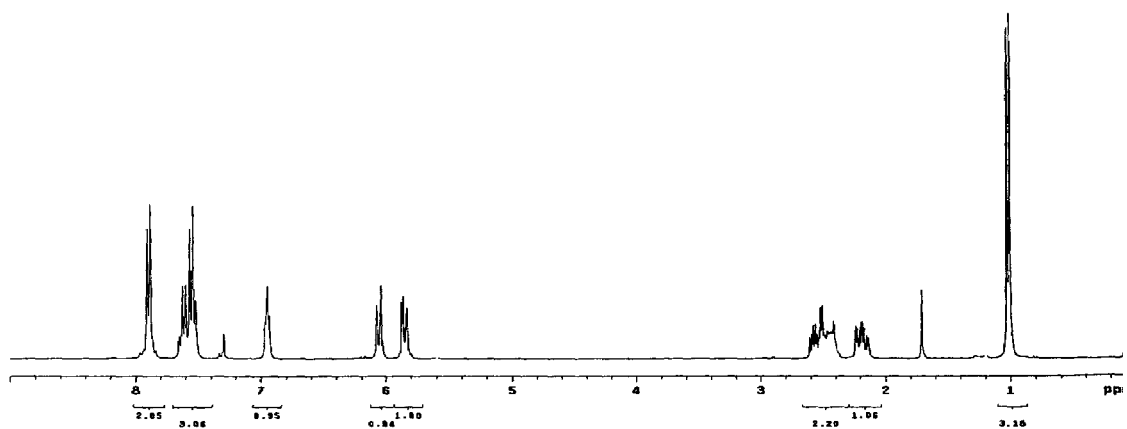
300MHz ¹H NMR of compound 29 in $CDCl_3$

FIGURE 8 (Cont'd)
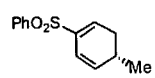
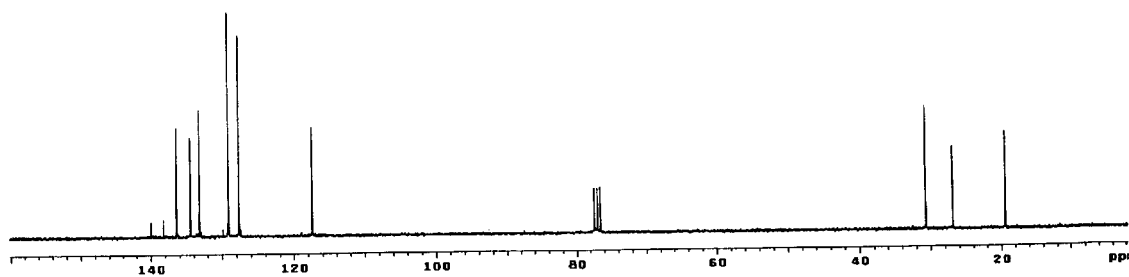
75MHz $^{13}$C NMR of compound 29 in CDCl$_3$ 300MHz ¹H NMR of compound 30 in CDCl₃

75MHz $^{13}$C NMR of compound 30 in CDCl$_3$

FIGURE 8 (Cont'd)
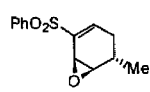
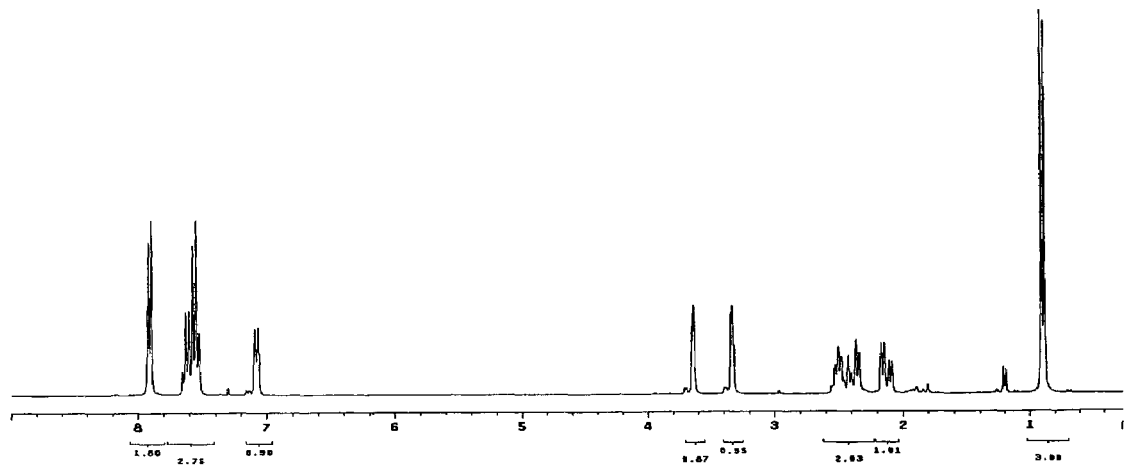
300MHz $^1$H NMR of compound 31 in CDCl$_3$ FIGURE 8 (Cont'd)
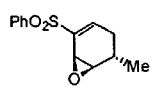
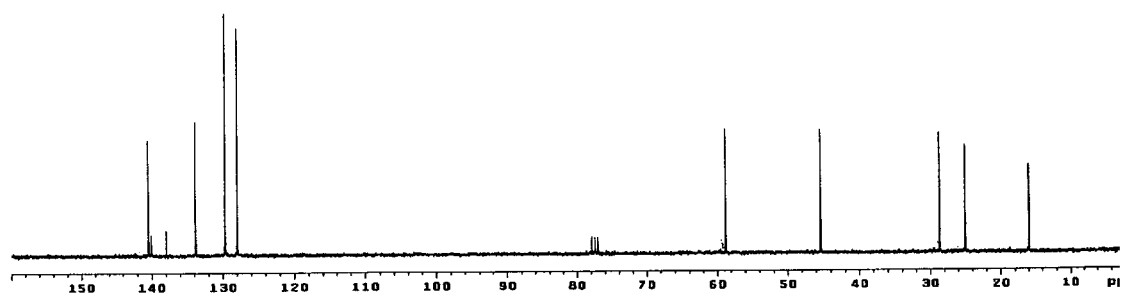
75MHz $^{13}$C NMR of compound 31 in CDCl$_3$ 300MHz $^1$H NMR of compound 32 in CDCl$_3$ 75MHz $^{13}$C NMR of compound 32 in CDCl$_3$ 300MHz ¹H NMR of compound 33 in CDCl₃

75MHz $^{13}$C NMR of compound 33 in CDCl$_3$

300MHz ¹H NMR of compound 35 in CDCl₃

FIGURE 8 (Cont'd)
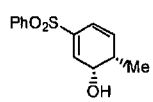
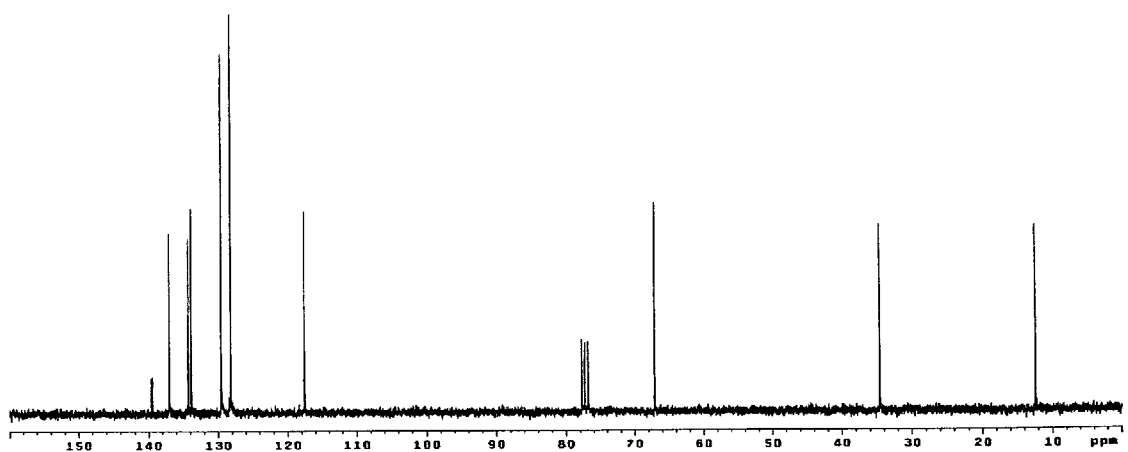
75MHz $^{13}$C NMR of compound 35 in CDCl$_3$ 300MHz $^1$H NMR of compound 36 in CDCl$_3$ FIGURE 8 (Cont'd)
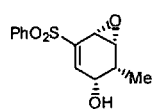
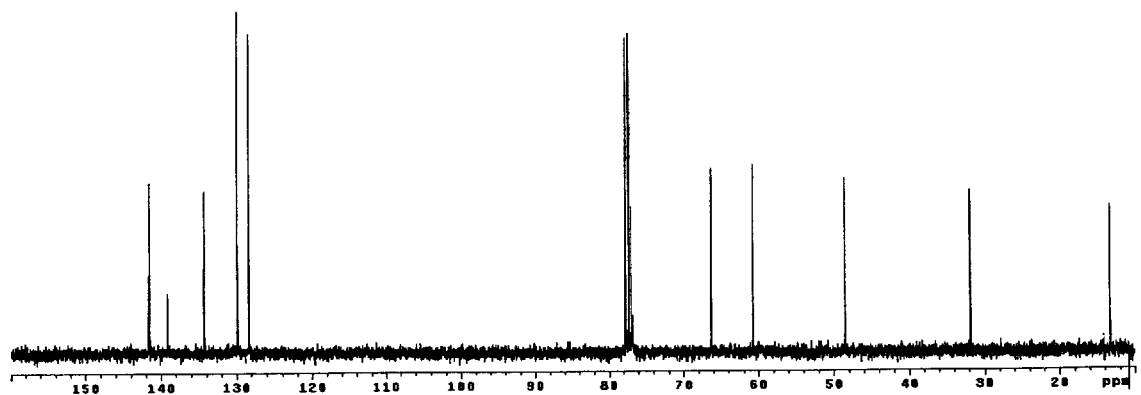
75MHz $^{13}$C NMR of compound 36 in CDCl$_3$

FIGURE 8 (Cont'd)
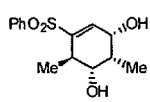
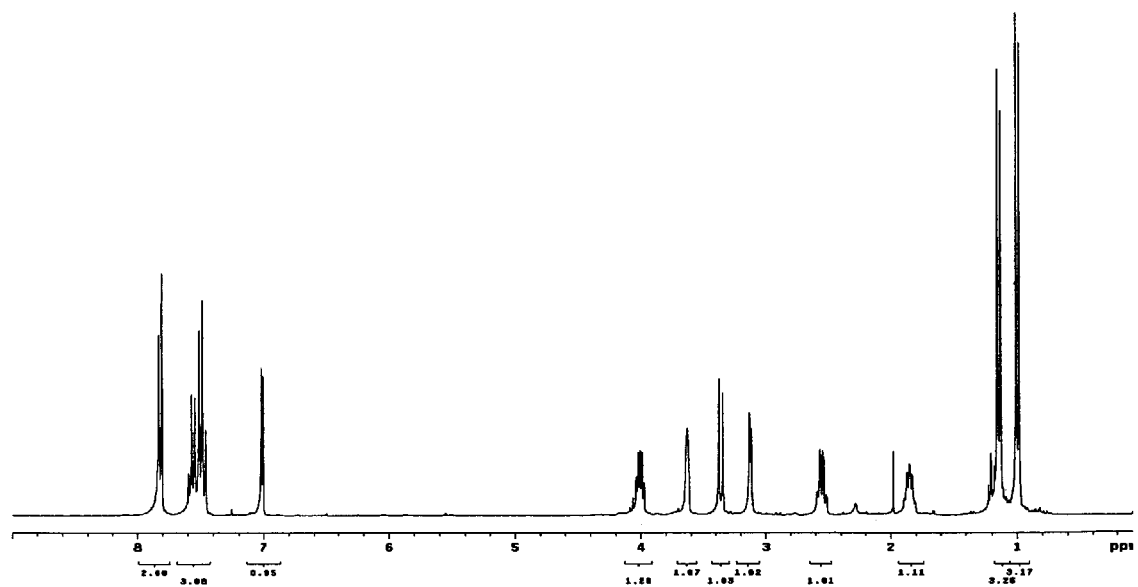
300MHz $^1$H NMR of compound 37 in CDCl$_3$ FIGURE 8 (Cont'd)
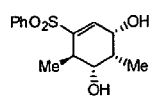
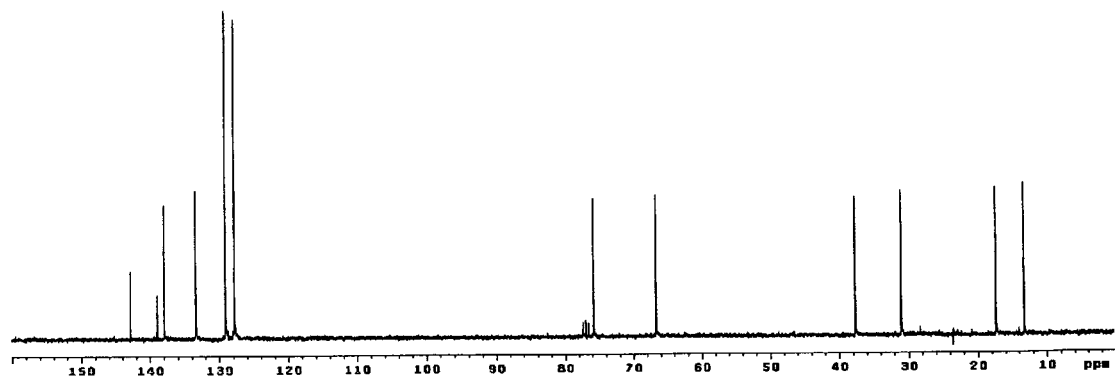
75MHz $^{13}$C NMR of compound 37 in CDCl$_3$ 300MHz ¹H NMR of compound 38 in CDCl₃

FIGURE 8 (Cont'd)
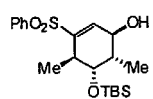
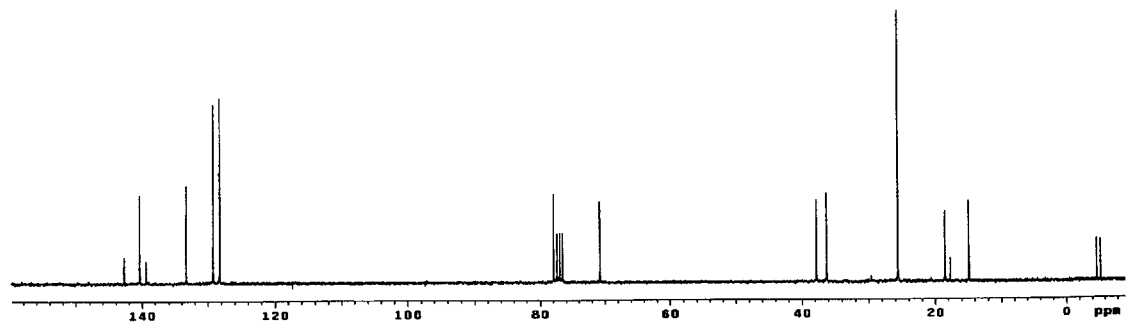
75MHz $^{13}$C NMR of compound 38 in CDCl$_3$ 300MHz $^1$H NMR of compound 39 in CDCl$_3$

FIGURE 8 (Cont'd)
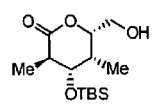
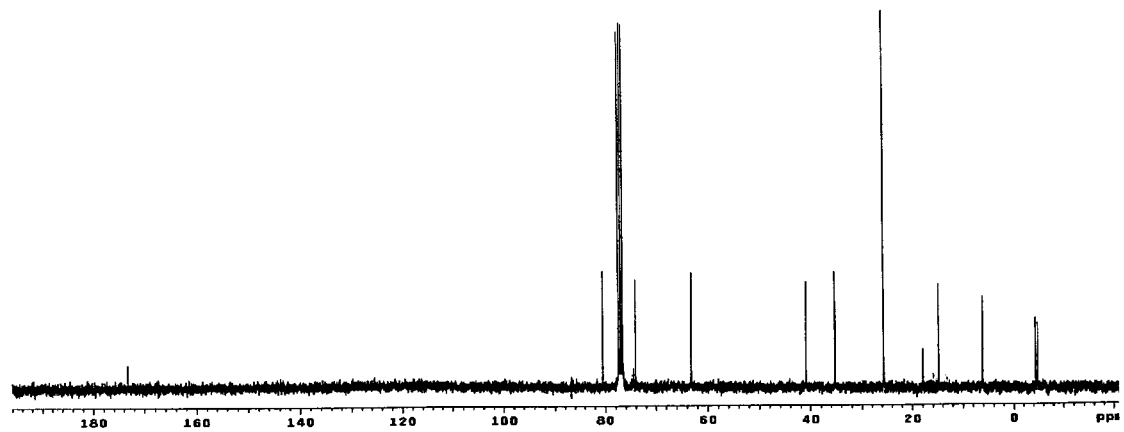
75MHz $^{13}$C NMR of compound 39 in CDCl$_3$ FIGURE 8 (Cont'd)
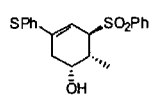
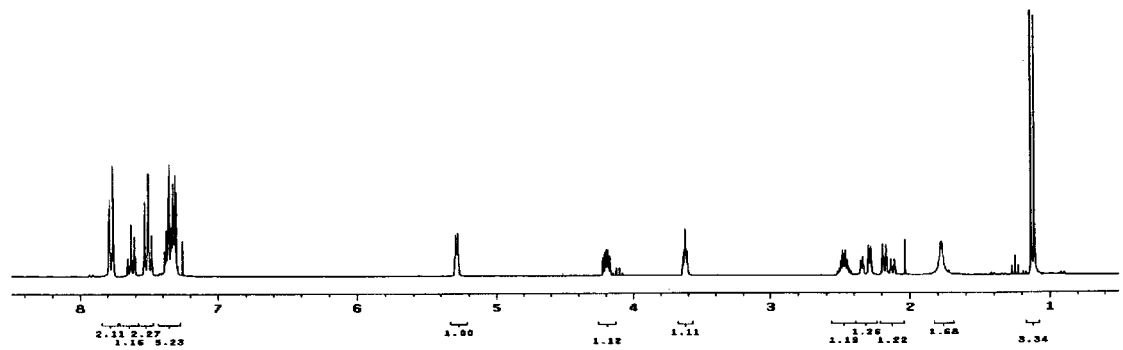
300MHz $^1$H NMR of compound 43β in CDCl$_3$ FIGURE 8 (Cont'd)
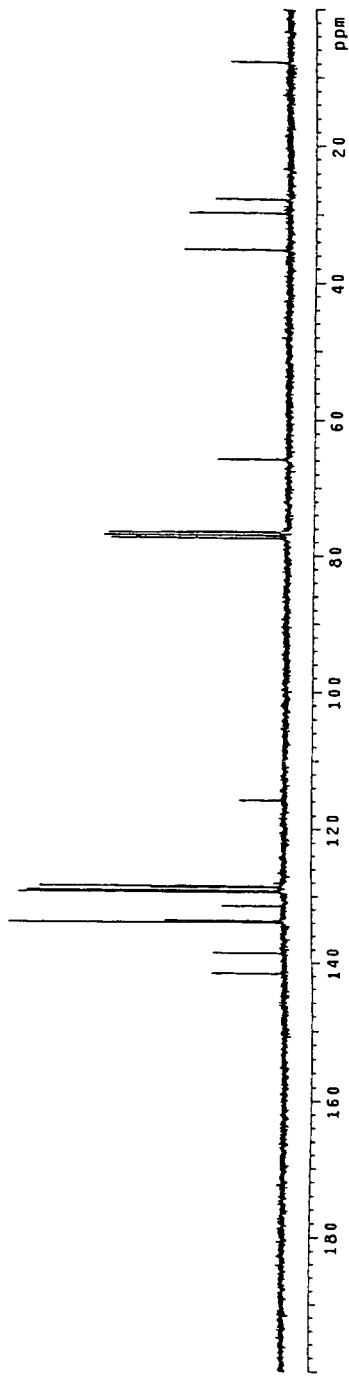
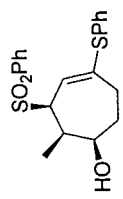
75MHz $^{13}$C NMR of compound 21 in CDCl$_3$ 300MHz $^1$H NMR of compound 23 α in CDCl$_3$ FIGURE 8 (Cont'd)
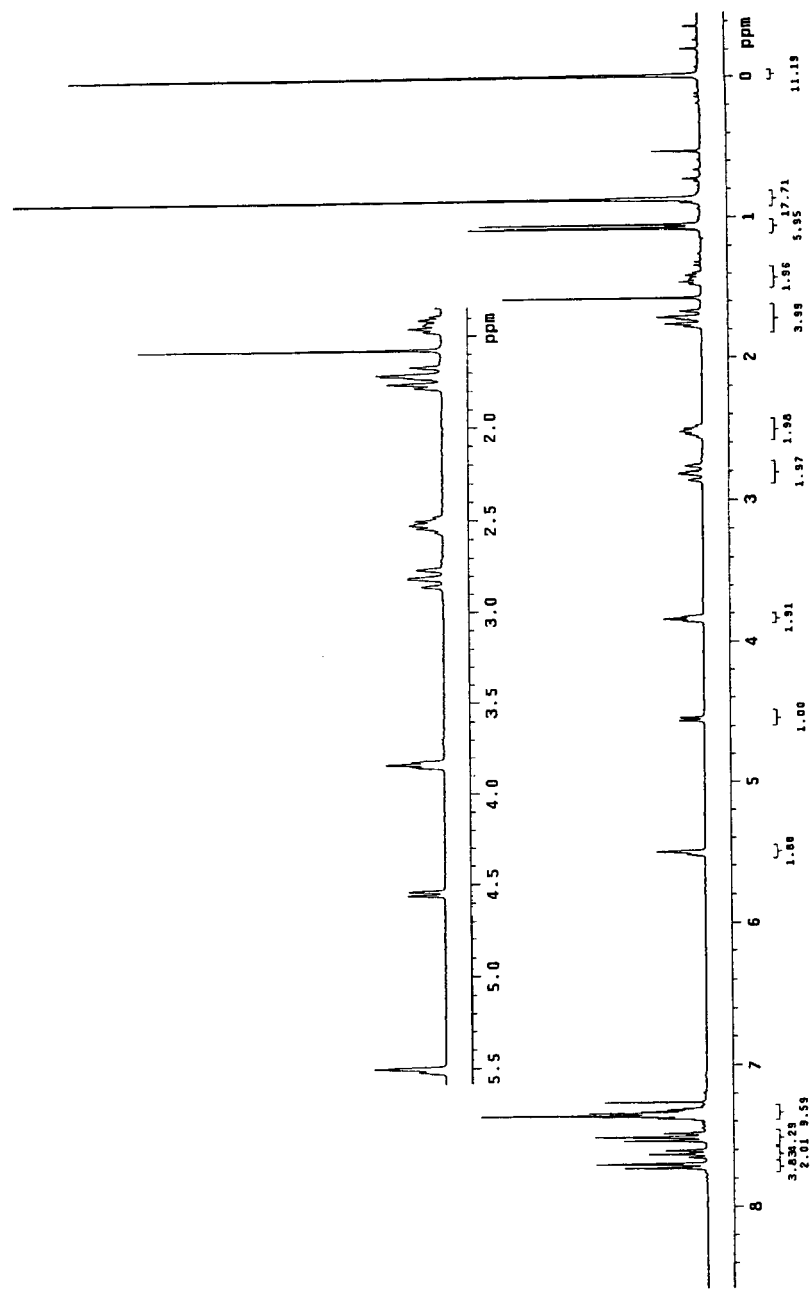
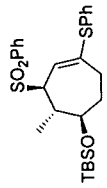
300MHz 1H NMR of compound 22 in CDCl$_3$

FIGURE 8 (Cont'd)
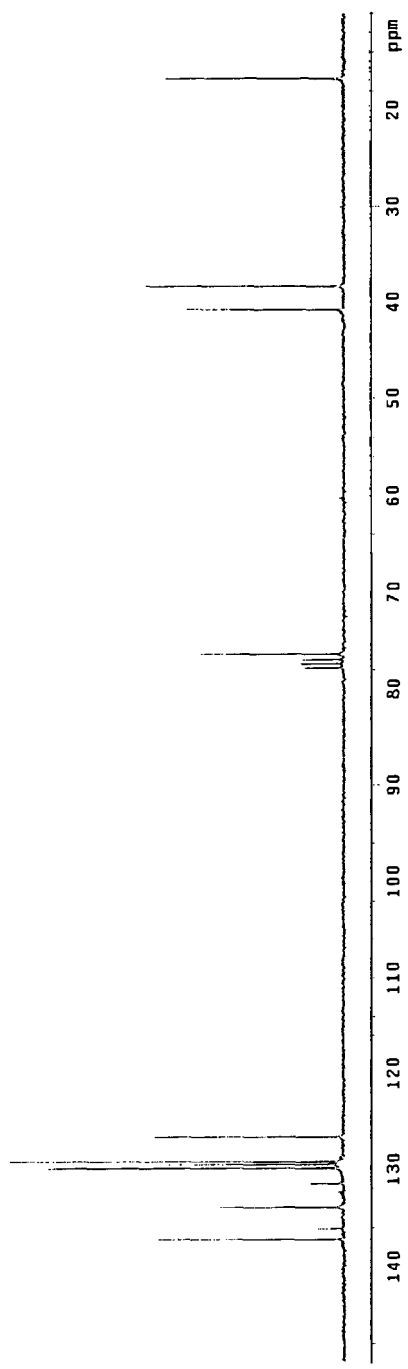
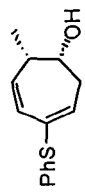

FIGURE 8 (Cont'd)
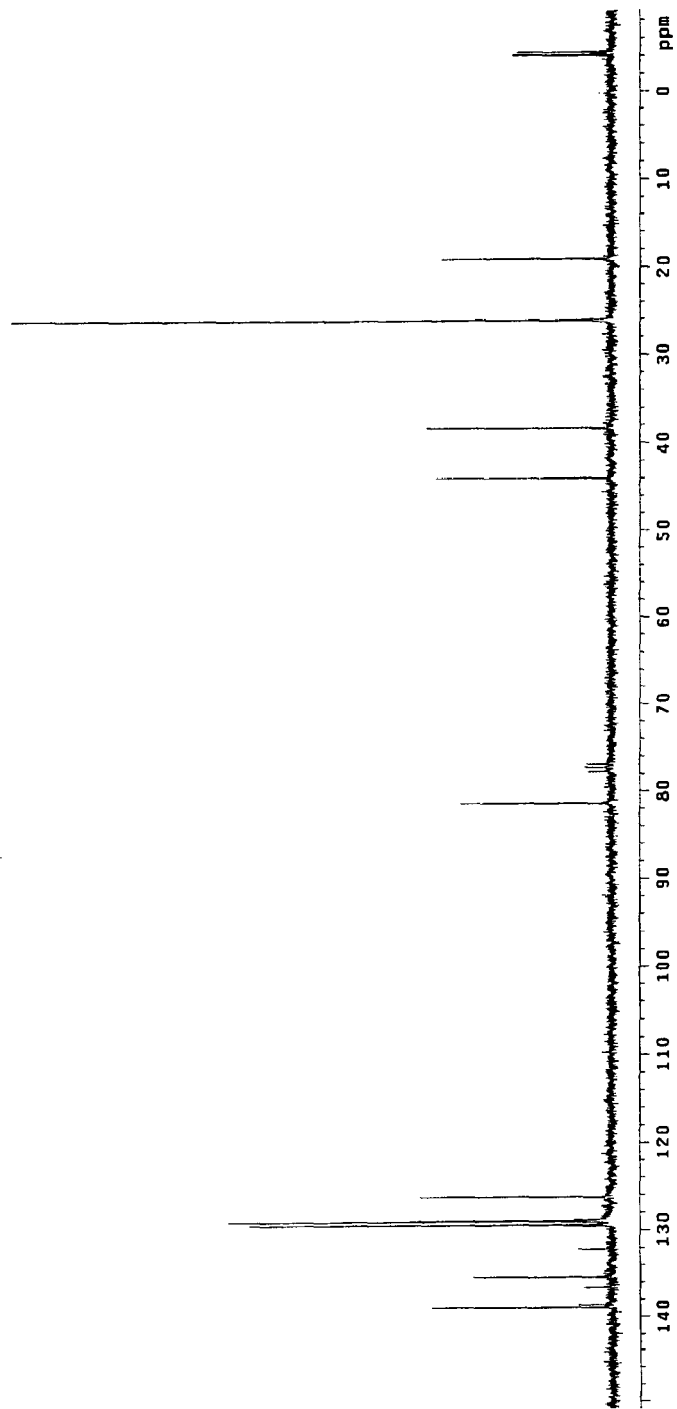
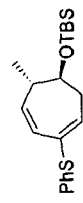
75MHz 13C NMR of compound 27 in CDCl$_3$ FIGURE 8 (Cont'd)
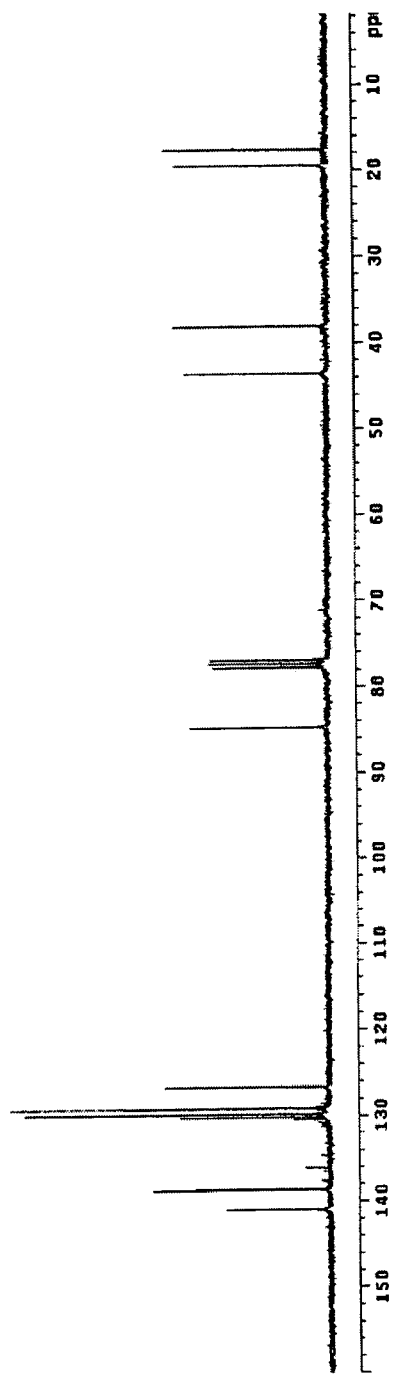
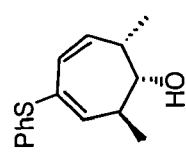
75MHz ¹³C NMR of compound 31 in CDCl₃

300MHz ¹H NMR of compound 32 in CDCl₃

75MHz $^{13}$C NMR of compound 32 in CDCl$_3$

300MHz $^1$H NMR of compound 33 in CDCl$_3$

FIGURE 8 (Cont'd)
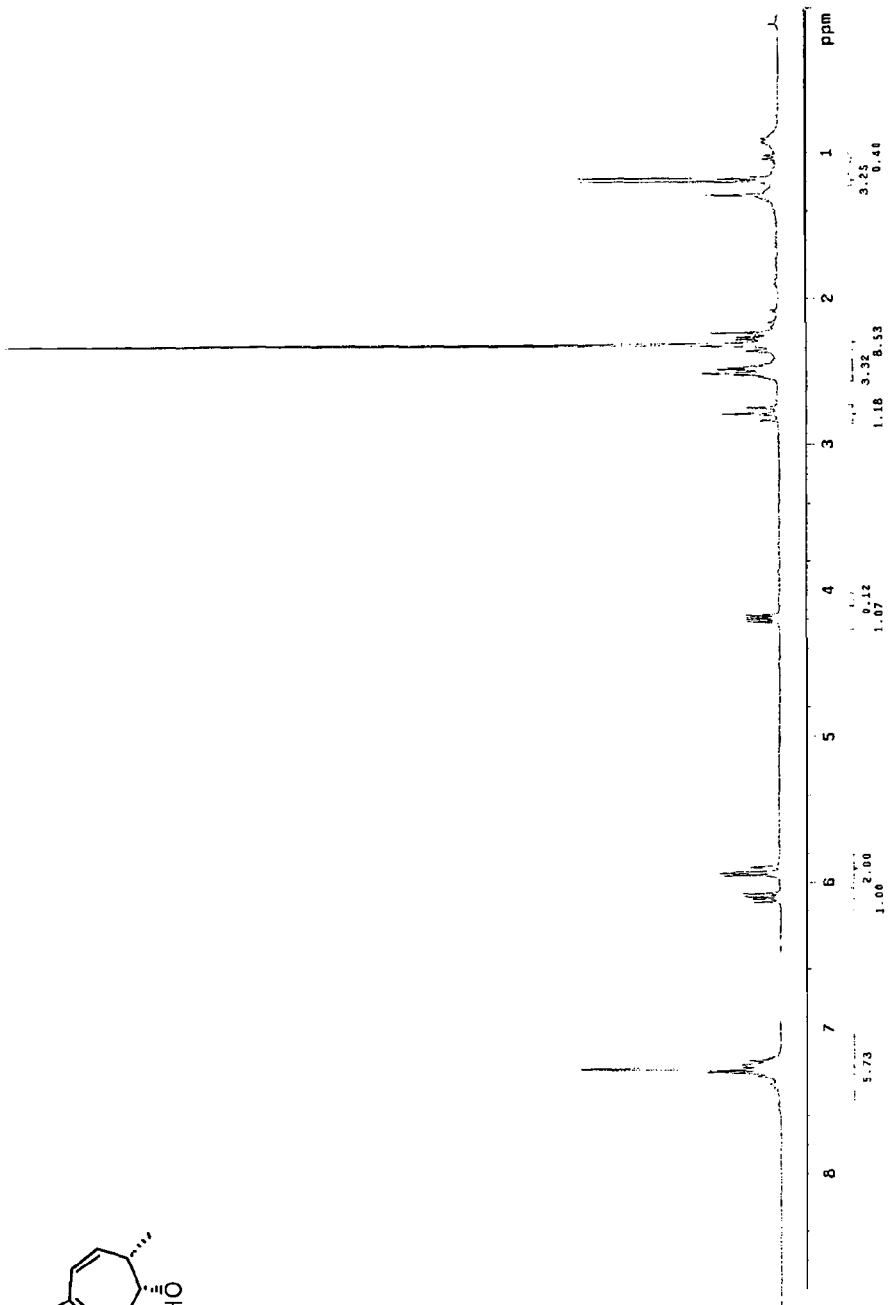
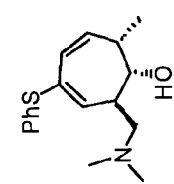
300MHz ¹H NMR of compound 34 in CDCl₃

FIGURE 8 (Cont'd)
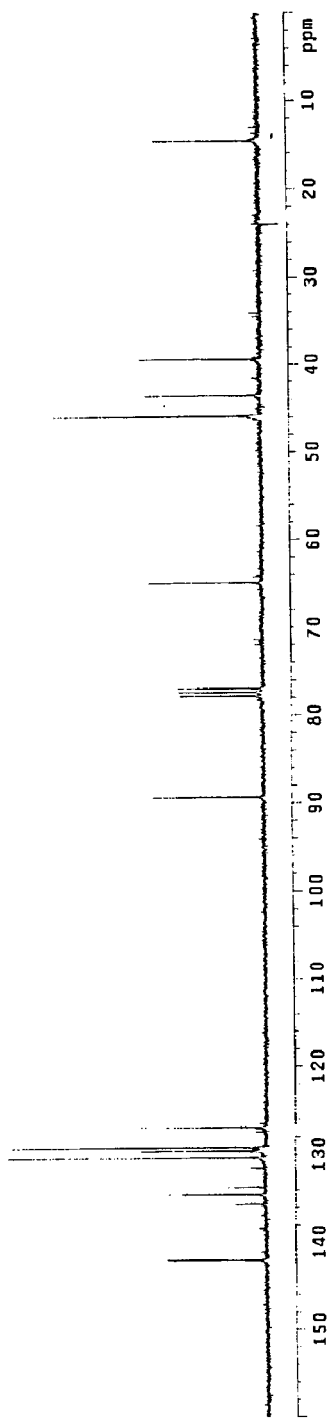
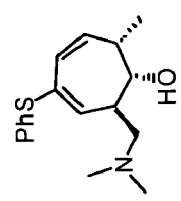
75MHz $^{13}$C NMR of compound 34 in CDCl$_3$ FIGURE 8 (Cont'd)
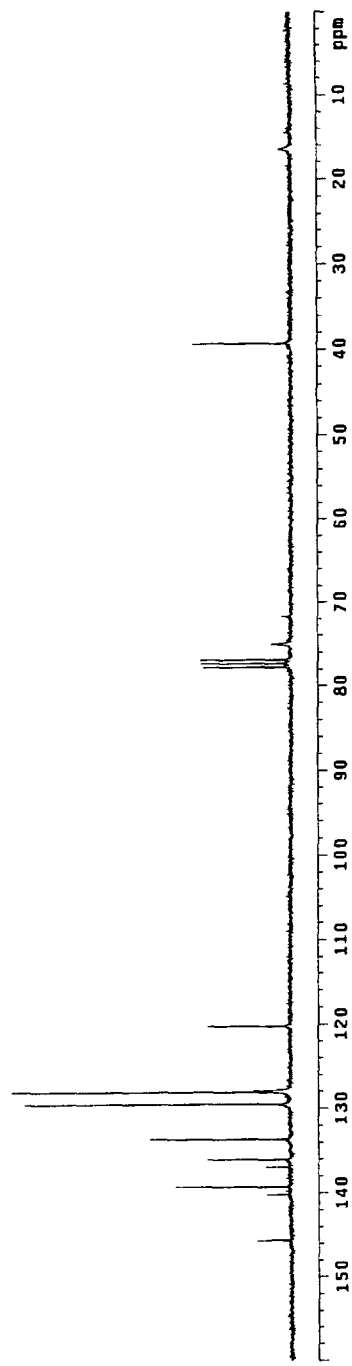
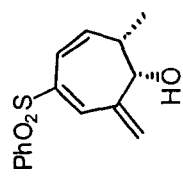
75MHz $^{13}$C NMR of compound 35 in CDCl$_3$ FIGURE 8 (Cont'd)
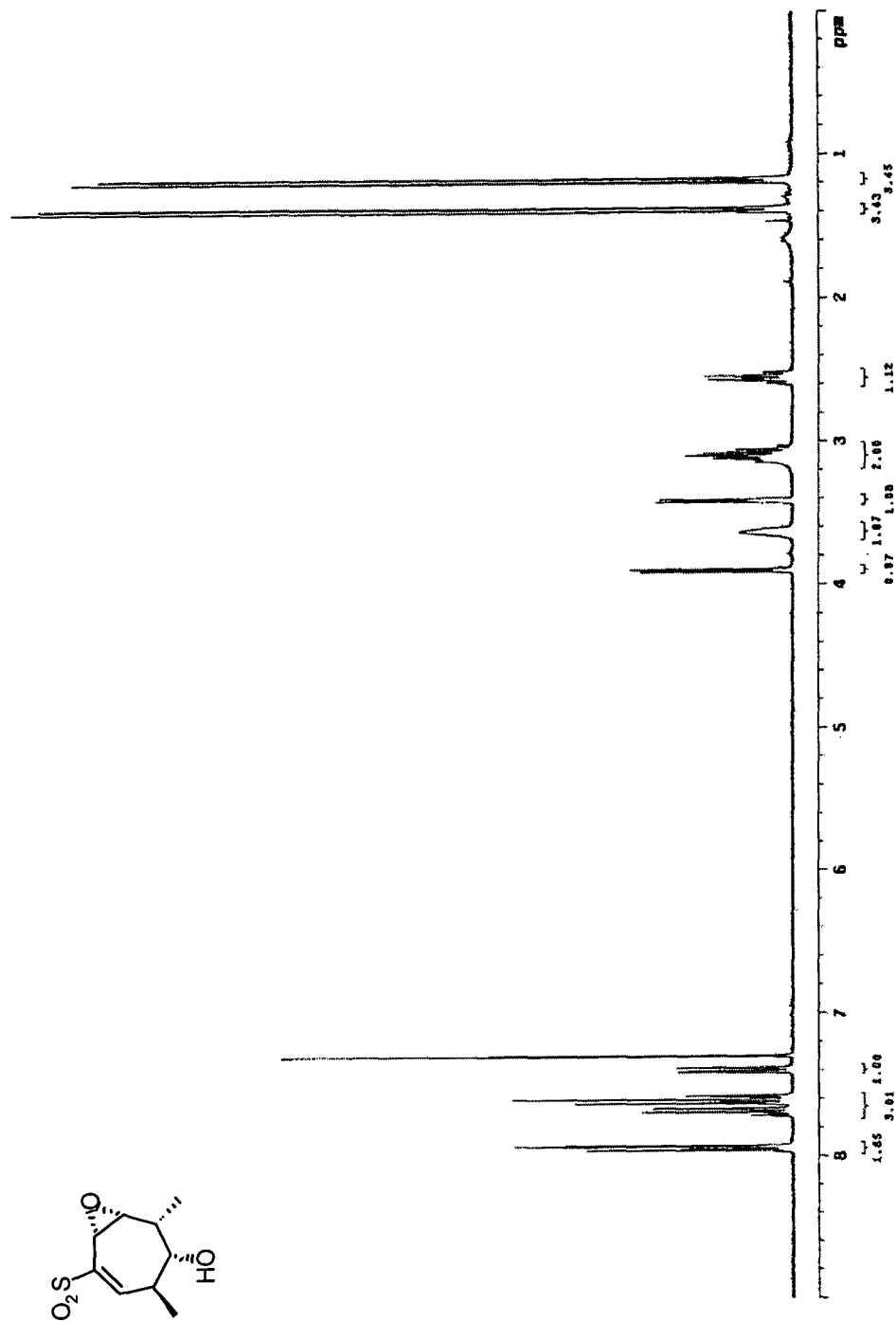
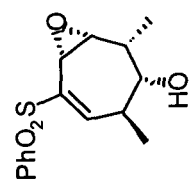

300MHz ¹H NMR of compound β36 in CDCl₃

FIGURE 8 (Cont'd)
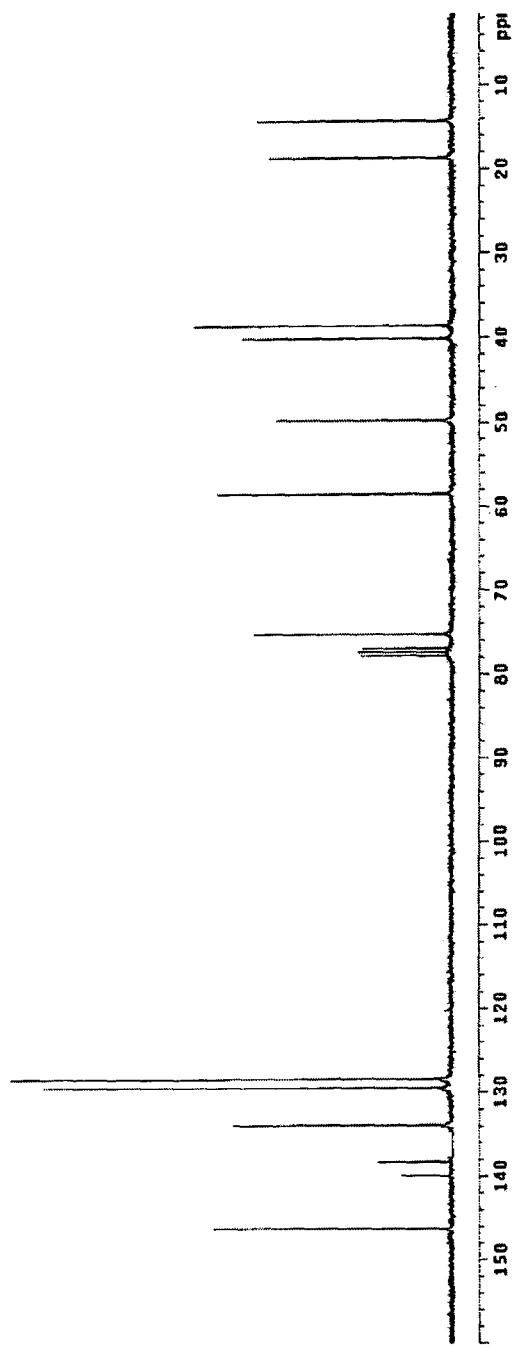
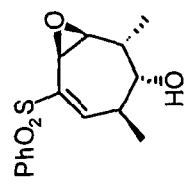
75MHz $^{13}$C NMR of compound β36 in CDCl$_3$ 300MHz ¹H NMR of compound α37 in CDCl₃

FIGURE 8 (Cont'd)
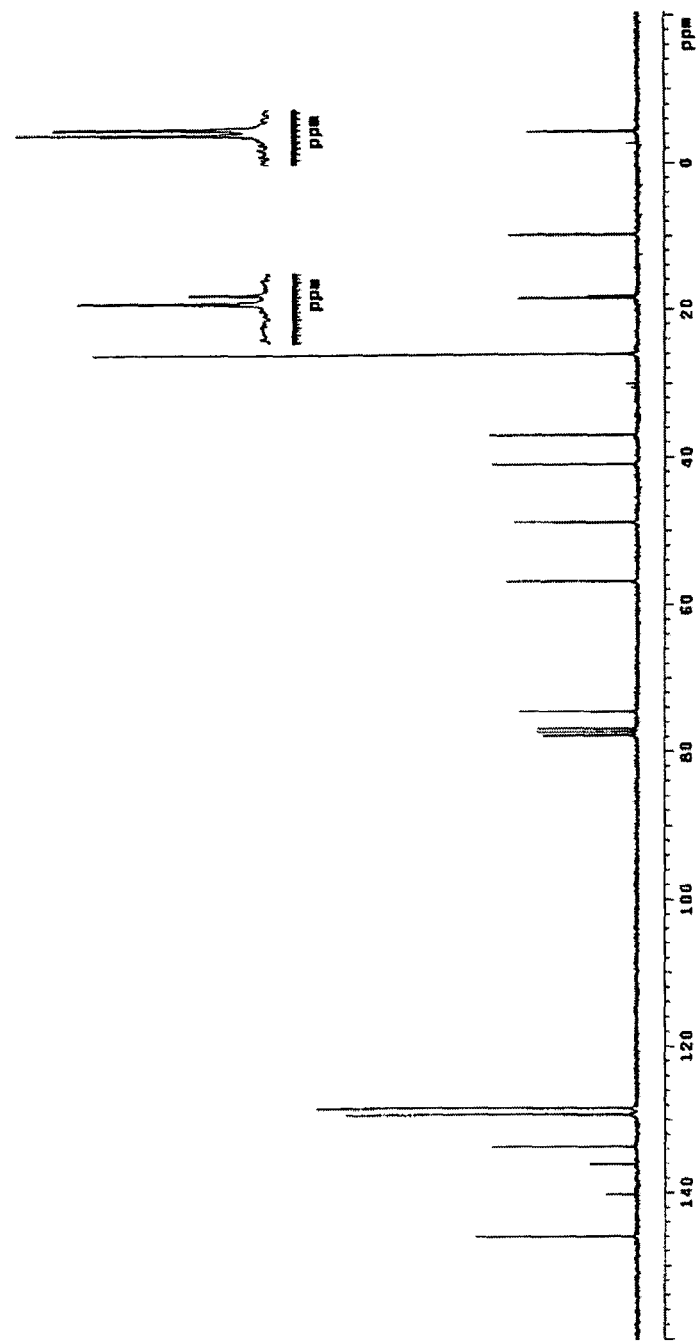
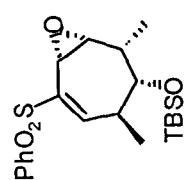
75MHz $^{13}$C NMR of compound α37 in CDCl$_3$ FIGURE 8 (Cont'd)
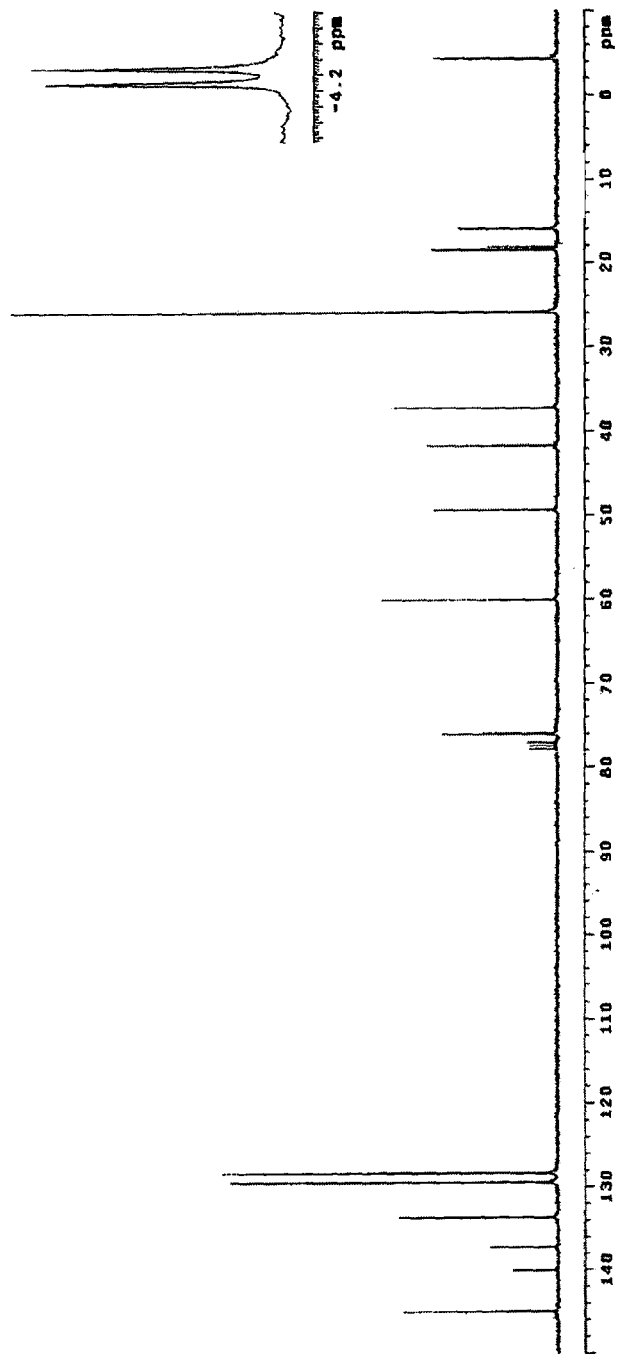
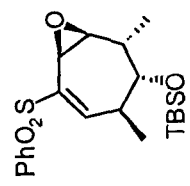
75MHz $^{13}$C NMR of compound β37 in CDCl$_3$ FIGURE 8 (Cont'd)
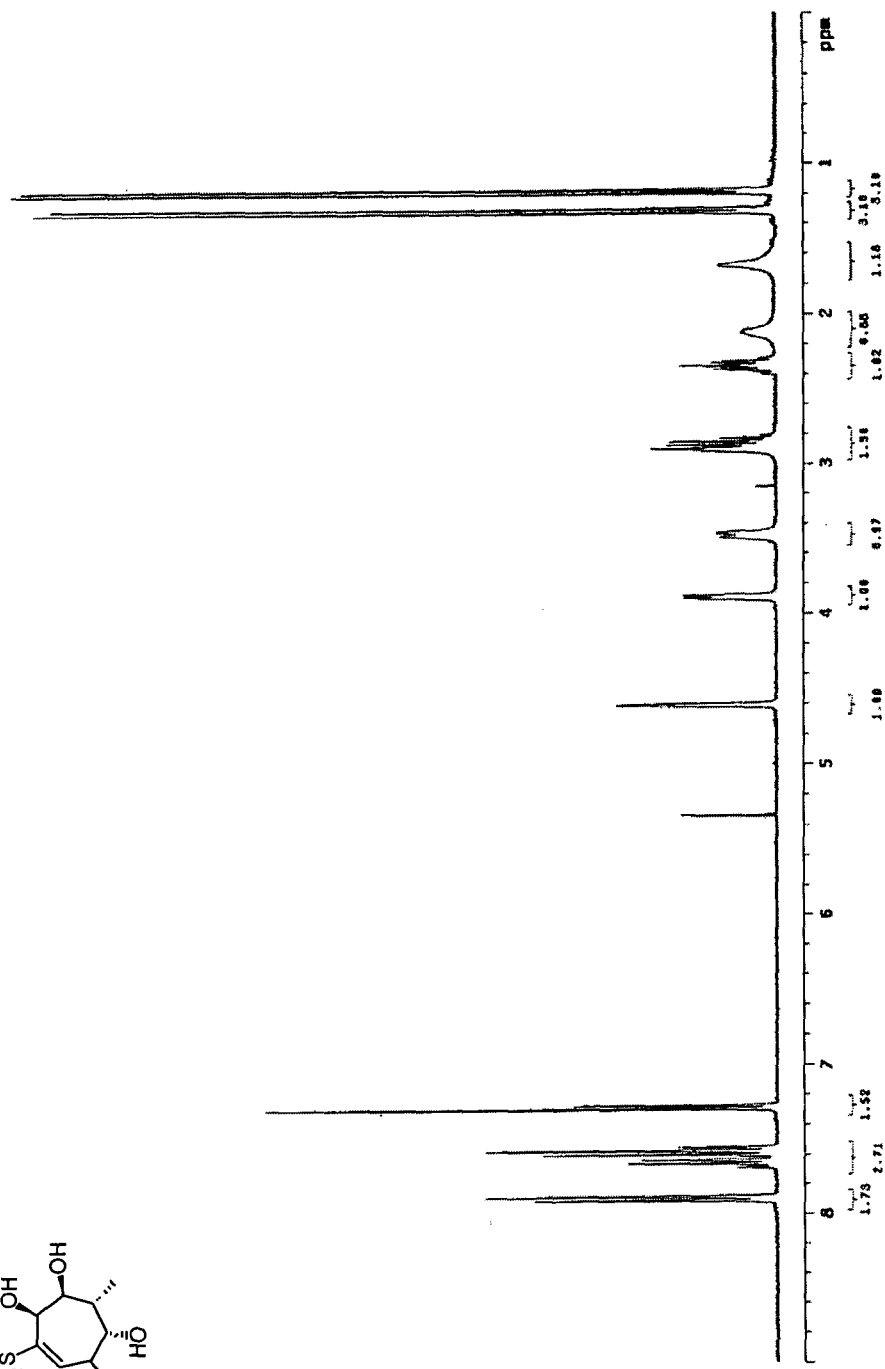
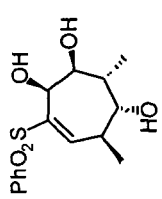
300MHz $^1$H NMR of compound 38 in CDCl$_3$ FIGURE 8 (Cont'd)
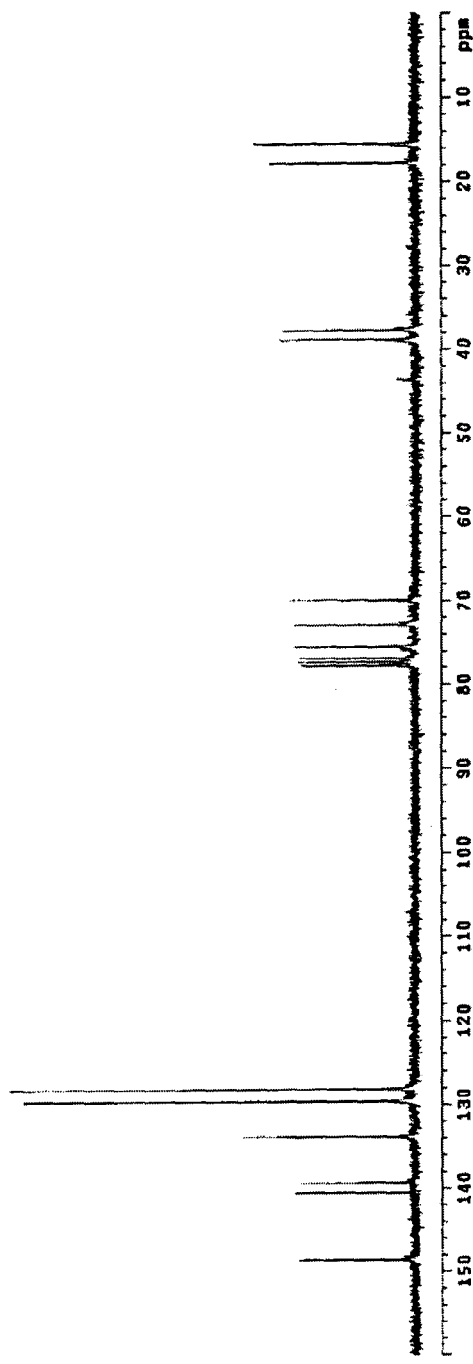
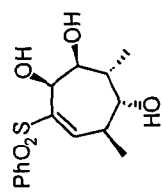

300MHz ¹H NMR of compound 39 in CDCl₃

FIGURE 8 (Cont'd)
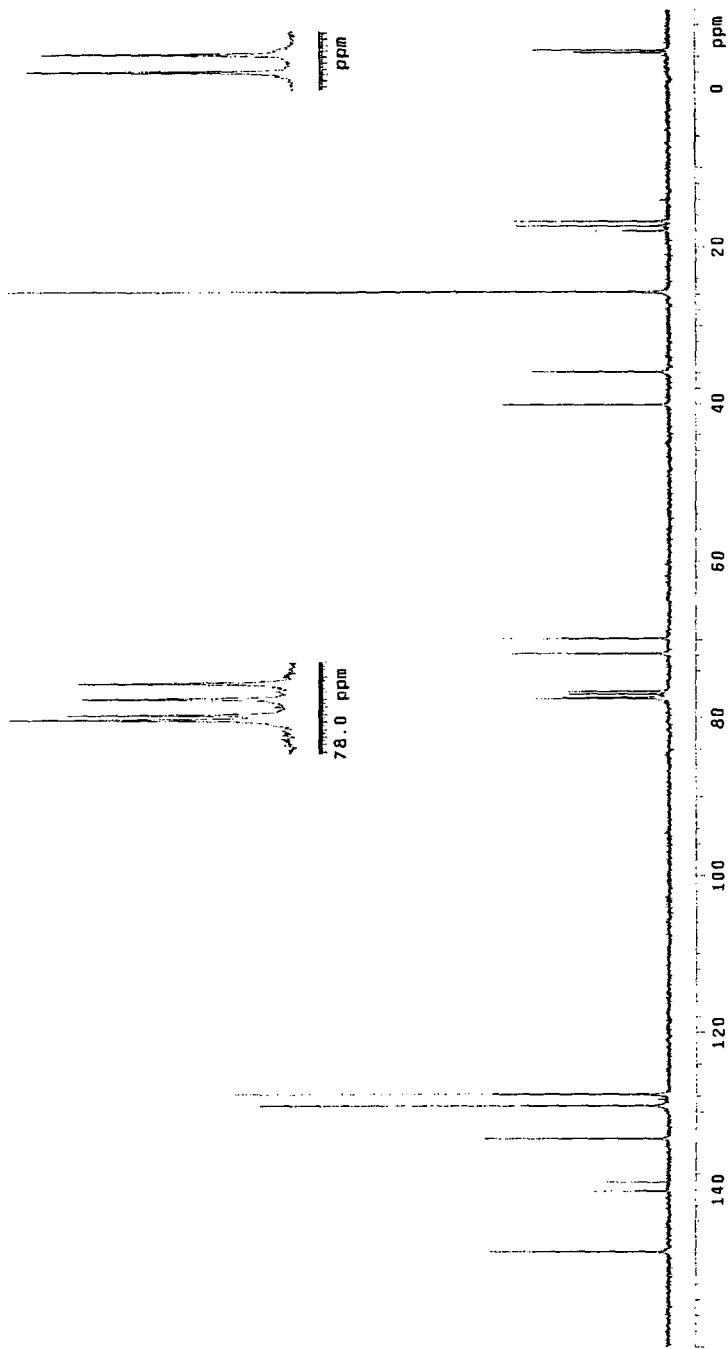
75MHz $^{13}$C NMR of compound 39 in CDCl$_3$
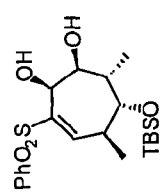

FIGURE 8 (Cont'd)
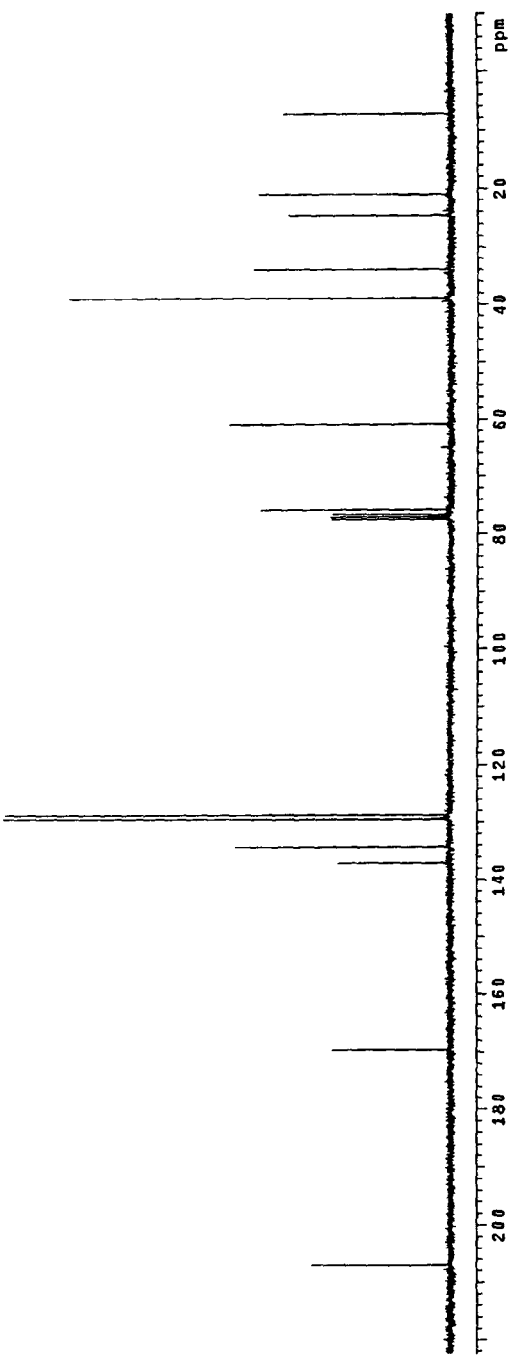
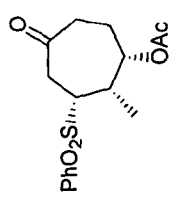
75MHz ¹³C NMR of compound 41 in CDCl₃

FIGURE 8 (Cont'd)
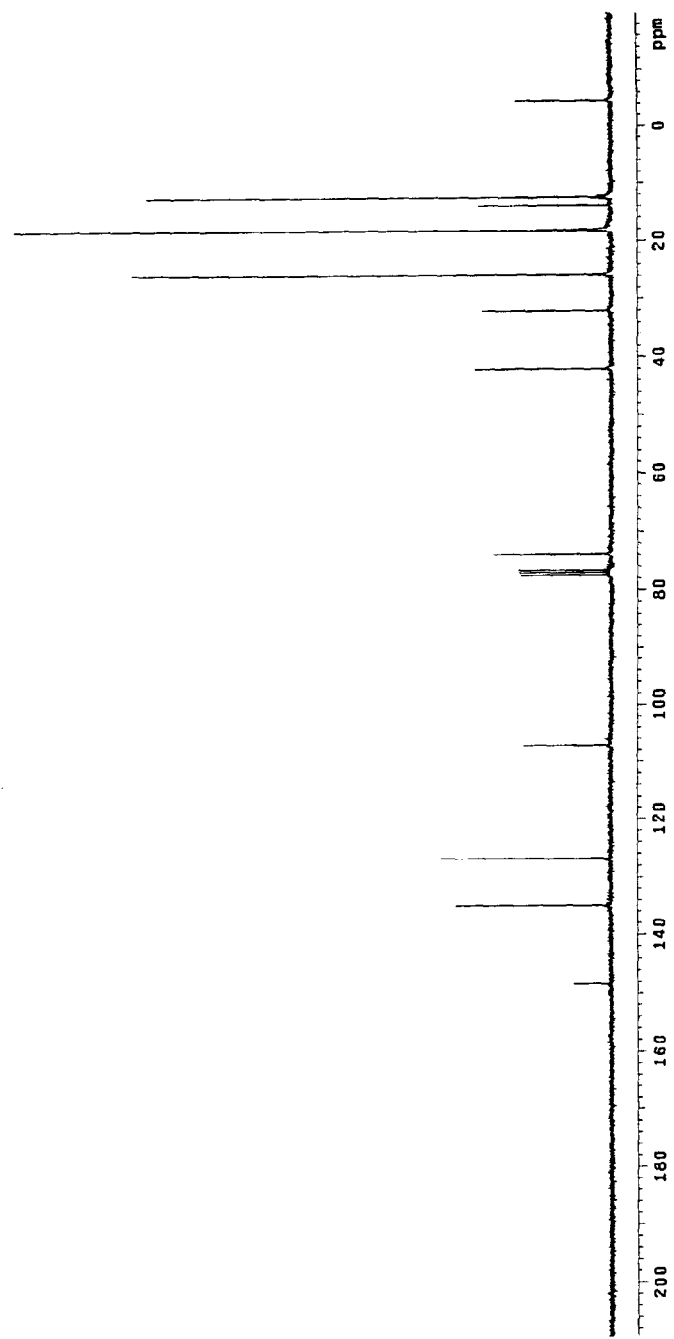
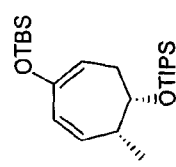
75MHz $^{13}$C NMR of compound 42 in CDCl$_3$ 300MHz $^1$H NMR of compound 43 in CDCl$_3$ FIGURE 8 (Cont'd)
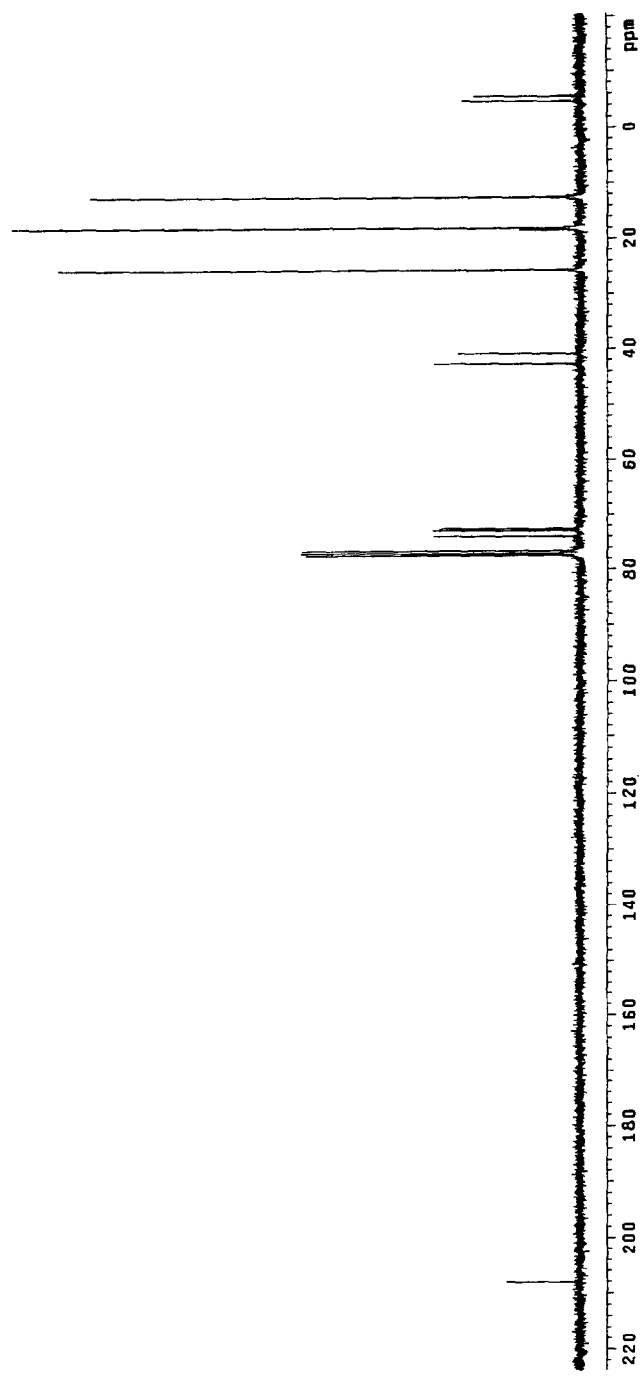
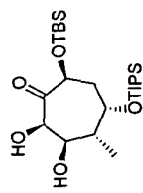
75MHz $^{13}$C NMR of compound 46 in CDCl$_3$ 300MHz $^1$H NMR of compound 47 in CDCl$_3$ 300MHz $^1$H NMR of compound 48 in CDCl$_3$ FIGURE 8 (Cont'd)
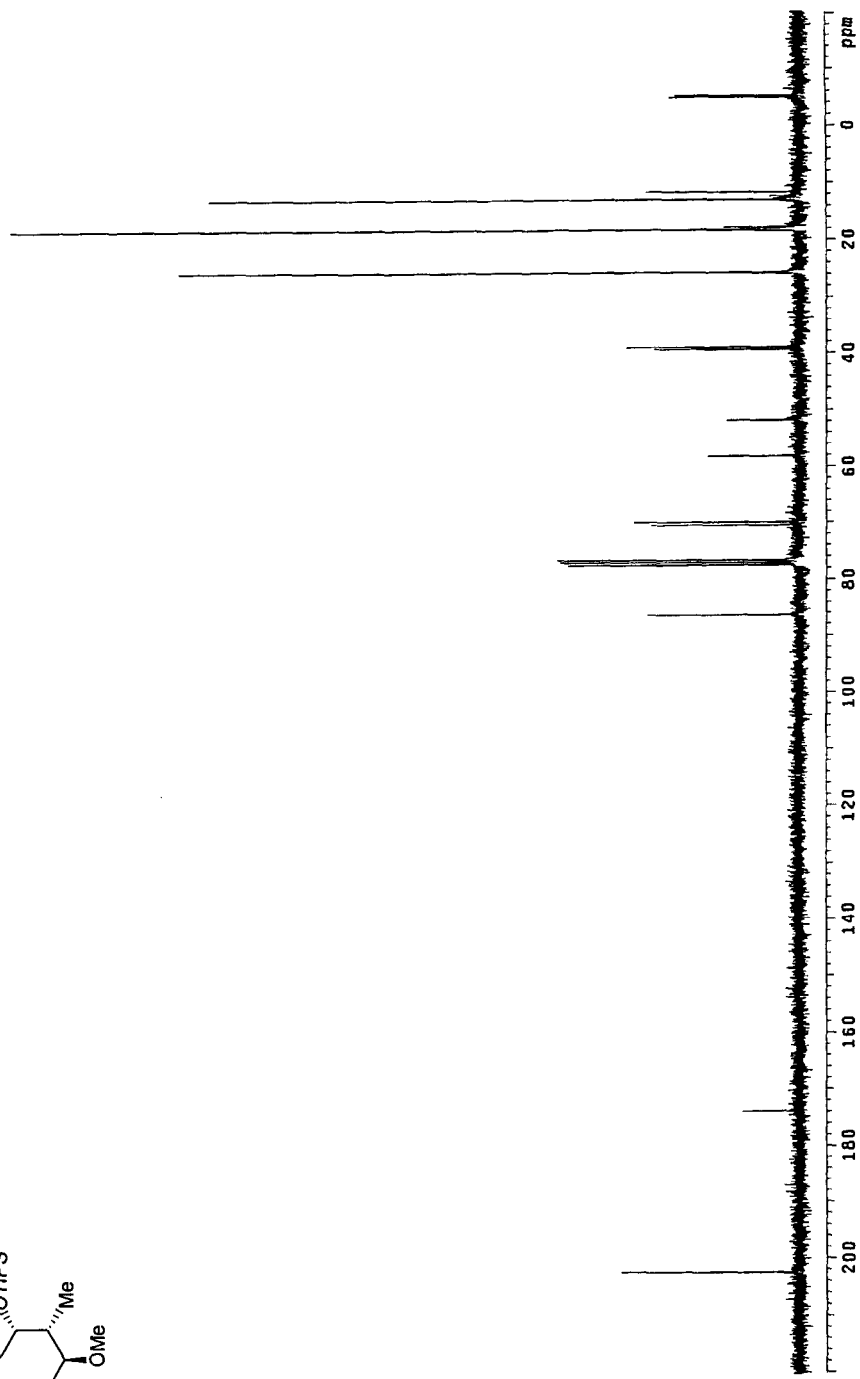
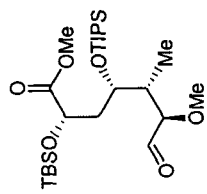

FIGURE 8 (Cont'd)
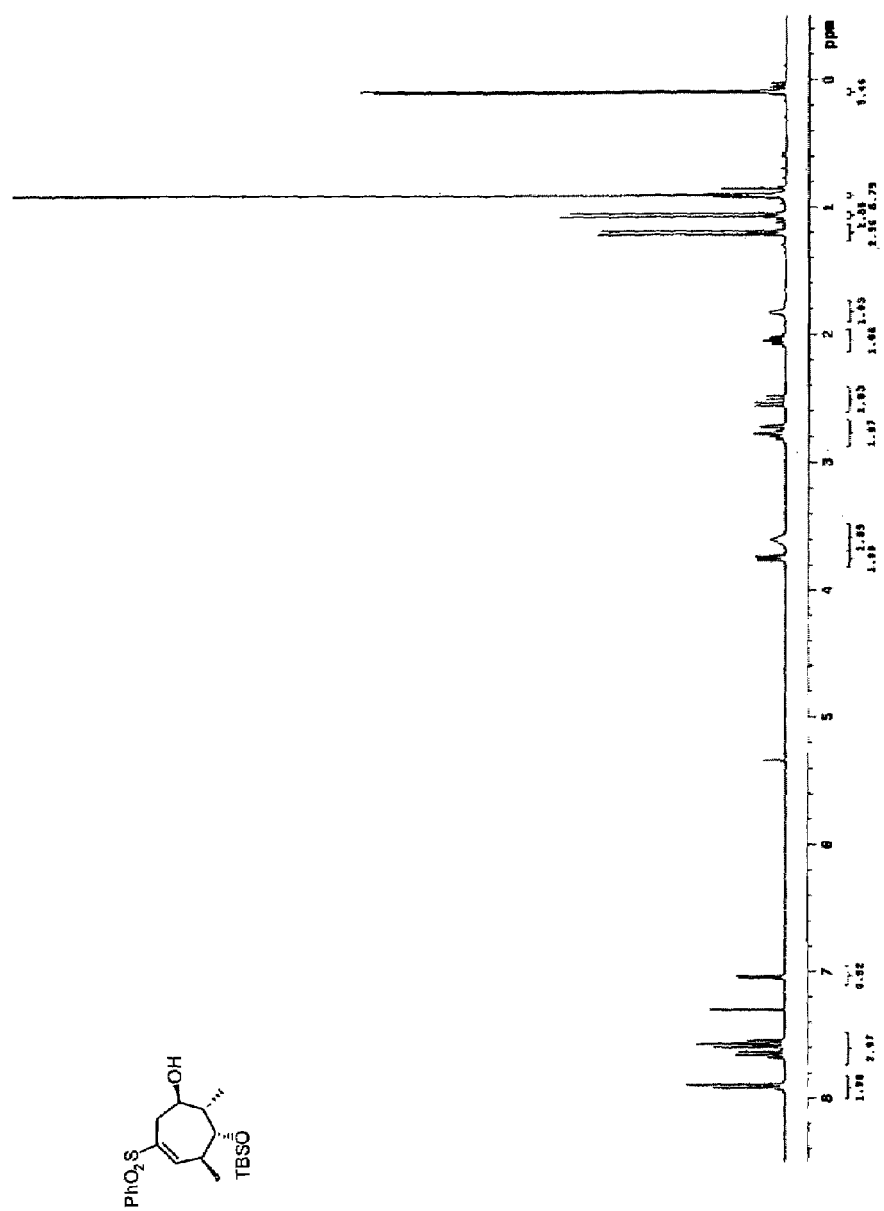
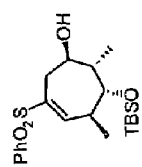

FIGURE 8 (Cont'd)
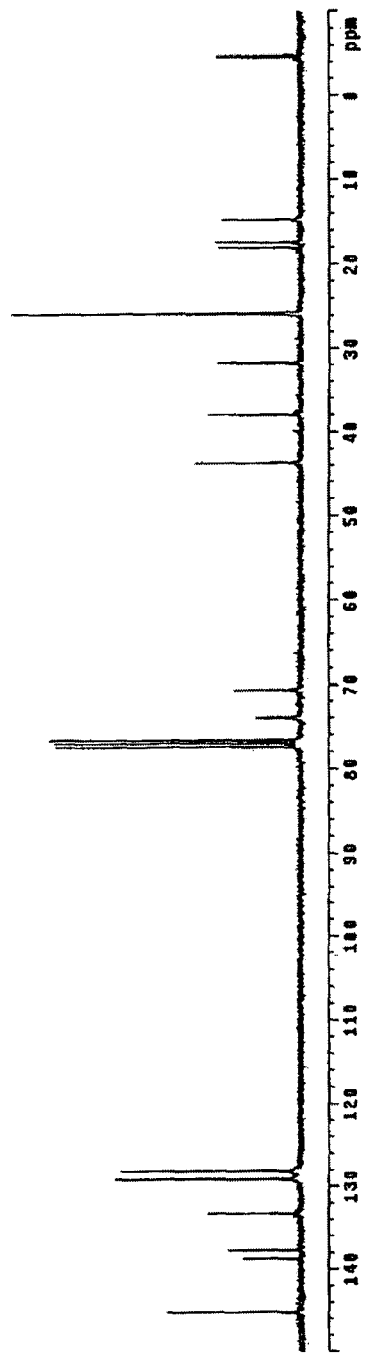
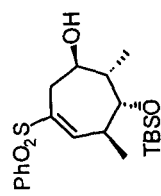
75MHz $^{13}$C NMR of compound 56 in CDCl$_3$ FIGURE 8 (Cont'd)
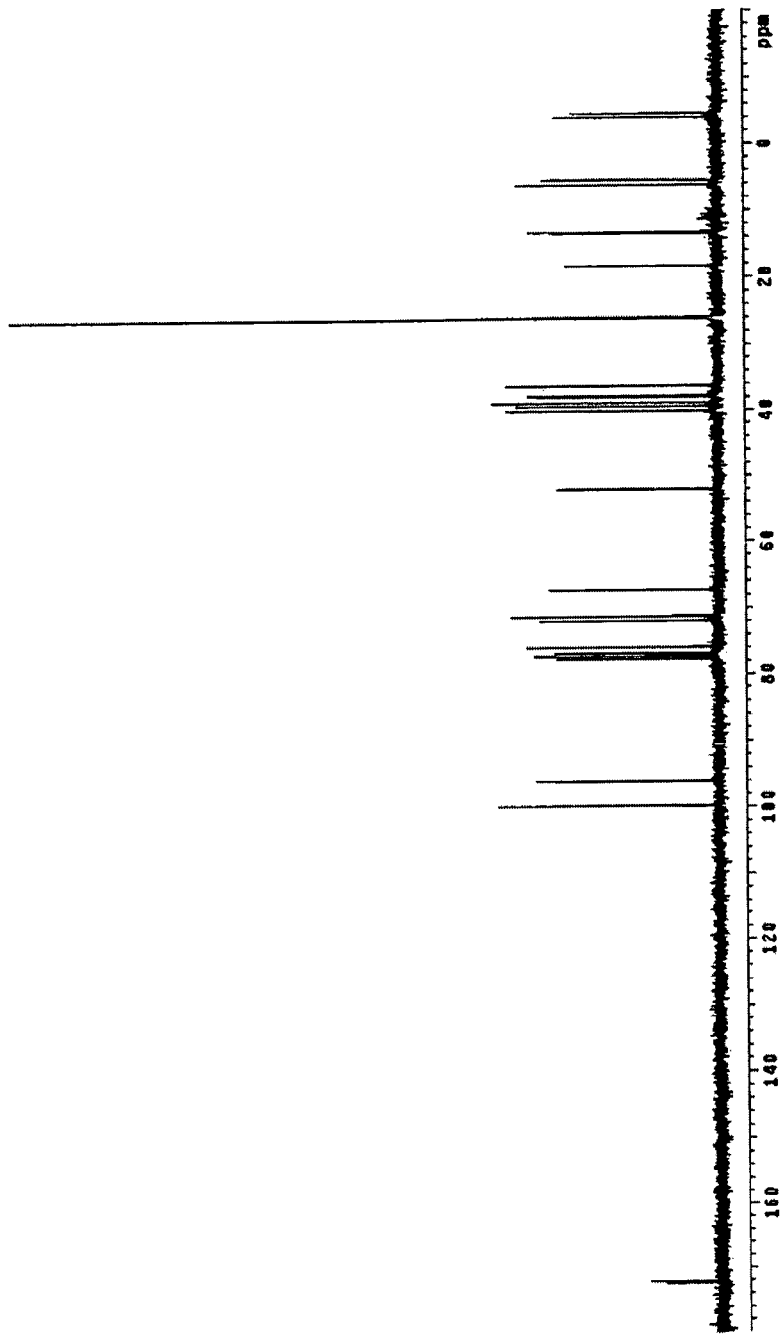
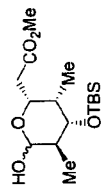

300MHz $^1$H NMR of compound 58α in CDCl$_3$

300MHz $^1$H NMR of compound 58β in CDCl$_3$

FIGURE 8 (Cont'd)
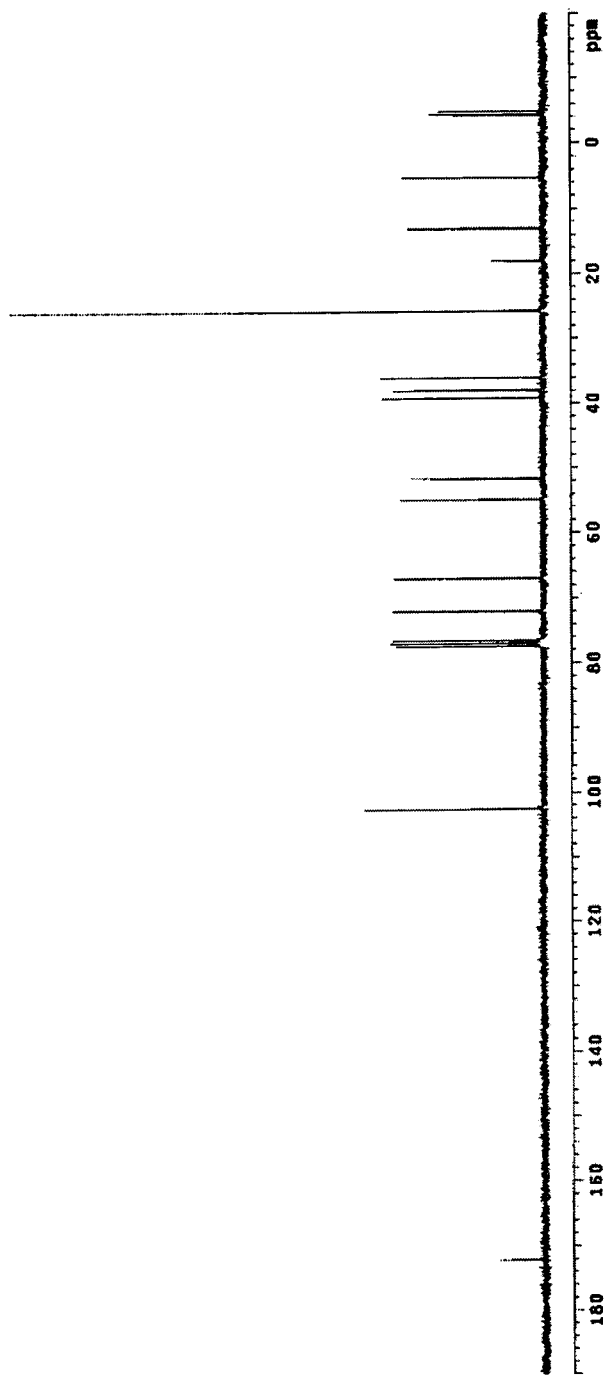
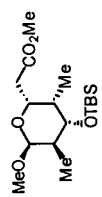
75MHz $^{13}$C NMR of compound 58β in CDCl$_3$ 75MHz $^{13}$C NMR of compound 59 in CDCl$_3$ FIGURE 8 (Cont'd)
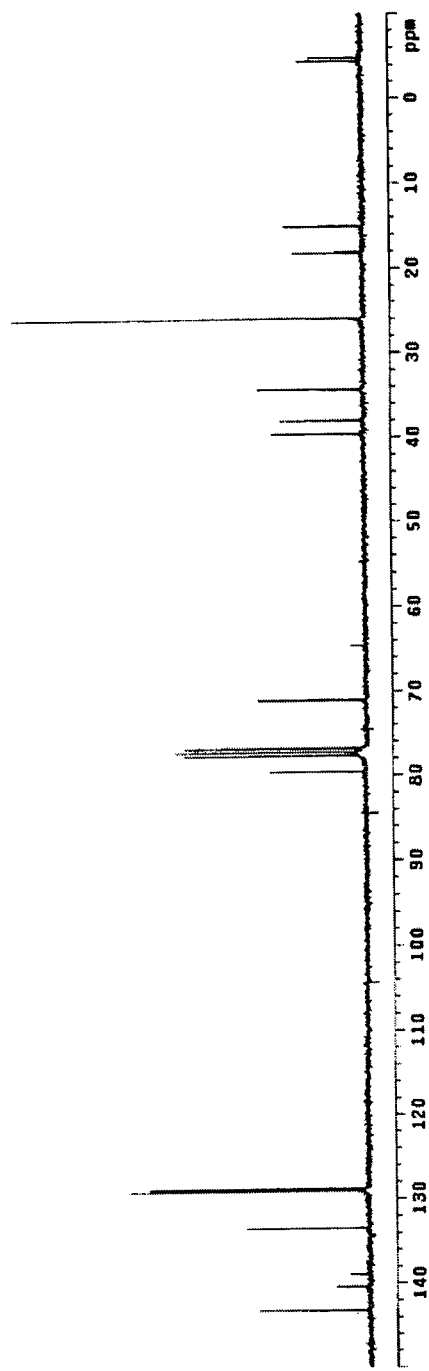
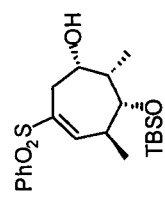
75MHz $^{13}$C NMR of compound 60 in CDCl$_3$ FIGURE 8 (Cont'd)
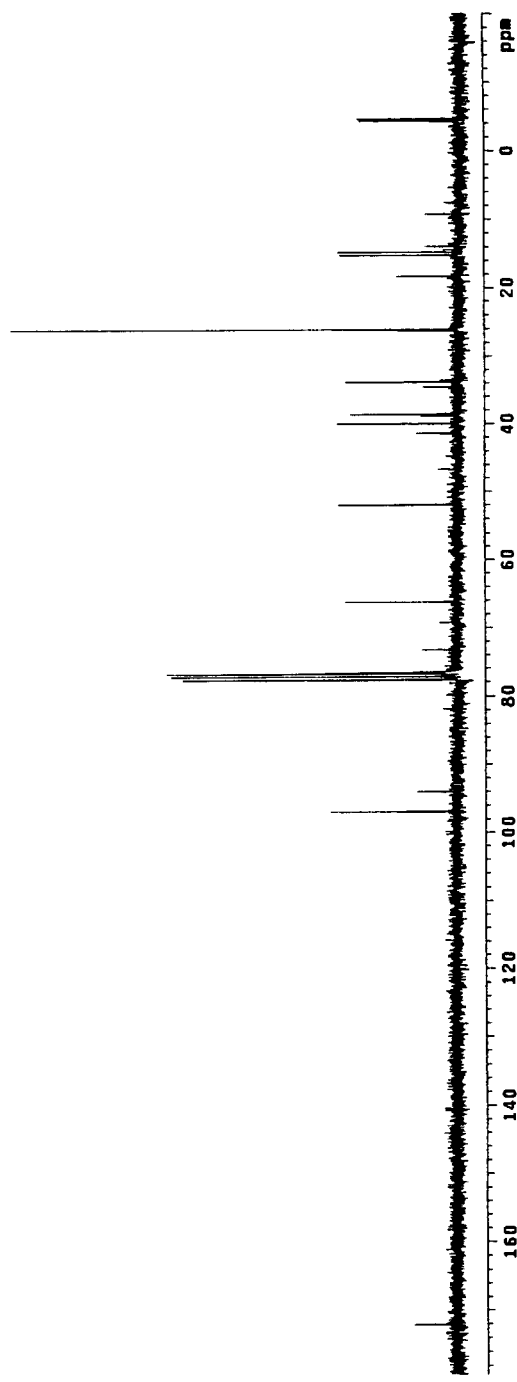
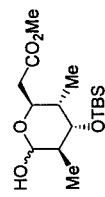
75MHz $^{13}$C NMR of compound 61 in CDCl$_3$ FIGURE 8 (Cont'd)
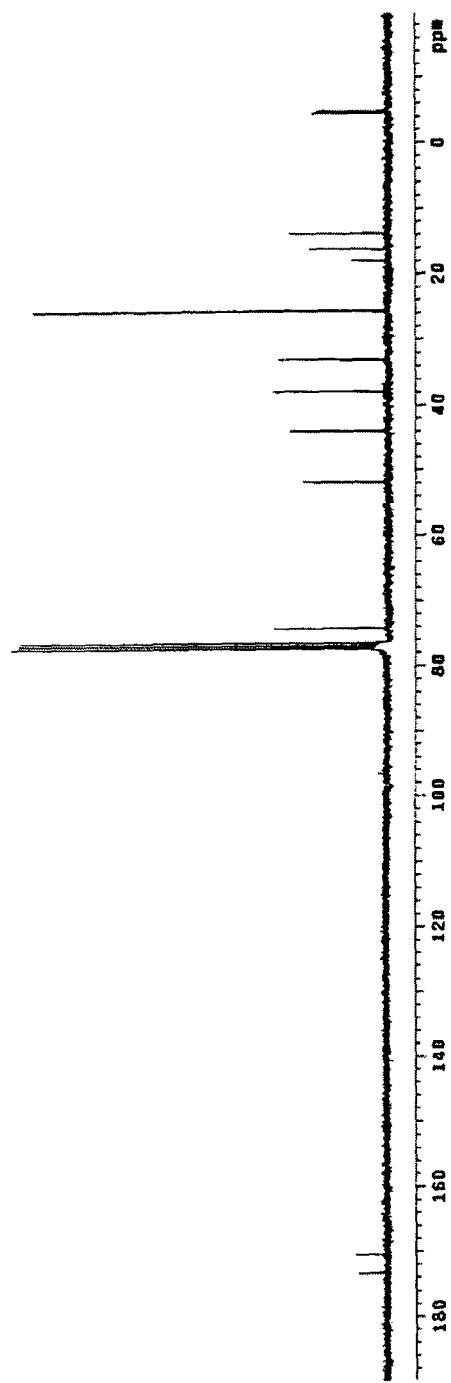
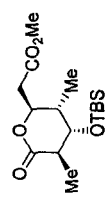
75MHz ¹³C NMR of compound 62 in CDCl₃

75MHz $^{13}$C NMR of compound 53 in CDCl$_3$

75MHz ¹³C NMR of compound 51 in CDCl₃

CHEMICAL SYNTHONS AND INTERMEDIATES

RELATED APPLICATIONS

This application claims the benefit of priority from provisional application No. 60/410,421, filed Sep. 13, 2002, which is incorporated in its entirety by reference herein.

The present invention was made with support from a grant of the National Institutes of Health. Consequently, the government retains certain rights in the invention.

FIELD OF THE INVENTION

The invention provides novel six and seven-carbon termini-differentiated polypropionate stereotetrads and stereopentads useful in syntheses of natural products, including bioactive agents, or for use in the synthesis of bioactive agents or other compounds. The invention also provides a novel alkylative sulfenylation-desulfonylation process that efficiently transforms enantiopure epoxyvinyl sulfones to syn and anti dienylsulfides in two operations.

BACKGROUND OF THE INVENTION

The trimethyldiol stereopentad is a polypropionate sequence found in many medicinally active natural products. It is possible that the pair of hydrogen bond donors/acceptors in conjunction with the conformation-influencing characteristics of the methyl groups is responsible for recognition and binding of these materials at the active site of various biological targets. While the five-center stereopentad can exist in 32 stereoisomeric forms, it appears, based upon examination of the structure-searchable databases, that only 5 of these possibilities appear in natural products reported thus far. This number can be expanded to 10 by adding those compounds which bear a keto or an ethyl group at one of the alcohol or methyl positions, respectively.

The synthesis of biologically significant structures that incorporate polypropionate sequences has been the focal point of recent research efforts. The ever-increasing need for the preparation of chiral drugs as single enantiomers has fostered the evolution of methods of polypropionate segment synthesis including asymmetric aldol and asymmetric allyl metal additions to aldehydes.

All syntheses that target a single enantiomer ultimately must be related to one or more substances obtained from the chiral pool. It is recognized that syntheses that generate their asymmetry via a chiral catalyst are desirable because one molecule of catalyst is responsible for the creation of a multitude of new chiral progeny. For maximum effect, the chiral catalyst must be commercially available, deliver product in high yield, high ee, and exhibit high turnover numbers.

Multiply-convergent syntheses that combine stereochemically defined, functionality rich segments are often inefficient. Adoption of an easily scaled segment synthesis primarily impacts the probability of success of a synthetic project. Enantiopure segments prepared via catalytic processes have intrinsic advantages over stoichiometric use of enantiopure auxiliaries or reagents as these strategies are 'high overhead,' in that they generate added time and expense. Even successful syntheses that adopt the latter approach may be limited with respect to potential scale-up.

Cross-conjugated 6 and 7-membered dienyl sulfones have been developed and now comprise a collection of termini-differentiated acyclic arrays bearing 2-5 stereocenters. As illustrated in FIG. 1, scheme 1, Jacobsen asymmetric epoxidation of dienylsulfone of 2 with about 1% catalyst loading can give greater than 80% yields of epoxides RR-3 or SS-3 with greater than 97% ee. Reapplication of the catalytic Jacobsen epoxidation protocol to 5 effects greater than 12:1 double stereoselection, providing greater than 75% isolated crystalline yields of the individual members of the 6 and 7 family with 97% de (Scheme 1). Trimethylaluminum or dimethylcuprate undergoes complementary addition to silyl ether syn-7, giving alcohols 8 and 10, respectively. Alternatively, reaction of alcohol syn-6 with methyl lithium provided the α-methylated product 9α. While cleavage of the vinyl sulfones 8 and 10β gave the pseudoenantiomers (enantiomers with protecting group reversal) 11 and 12β, respectively, further evolution of these compounds in order to access polypropionates having $C_{4,5}$ (arrows, scheme 1) functionalized would not be easily accomplished.

Accordingly, the need exists for improved stereospecific, efficient syntheses of sulfides and sulfones, including dienyl sulfides and sulfones. Novel enantiopure diastereomers made by such syntheses would also prove useful in a number of applications. For example, they could serve as bioactive agents, including pharmaceutical compositions which have stereochemical requirements. Such compounds could also be used as standards for determining the stereochemistry of segments of natural products and other compounds which are suspected of having set stereochemistries within their chemical structuces.

SUMMARY OF THE INVENTION

The invention provides novel six and seven-carbon termini-differentiated polypropionate stereotetrads and stereopentads useful in syntheses of natural products or other chemical compounds or as bioactive agents. The invention also provides a novel alkylative sulfenylation-desulfonylation process that efficiently transforms enantiopure epoxyvinyl sulfones to syn and anti dienylsulfides in two operations. This process permits the stereospecific functionalization of all six or seven carbons of a cyclohexyl or cycloheptyl system, ultimately providing six or seven-carbon termini-differentiated polypropionate stereotetrads and stereopentads appropriate for natural product synthesis.

More specifically, the invention in one embodiment employs epoxy vinylsulfone chemistry to provide improved processes for the general synthesis of both chiral 4-alkylcycloalkenones and enantiopure 2,5-cyclohexadienone synthons. Epoxyvinyl sulfones are employed as a synthon for both unpoled enones as well as chiral 2,5-cyclohexadienone equivalents in which one masked enone is charge-inverted, and the latent enone is normally polarized.

Referring to schemes 1-4, FIGS. 1-2, and the detailed description provided hereinafter, the invention in one embodiment provides enantiopure stereodiads 27 and 29 in five operations from cycloheptanone 1, with overall yields in excess of around 40% on the 100 g scale. These key substrates serve as progenitors to materials bearing up to five stereocenters on the 7-membered ring, thereby enabling synthesis of an entire collection of enantiopure diastereomers from catalytically-generated epoxide 3 (or ent-3). Enantiopure anti and syn stereodiads 27 and 29 can be used to prepare a group of termini-differentiated seven-carbon segments useful in syntheses of bioactive polypropionate derived natural products.

Further, in accordance with the invention and schemes 4a, 6a, 7a, 8a, and 9a described hereinafter in the detailed description, epoxy vinylsulfone chemistry provides improved methodology for the general synthesis of chiral 4-alkylcycloalkenones and for enantiopure 2,5-cyclohexadienone synthons.

Accordingly, the invention includes, but is not limited to, compounds of the following formulae:

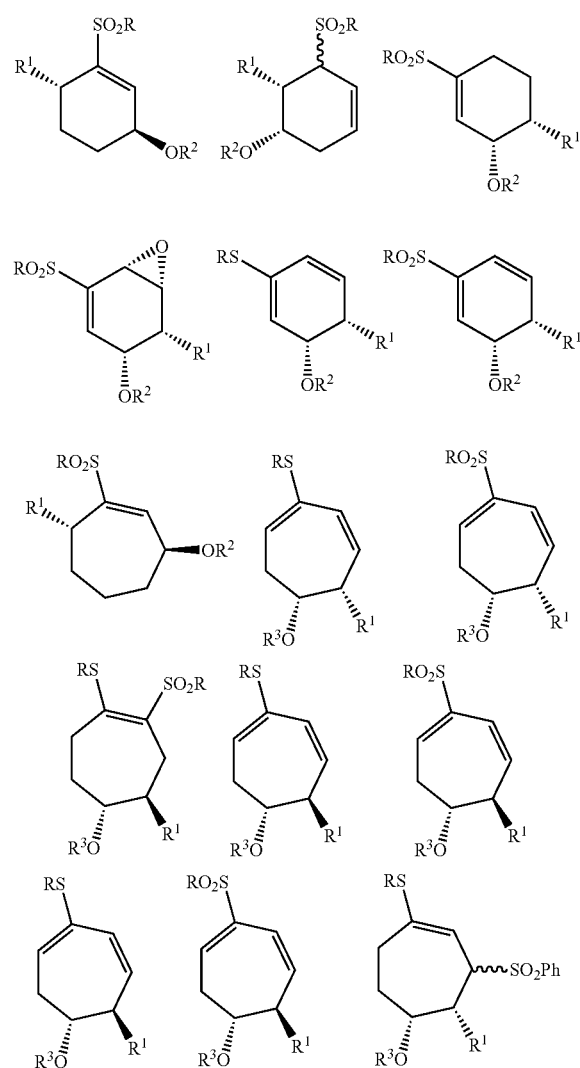

Where $R^1$ is a $C_1$-$C_5$ alkyl group;

$R^2$ and $R^3$ are independently selected from H, a $C_1$-$C_4$ alkyl group or a blocking group, preferably a silyl-containing blocking group such as a trimethyl silyl group or a t-butyl dimethyl silyl group; and R is a phenyl or substituted phenyl group wherein the substituted phenyl group is substituted in one instance at the ortho, meta or para position of the phenyl group with a $C_1$-$C_4$ alkyl group, a halogen (F, Cl, Br, I) a nitro group, an amine, hydroxyl, alkyl ester (wherein the alkyl group on the ester is a $C_1$-$C_4$ alkyl group), alkylether (wherein the alkyl group on the ester is a $C_1$-$C_4$ alkyl group) or acyl group.

More preferred compounds according to the present invention are selected from the following chemical compounds:

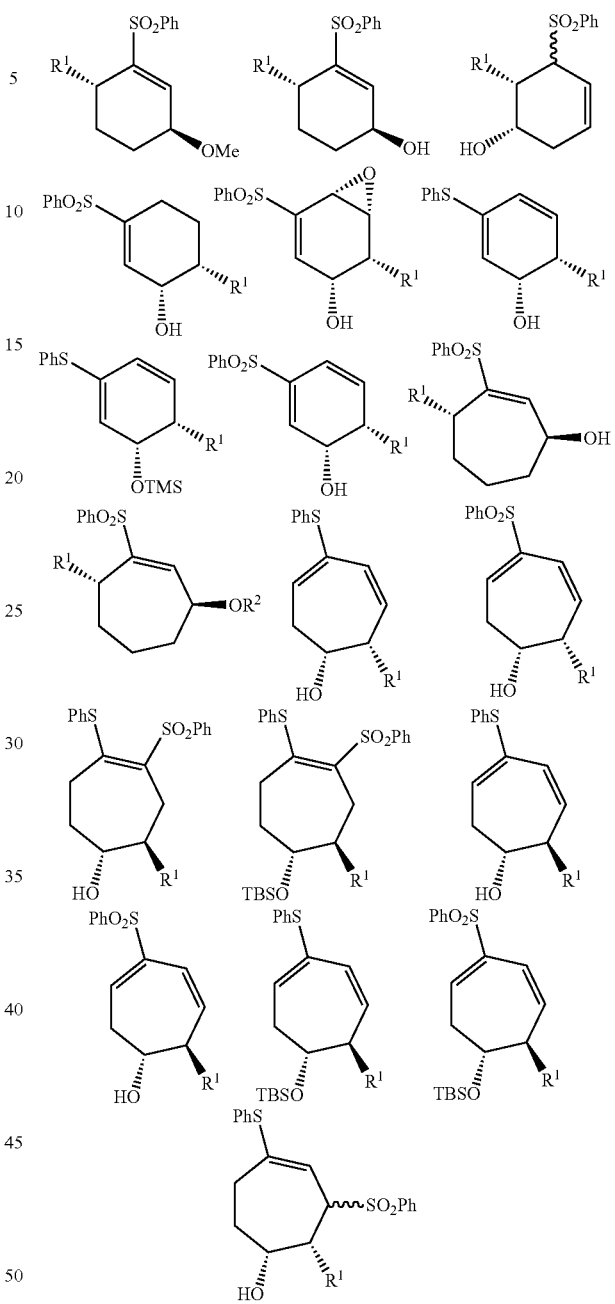

Wherein $R^1$ is as described above.

Methods of making and using these compounds in the synthesis of bioactive agents, pharmaceutical compounds and other chemical compounds which contain chiral centers and specific stereochemistry are provided by the present invention.

The syntheses of the claimed compounds may be carried out readily using the methods which are identified hereinafter. Alternatives to the disclosed methods are contemplated by relying on analogous applications of the disclosed methods which are presented in significant detail hereinafter.

The present invention also relates to compounds according to the present invention wherein the compound is made by a process in which reaction of allyl sulfones with TMS triflate and an amine, preferably an organic amine such as triethylamine in a solvent such as methylene chloride at reflux effects regiospecific elimination to yield dienylsulfides; the dienylsulfides are oxidized through addition of an oxidizing agent, preferably a peroxide oxidizing agent such as mCPBA; and wherein the process can be done one pot or in steps.

The present invention also relates to methods of making a compound according to the present invention by:

(a) reacting allyl sulfones of the formula

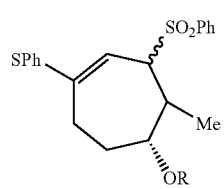

with TMS triflate and an amine, such as an organic amine including triethylamine in a solvent, such as methylene chloride, at reflux to yield a dienylsulfide of the formula

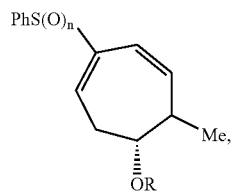

and oxidizing the dienylsulfide with an oxidizing agent, preferably a peroxide oxidizing agent such as mCPBA, where R is $C_1$-$C_5$ alkyl, phenyl, substituted phenyl, vinyl, alkynyl, trimethylsilyl or t-butyldimethylsilyl and wherein the reaction can be done one pot or in steps.

The present invention also relates to compounds according to the present invention as otherwise described herein and methods of making such compounds, wherein the compound is made by alkylating an epoxyvinylsulfone of the formula

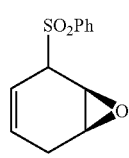

in a reaction medium comprising $(R)_2CuLi$, a solvent, such as an ether solvent, such as THF, $ET_2O$ or a mixture of THF and $Et_2O$, where R is a $C_1$ to $C_5$ alkyl and wherein the reaction can be done one pot or in steps.

In other aspects of the present invention a compound according to the present invention is made by oxidizing an allylic alcohol of the formula

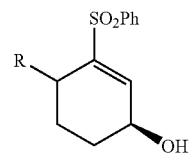

where R is a $C_1$ to $C_5$ alkyl, phenyl, substituted phenyl, vinyl, alkynyl, trimethylsilyl or t-butyldimethylsilyl to yield a β-sulfonyl enone of the formula

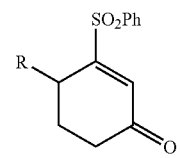

wherein the β-sulfonyl enone is subjected to Michael addition of heterocuprates and subsequent β-elimination of sulfinate, and wherein the reactions are done one pot or in steps.

In still other aspects, a compound according to the present invention is made by reacting a sulfone of the formula

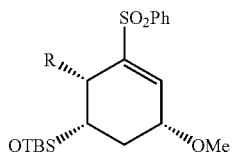

where R is a $C_1$ to $C_5$ alkyl, phenyl, substituted phenyl, vinyl, alkynyl, trimethylsilyl or t-butyldimethylsilyl with one or more alkyl halides.

In still other aspects, the present invention relates to a cleavage process comprising using a tetraacetate cleavage such as lead tetraacetate to promote oxidative cleaveage cleavage of a compound of the formula

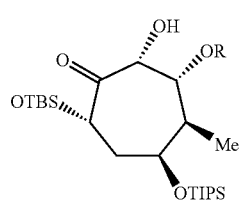

to yield an enantiopure aldehyde-ester of the formula

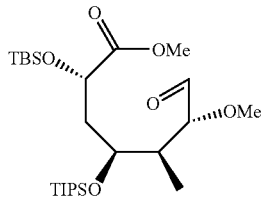

where R is a $C_1$ to $C_5$ alkyl, phenyl, substituted phenyl, vinyl, alkynyl, trimethylsilyl or t-butyldimethylsilyl, the process is done one pot or in steps, and wherein the enantiopure aldehyde-ester is used in the synthesis of the $C_{12}$-$C_{18}$ fragment of rhizoxin D.

In still other aspects, the present inventon relates to a synthetic method comprising:
(a) reacting allyl sulfones of the formula

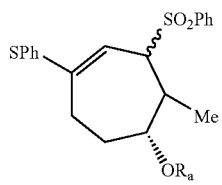

with TMS triflate and an amine, preferably, triethylamine in a solvent, preferably, methylene chloride, at reflux to yield a dienylsulfide of the formula

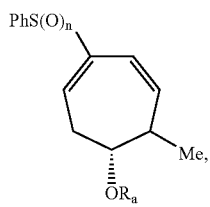

and oxidizing the dienylsulfide with an oxidizing agent, preferably a peroxide oxidizing agent such as mCPBA, where $R_a$ is $C_1$-$C_5$ alkyl, phenyl, substituted phenyl, vinyl, alkynyl, trimethylsilyl or t-butyldimethylsilyl to yield a compound of the formula

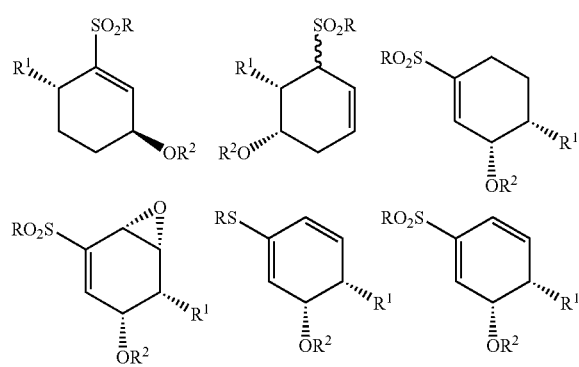

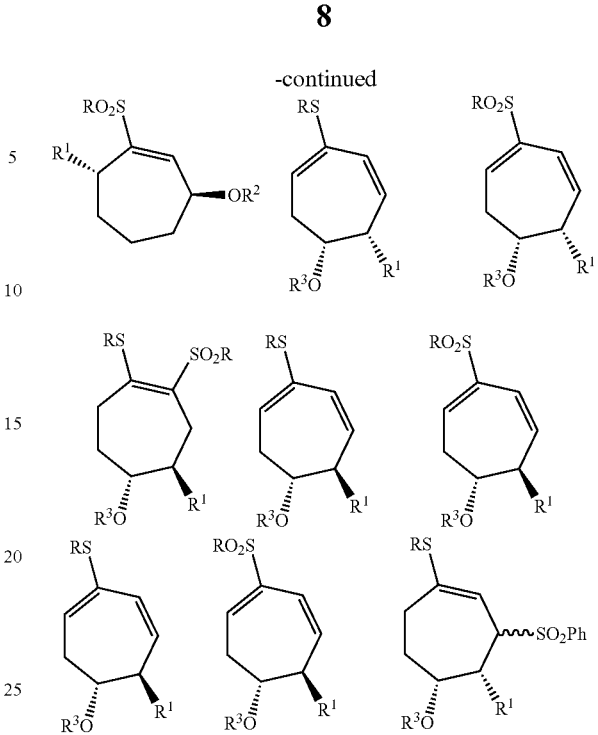

wherein:
$R^1$ is a $C_1$-$C_4$ alkyl group;
$R^2$ and $R^3$ are independently selected from H, a $C_1$-$C_4$ alkyl group or a blocking group, preferably a silyl-containing blocking group such as a trimethyl silyl group or a t-butyl dimethyl silyl group; and
R is a phenyl or substituted phenyl group wherein the substituted phenyl group is substituted in one instance at the ortho, meta or para position of the phenyl group with a $C_1$-$C_4$ alkyl group, a halogen (F, Cl, Br, I) a nitro group, an amine, hydroxyl, alkyl ester (wherein the alkyl group on the ester is a $C_1$-$C_4$ alkyl group), alkylether (wherein the alkyl group on the ester is a $C_1$-$C_4$ alkyl group) or acyl group,
and wherein the reaction can be done one pot or in steps.

These and other aspects of the instant invention are described further in the following detailed description.

BRIEF DESCRIPTION OF THE DRAWINGS

FIG. 1 illustrates preparation of acyclic arrays (scheme 1) and attempted sulfenylation (scheme 2).

FIG. 2 illustrates novel gamma sulfenylation and diene transposition (scheme 3).

FIG. 4 illustrates synthesis of $C_{12}$-$C_{18}$ fragment of rhizoxin D (scheme 5).

FIG. 5 illustrates synthesis of the ent-$C_{15}$-$C_{21}$ fragment of conanamycin F (scheme 6).

FIG. 6 illustrates preparation of a C21-C27 fragment of apoptolidin and C1-C7 fragment of discodermolide (scheme 7).

DETAILED DESCRIPTION OF THE INVENTION

Figure 3:
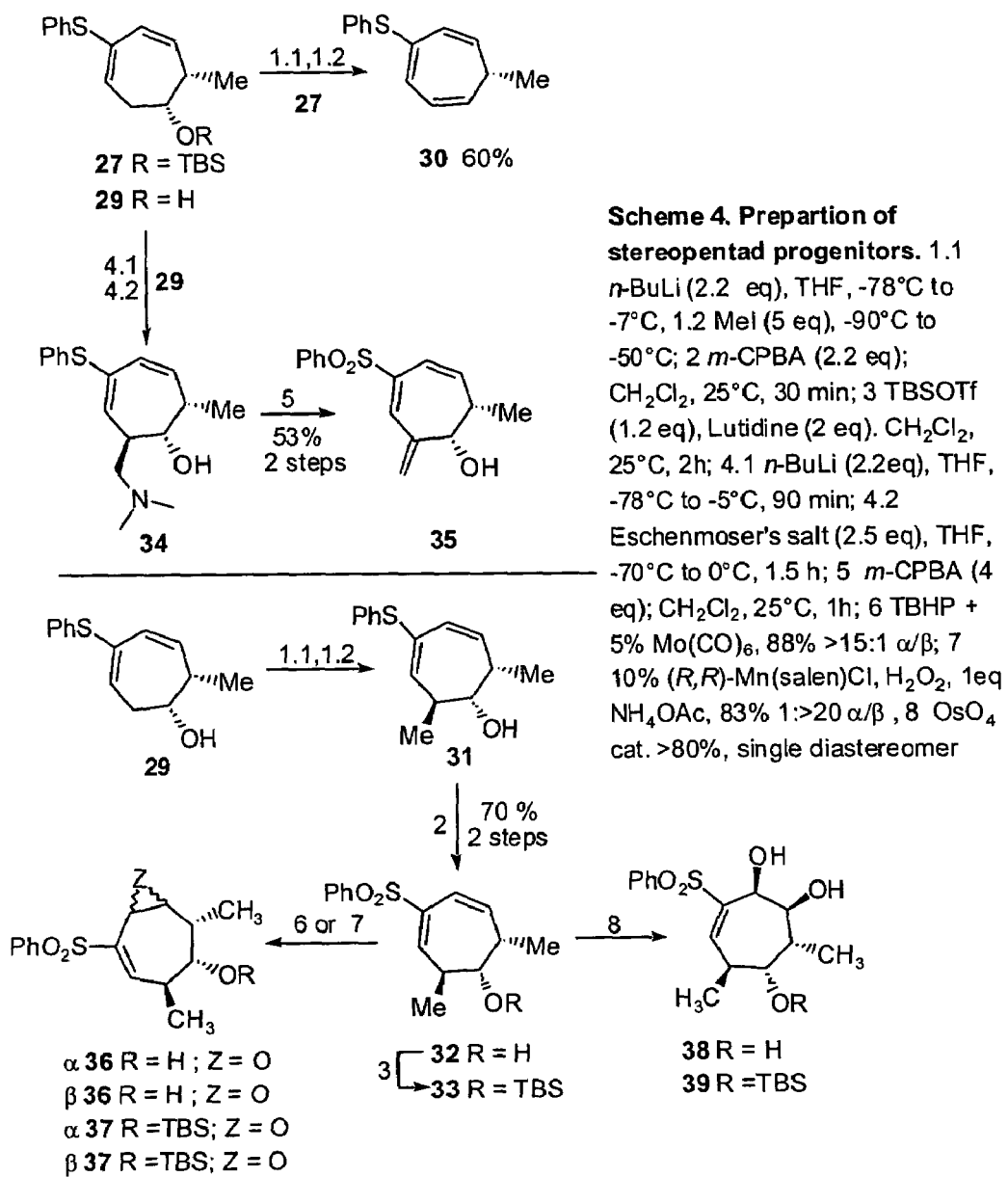
FIG. 3 illustrates preparation of steropentad progenitors (scheme 4).

As used herein, the following terms have the following respective meanings. Other terms that are used to describe the present invention have the same definitions as those generally used by those skilled in the art. Specific examples recited in any definition are not intended to be limiting in any way.

"Hydrocarbon" refers to a substituted or unsubstituted organic compound.

"Acetal" refers to a compound in which two ether oxygens are bound to the same carbon. A "ketal" is an acetal derived from a ketone.

"Acyl" means a compound of the formula RCO, where R is aliphatic (characterized by a straight chain of carbon atoms), alicyclic (a saturated hydrocarbon containing at least one ring), or aromatic.

"Acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein "Alkyl" refers to a fully saturated monovalent hydrocarbon radical containing carbon and hydrogen which may be a straight chain, branched, or cyclic. Examples of alkyl groups are methyl, ethyl, n-butyl, n-heptyl, isopropyl, 2-methylpropyl, cyclopropyl, cyclopropylmethyl, cyclobutyl, cyclopentyl, cyclopentylethyl and cyclohexyl. "Cycloalkyl" groups refer to cyclic alkyl groups such as cyclopropyl, cyclobutyl, cyclopentyl and cyclohexyl. $C_1$-$C_7$ alkyl groups are preferably used in the present invention.

"Substituted alkyl" refers to alkyls as just described which include one or more functional groups such an alkyl containing from 1 to 6 carbon atoms, preferably a lower alkyl containing 1-3 carbon atoms, aryl, substituted aryl, acyl, halogen (i.e., alkyl halos, e.g., $CF_3$), hydroxy, alkoxy, alkoxyalkyl, amino, alkyl and dialkyl amino, acylamino, acyloxy, aryloxy, aryloxyalkyl, carboxyalkyl, carboxamido, thio, thioethers, both saturated and unsaturated cyclic hydrocarbons, heterocycles and the like. The term "substituted cycloalkyl" has essentially the same definition as and is subsumed under the term "substituted alkyl" for purposes of describing the present invention.

"Amine" refers to aliphatic amines, aromatic amines (e.g., aniline), saturated heterocyclic amines (e.g., piperidine), and substituted derivatives such as an alkly morpholine. "Amine" as used herein includes nitrogen-containing aromatic heterocyclic compounds such as pyridine or purine.

"Aralkyl" refers to an alkyl group with an aryl substituent, and the term "aralkylene" refers to an alkenyl group with an aryl substituent. The term "alkaryl" refers to an aryl group that has an alkyl substituent, and the term "alkarylene" refers to an arylene group with an alkyl substituent. The term "arylene" refers to the diradical derived from aryl (including substituted aryl) as exemplified by 1,2-phenylene, 1,3-phenylene, 1,4-phenylene, 1,2-naphthylene and the like.

"Alkenyl" refers to a branched or unbranched hydrocarbon group typically although not necessarily containing 2 to about 24 carbon atoms and at least one double bond, such as ethenyl, n-propenyl, isopropenyl, n-butenyl, isobutenyl, octenyl, decenyl, and the like. Generally, although again not necessarily, alkenyl groups herein contain 2 to about 12 carbon atoms.

The term "lower alkenyl" intends an alkenyl group of two to six carbon atoms, preferably two to four carbon atoms.

"Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

"Aryl" refers to a substituted or unsubstituted monovalent aromatic radical having a single ring (e.g., phenyl) or multiple condensed rings (e.g., naphthyl). Other examples include heterocyclic aromatic ring groups having one or more nitrogen, oxygen, or sulfur atoms in the ring, such as imidazolyl, furyl, pyrrolyl, pyridyl, thienyl and indolyl, among others. Therefore, "aryl" as used herein includes "heteroaryls" having a mono- or polycyclic ring system which contains 1 to 15 carbon atoms and 1 to 4 heteroatoms, and in which at least one ring of the ring system is aromatic. Heteroatoms are sulfur, nitrogen or oxygen.

"Substituted aryl" refers to an aryl as just described that contains one or more functional groups such as lower alkyl, acyl, aryl, halogen, alkylhalos (e.g., $CF_3$), hydroxy, alkoxy, alkoxyalkyl, amino, alkyl and dialkyl amino, acylamino, acyloxy, aryloxy, aryloxyalkyl, carboxyalkyl, carboxamido, thio, thioethers, both saturated and unsaturated cyclic hydrocarbons, heterocycles and the like.

"Alkynyl" as used herein refers to a branched or unbranched hydrocarbon group typically although not necessarily containing 2 to about 24 carbon atoms and at least one triple bond, such as ethynyl, n-propynyl, isopropynyl, n-butynyl, isobutynyl, octynyl, decynyl, and the like. Generally, although again not necessarily, alkynyl groups herein contain 2 to about 12 carbon atoms. The term "lower alkynyl" intends an alkynyl group of two to six carbon atoms, preferably three or four carbon atoms. "Substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

"Alkoxy" as used herein refers to an alkyl group bound through an ether linkage; that is, an "alkoxy" group may be represented as —O-alkyl where alkyl is as defined above. A "lower alkoxy" group intends an alkoxy group containing one to six, more preferably one to four, carbon atoms.

"Allenyl" is used herein in the conventional sense to refer to a molecular segment having the structure —CH=C=CH$_2$. An "allenyl" group may be unsubstituted or substituted with one or more non-hydrogen substituents.

"Anomer" as used herein means one of a pair of isomers of a cyclic carbohydrate resulting from creation of a new point of symmetry when a rearrangement of atoms occurs at an aldehyde or ketone position.

"Halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

"Heterocycle" or "heterocyclic" refers to a carbocylic ring wherein one or more carbon atoms have been replaced with one or more heteroatoms such as nitrogen, oxygen or sulfur. A substitutable nitrogen on an aromatic or non-aromatic heterocyclic ring may be optionally substituted. The heteroatoms N or S may also exist in oxidized form such as NO, SO and $SO_2$. Examples of heterocycles include, but are not limited to, piperidine, pyrrolidine, morpholine, thiomorpholine, piperazine, tetrahydrofuran, tetrahydropyran, 2-pyrrolidinone, δ-velerolactam, δ-velerolactone and 2-ketopiperazine, among numerous others.

"Heteroatom-containing" refers to a molecule or molecular fragment in which one or more carbon atoms is replaced with an atom other carbon, e.g., nitrogen, oxygen, sulfur, phosphorus or silicon. "Substituted heterocycle" refers to a heterocycle as just described that contains one or more functional groups such as lower alkyl, acyl, aryl, cyano, halogen, hydroxy, alkoxy, alkoxyalkyl, amino, alkyl and dialkyl amino, acylamino, acyloxy, aryloxy, aryloxyalkyl, carboxyalkyl, carboxamido, thio, thioethers, both saturated and unsaturated cyclic hydrocarbons, heterocycles and the like. In other instances where the term "substituted" is used, the substituents which fall under this definition may be readily gleaned from the other definitions of substituents which are presented in the specification as well the circumstances under which such substituents occur in a given chemical compound. One having ordinary skill in the art will recognize that the maximum number of heteroatoms in a stable, chemically feasible heterocyclic ring, whether it is aromatic or non-aromatic, is determined by the size of the ring, degree of unsaturation, and valence of the heteroatoms. In general, a heterocyclic ring may have one to four heteroatoms so long as the heterocyclic ring is chemically feasible and stable.

"Isostere" refers to compounds that have substantially similar physical properties as a result of having substantially similar electron arrangements.

"Substituted", as in "substituted alkyl" or "substituted alkenyl", means that in the hydrocarbyl, hydrocarbylene, alkyl, alkenyl or other moiety, at least one hydrogen atom bound to a carbon atom is replaced with one or more substituents that are functional groups such as hydroxyl, alkoxy, thio, amino, halo, silyl, and the like. When the term "substituted" appears prior to a list of possible substituted groups, it is intended that the term apply to every member of that group.

"Effective amount" refers to the amount of a selected compound, intermediate or reactant which is used to produce an intended result. The precise amount of a compound, intermediate or reactant used will vary depending upon the particular compound selected and its intended use, the age and weight of the subject, route of administration, and so forth, but may be easily determined by routine experimentation. In the case of the treatment of a condition or disease state, an effective amount is that amount which is used to effectively treat the particular condition or disease state. Therefore, "effective amount" includes amounts of compounds of the instant invention that are effective in treating: anxiolytic disorders; a condition requiring treatment of injured mammalian nerve tissue; a condition amenable to treatment through administration of a neurotrophic factor; a neurological disorder; obesity; an obesity-related disorder; or a condition related to an endocrine function including inovulation and infertility.

The term "subjects" is used throughout the specification to describe an animal, preferably a human, to whom treatment, including prophylactic treatment, with the compositions according to the present invention is provided. For treatment of those infections, conditions or disease states which are specific for a specific animal such as a human patient, the term patient refers to that specific animal.

Reference to one or more of the following references in relevant part provides background and other information which may prove useful in synthesizing the present compounds and employing the invention of the present application. See, for example:

Hentenmann and Fuchs, *Tetrahedron Lett.*, 40, 2699-2701 (1999);

Evarts and Fuchs, *Tetrahedron Lett.*, 40, 2703-2706 (1999);

Hentenmann and Fuchs, *Organic Lett.*, 1, 355-357 (1999);

Jiang, et al., *Organic Lett.*, 2, 2181-2184 (2000);

Tong, et al., *Tetrahedron Lett.*, 41, 7795-7799 (2000);

Evarts and Fuchs, *Tetrahedron Lett.*, 42, 3673-3675 (2001);

Myers and Fuchs, *J. Org. Chem.*, 60, 200-204, (2002);

Evarts, et al., *J. Am. Chem. Soc.*, 124, 11093-11101 (2002); and

Torres, et al., *Angew. Chem. Int. Ed.*, 27, 3124-3131 (2003), relevant portions of which are incorporated by reference herein.

Chemistry

Referring to FIG. 1, schemes 1 and 2, compounds 4 and 5 were treated with methyl lithium to generate allyl sulfonyl anions 4Li$_2$ and 5Li, respectively. Quenching of these anions at low temperature delivered 14α and 15β, (as mixtures of sulfone diastereomers, E=H) in excess of 85% yield. HPLC analysis revealed that methylation of both intermediates occurred with complementary greater than 10:1 diastereoselectivity. Sulfenylation with dimethyldisulfide or methylthiolsulfonate gave a complicated mixture of products, which appeared to involve both α and γ-sulfenylation of the intermediate allylic anions. Attempted hydrolysis of these mixtures to enones 16 or 17 was unrewarding (FIG. 1, Scheme 2).

Reaction of the allylic anions 4Li$_2$ and 5Li with the more sterically-demanding diphenyldisulfide suffered regiospecific quenching at the γ-position, initially affording syn-18 and anti-19, as a mixture of sulfide diastereomers. Monitoring of the reaction revealed that isomerization of intermediate vinylsulfones syn-18 and anti-19 to allyl sulfones syn-21 and anti-22 occurs under the basic reaction conditions (FIG. 2, Scheme 3). While ionization of the γ-phenylsulfonyl moiety of acyclic vinyl ethers and vinyl sulfides is known to generate enones and enals, the corresponding reaction for cyclic substrates is far less common.

Reaction of allyl sulfones syn-21 and anti-22 with TMS triflate and triethylamine in methylene chloride at reflux effected regiospecific elimination to dienylsulfides syn-29 and anti-27. This transformation relies upon the unique amphoteric nature of the sulfone moiety. While sulfones are used as withdrawing groups to polarize olefins and inductively stabilize anions, it is the leaving group ability of phenyl sulfinic acid (pKa 7.1), which enables the lone pair of phenylvinyl sulfide group to expel sulfinate.[*r*] Presumably the silyl triflate serves to activate the sulfone moiety by reversible oxygen silylation (to 24, 25), thereby also preventing readdition of silyl sulfinate 26 once the vinyl thionium ion loses proximal proton H$_a$. Oxidation of 27 and 29 to key dienyl sulfones 27ox and 29ox can be achieved by addition of mCPBA to the crude reaction mixture. This two-operation sequence enables stereoselective methylation with simultaneous establishment of a new, transposed diene (FIG. 1, Scheme 3). This transformation provides enantiopure stereodiads 27 and 29 in five operations from cycloheptanone 1 (overall yields are in excess of 40% on the 100 g scale).

The dienyl sulfone strategy proves useful in those cases where 4-5 stereocenters are required. As described, these key substrates serve as progenitors to materials bearing up to five stereocenters on the 7-membered ring, thereby enabling synthesis of an entire collection of enantiopure diastereomers from catalytically-generated epoxide 3 (or ent-3). Employing the TMS ether 13 afforded the unexpected syn-28 after elimination of the sulfone moiety. Syn-addition via direction by OLi groups has been demonstrated on many occasions, but since silyloxy groups are generally held not to promote oxygen-coordinated direction, it appeared possible that more subtle conformational effects were involved. Conformational modeling show the TMS ether 19 preferred an equatorial oxygen, which placed the TMS group away from the α-face of the vinyl sulfone, providing unencumbered access for conjugate addition.

To demonstrate the value of enantiopure anti and syn stereodiads 27 and 29, applicants prepared a group of termini-differentiated seven-carbon segments projected to be of use in synthesis of bioactive polypropionate derived natural products. Targets initially investigated used syn-intermediates 21, 23, 29 as enantiopure starting materials; anti-intermediates 19, 22, 27 could also be used.

Further functionalization of these substrates gives cycloheptenyl sulfones, which afford termini-differentiated aldehyde segments after oxidative cleavage. For example, referring to FIG. 3, scheme 4, direct methylation of the dianion of alcohol 29 produced dienylsulfide 31 (confirmed by X-ray). Oxidation of 31 affords dienyl sulfone 32 in 70% overall yield from 29. The necessity of 'protection' of the alcohol moiety as an oxido anion is apparent from attempted alkylation of TBS ether 29, which suffers β-elimination to trienylsulfide 30. Treatment of the dianion of 29 with Eschenmoser's reagent gives amine 34, which undergoes smooth tris-oxidation to trienylsulfone 35 upon exposure to excess mCPBA. Oxidation of dienylsulfones 32 and 33 using mCPBA was unselective, but high diastereoselectivity could be obtained using Molybdenum, Manganese, and Osmium catalyzed oxidations to prepare 36-39 (Scheme 4).

Approach to Rhizoxin

Rhizoxin, the bis epoxide of rhizoxin D 40, was isolated by Okuda from *Rhizopus chinensis* infected rice seedlings (Scheme 5). Eight total and/or formal syntheses of rhizoxin (four via rhizoxin D) have been reported.

The plan for the synthesis of rhizoxin D 40 in accordance with the invention involves a 1-2 pot method of sequentially joining a pair of carbonyl compounds with a two-carbon bis-olefination splicer (FIG. 4, Scheme 5). Acylation of ent-21 followed by hydrolysis gives β-sulfonyl ketone 41, which was then transformed to silyl dienylether 42. Singlet oxygen addition to 42 effected stereospecific (OTIPS necessary for greater than 95% β-face addition) formation of stable bicyclic peroxide 43. Dimethyl dioxirane (DMDO) epoxidation of silyl enolether 43 provided the isolable α-epoxysilyl ether 44. Hydrogenation of 44 proceeded, as desired, with silicon migration to give diol 46 in 83% yield. Methylation of the keto-diol 46 required dimethyltin chloride catalysis to effect regiospecific O-methylation at the more electron-rich distal alcohol, rapidly providing ketone 47 in high yield (first example for a 1-keto-2,3-diol). Methylation or silylation without the tin catalyst was very slow and strongly favored functionalization of the opposite alcohol. Lead tetraacetate cleavage of 47 in methanol completed the synthesis of enantiopure aldehyde-ester 48 (Scheme 5).

Concanamycin F

Concanamycin F 49, also called concanolide A, is the most intricate parent aglycone of a series of related macrocyclic lactones bearing considerable structural homology (Scheme 6). This family also includes biafilomycin A and hygrolidin. Concanamycin F 49 has been synthesized by the groups of Paterson in 2000 and Toshima in 2001 in 44 and 53 operations, respectively. Paterson, V. A. Doughty, M. D. McLeod, T. Trieselmann, *Angew. Chem. Int. Ed. Engl.* 2000, 39, 1308-1312; *Angew. Chem.* 2000, 1364-1368.

Referring to FIG. 5, scheme 6, analysis of concanamycin F 49 envisages the construction of a pair of stereopentads to be derived from vinyl sulfones 50 and 53. Diol 39 is used to generate stereopentad 51. Silylation of 39 provided vinylsulfone 52 in quantitative yield which was directly methylated in DMSO to give vinylsulfone 53 in 94% overall yield. Ozonolysis of 53 afforded ester-aldehyde 51 in 92% yield. Compound 51 is the enantiomer of the C15-C21 stereopentad of concanamycin F 49 (Scheme 6).

Apoptolidin

Apoptolidin 54 is a 20-membered macrocyclic lactone isolated from *Norcardiopsis* sp (FIG. 6, Scheme 7). Apoptolidin induced apoptotic cell death in rat gila cells transformed with the E1A oncogene at 11 ng/mL but did not cause cell death in normal gila cells or fibroblasts at greater than 100 g/mL.

Discodermolide 55, like paclitaxel (taxol), has been shown to stabilize microtubules, but is more potent and inhibits the grown of paclitaxel-resistant cells. The material is in high demand for clinical trials, and synthesis is the only option. Five total syntheses and related synthetic approaches all using aldol-based acyclic stereoselection strategies beginning with enantiopure 3-hydroxy 2-methylpropionate have been reported. The second generation Smith synthesis utilized 34 total operations and enabled delivery of the first gram of (+)-discodermolide 55 with a linear supply line of only 24 operations. The overall yield was 6%.

Referring to FIG. 6, synthesis of apoptolidin 54 and discodermolide 55 in accordance with the invention makes use of the central stereotriads 32 and 33 as precursors to key epoxides α36 and β36, respectively. Preparation of the C21-C27 segment of apoptolidin 54 is accomplished from epoxide β36 beginning with selective 1,2-reduction with DIBAL-H to provide alcohol 56. The complementary 1,4-reduction process to produce alcohol 59 can be selectively achieved using borane-THF. Completion of the apoptolidin segment synthesis simply involves ozonolysis of 56 to a δ-hydroxy aldehyde intermediate, which suffers cyclization to hemiacetal 57. Protection of 57 as acetal 58 gave a 4:1 mixture of anomers, which can be easily separated by silica column chromatography (Scheme 7). Acetal 58 is also the C20-26 segment of phorboxazole (not shown).

In parallel fashion to the synthesis of 58, it was possible to prepare the C1-C7 segment of discodermolide 55 by employing epoxide α36 for 1,2-reduction with DIBAL-H. This afforded alcohol 60 in 65% yield. Subsequent ozonolysis afforded hemiacetal 61, which smoothly underwent PDC oxidation to give lactone-ester 62 in 75% yield (Scheme 7).

Evaluation of the Cycloheptadienyl Sulfone 2 as a Stereopentad Precursor

Figure 7:
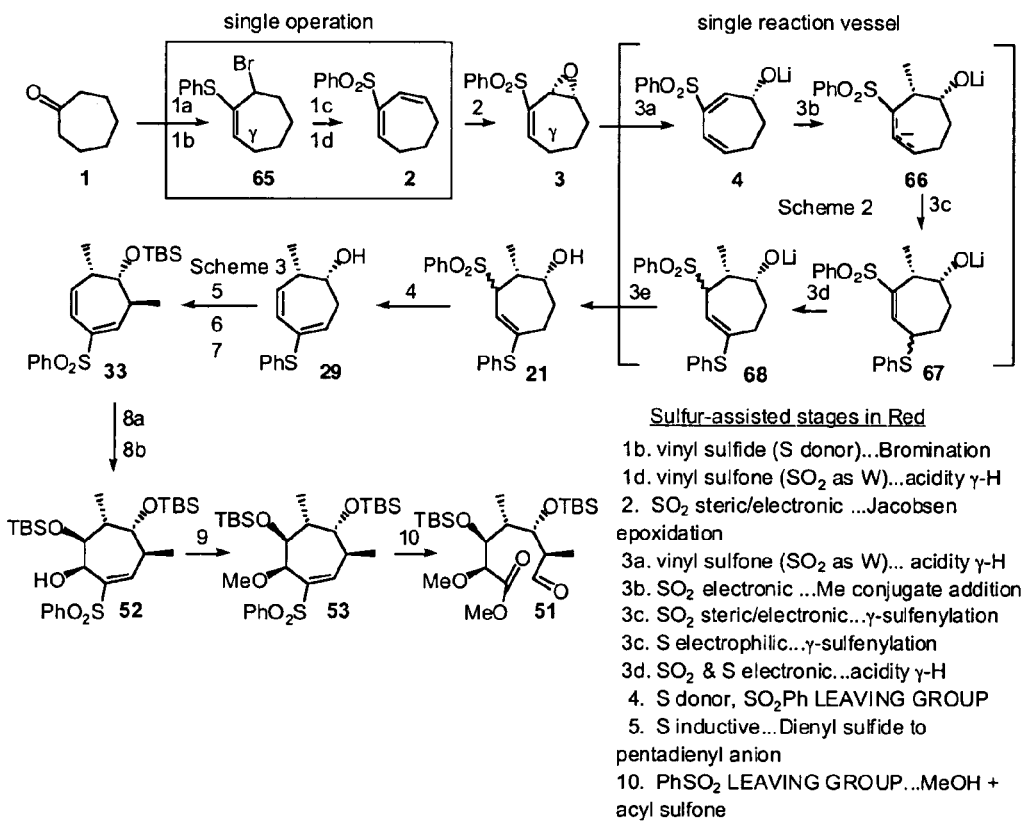
FIG. 7 illustrates the importance of the sulfur atom in the depicted synthesis.
Figure 8:
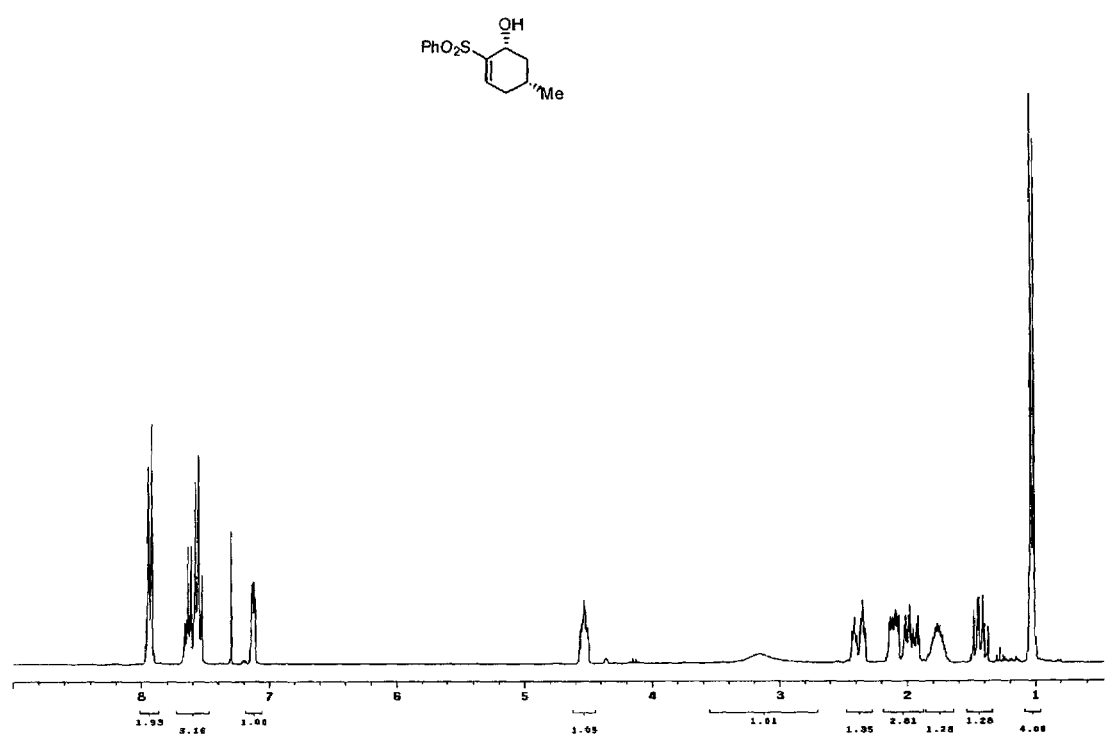
FIG. 8 illustrates NMR data for compounds of the invention.
Figure 8:
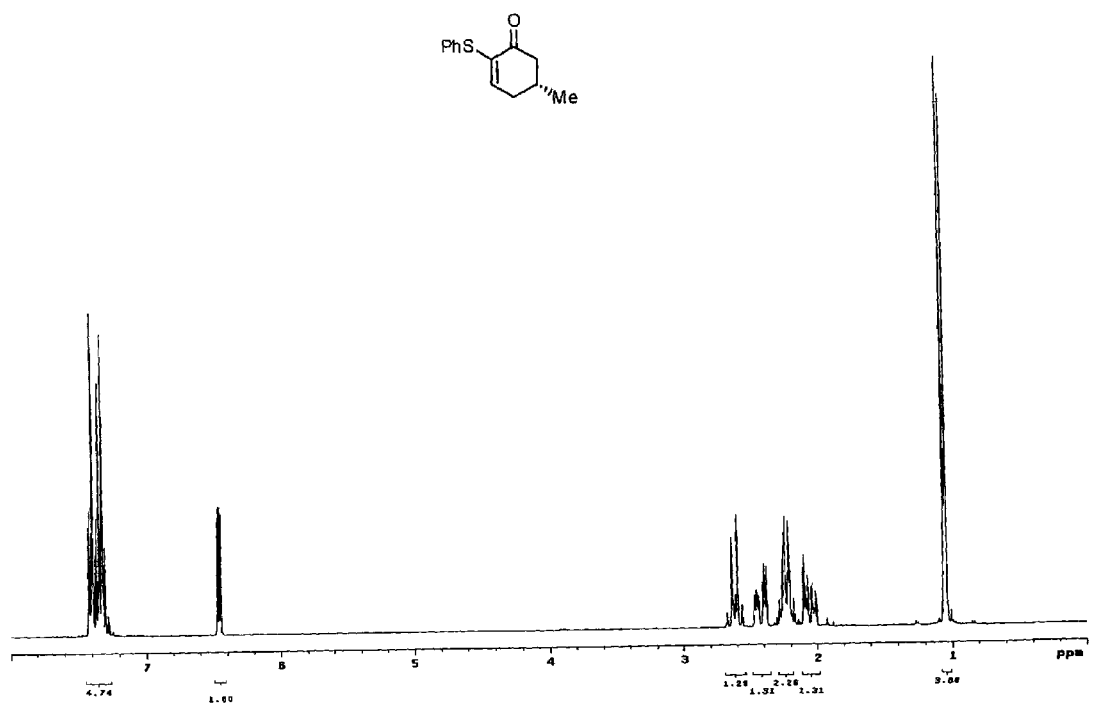
Figure 8:
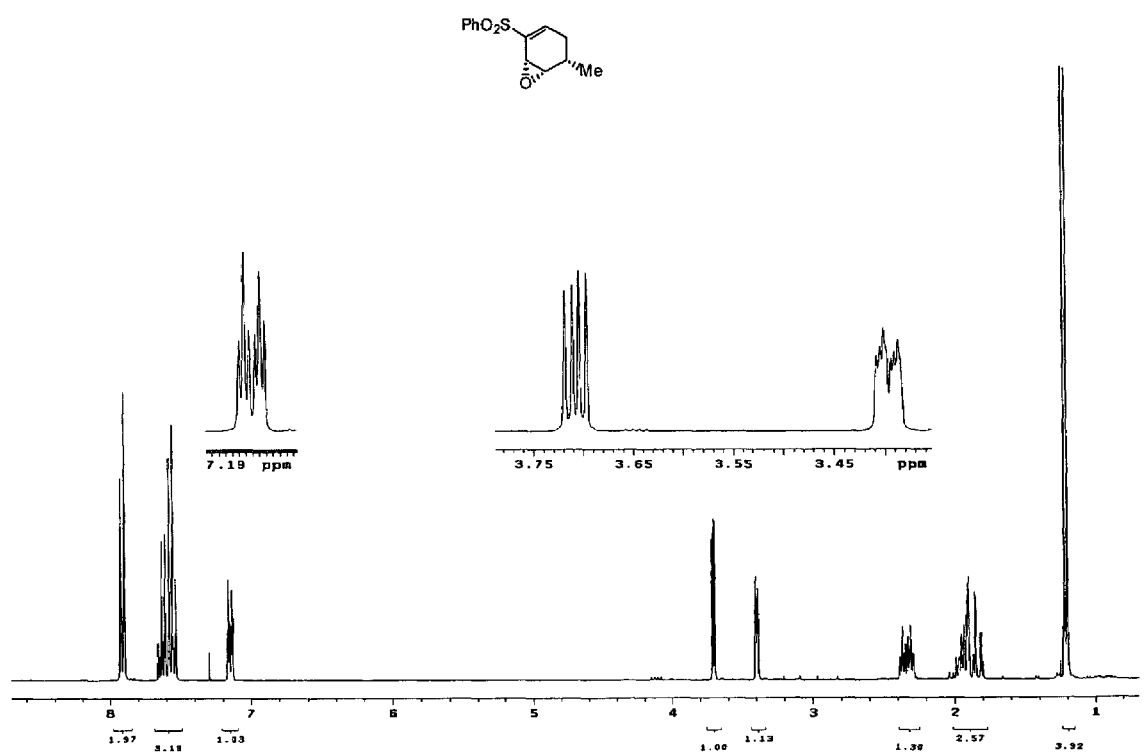
Figure 8:
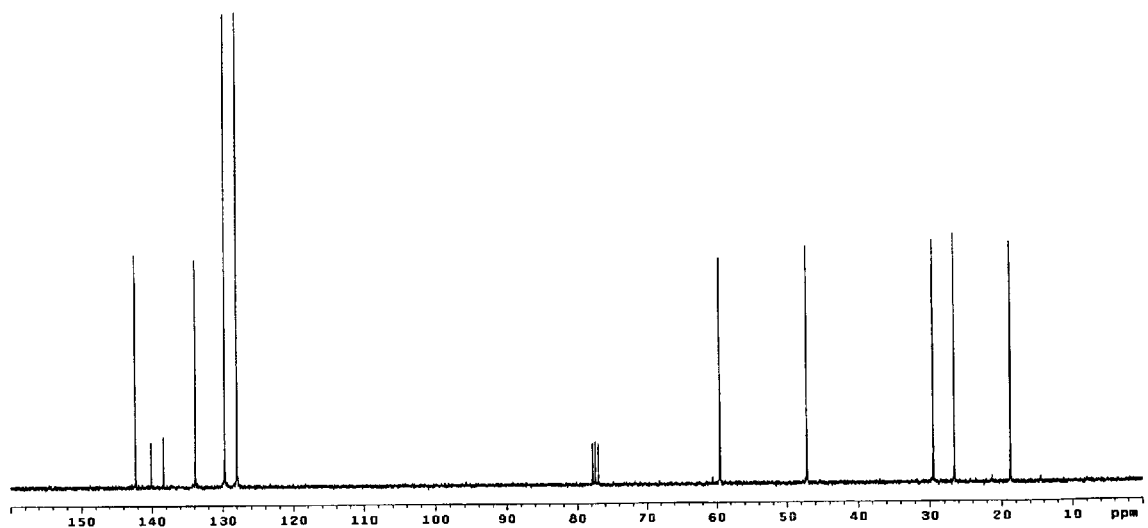
Figure 8:
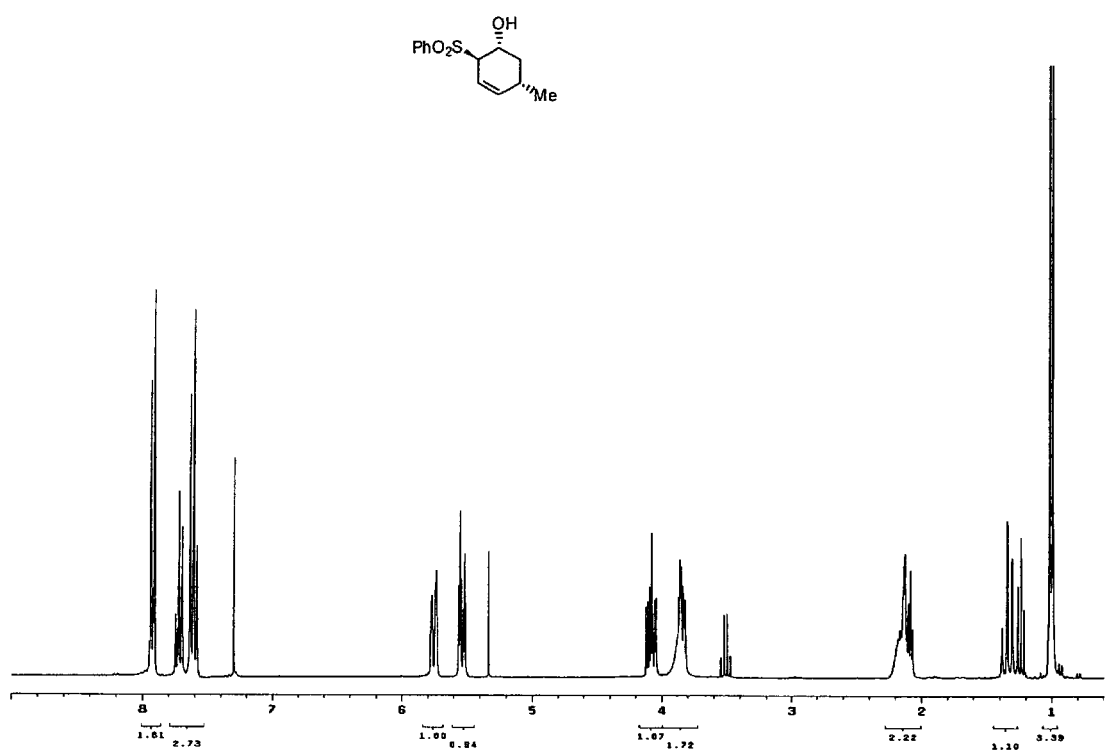
Figure 8:
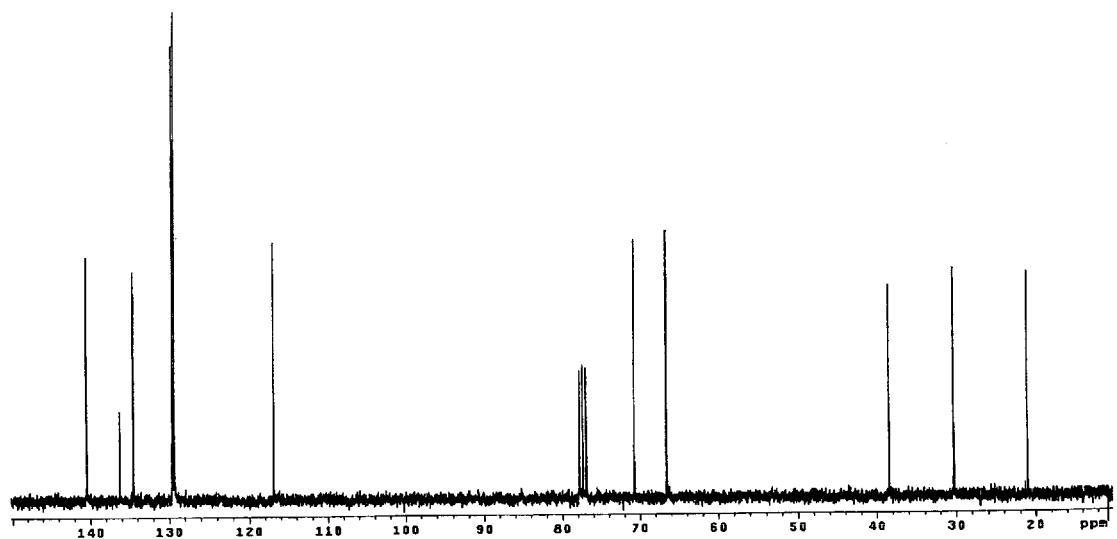
Figure 8:
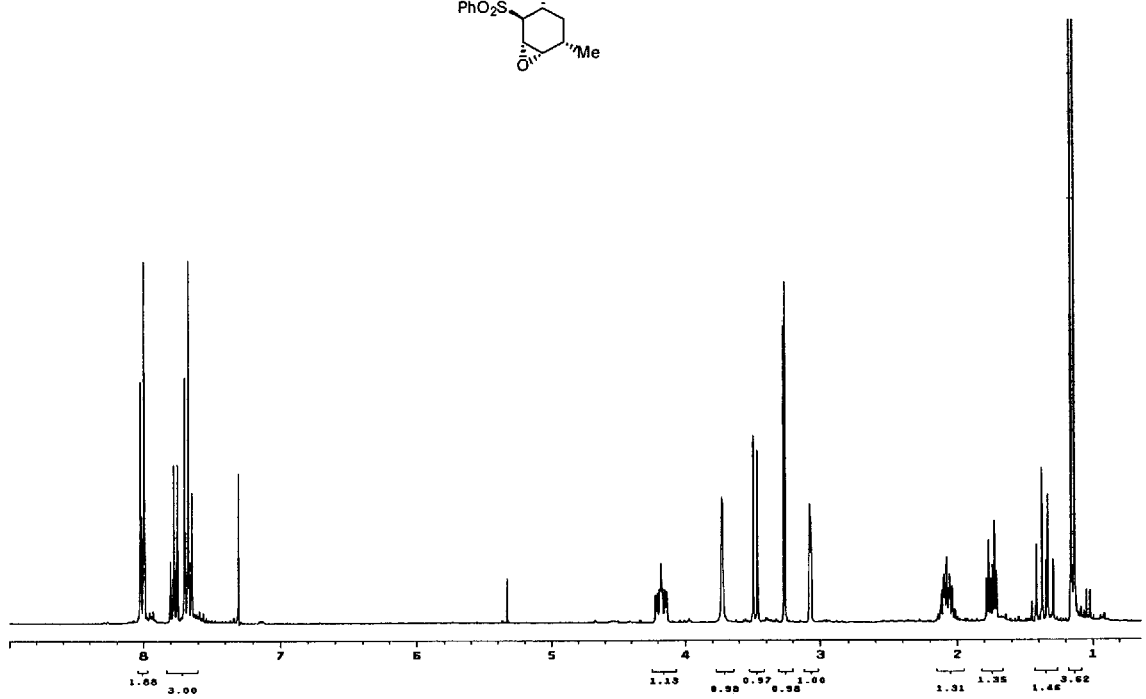
Figure 8:
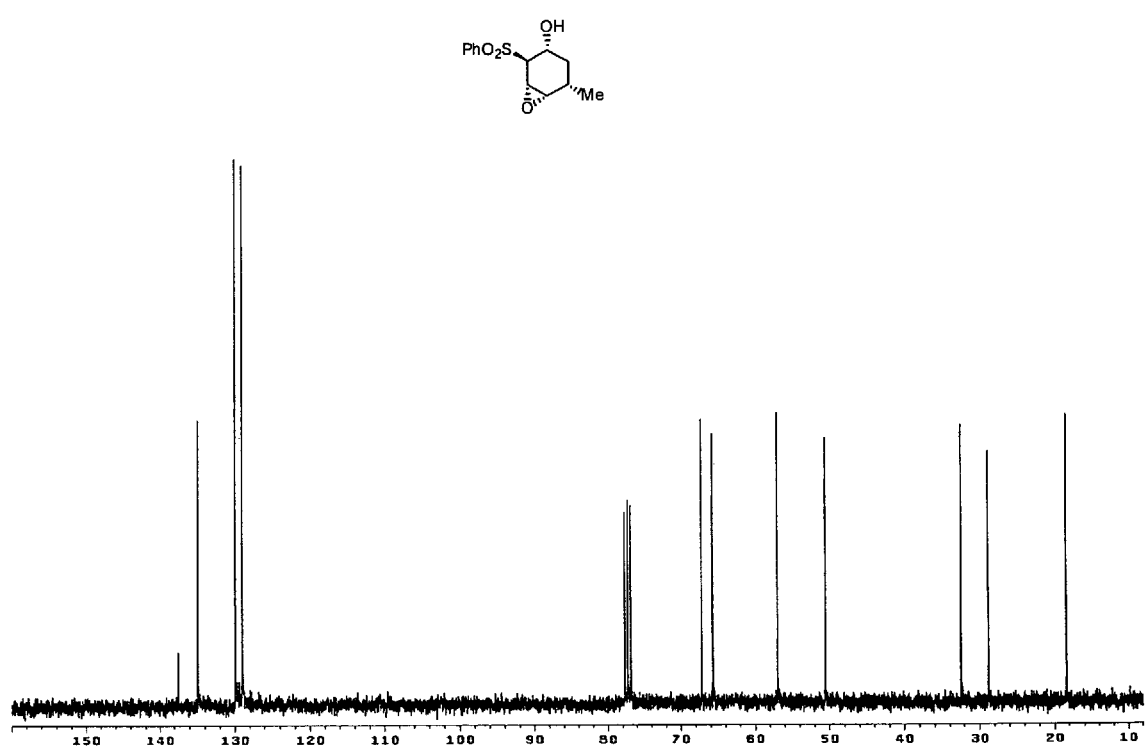
Figure 8:
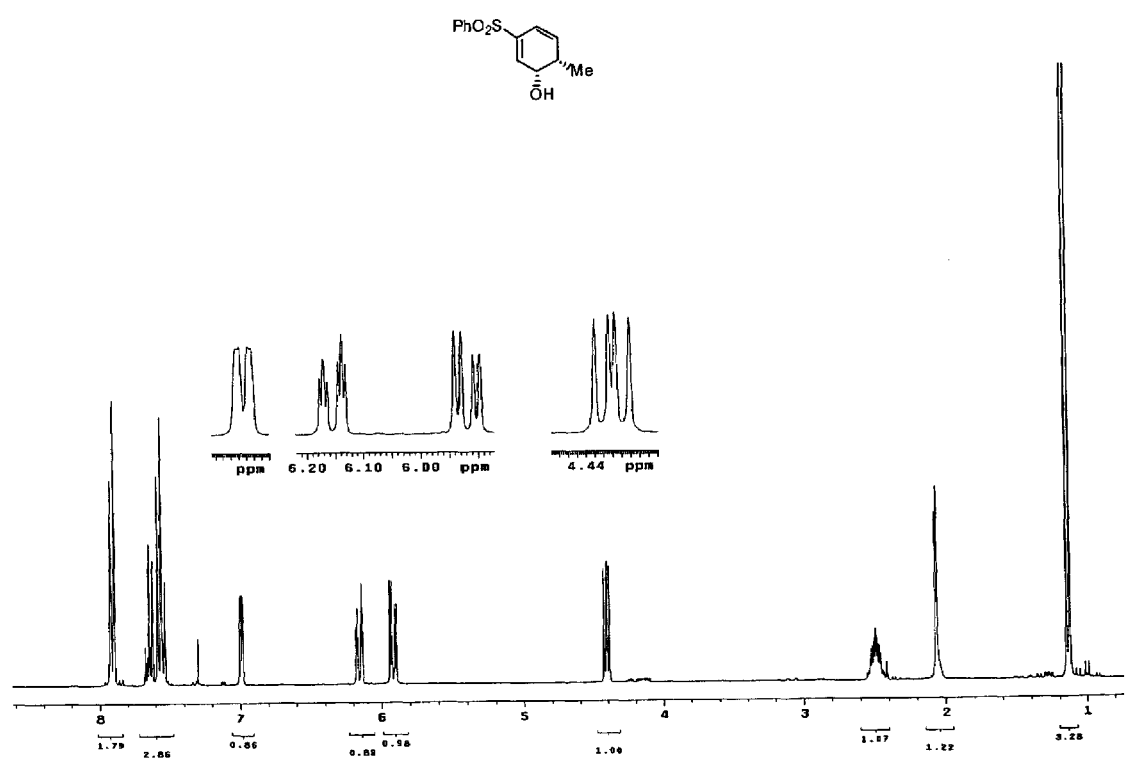
Figure 8:
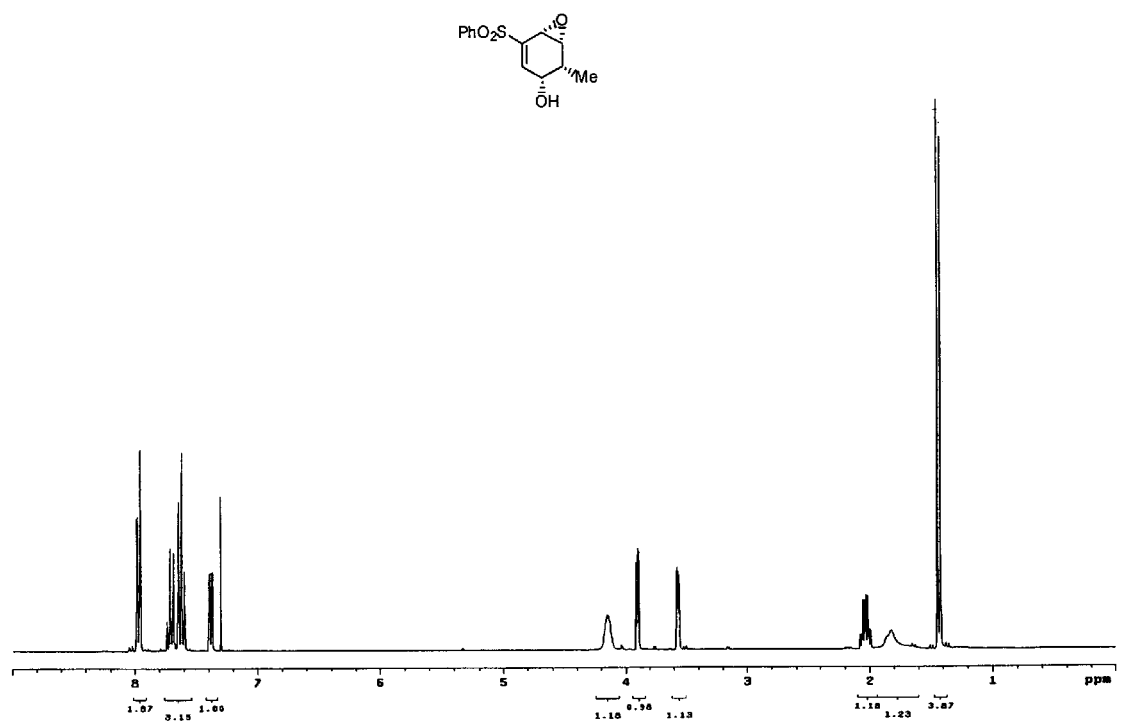
Figure 8:
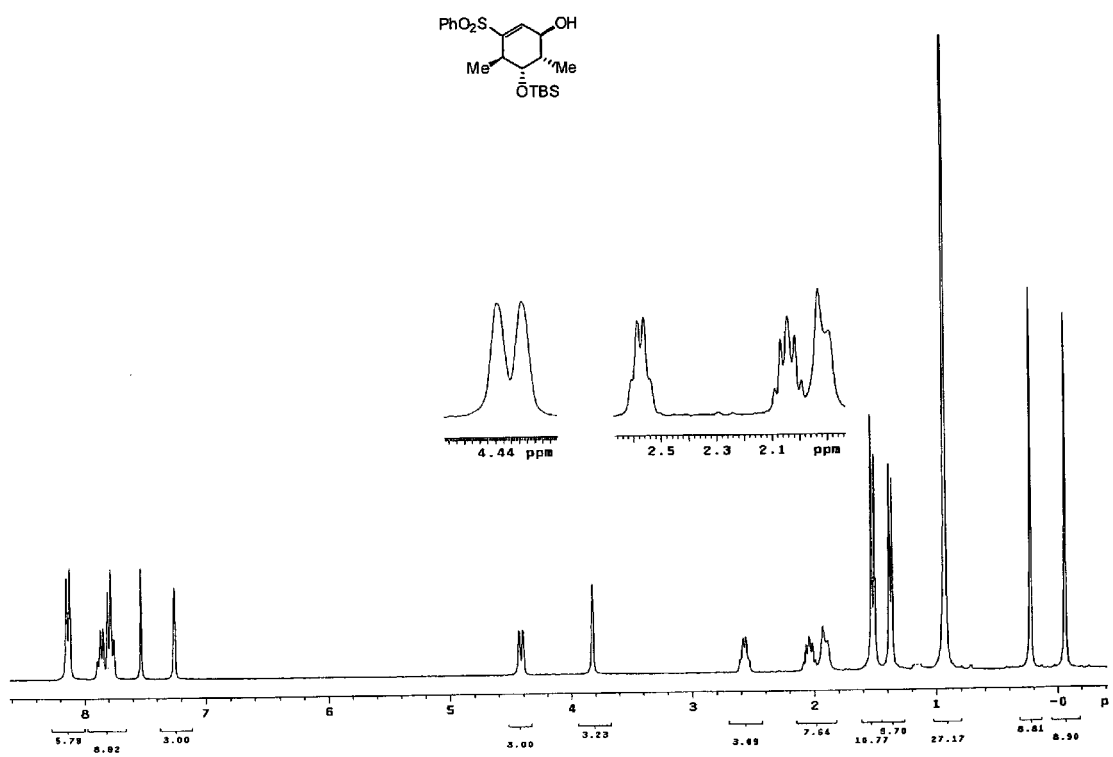
Figure 8:
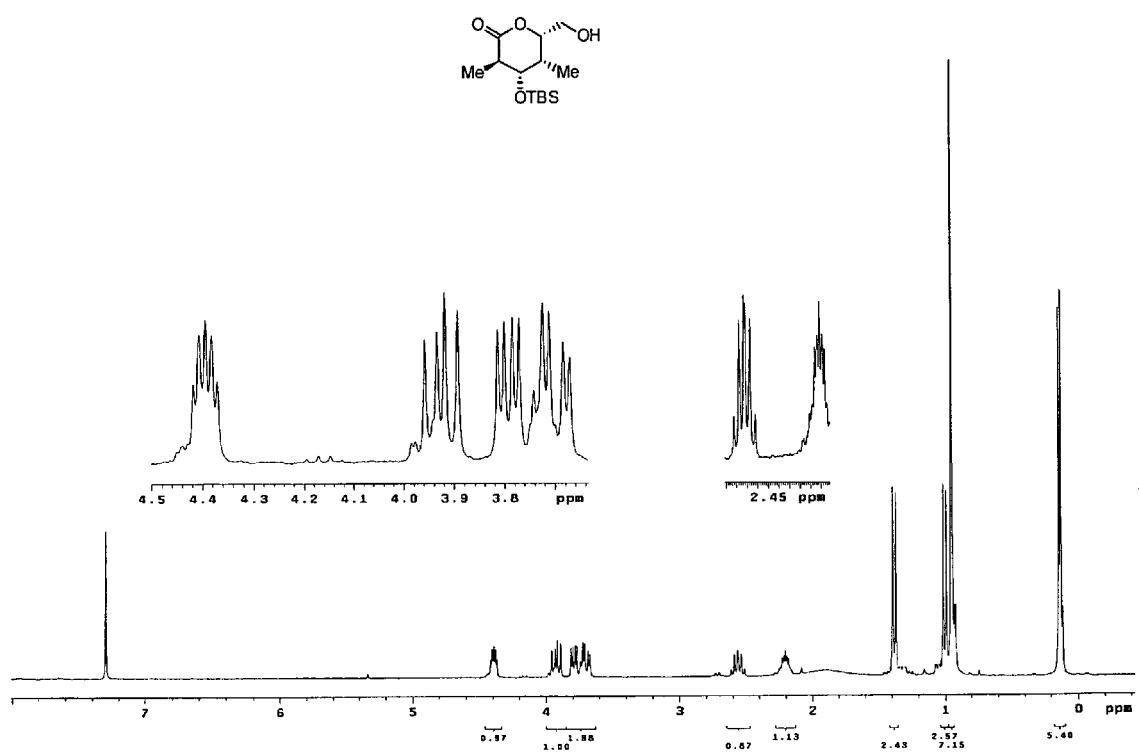
Figure 8:
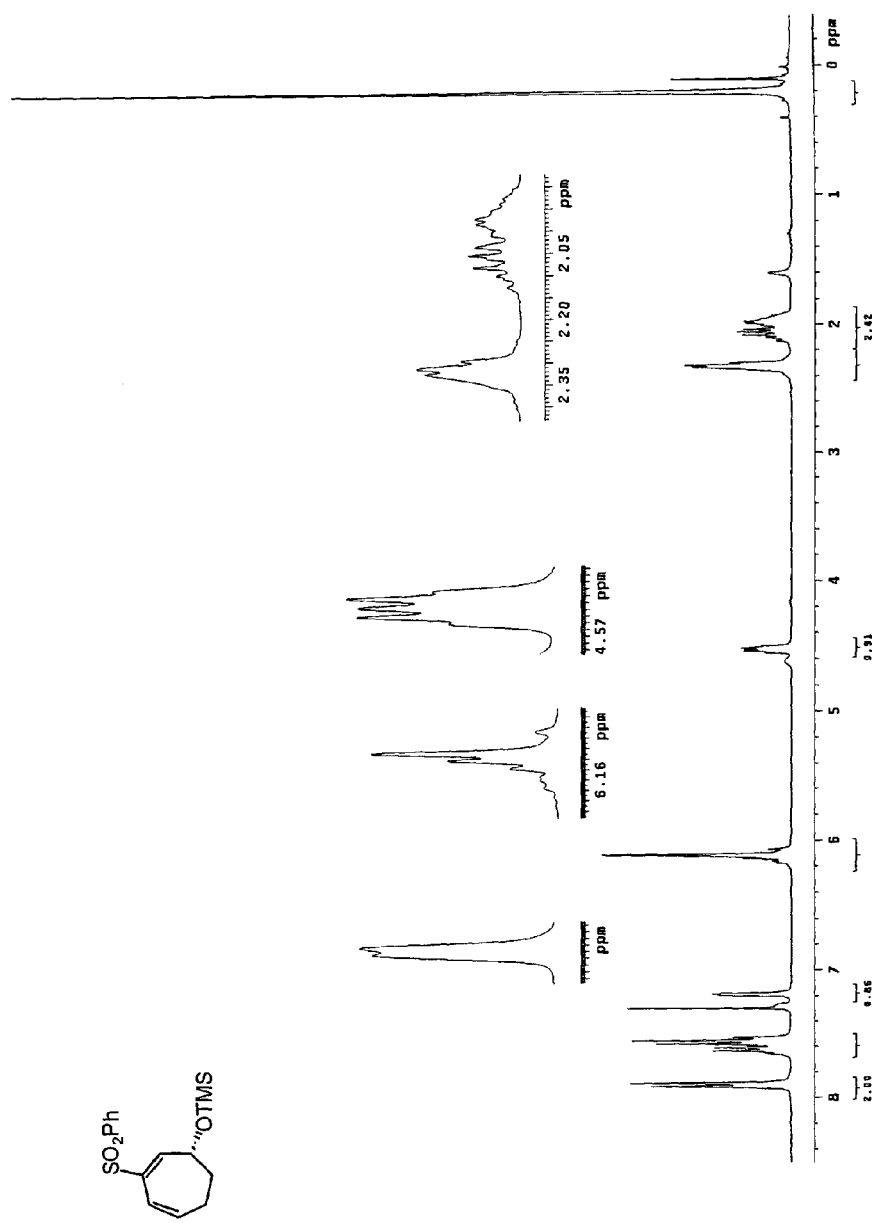
Figure 8:
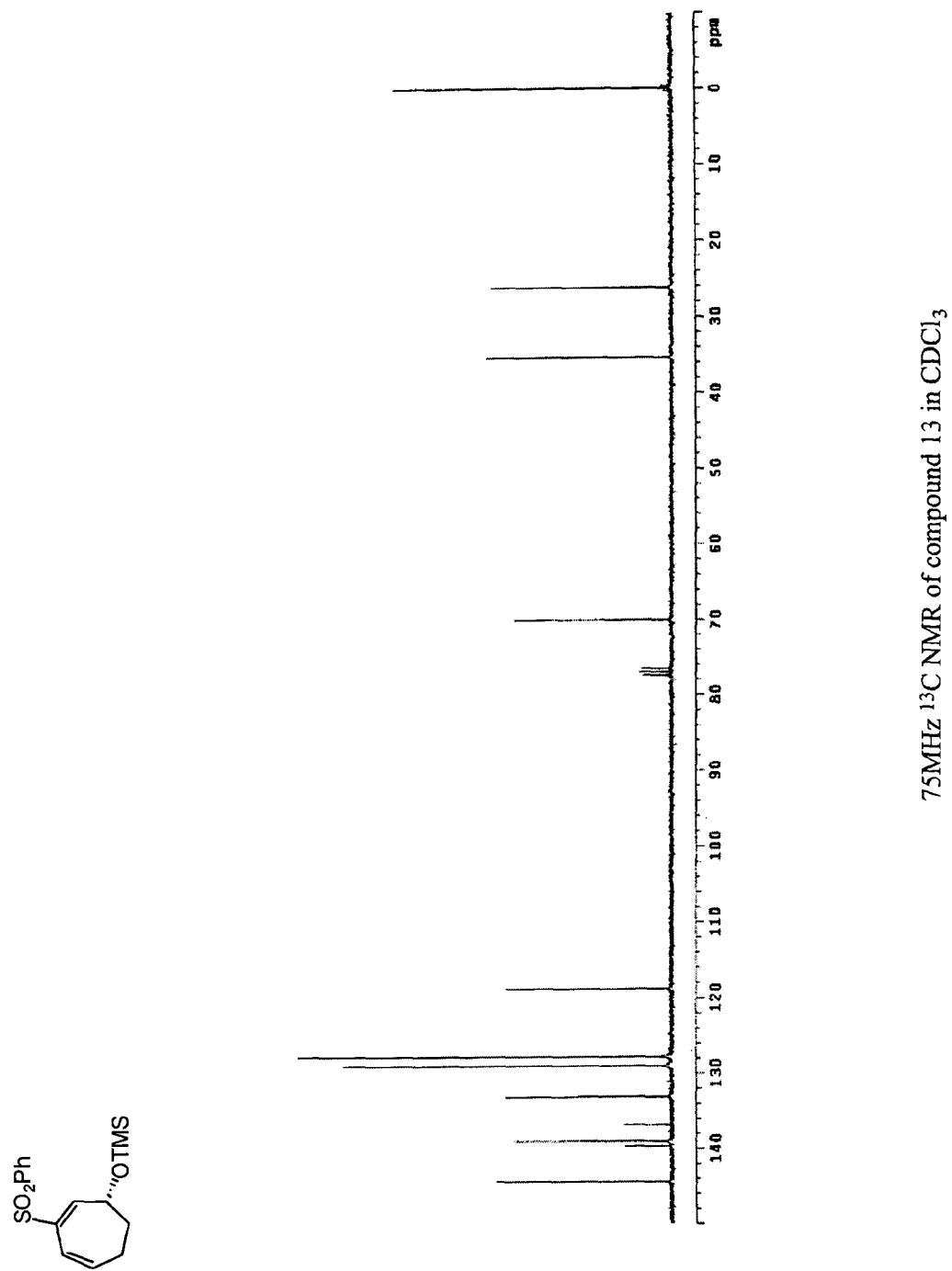
Figure 8:
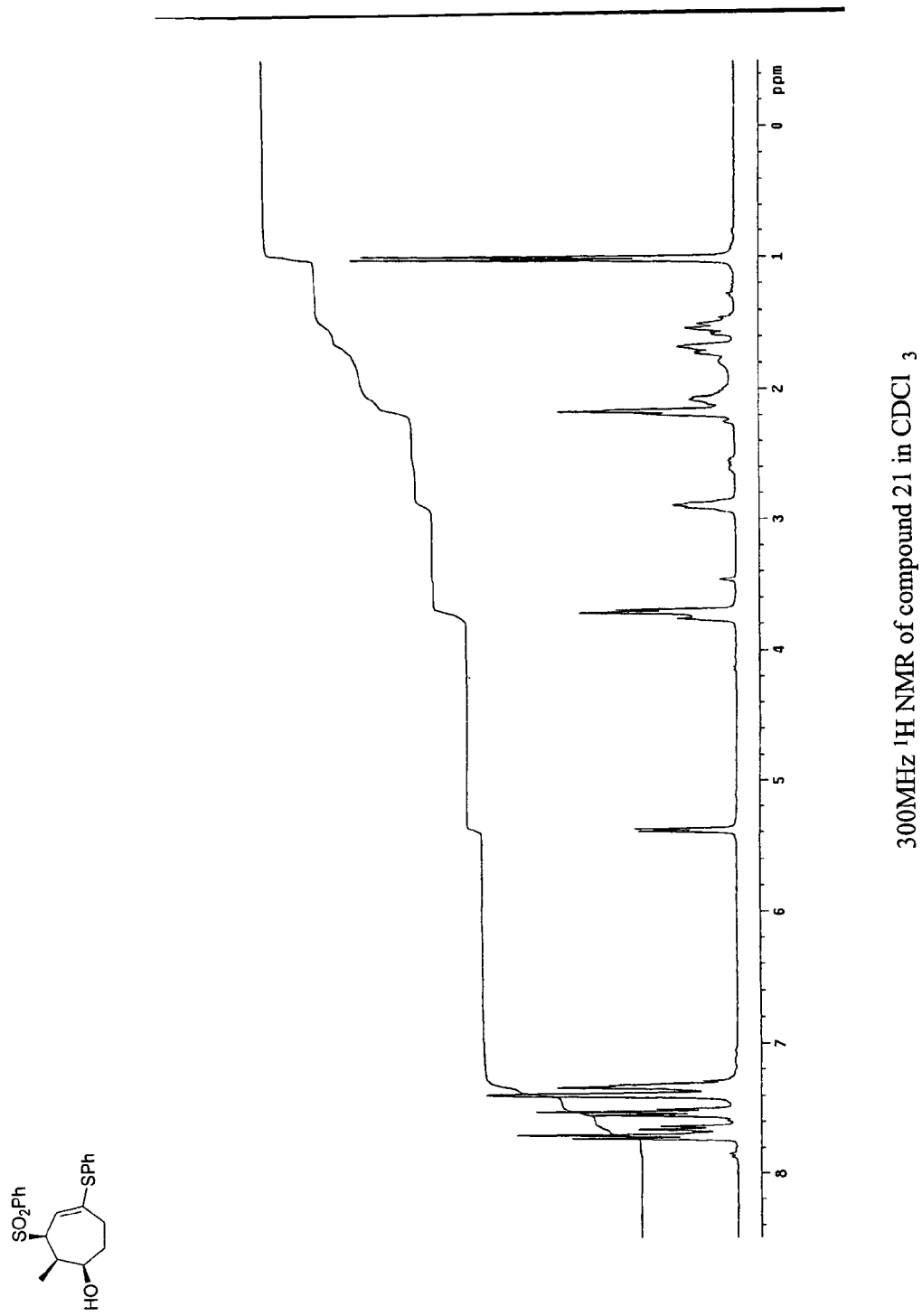
Figure 8:
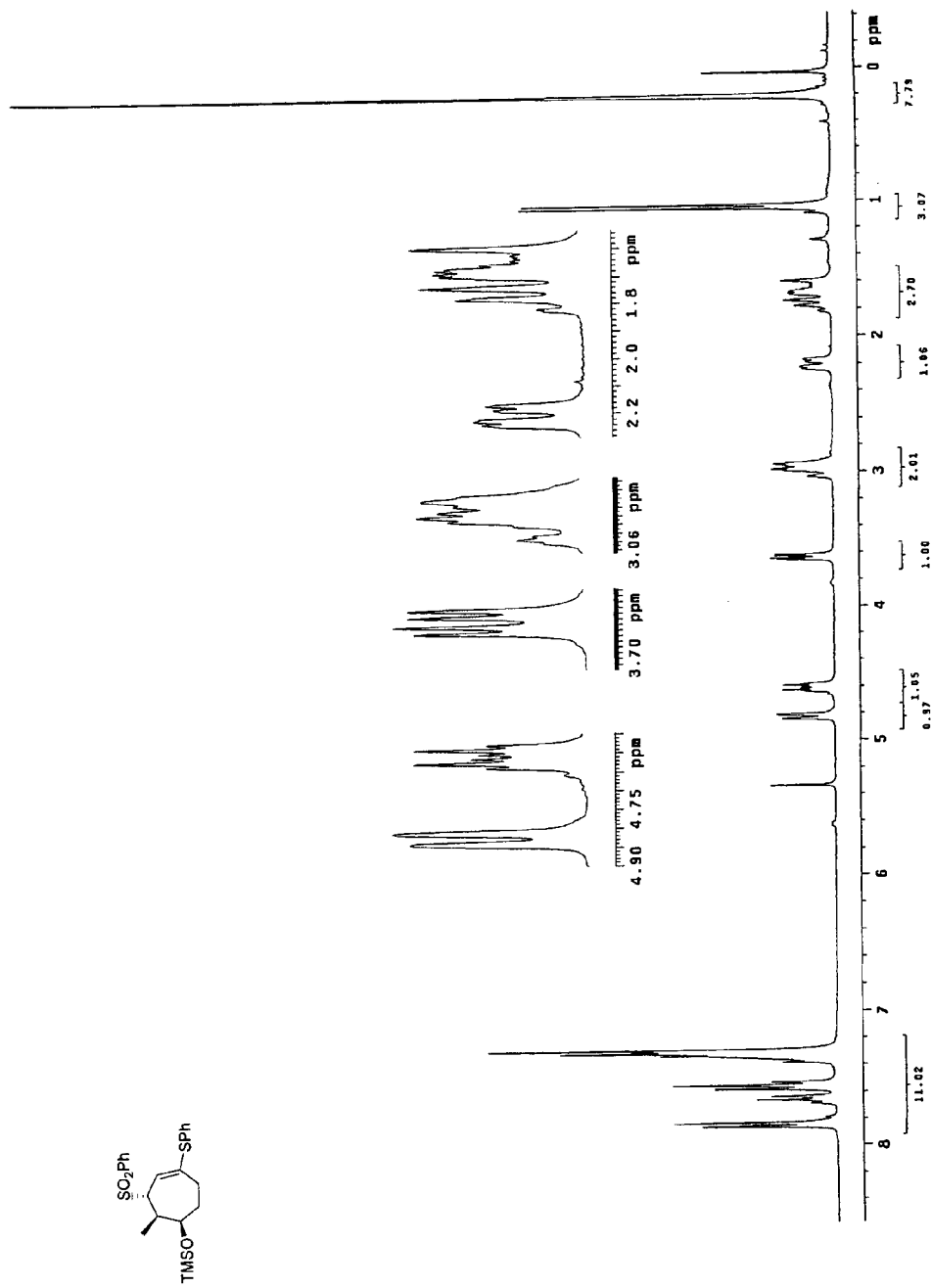
Figure 8:
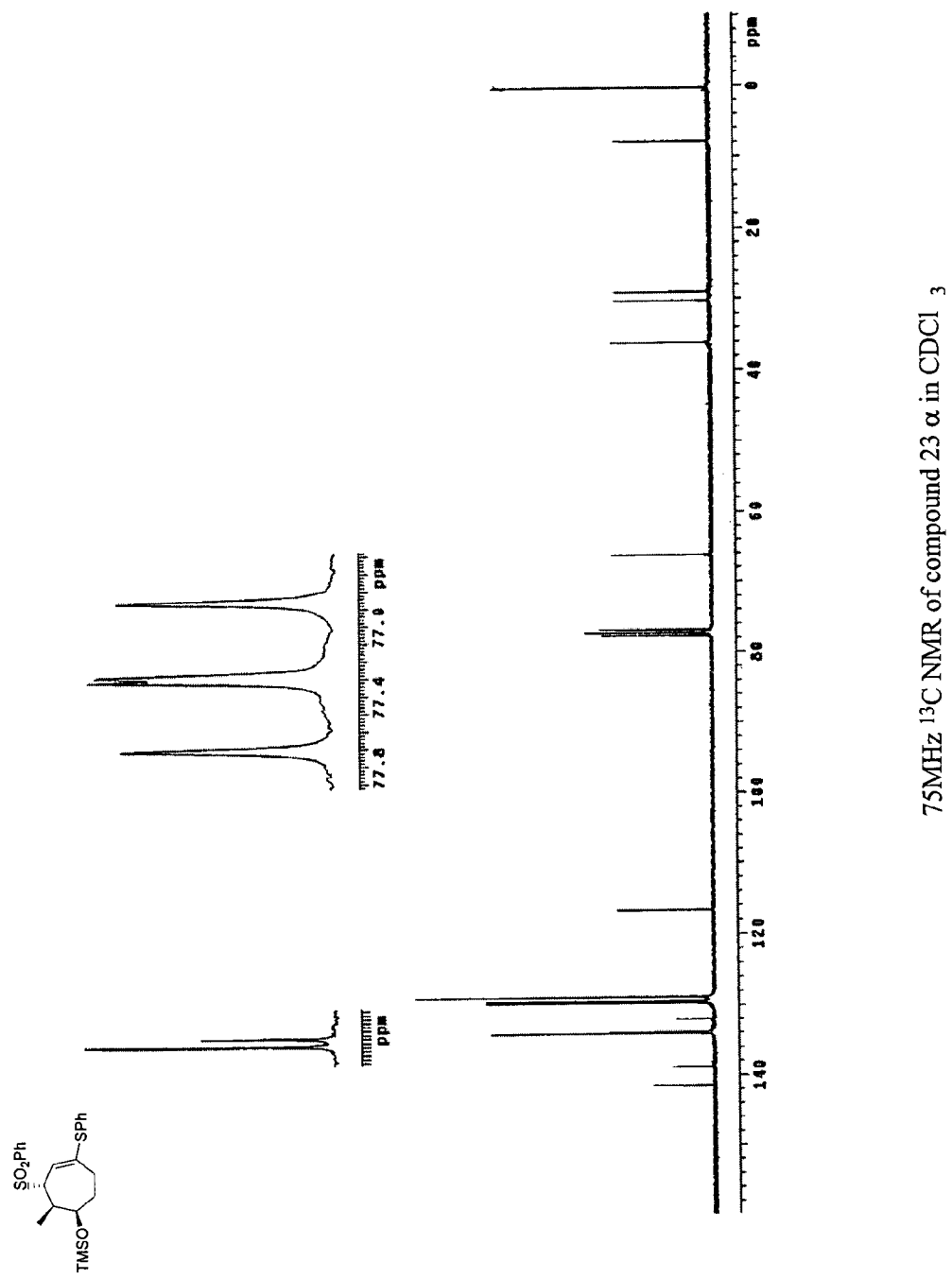
Figure 8:
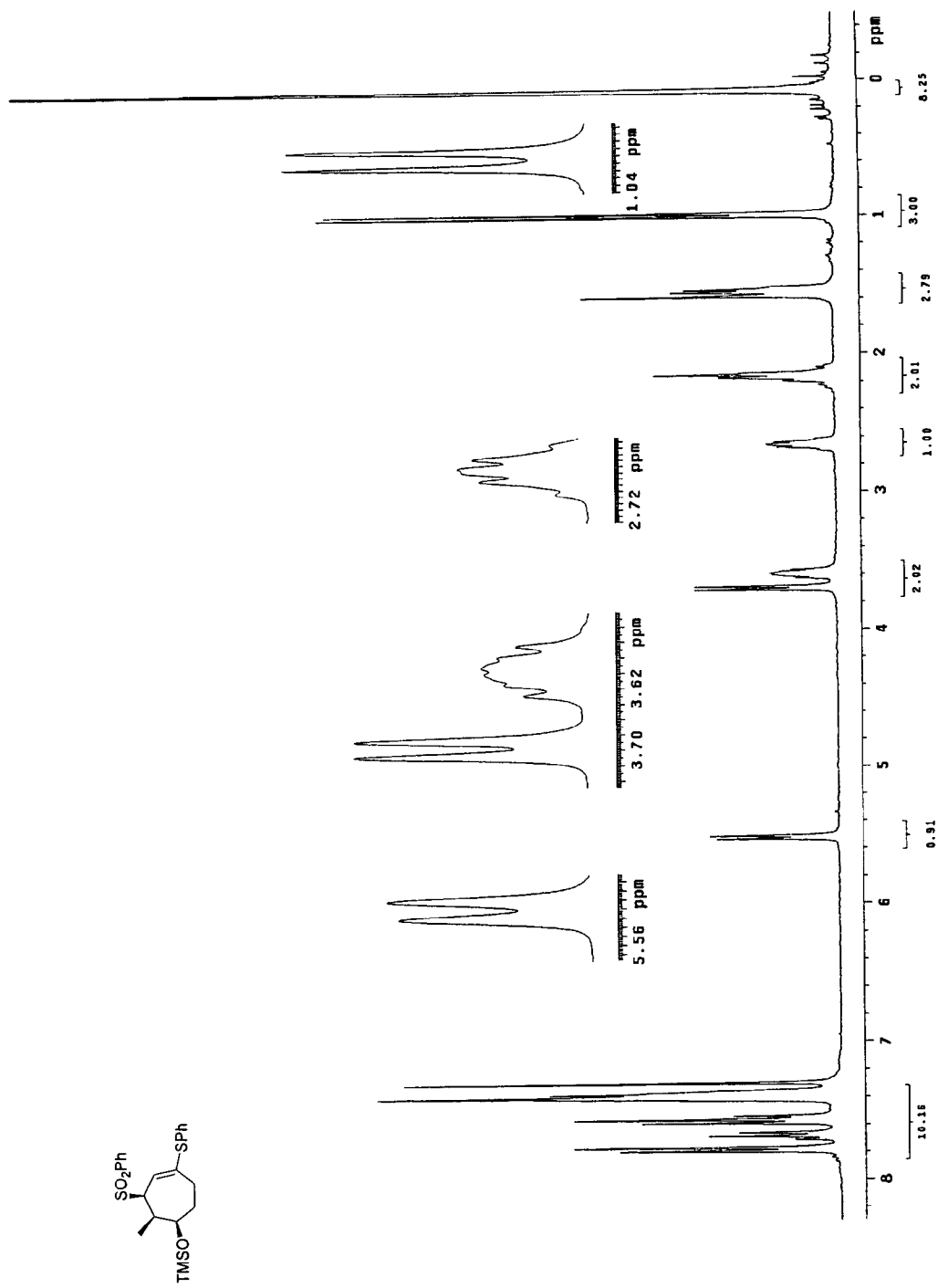
Figure 8:
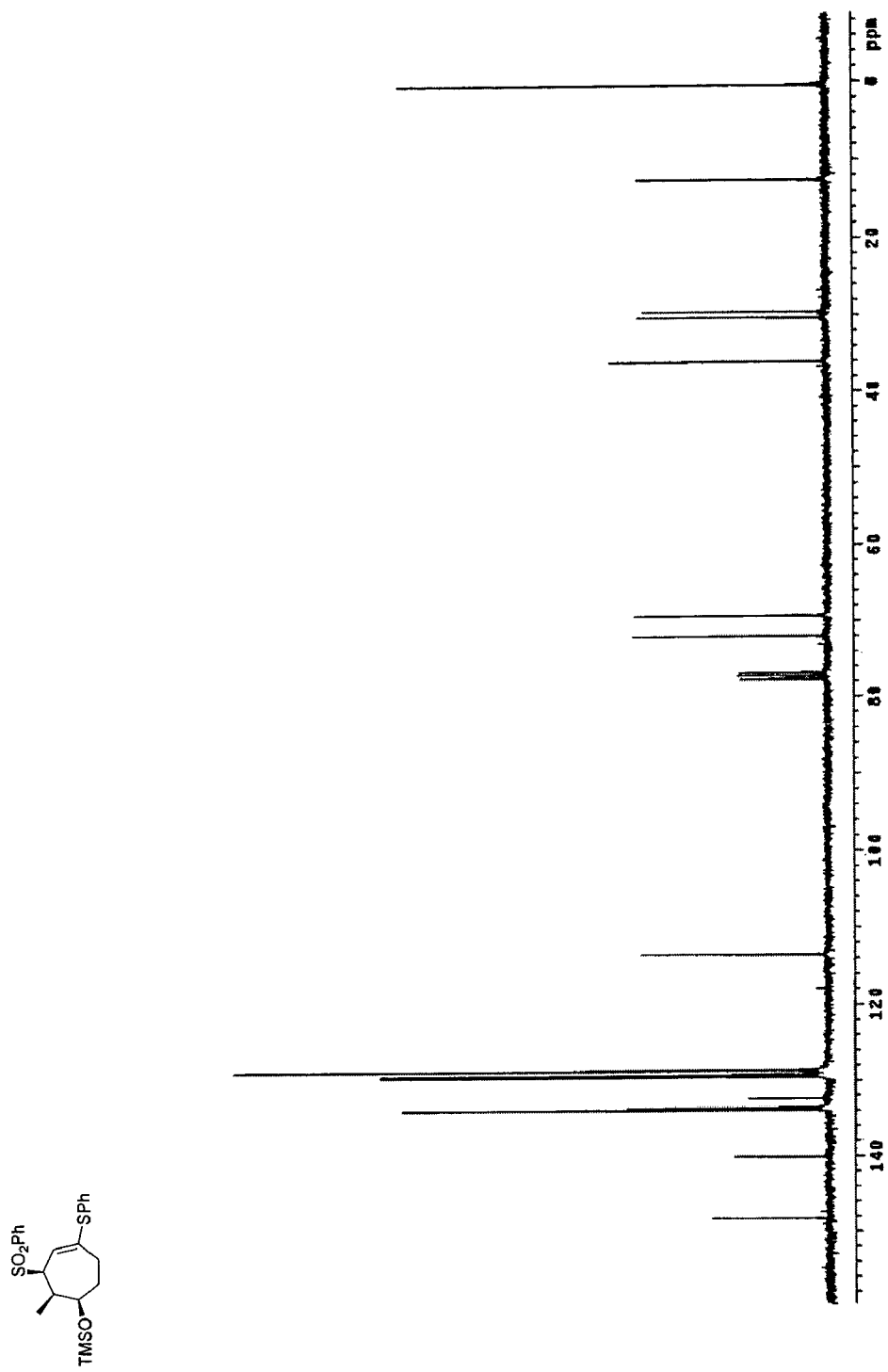
Figure 8:
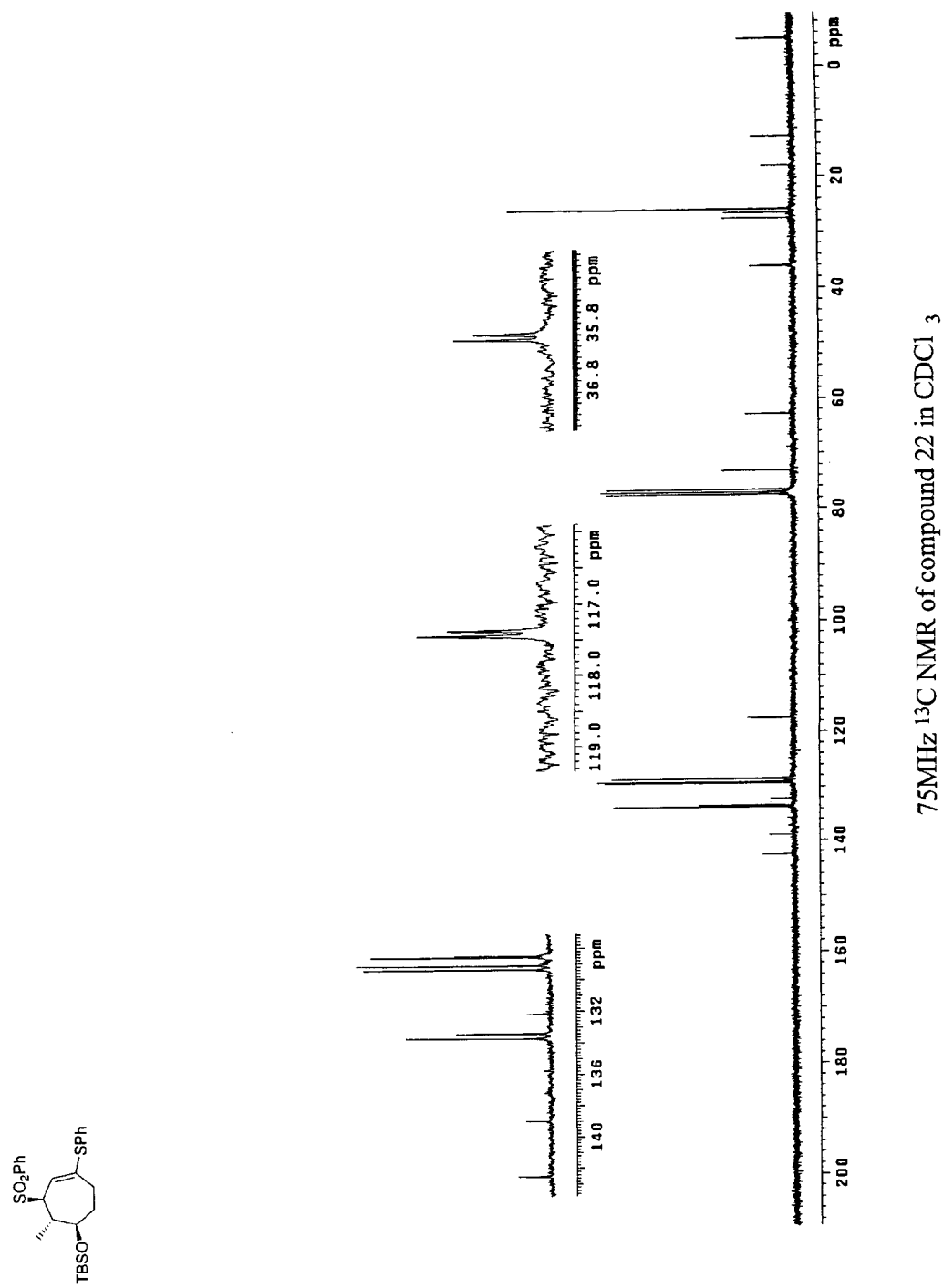
Figure 8:
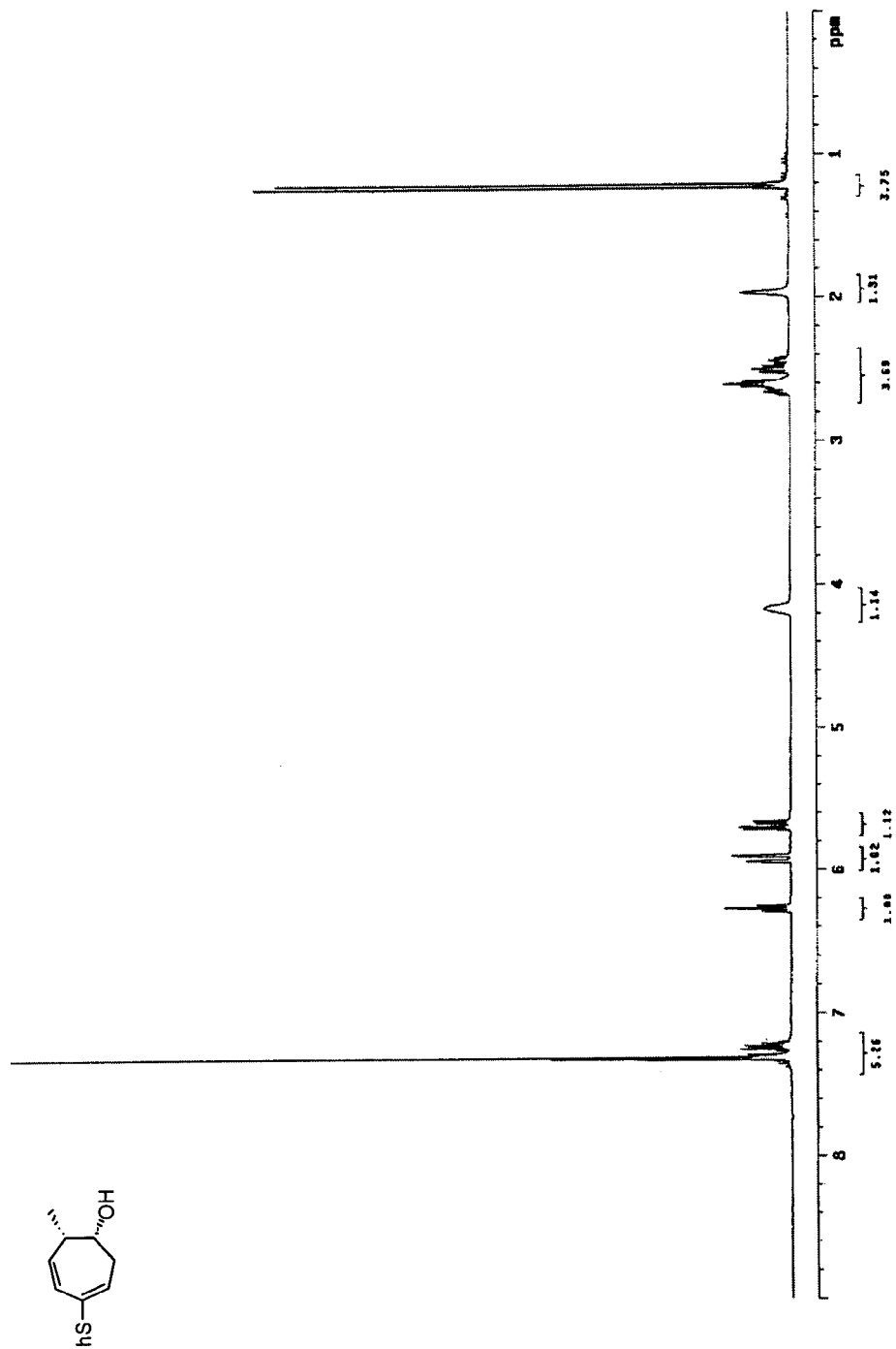
Figure 8:
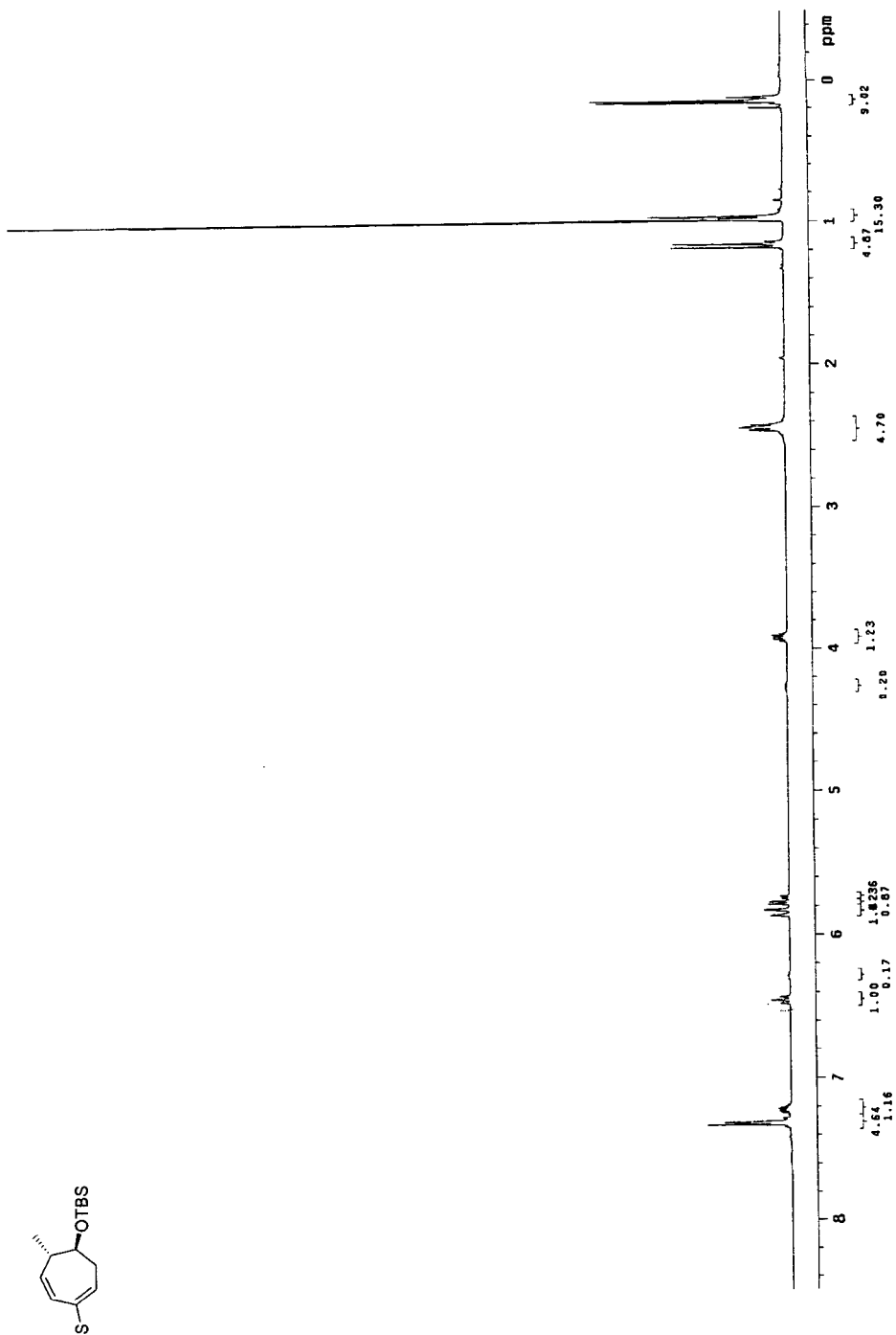
Figure 8:
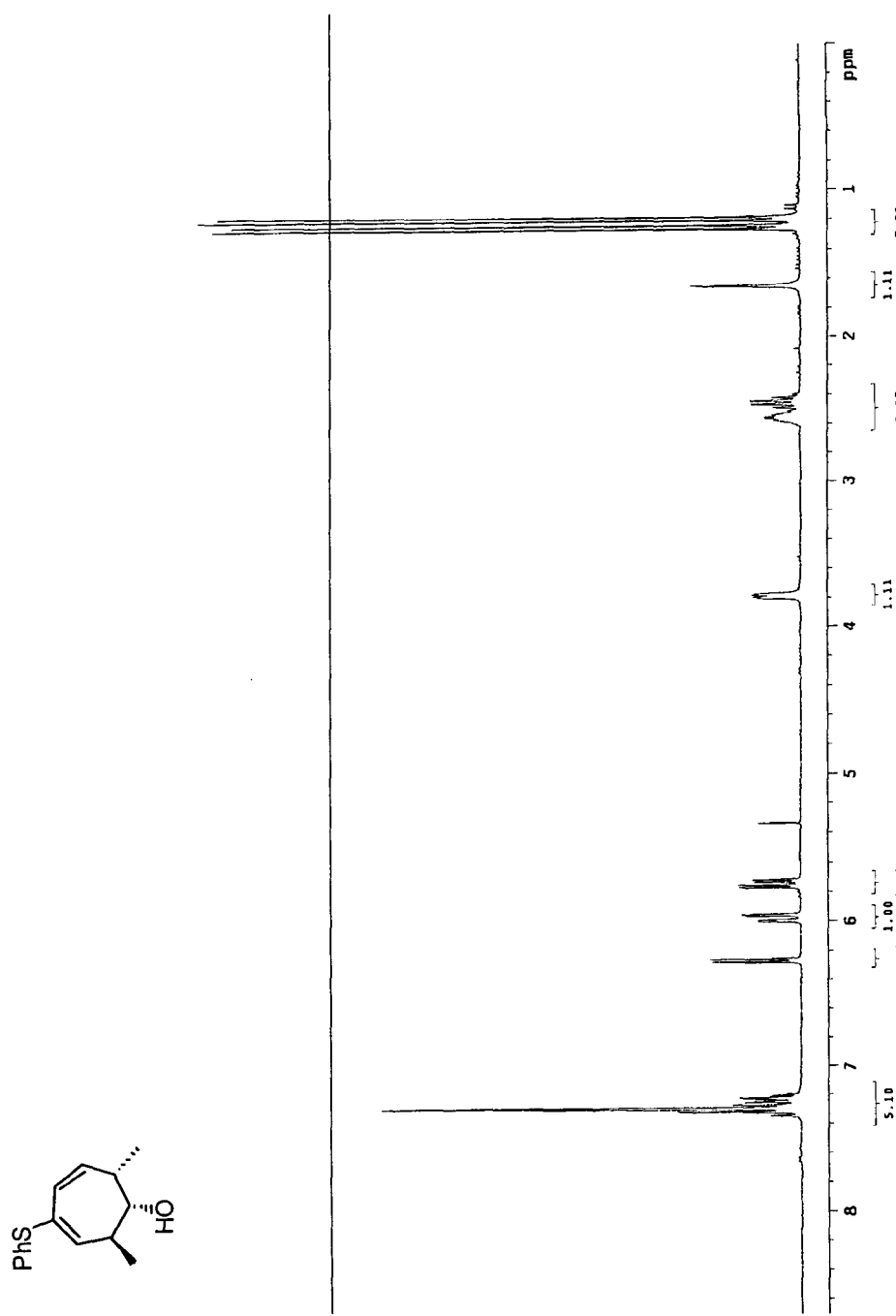
Figure 8:
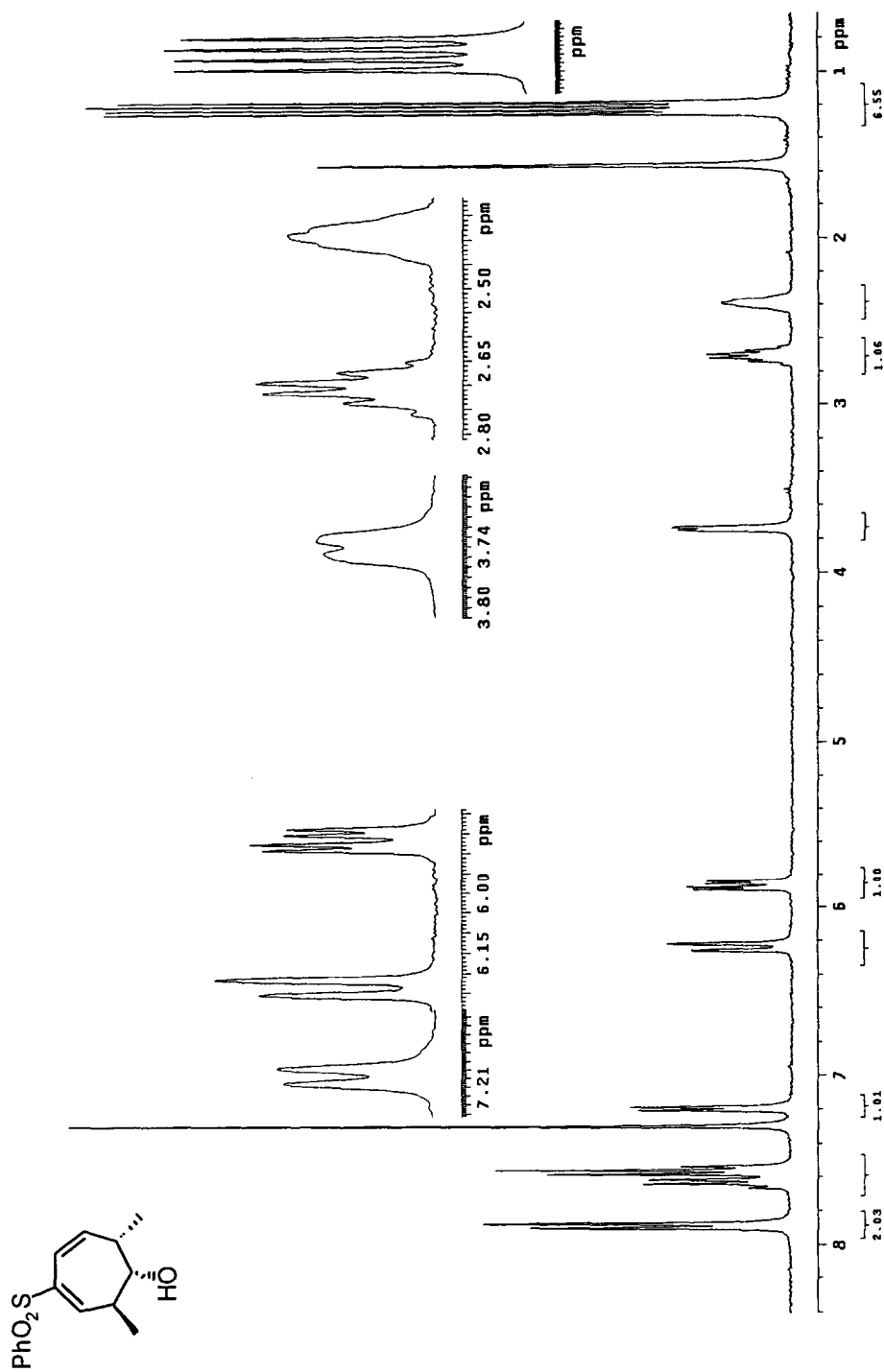
Figure 8:
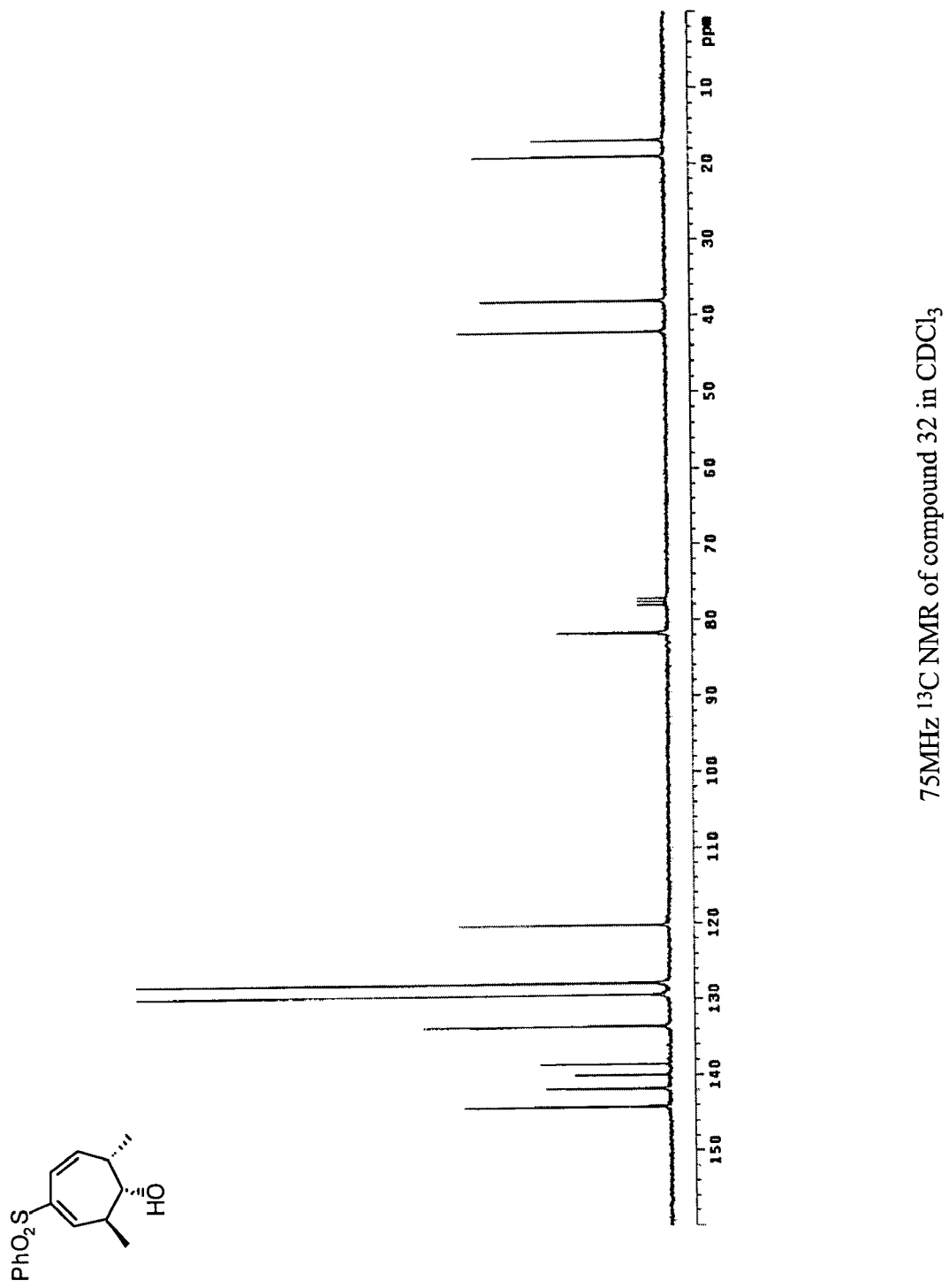
Figure 8:
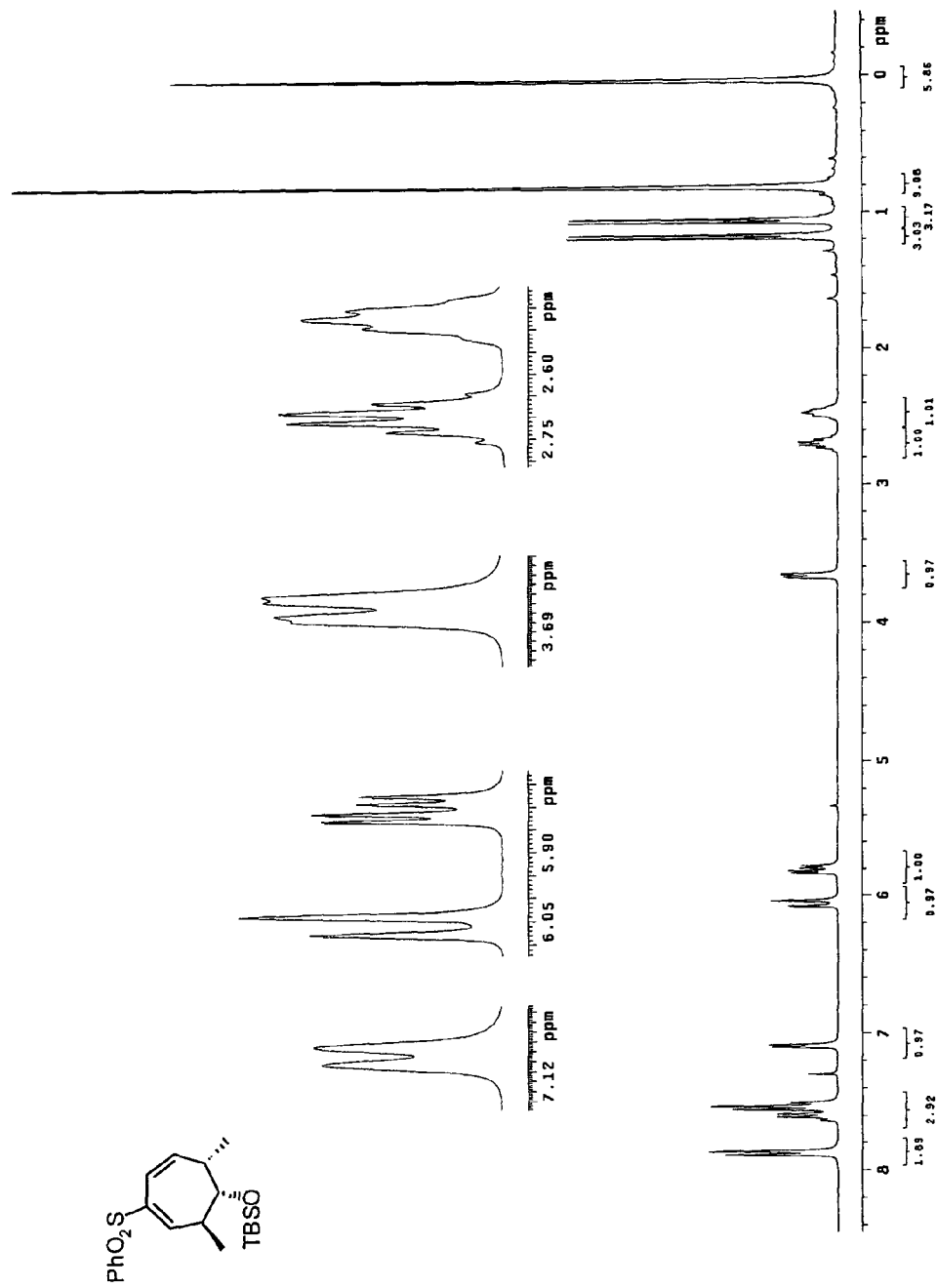
Figure 8:
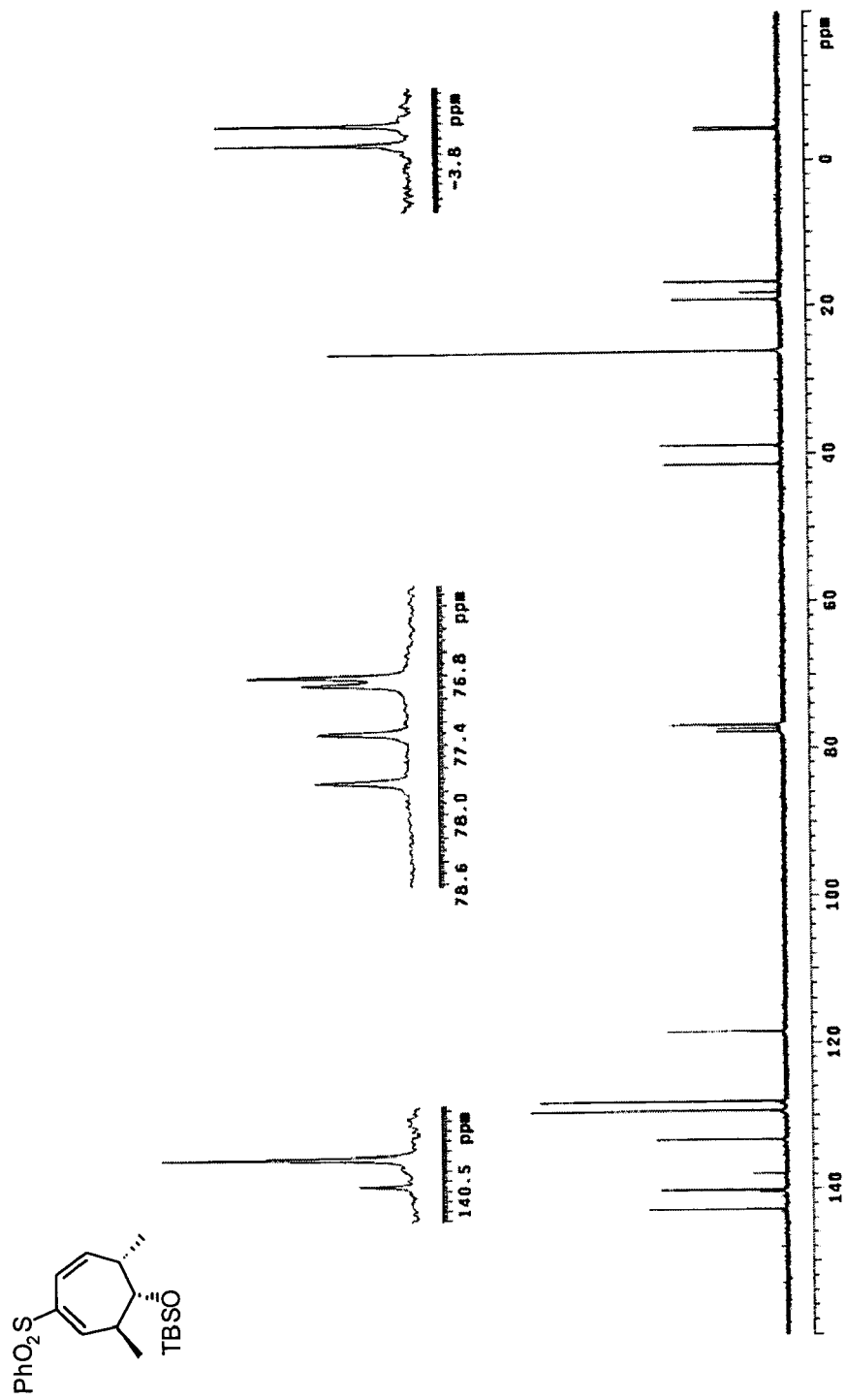
Figure 8:
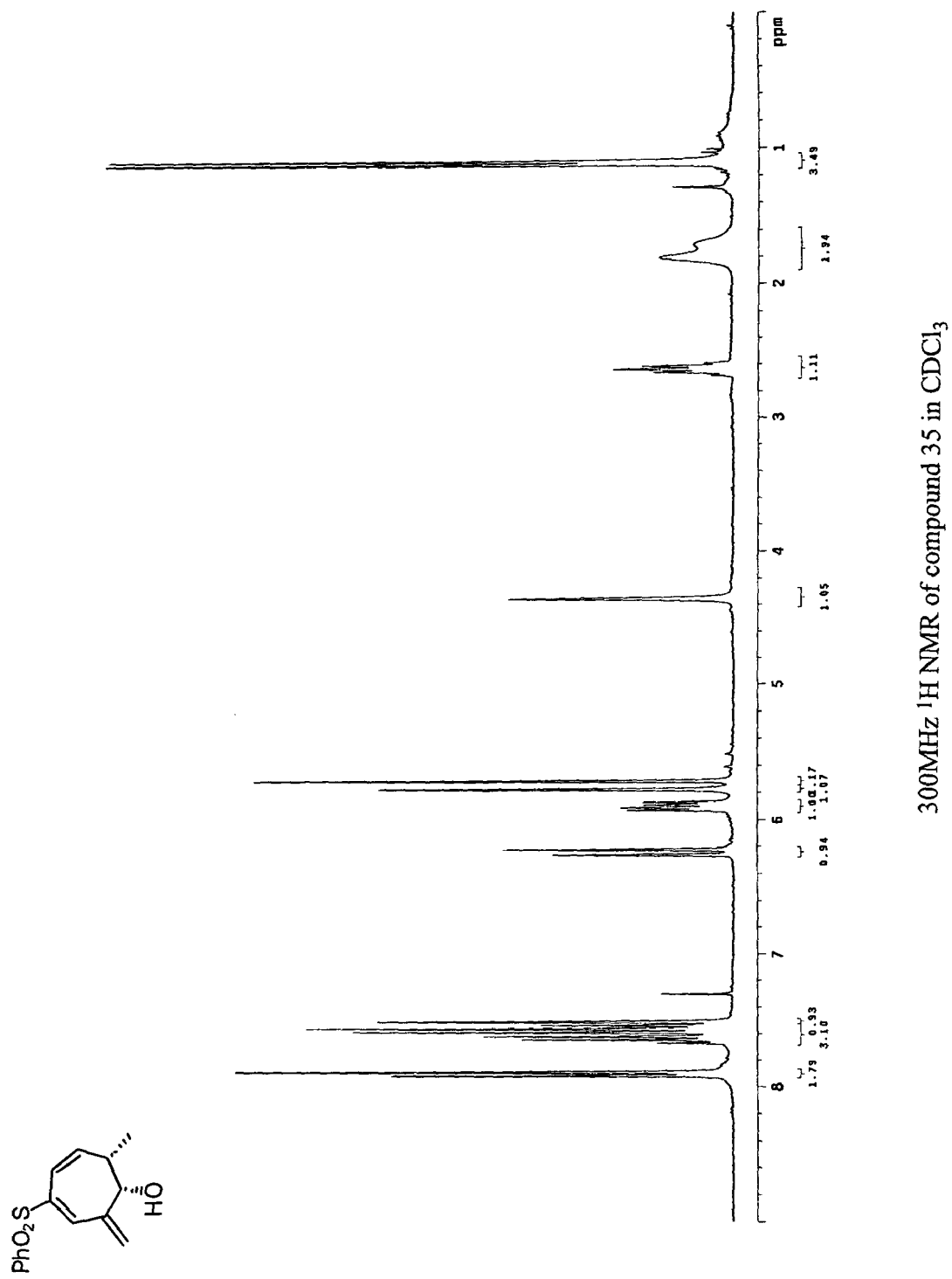
Figure 8:
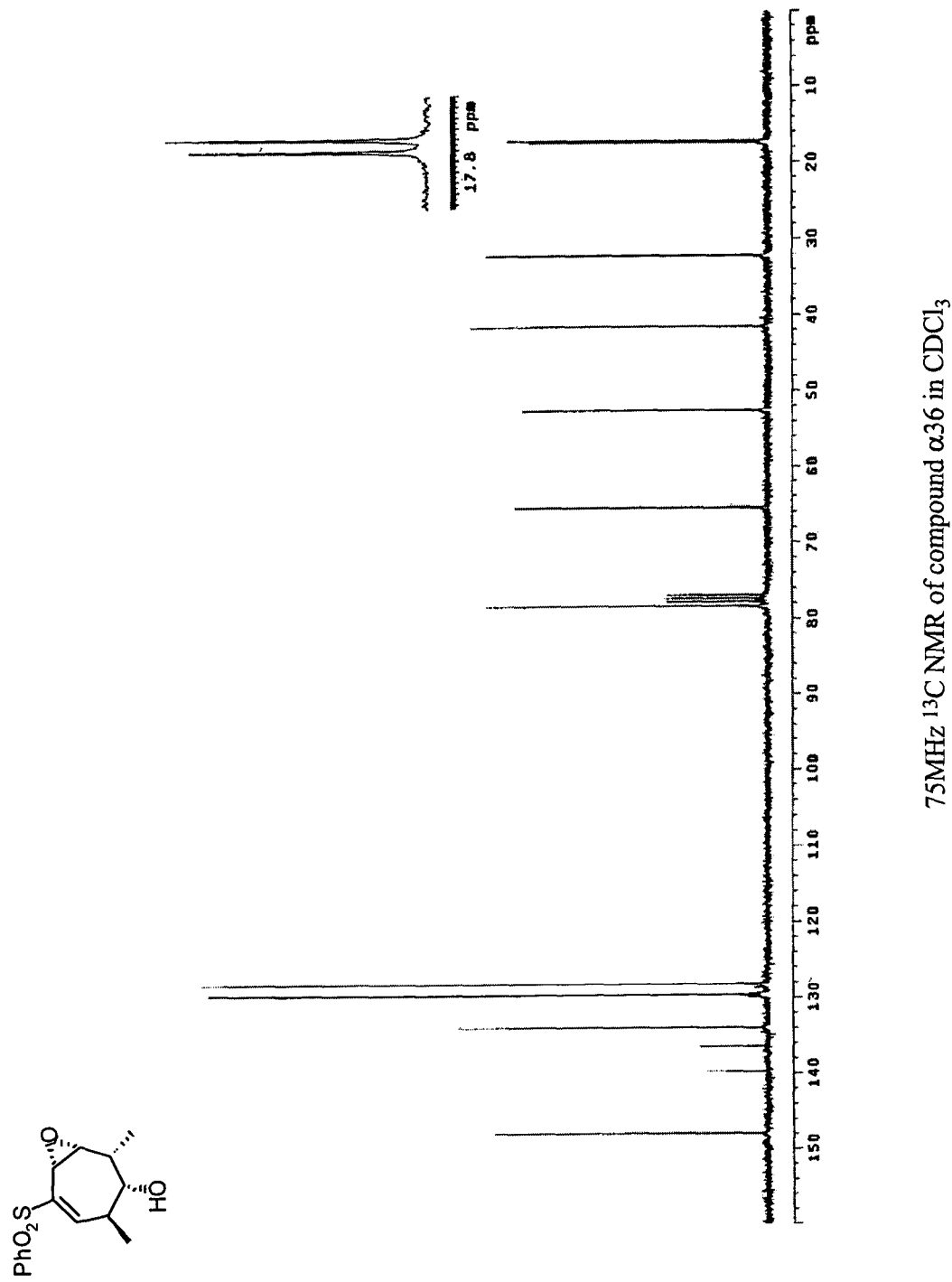
Figure 8:
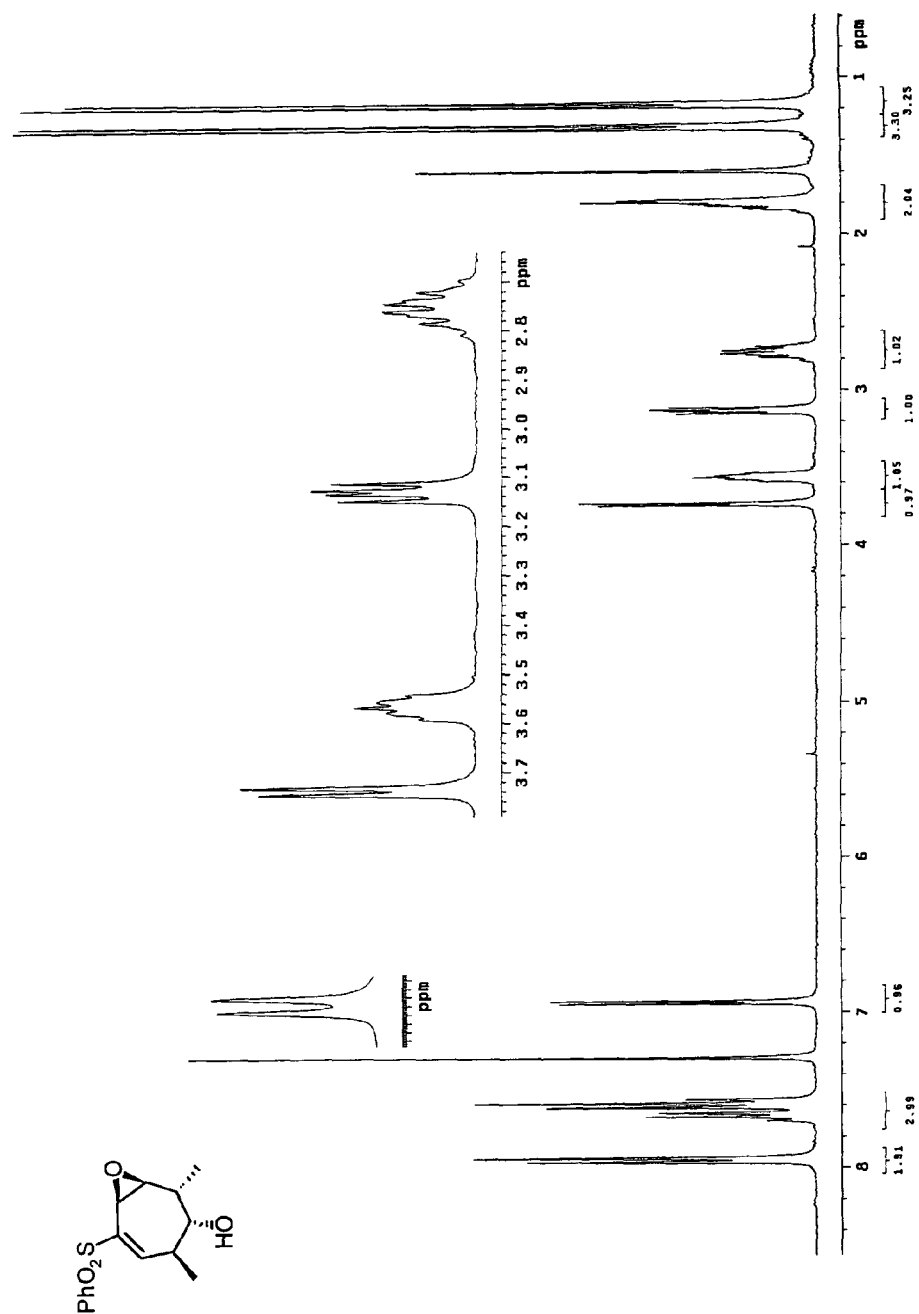
Figure 8:
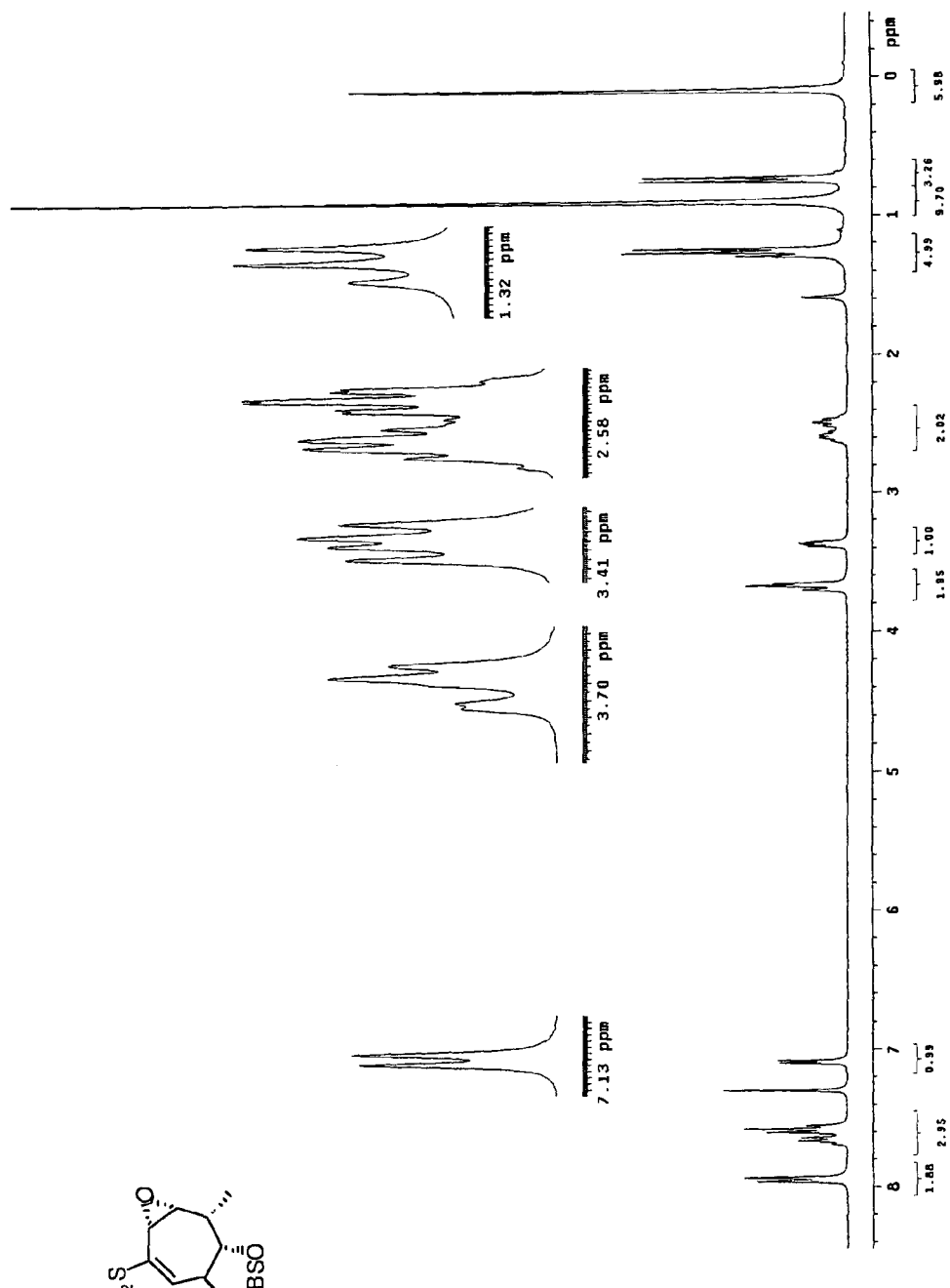
Figure 8:
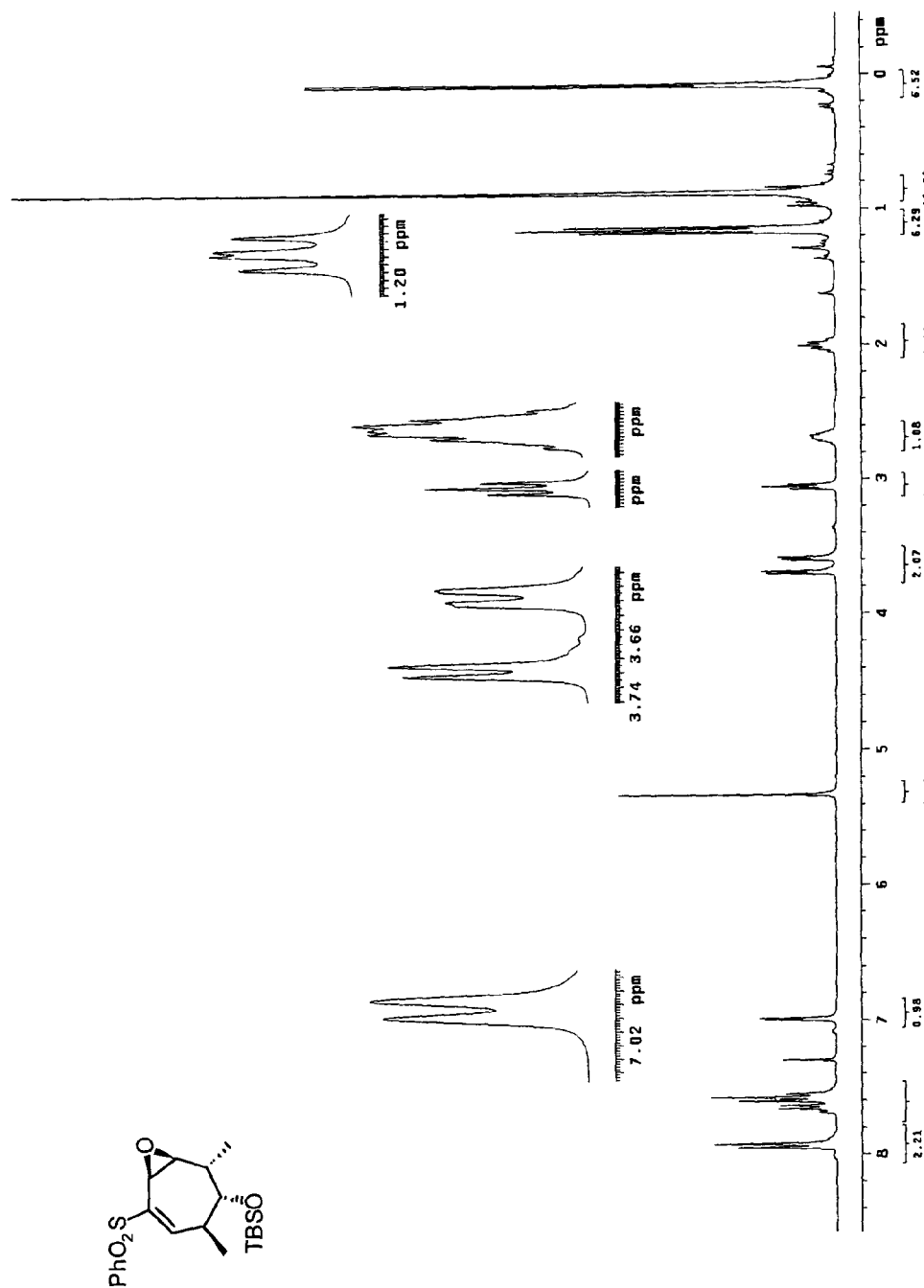
Figure 8:
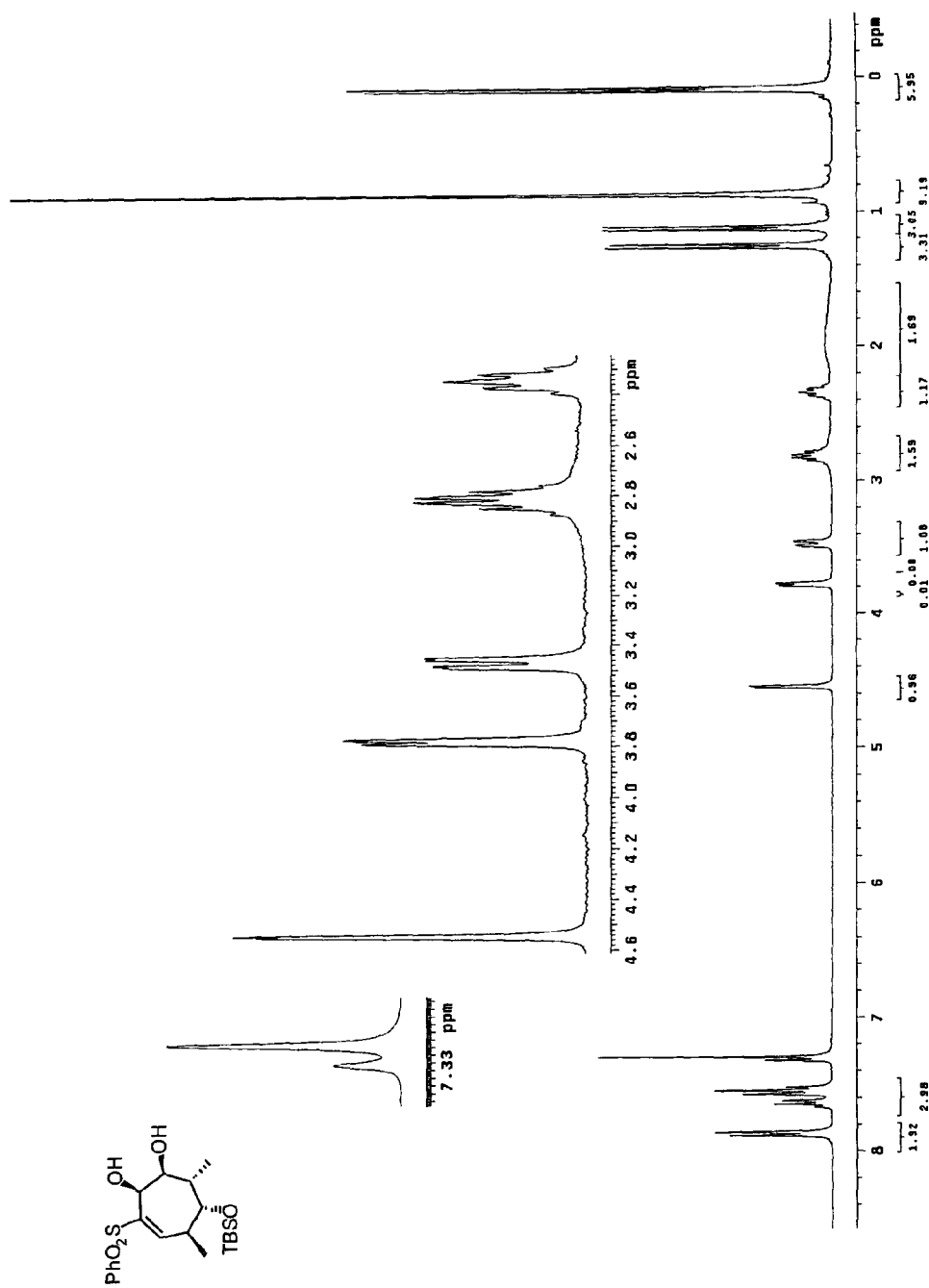
Figure 8:
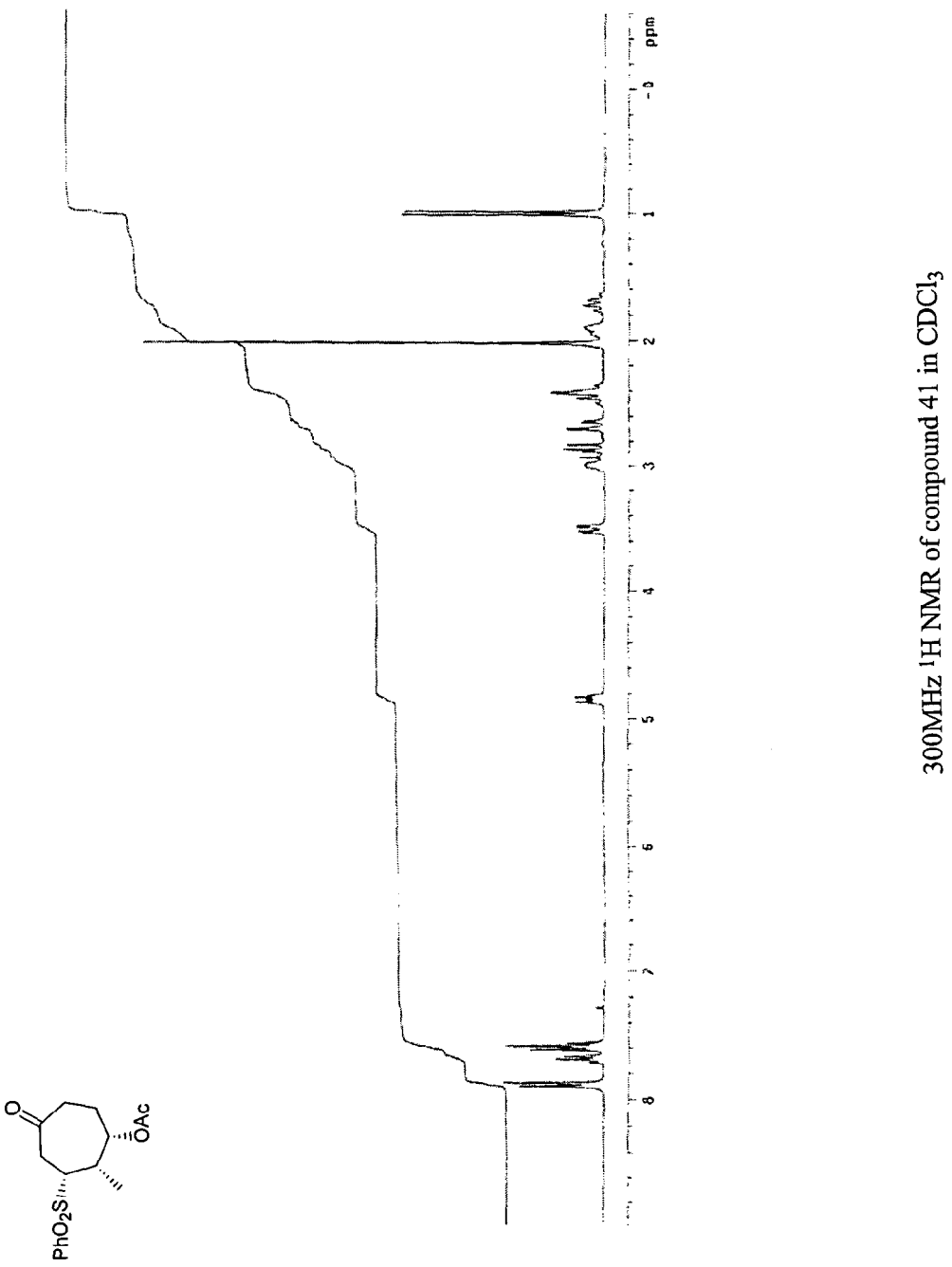
Figure 8:
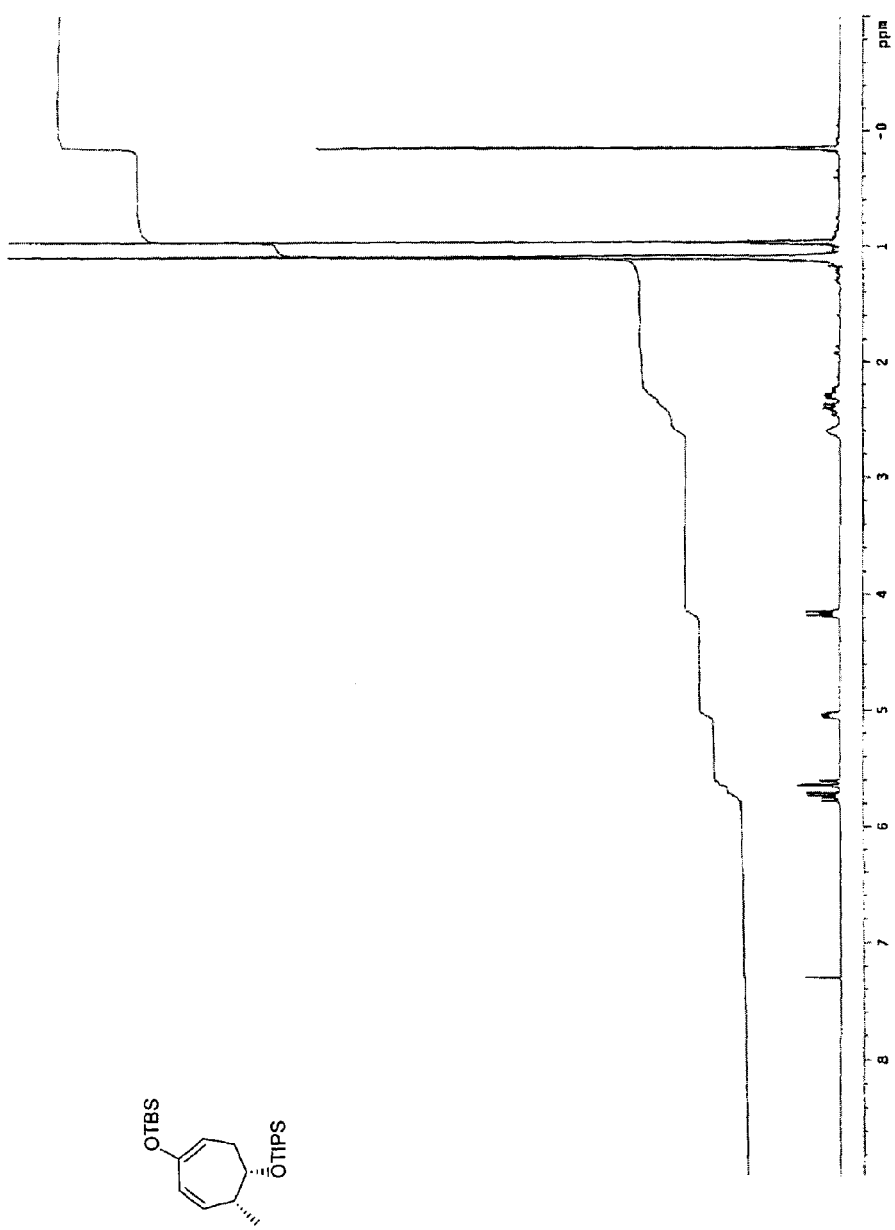
Figure 8:
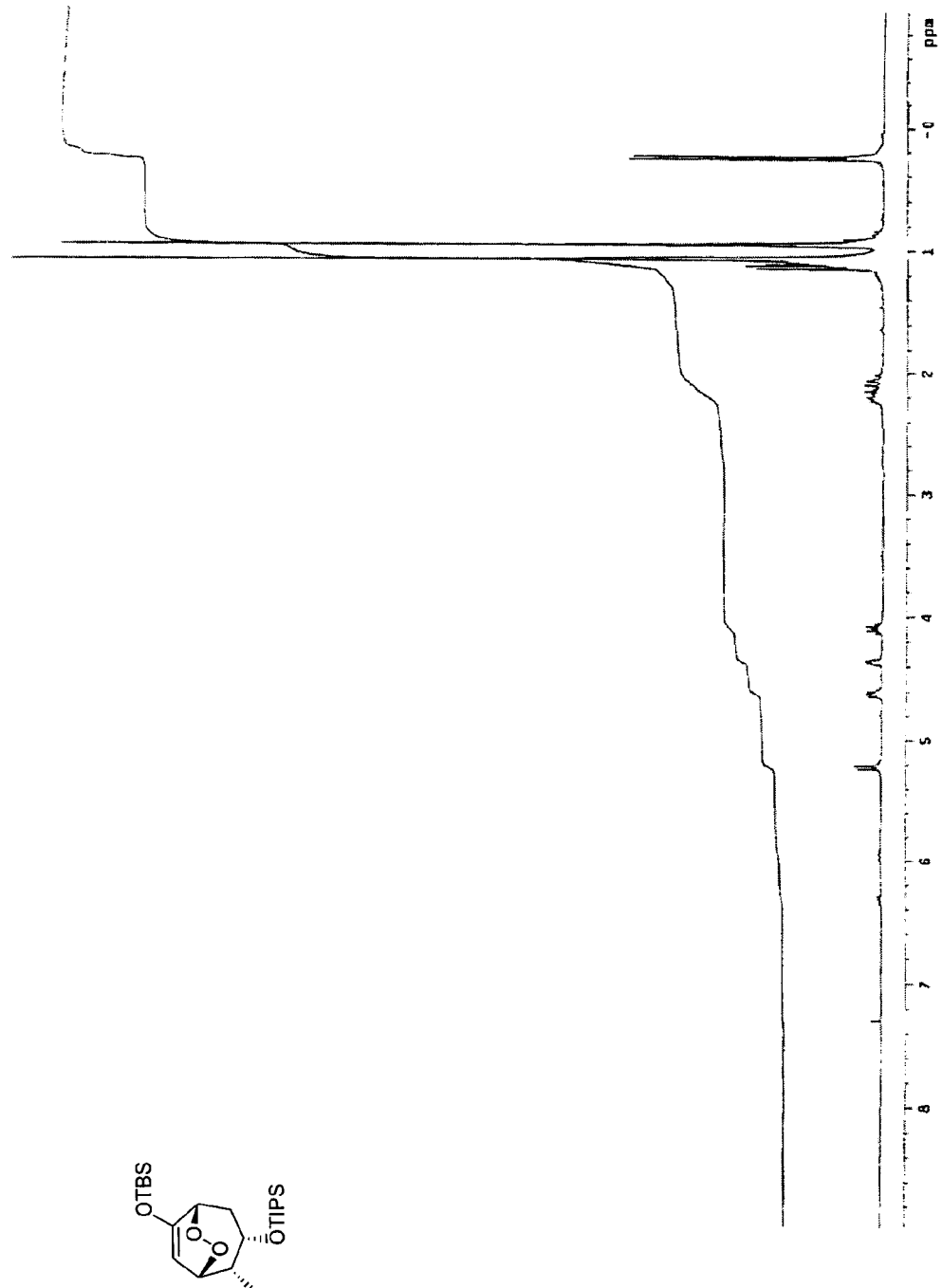
Figure 8:
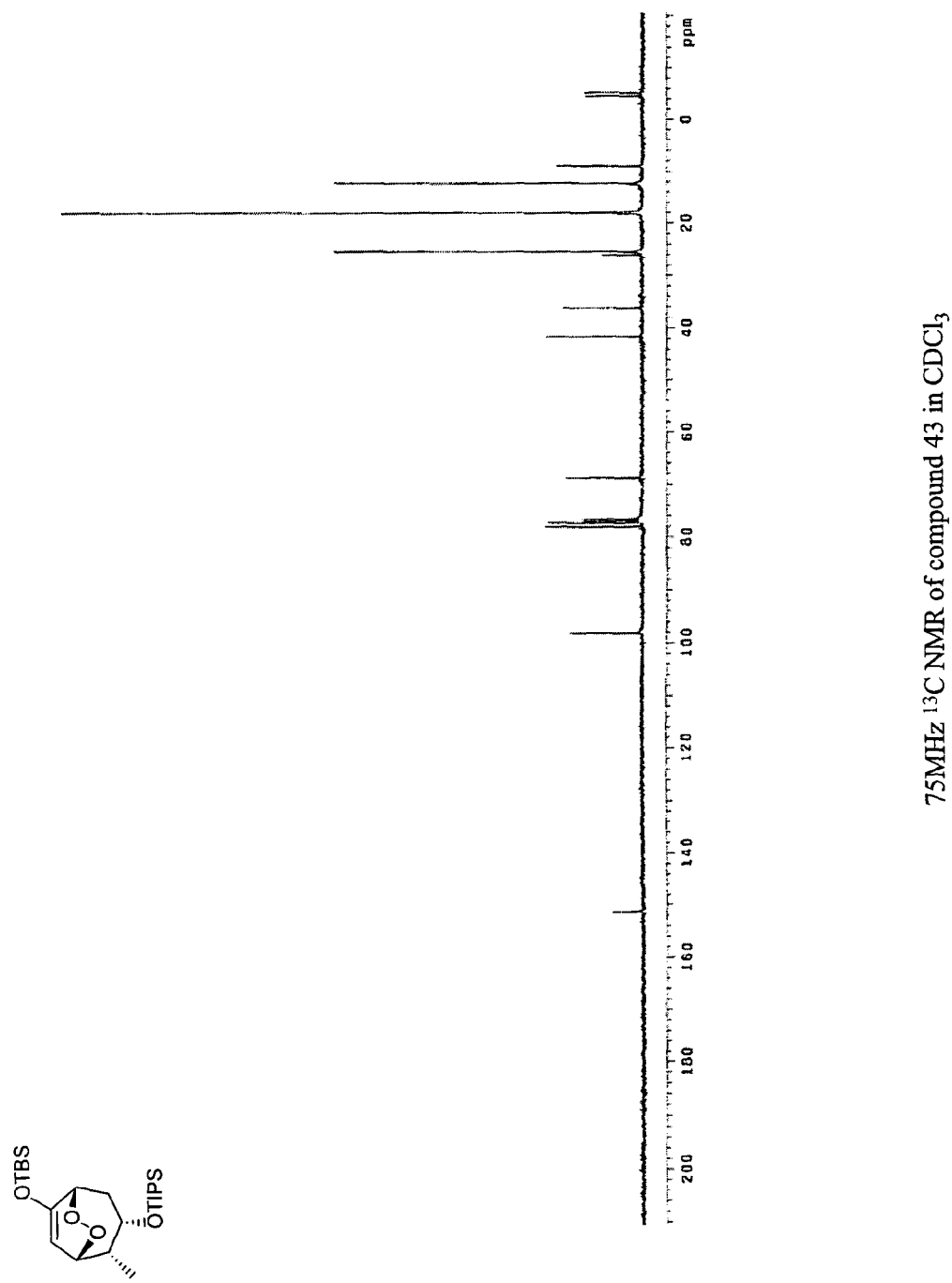
Figure 8:
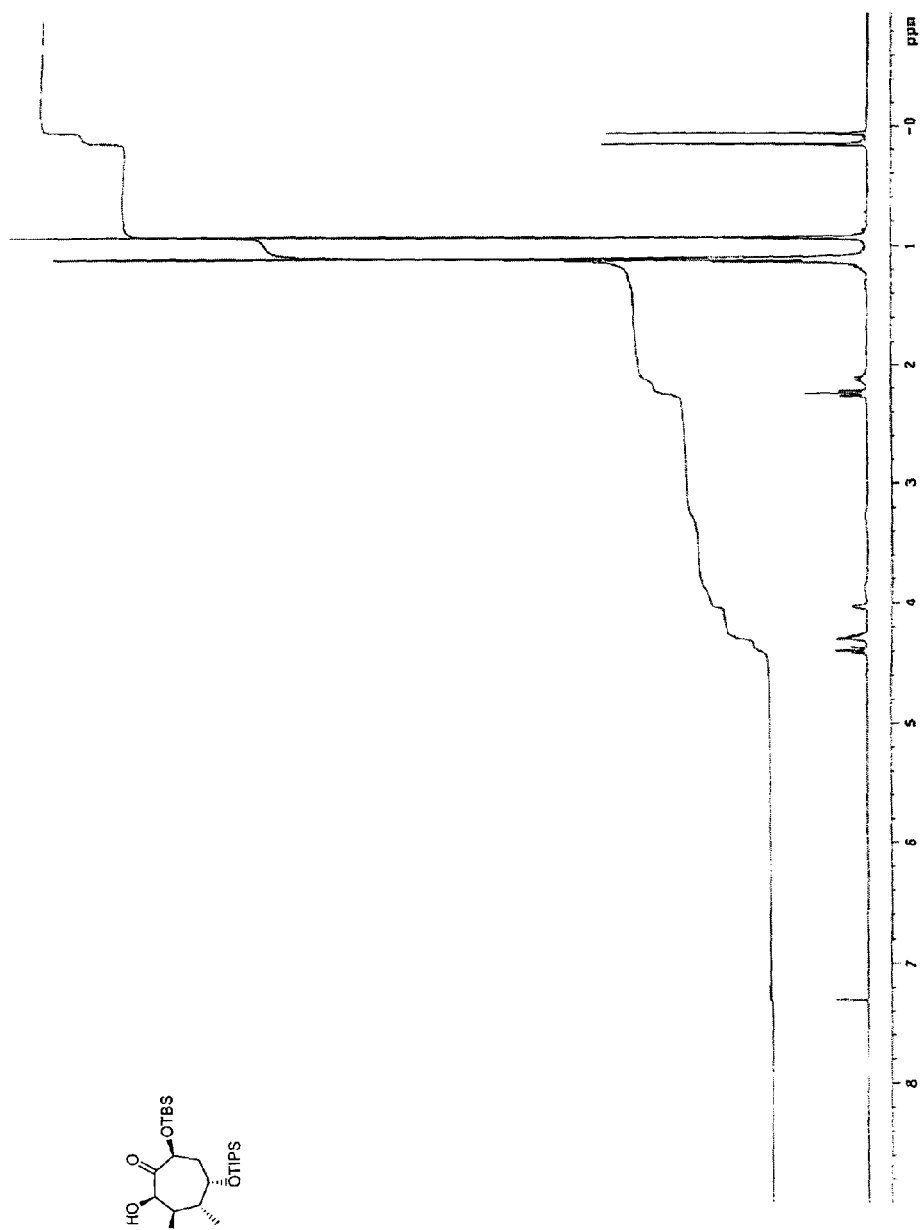
Figure 8:
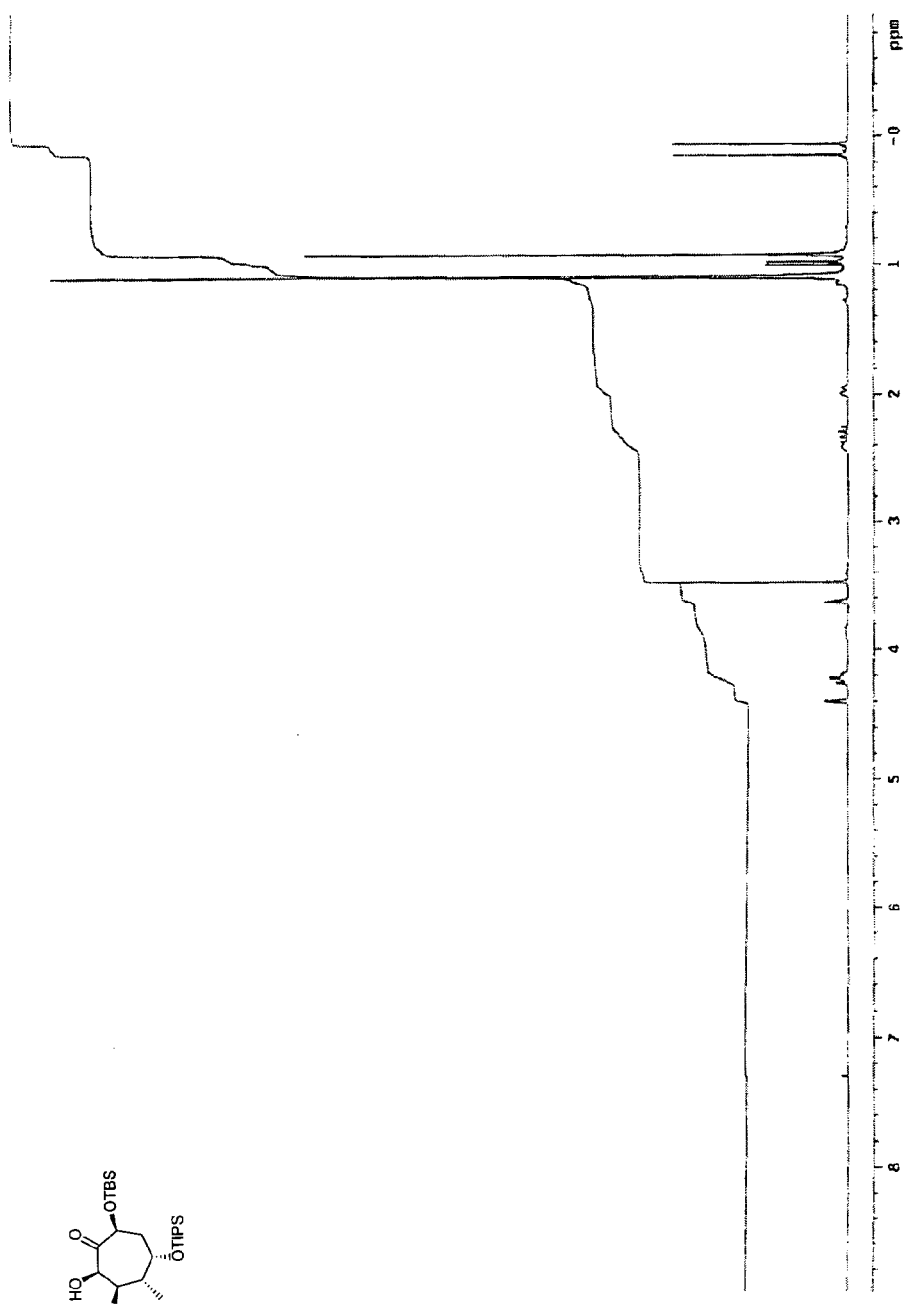
Figure 8:
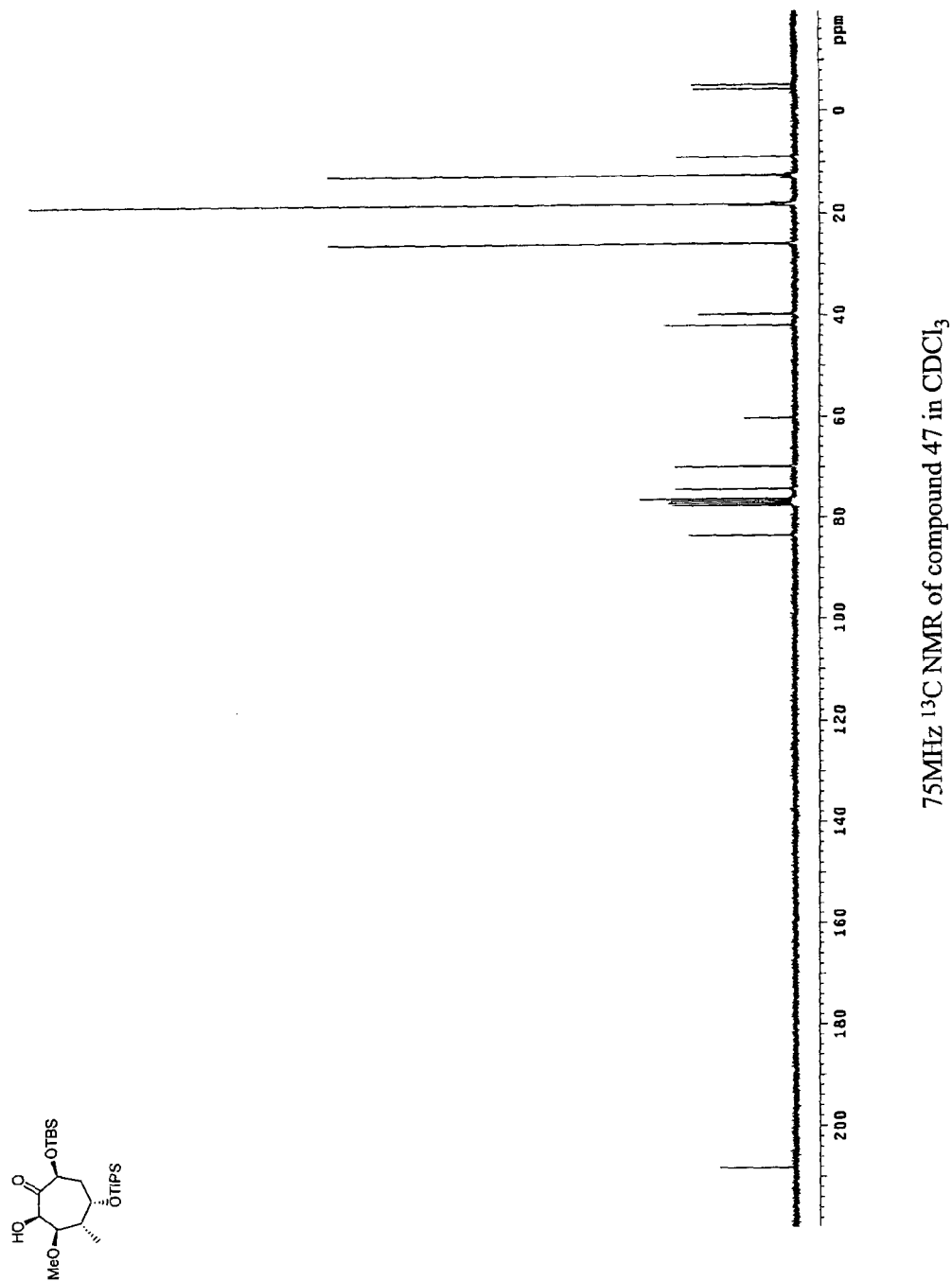
Figure 8:
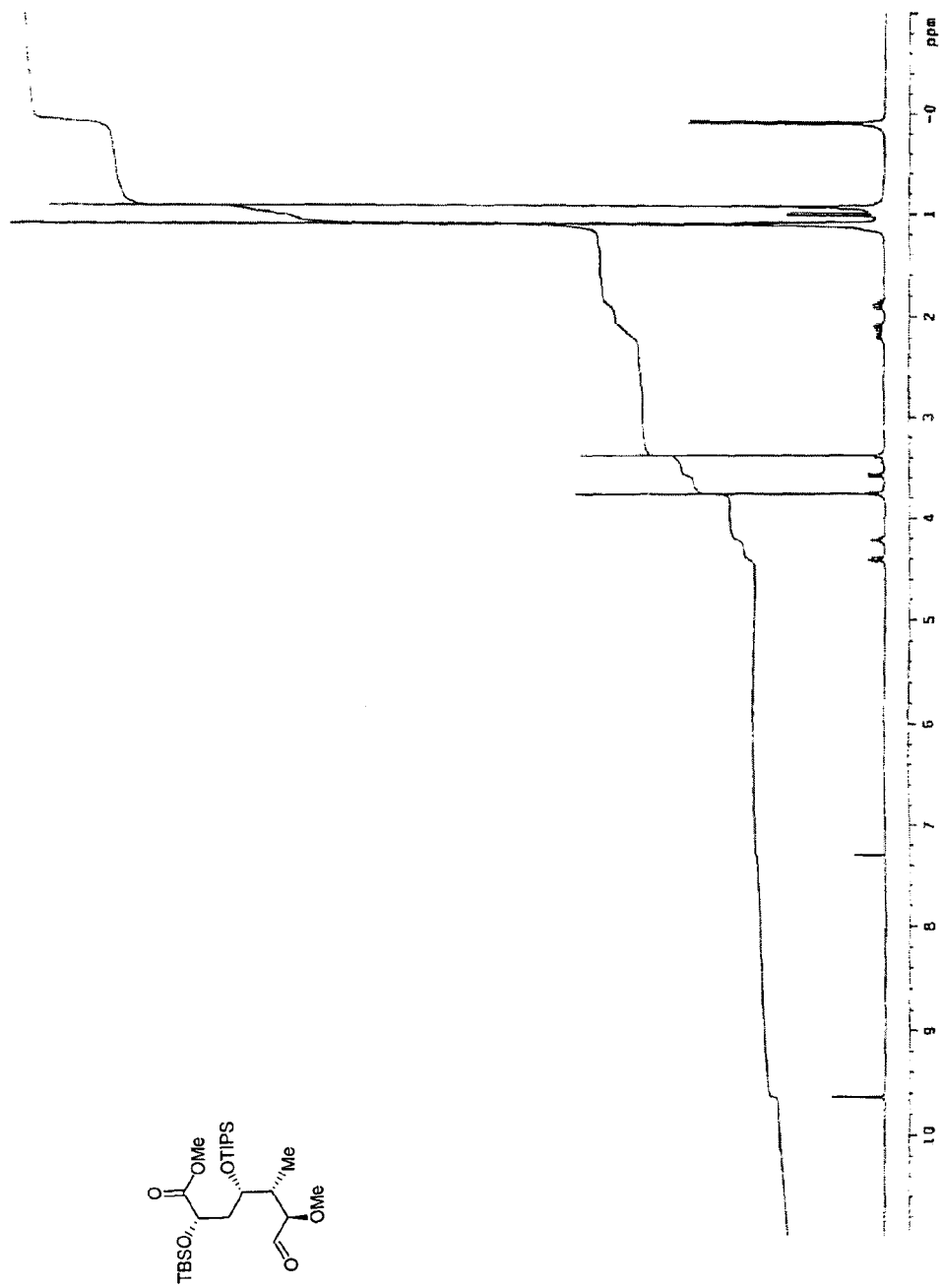
Figure 8:
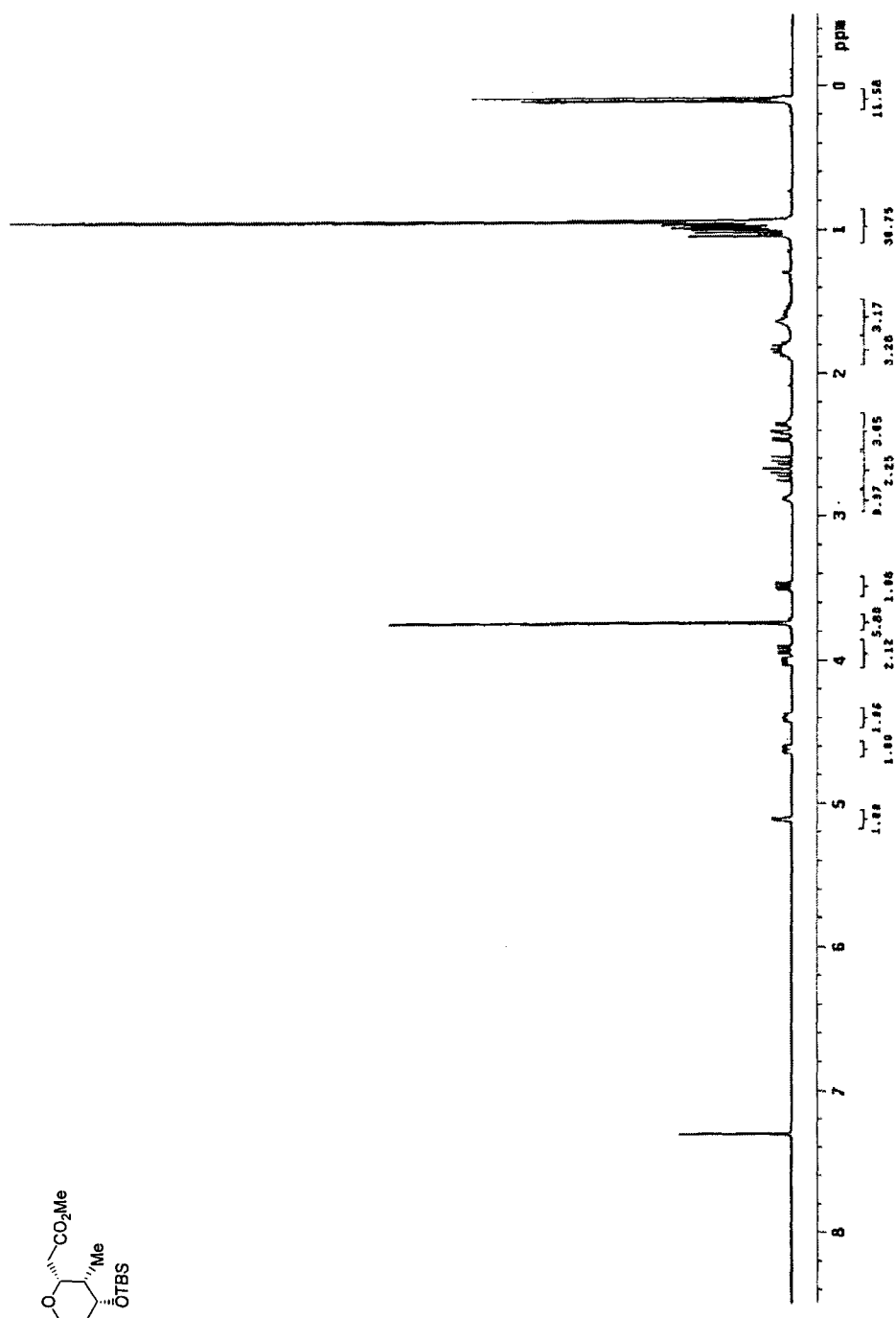
Figure 8:
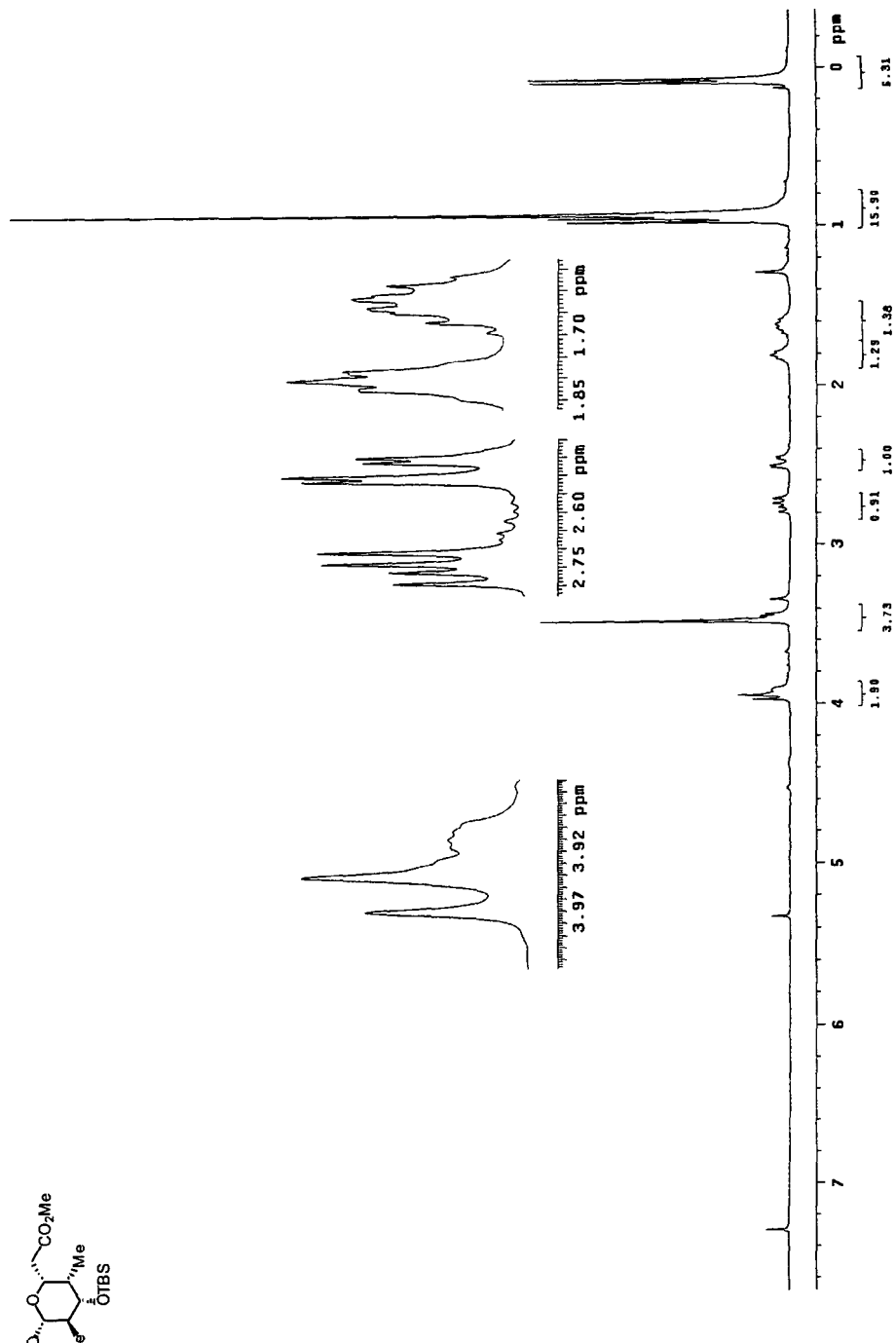
Figure 8:
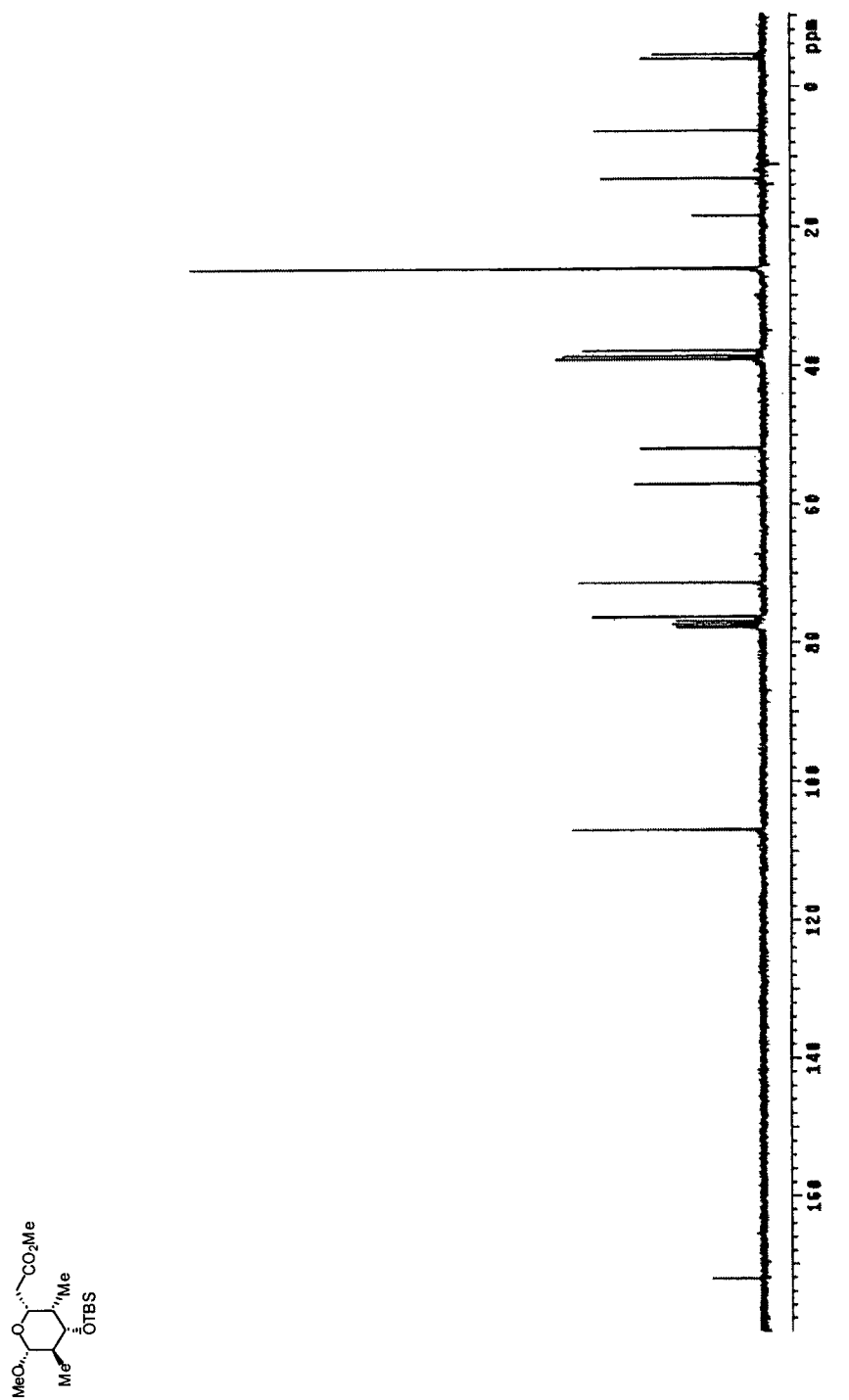
Figure 8:
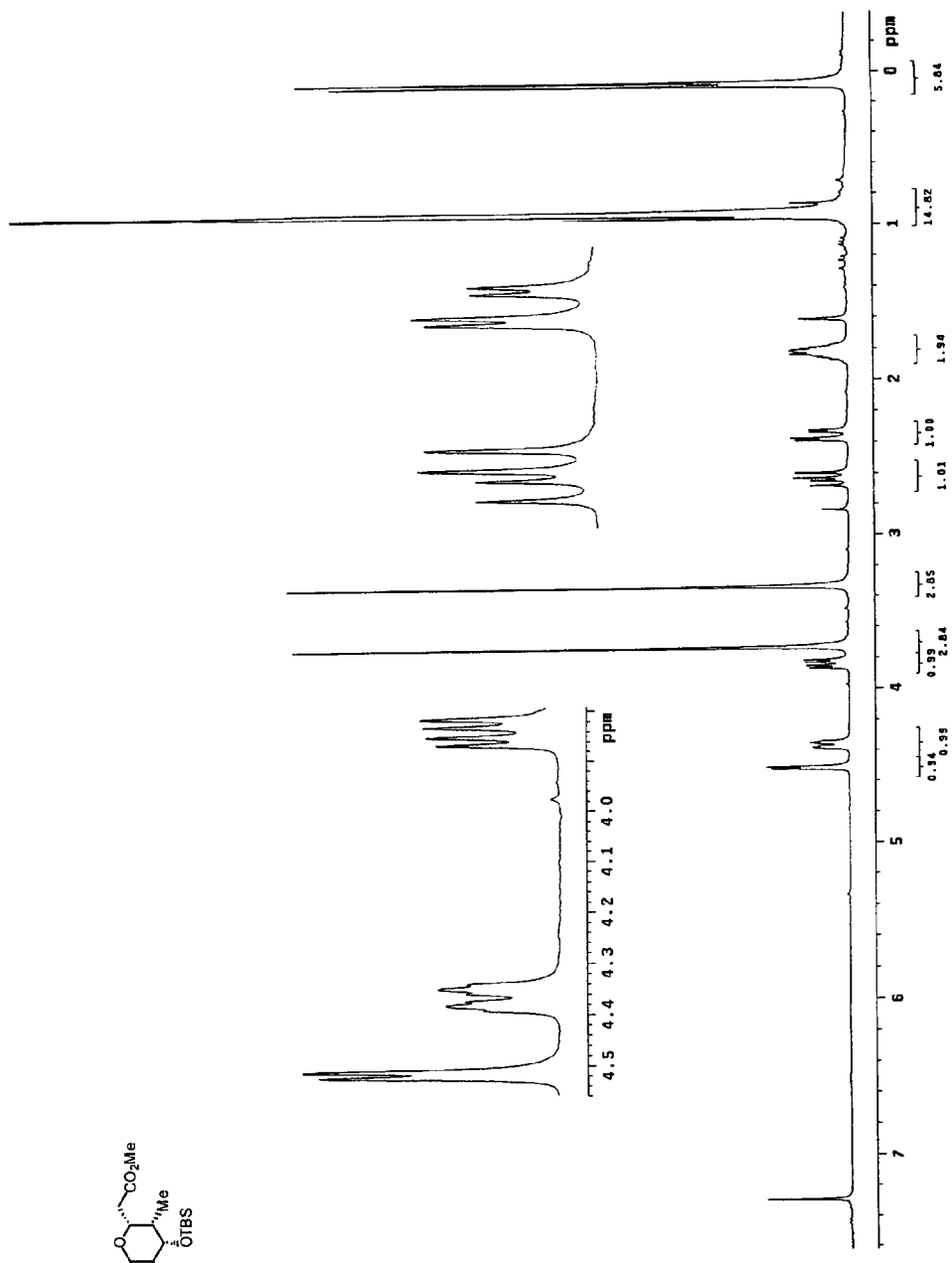
Figure 8:
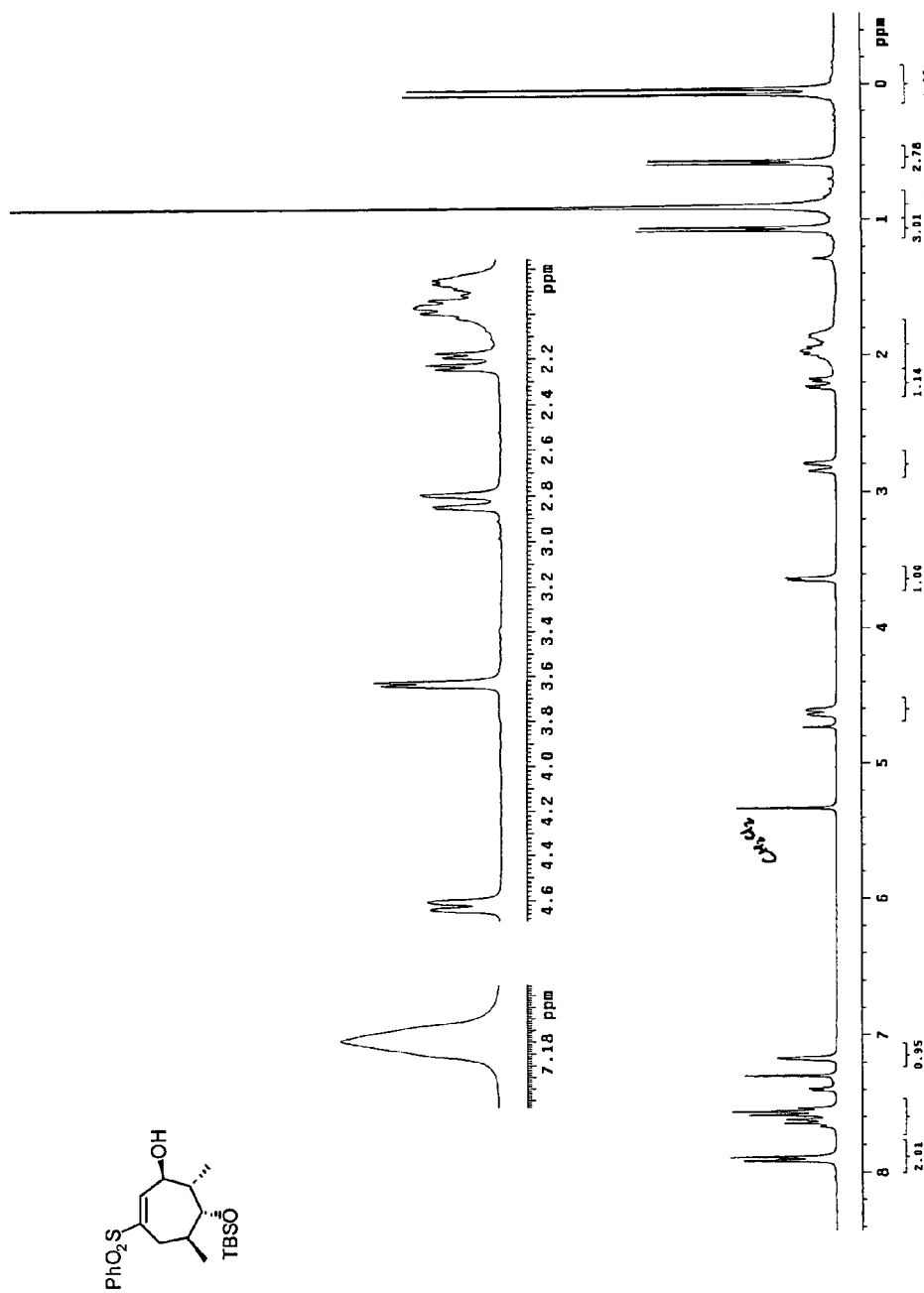
Figure 8:
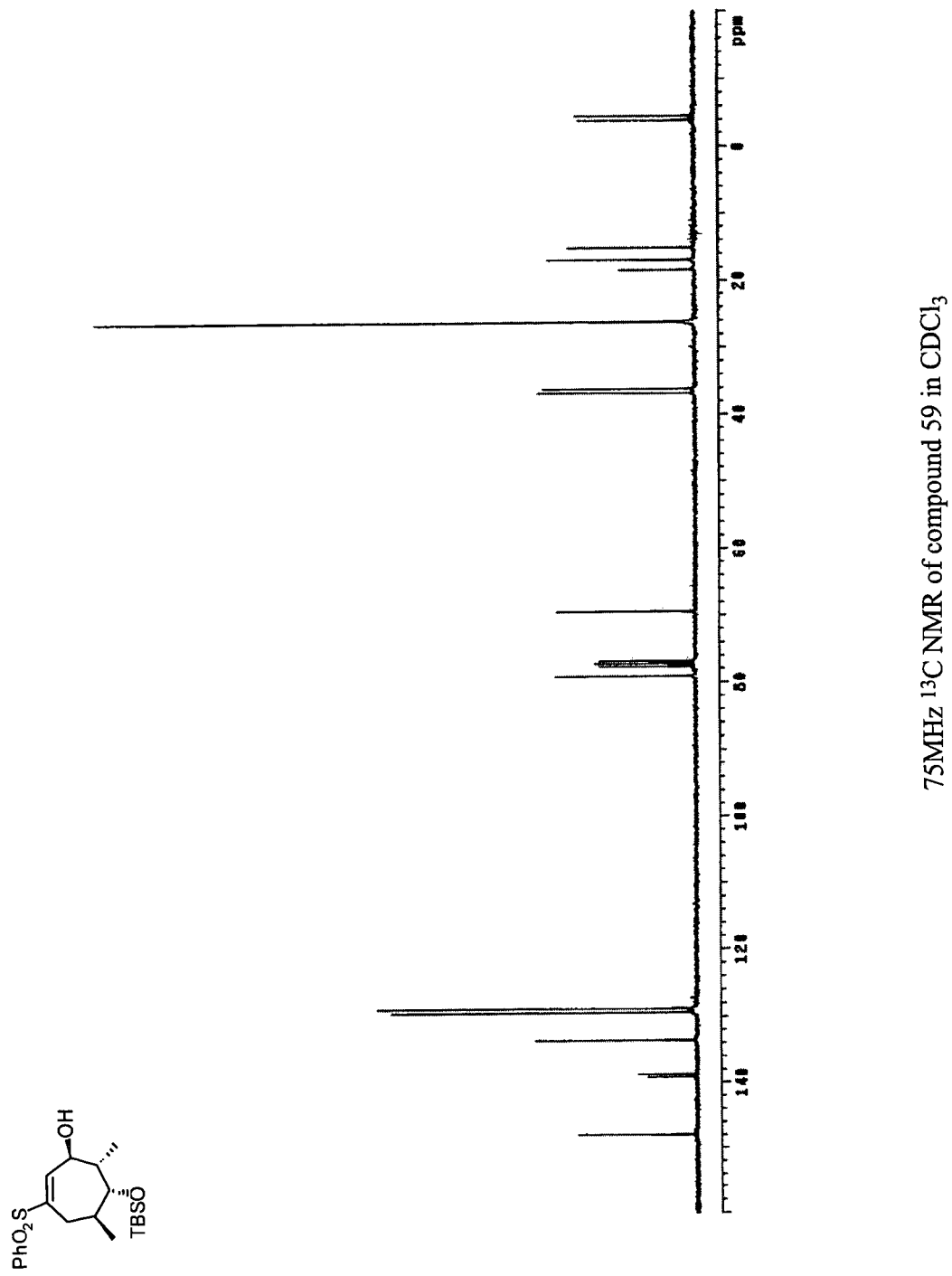
Figure 8:
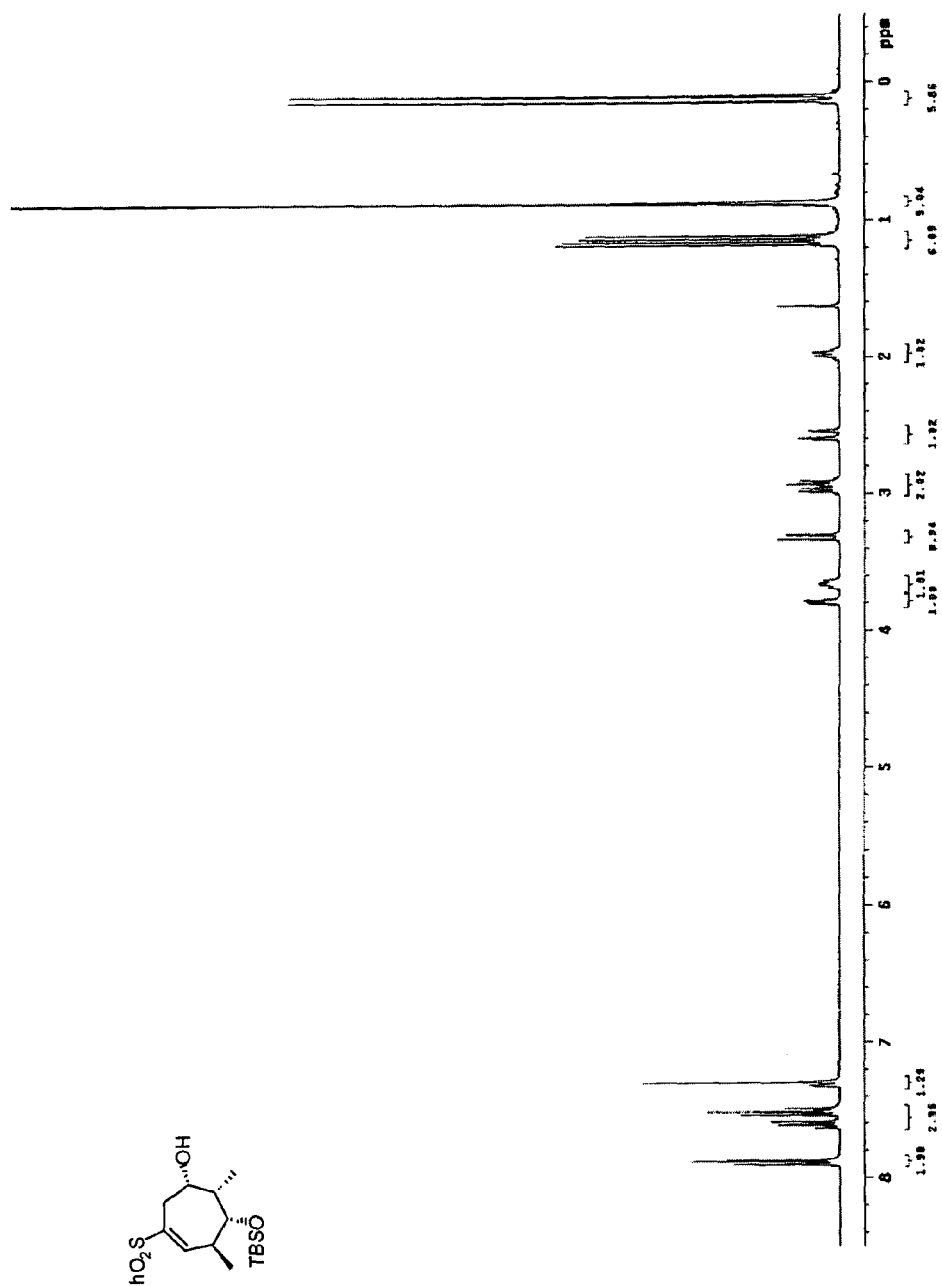
Figure 8:
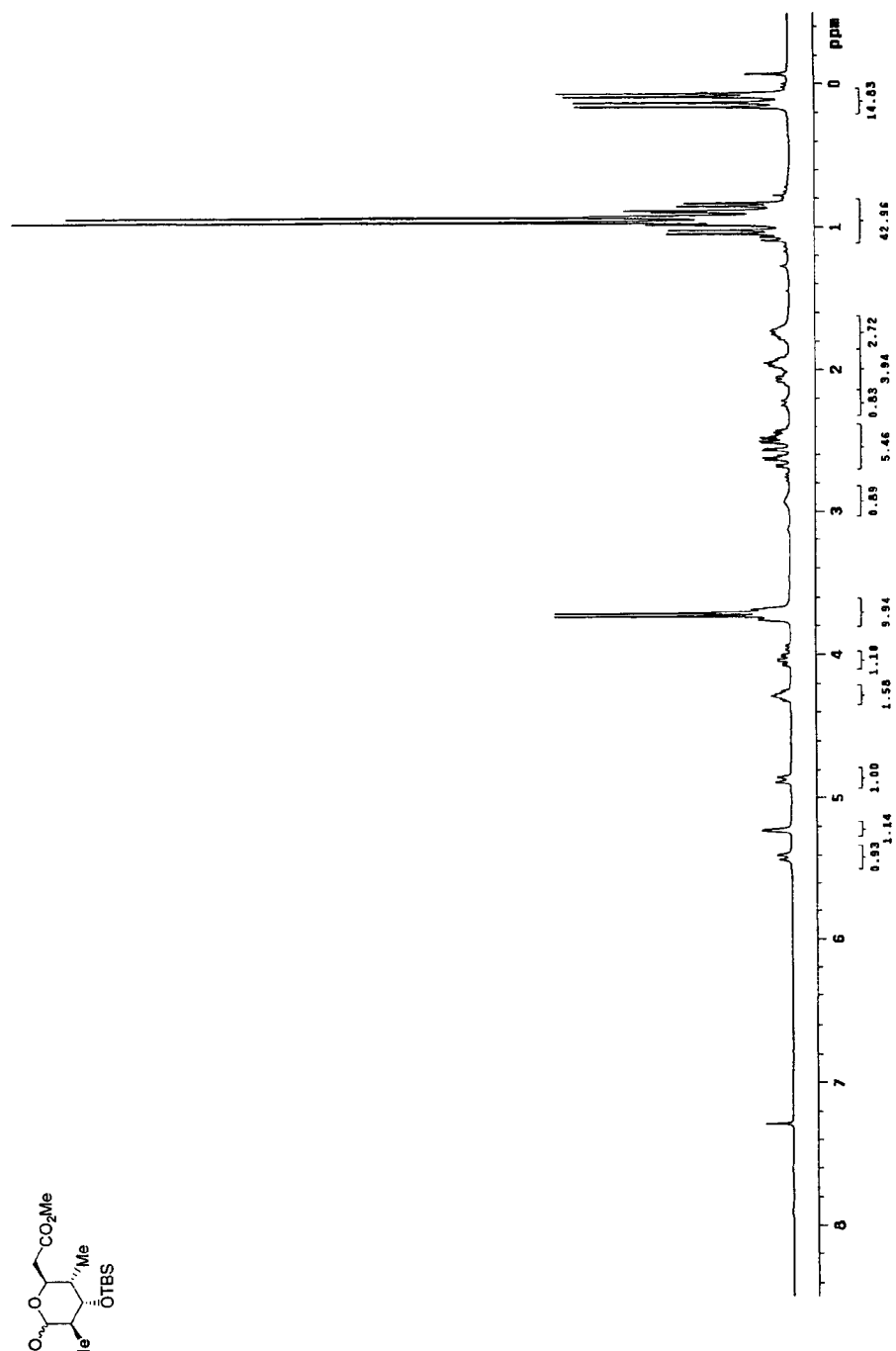
Figure 8:
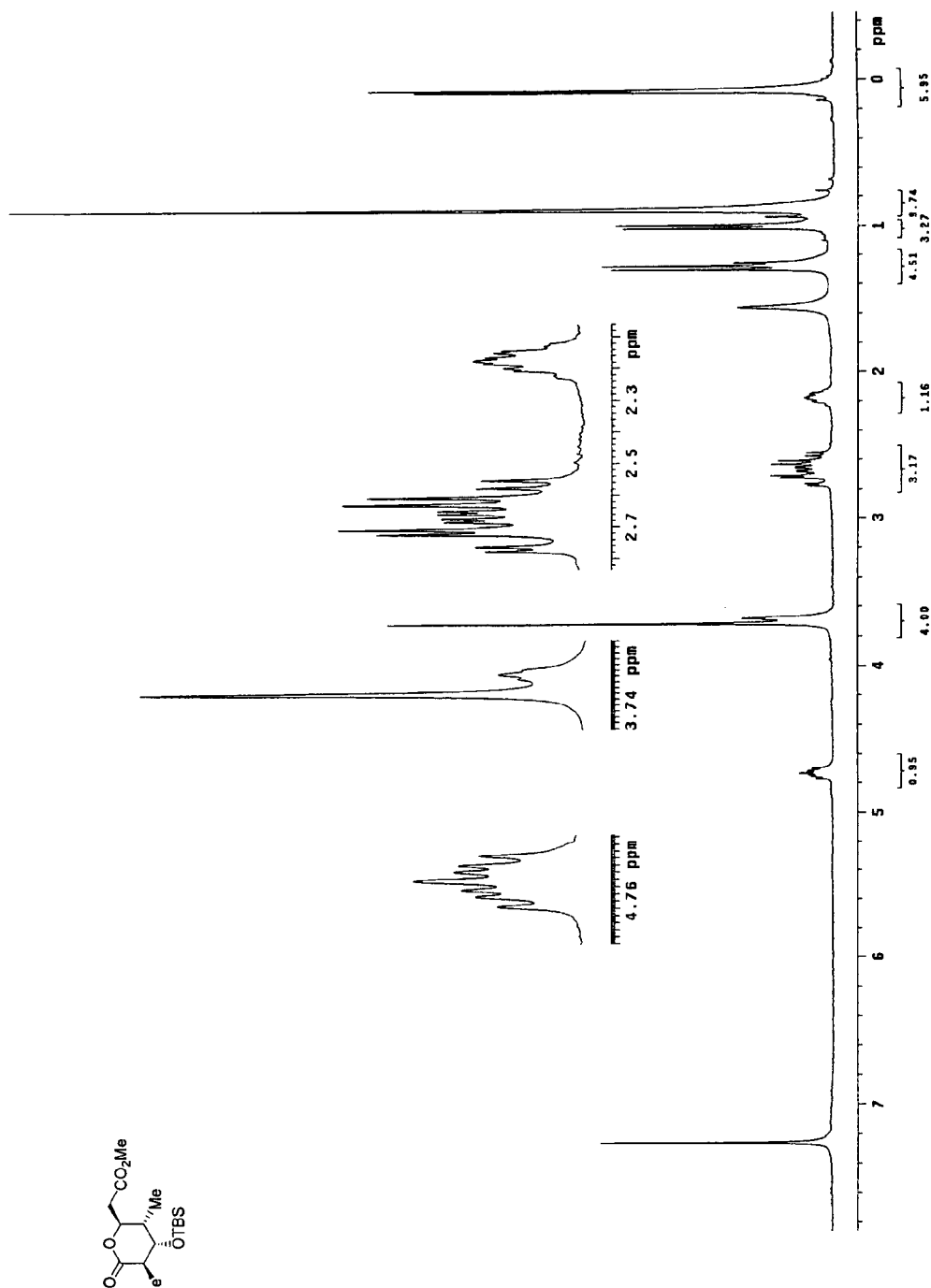
Figure 8:
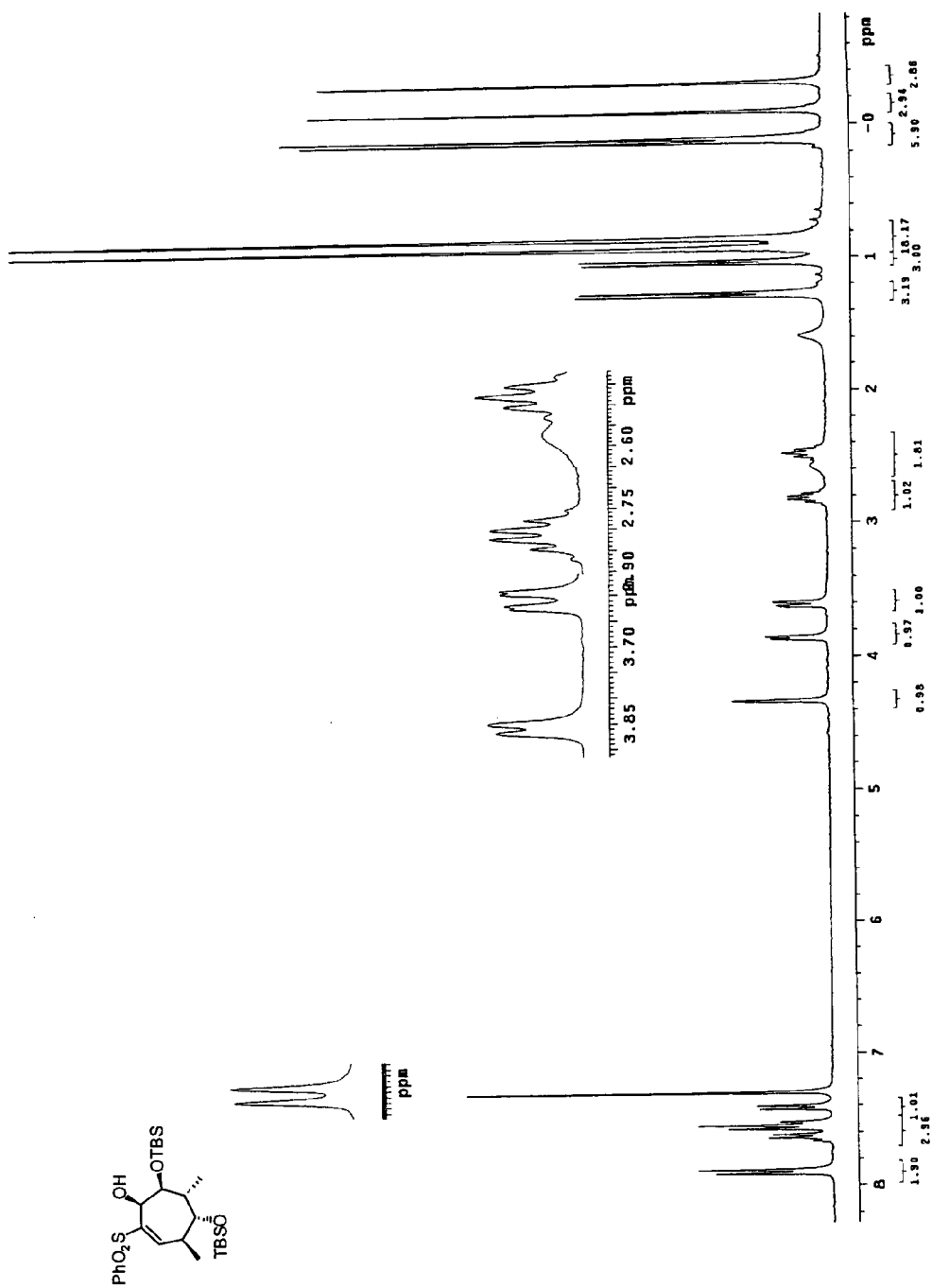
Figure 8:
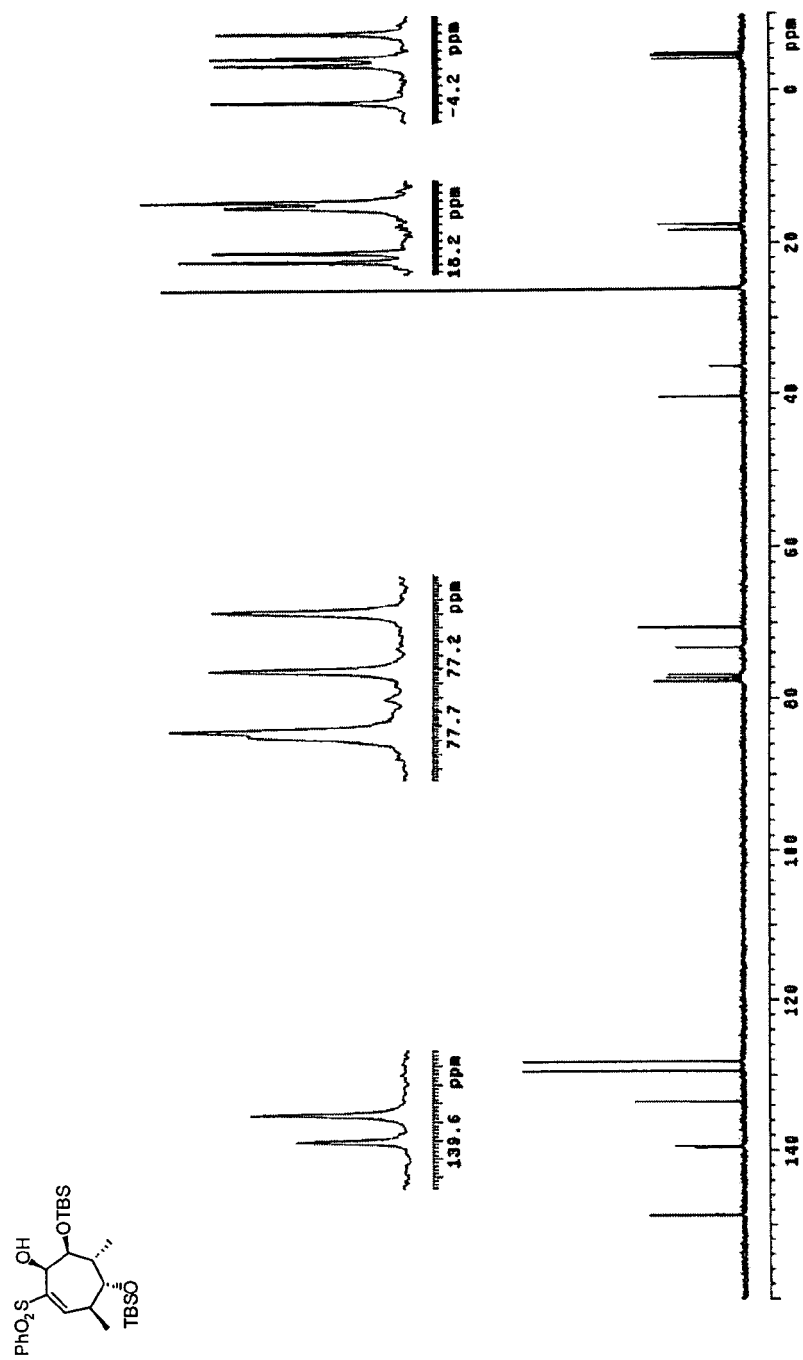
Figure 8:
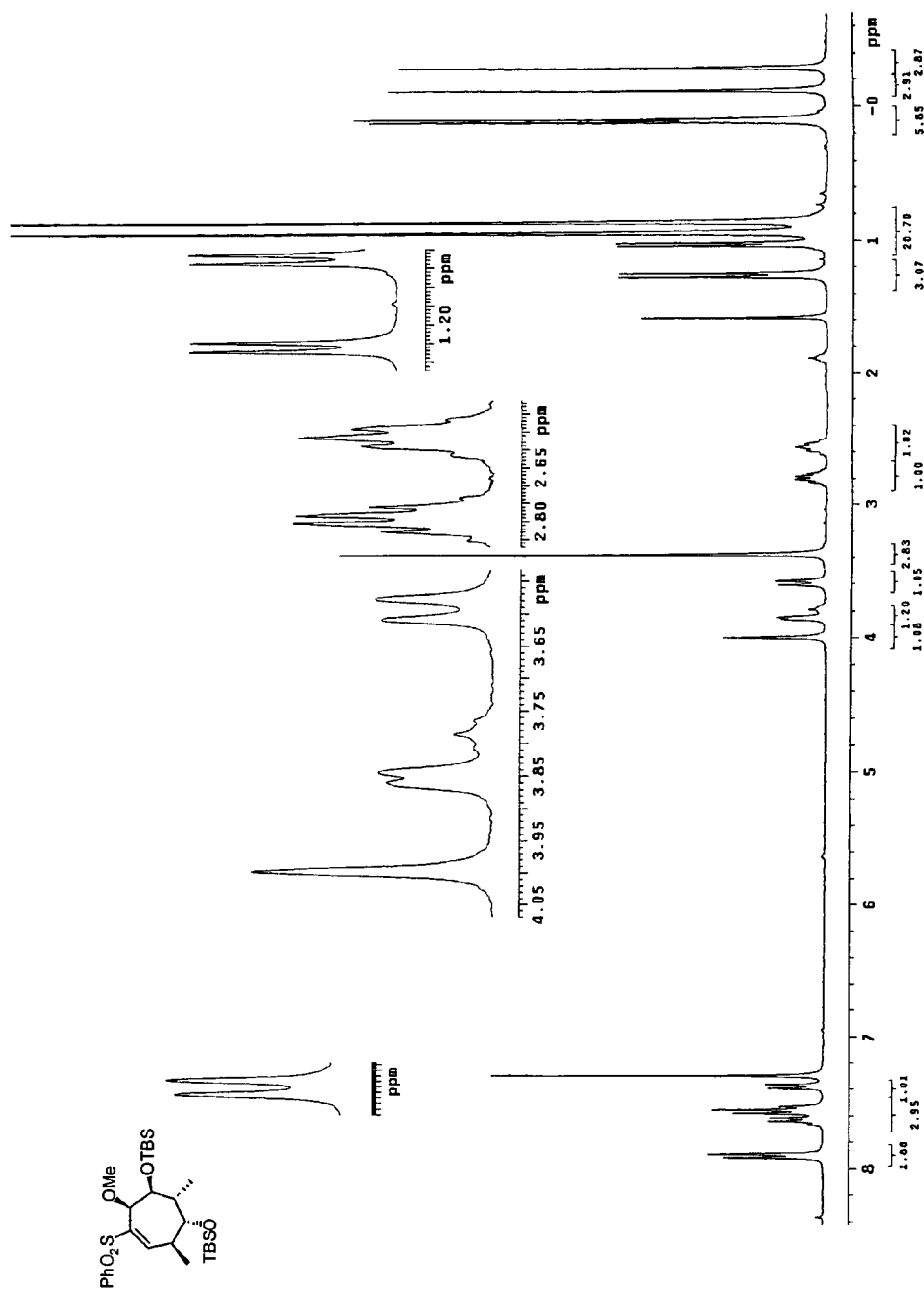
Figure 8:
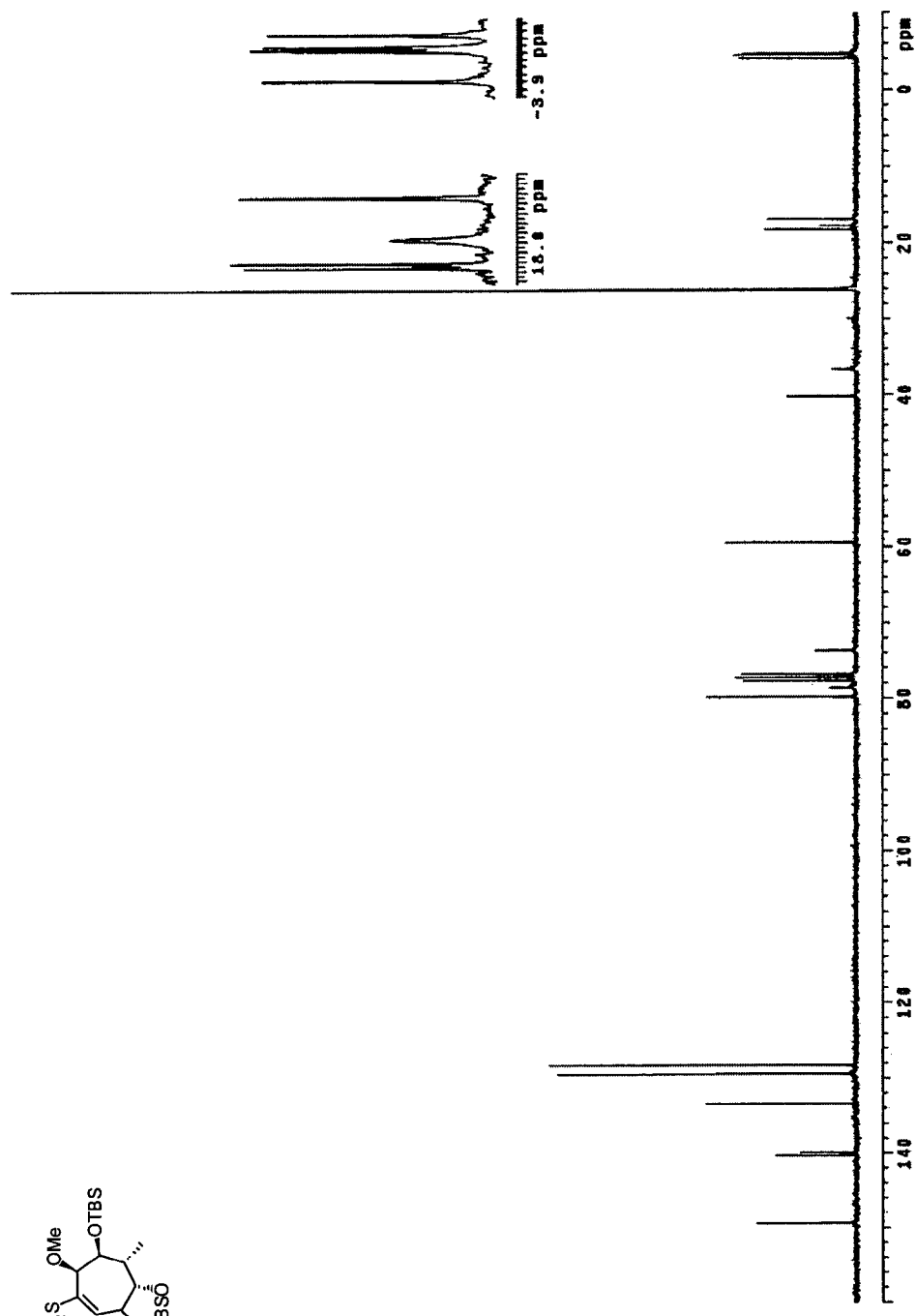
Figure 8:
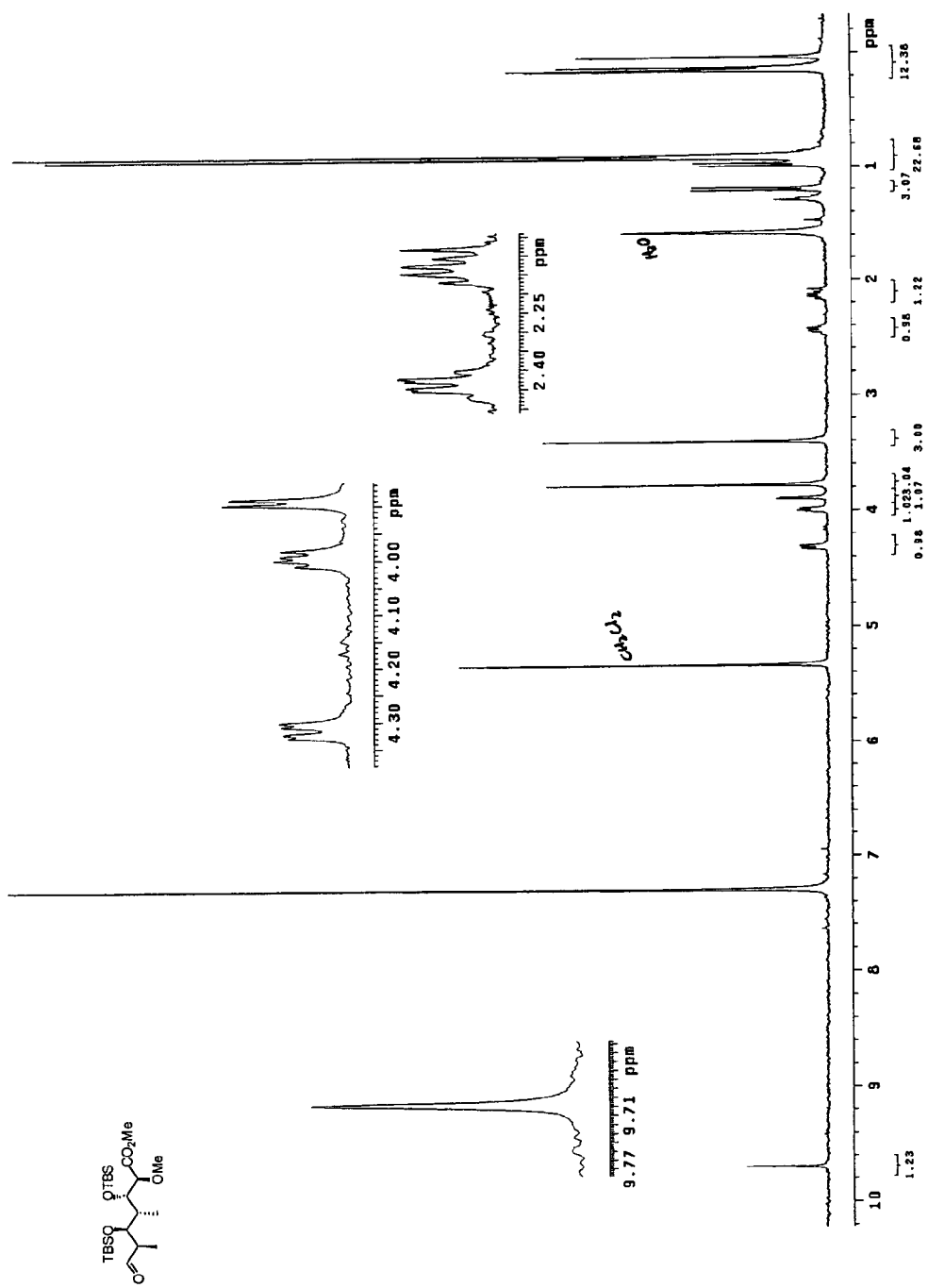
Figure 8:
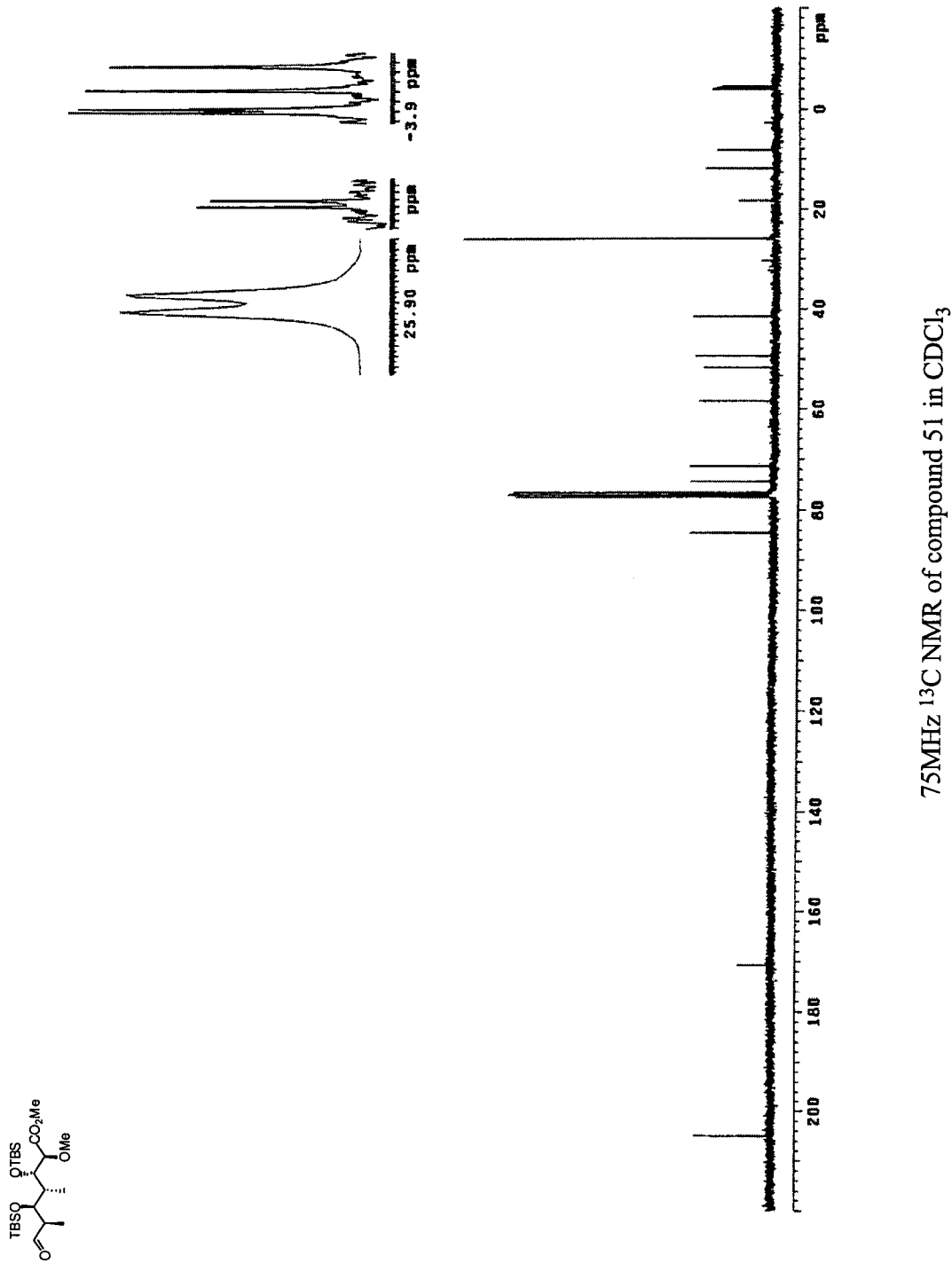

Referring to FIGS. 1 and 7, synthesis of segment 51, in accordance with the invention begins with cycloheptanone 1. The sulfur atoms used in this strategy are essential for the synthesis (FIG. 1). The initial vinyl sulfide activates the olefin for bromination in operation 1b, after being oxidized to sulfone in 1c, the resultant sulfone regiospecifically activates the allylic position for base promoted 1,4 elimination in operation 1d to dienyl sulfone 2. The electrophilic olefin of cross-conjugated dienyl sulfone 2 is flanked by a sterically demanding $sp^3$-hybridized sulfone moiety, which has been shown to be crucial for obtaining the high enantiomeric excess obtained in the Jacobsen epoxidation. Once again, in operation 3a the epoxy vinyl sulfone 3 undergoes 1,4 elimination to provide intermediate 4 which suffers conjugate-addition with methyl lithium in operation 3b to provide an allyl sulfonyl anion 66, which is directly sulfenylated to 67 in stage 3c. Vinyl sulfone 67 equilibrates to 68 at stage 3d and is finally protonated to 21 at stage 3e. Vinylogous dioxythioacetal 21 undergoes vinyl sulfide promoted loss of sulfinic acid at operation 4 to afford cross-conjugated dienyl sulfide 29 after workup. Methylation of the dianion of 29, followed by oxidation of sulfide, and alcohol protection gives 33. Catatytic substrate-based dihydroxylation followed by regiospecific silylation of the more available alcohol generates alcohol 52, which undergoes O-methylation to 53, then cleavage of the final vinyl sulfone to deliver the target stereopentad 51.

In the course of this synthesis, applicants have introduced and ultimately removed two phenyl sulfone moieties; and while these factors are negative from the viewpoint of atom-economy, they are absolutely essential to achieve the chemistry. The dienyl sulfone synthesis of 51 exploits a chiral catalyst and then relates all further stereochemistry to the newly created stereocenter(s). This creates less costly 'overhead' than a synthesis employing an enantiopure starting material and then twice using either a chiral reagent or a chiral auxiliary. This difference will be especially significant in situations where reactions need to be conducted on a significant scale; since auxiliary or reagent cost, recycle, and/or disposal all strongly impact production cost.

General Synthesis of Chiral 4-alkylcycloalkenones and for Enantiopure 2,5-cyclohexadienone Synthons Methylation of epoxyvinylsulfone SS-9a (Scheme 4a below) proceeds with about 96/4 trans/cis specificity for trans adduct 14a. Duplication of this reaction with enantiopure SS-9a using chiral HPLC analysis reveals that the reaction is essentially stereospecific (Table 1a, entry 1). Repetition of the process for the additional alkyl groups shown in Table 1a can be conveniently conducted with cuprates derived from both lithium and Grignard reagents without the need for addition of any alkyl aluminum reagent (Scheme 4a). The reactions are all high yielding and the product can be directly O-methylated as crude material. Methylation using MeI in basic DMSO is high yielding, fast, and does not require chromatography either before or after the process (Table 1a). Substantial empirical efforts failed to increase the selectivity of phenyl addition beyond 3:1.

TABLE 1a

Alkyl Cuprate additions to SS-9a

| R = | M = | % Yield 12at, c | HPLC Ratio 12at/12c | % Yield |
|---|---|---|---|---|
| Me* | Li | 98 | >50/1 | 13at-Me 99 |
| Et | MgBr | 92 | >50/1 | 13at-Et 97 |
| i-Pr | MgCl | 94 | >50/1 | 13at-Pr 99 |
| t-Bu | Li | 93 | >50/1 | 13at-tBu 98 |
| PhMe2Si | Li | 87 | >50/1 | 13at-PhMe$_2$Si 93 |
| Ph | MgBr | 90 | 3/1 | not run |

*20% MeLi/20% CuI, 1.2 equiv. Me$_3$Al.

Addition of t-BuLi at −78° C. to 13at generates a bright orange solution which, after 15 minutes, is quenched with saturated NaHCO$_3$ providing a mixture of sulfone diastereomers 15a in high yield accompanied by less than 3% of the desired enone 14aMe by NMR (Scheme 5a). An attempt to hydrolyze diastereomeric vinyl ethers 15a to ketone 14aMe using 5% oxalic acid in 1:1 methanol/water was interrupted after 1 h at 25° C. TLC analysis incorrectly suggested that the reaction contained only the mixture of starting vinyl ethers 15a. It was later revealed that 15a, 14aMe, and 16a have the same Rf value on TLC in the assay system employed. During workup, 10% NaOH was added to the diluted reaction mixture, which was then extracted with CH$_2$Cl$_2$. NMR analysis showed that 15a had been completely hydrolyzed to 16a with about 40% conversion to enone 14aMe. Et$_3$N was added to a mixture of β-ketosulfones 16a and enone 14aMe in CH$_2$Cl$_2$. The ratio did not change. Heating the mixture to reflux in CH$_2$Cl$_2$, then in dichloroethane, and finally adding DBU did not positively affect the ratio and side products began to dominate the crude NMR. Since acidic conditions seemed to facilitate elimination, the process was repeated and the oxalic acid hydrolysis step was allowed to stir overnight. The ratio, as analyzed by NMR, was worse, 75% 16a and 25% 14aMe.

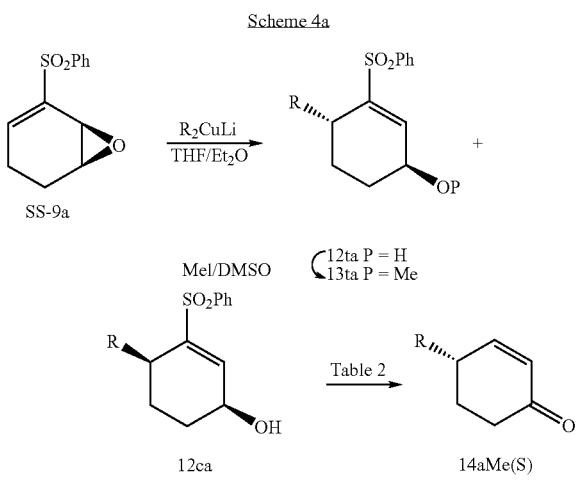

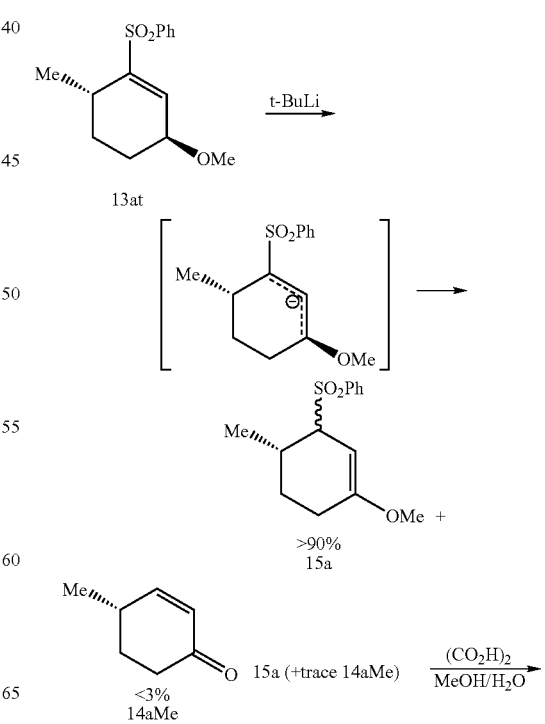

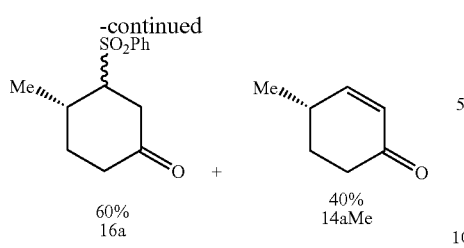

60% 16a + 40% 14aMe

Adding the crude 16a/14aMe mixture to THF/water containing 3% Et$_3$N and allowing the reaction to stir at 25° C. for 9 h was highly effective. The ratio of THF to water is critical. The substrate is dissolved in THF (approx. 0.09M), water is added until the reaction becomes slightly cloudy, then the minimum amount of THF is added to establish homogeneity. This process is ineffective without an aqueous wash of the initial reaction, because the lithium salt content does not allow the THF and water to be completely miscible.

Presumably, the basic aqueous conditions are more effective than in CH$_2$Cl$_2$ because of the greater polarity of the media. Furthermore, the literature reveals that elimination of sulfinate from γ ketosulfones is a reversible process, and that the equilibria lies far towards the side of the β-ketosulfone under acidic conditions.

With a convenient method for conversion of the isomerized allyl sulfone to the desired enone finally in hand, 4-methylcyclohex-2-en-1-one 14aMe was produced in 93% yield. It is significant that the sp$^3$ cuprate additions to SS-9a are about 100% anti throughout the series of methyl, ethyl, isopropyl, and t-butyl substituents as assayed by chiral HPLC of the resulting enones (14a) shown in Table 2a.

TABLE 2a

Cyclohexenones from γ-MeO-Vinyl Sulfones.

| R | % Yield | % ee† | % de |
|---|---|---|---|
| Me | 14aMe 93 | 93* | >99 |
| Et | 14aEt 93 | 93.7 | >99 |
| i-Pr | 14aPr 94 | 94.8§ | >99§ |
| t-Bu | 14atBu 89 | 91.2 | 98 |
| PhMe$_2$Si | NR | — | — |

†HPLC analysis;
*By rotation, HPLC inseparable;
§Enriched by crystallization.$^{ii}$ Epoxy vinylsulfone SS-9a can be obtained in excess of 99% ee, but in this experiment the ee of epoxide SS-9a was fixed at 93% by doping with racemic material, providing an unambiguous HPLC control. Except for 14Mea (chiral HPLC inseparable; 93% by rotation), all the ee values in Table 2a were determined by HPLC analysis. With the possible exception of the t-butyl experiment, the reactions in Table 2a are held to be 100% enantiospecific within the limits of experimental detection.

γ-methoxyallyl sulfone anions can be quenched with electrophiles. Extension of this method to the more highly functionalized materials prepared in this study reveals that alkylations of proximally substituted γ-methoxyallyl sulfone anions are strongly influenced by the steric demands of the electrophile (Scheme 6a). As can be seen in Table 3a, synthesis of 3-substituted-4-alkyl cyclohex-2-en-1-ones bearing a secondary substituent in the 4-position are reluctant to alkylate under 'standard' conditions, but can be successfully alkylated provided that HMPA is added to the γ-methoxyallyl sulfone anion during the alkylation phase. Still, these conditions cannot overcome the steric demands of the electrophile, with the 3,4-bisisopropyl adduct only being formed in 5-10% yield even using the HMPA protocol.

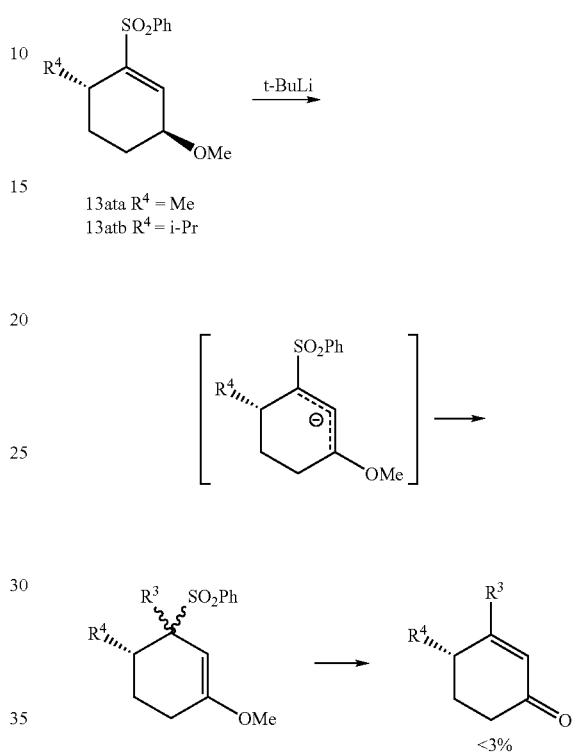

Scheme 6a

13ata R$^4$ = Me
13atb R$^4$ = i-Pr

15aa R$^3$ = R$^4$ = Me
15ab R$^3$ = allyl; R$^4$ = Me
15ad R$^3$ = Me; R$^4$ = i-Pr
15ae R$^3$ = allyl; R$^4$ = i-Pr
15af R$^3$ = i-Pr; R$^4$ = i-Pr
15ag R$^3$ = Bu; R$^4$ = i-Pr 14aa
14ab
14ac
14ad
14ae
14af
14ag

<3%

TABLE 3a

Enantiopure 3,4-Disubstituted Enones.

| R$^4$ | R$^3$ | % Yield | % ee or rotation |
|---|---|---|---|
| Me | Me* | 14a 92 | 106° |
| Me | Allyl* | 14b 96 | −153° |
| i-Pr | Me* | 14d 90 | 93% |
| i-Pr | Allyl* | 14e trace | — |
| i-Pr | i-Pr* | 14f no rxn | — |
| i-Pr | Bu* | 14g no rxn | — |
| i-Pr | Allyl$^\#$ | 14e 92 | −69° |
| i-Pr | i-Pr$^\#$ | 14f trace | — |
| i-Pr | Bu$^\#$ | 14g 84 | −12° |

*No HMPA added;
$^\#$HMPA added.

A complementary method for synthesis of 3-substituted-4-alkyl cyclohex-2-en-1-ones 14a involves reversing the role of nucleophile and electrophile. Oxidation of allylic alcohols t-12aa,ba to β-sulfonyl enones 17aa,ba using activated $MnO_2$ is high yielding. Michael addition of heterocuprates with subsequent β-elimination of sulfinate gives the desired 3,4-disubstituted enones 14a in fair yield (Table 4a, Scheme 7a). While cuprate reactions are well known for vinylogous thiolesters, this is apparently the first report with vinylogous acyl sulfones 17a (β-sulfonyl enones).

Scheme 7a

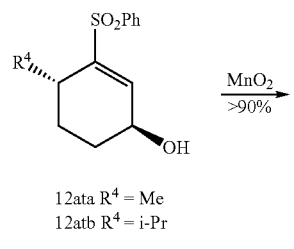

12ata R⁴ = Me
12atb R⁴ = i-Pr

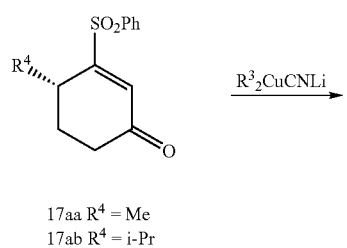

17aa R⁴ = Me
17ab R⁴ = i-Pr

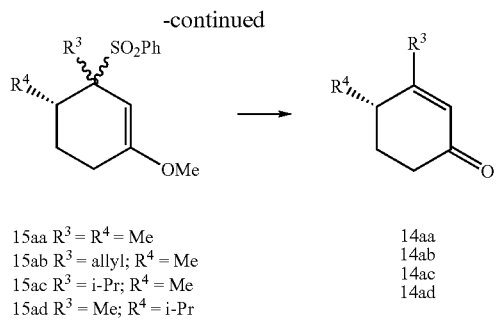

15aa R³ = R⁴ = Me
15ab R³ = allyl; R⁴ = Me
15ac R³ = i-Pr; R⁴ = Me
15ad R³ = Me; R⁴ = i-Pr 14aa
14ab
14ac
14ad TABLE 4a 3,4-Disubstituted Enones from 17a + Cuprates.

| | R⁴ | R³ | % Yield | % ee or rotation |
|---|---|---|---|---|
| 17aa | Me | Me | 14aa 92 | +106° |
| 17aa | Me | allyl | 14ba 96 | −153° |
| 17aa | Me | i-Pr | 14ca 45 | +119° |
| 17ba | i-Pr | Me | 14da 60 | 92% |

2-substituted 4-alkylcyclohexenones are also available by the addition of 2 equiv. of alkyl or aryl lithium followed by oxidation and elimination to the desired enone. Application of this process to t-12ba gives enone 19a in 90% yield (Scheme 8a). Extension of the strategy for synthesis of 2,3,4-trisubstituted enones was also examined beginning with alcohol t-12ba. In this instance, addition of the methyl lithium and subsequent capture of the anion with the methyl iodide produces 20a as a mixture of isomers. Oxidation of 20a followed by elimination furnishes trisubstituted enone 21a in excellent yield.

Scheme 8a

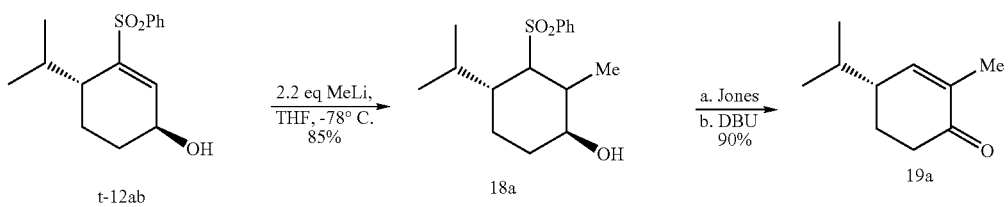

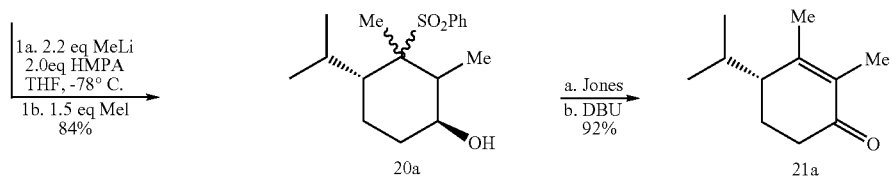

Enantiopure epoxyvinyl sulfone SS-9a also can serve as a synthon for differentiated cyclohexa-2,5-dienones. Treatment of SS-9a with one equivalent of LiHMDS followed by addition of methyl- or isopropyl-lithium proceeds via sequential γ-metalation/epoxide fragmentation followed by OM-directed conjugate-addition with quenching α to the sulfone moiety to generate 22a as shown in Table 5a and Scheme 9a. $Mo(CO)_3$ catalyzed directed epoxidation with tBu-OOH gives 23a; DBU treatment of 23a for the absolute minimal time (<1 h) cleanly effects β-elimination of the epoxide moiety. Methylation of the resulting γ-sulfonyl allyl alcohol may be done in the same operation to provide 24a in the yields indicated in Table 5a. Treatment of 24a with t-butyllithium affords an allylic anion which reacts with methyl iodide (HMPA essential) to give enantiopure enones 25a in greater than 92% yield.

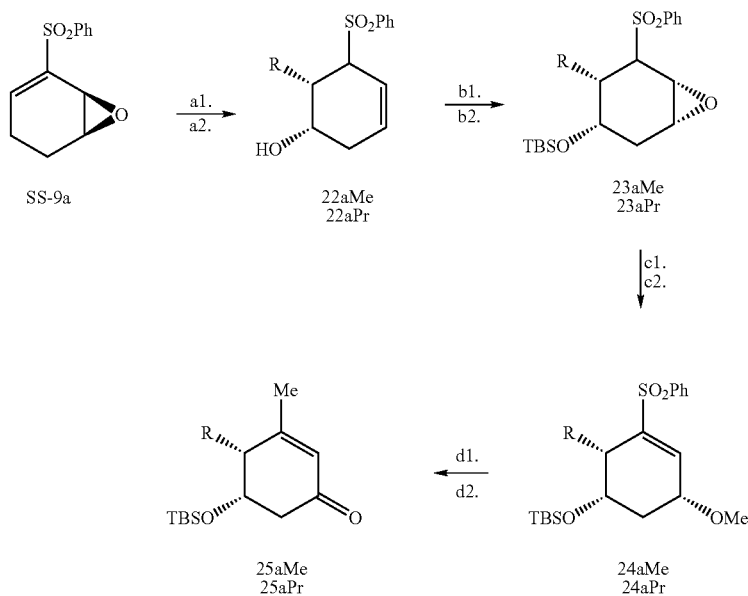

Scheme 9a

Me series, R = Me; Pr series, R = i-Pr a1. 1.1 eq LiHMDS, THF, -78° C.; a2. (4.0eq) MeLi or i-PrMgCl, THF, -78° C., 2h; b1. 2% $Mo(CO)_6$ 1.1eq TBHP, PhH, 80° C., 2h; b2. 1.2 eq TBSOTf, 1.5eq $Et_3N$, $CH_2Cl_2$, 0.5h, 25° C.; c1. 1.1 eq DBU, THF, reflux, 50 min; c2. 10 eq MeI, 10 KOH, DMSO, 25° C., 10 min.; d1. 2.0eq t-BuLi, 5.0eq HMPA, -78° C., 10 min then 5.0eq MeI; d2. $SiO_2$, $CHCl_3$, 3h 25° C.

TABLE 5a

Synthesis of enones 24.

| R = | Yield 21a | Yield 22a | Yield 23a | Yield 24a |
|---|---|---|---|---|
| Me | 90 | 96 | 87 | 93 |
| i-Pr | 94 | 98 | 99 | 92 |

Certain compounds of the invention were characterized and determined to have the structures or values presented in Tables 1-3.

TABLE 1

Compound Structures

| Compound structure | Number |
|---|---|
| (SO₂Ph cycloheptene with OTMS) | 13 |

TABLE 1-continued

Compound Structures

| Compound structure | Number |
|---|---|
| (SO₂Ph cycloheptene with HO and SPh) | 21 |

TABLE 1-continued

Compound Structures

| Compound structure | Number |
|---|---|
| (structure with SO₂Ph, TMSO, SPh) | 23 |
| (structure with SO₂Ph, TBSO, SPh) | 22 |
| (structure with PhS, OH) | 29 |
| (structure with PhS, OTBS) | 27 |
| (structure with PhS, HO) | 31 |
| (structure with PhO₂S, HO) | 32 |
| (structure with PhO₂S, TBSO) | 33 |
| (structure with PhS, N(Me)₂, HO) | 34 |
| (structure with PhO₂S, HO, =CH₂) | 35 |
| (structure with PhO₂S, epoxide, HO) | α36 |
| (structure with PhO₂S, epoxide, HO) | β36 |
| (structure with PhO₂S, epoxide, TBSO) | α37 |
| (structure with PhO₂S, epoxide, TBSO) | β37 |
| (structure with PhO₂S, OH, OH, HO) | 38 |
| (structure with PhO₂S, OH, OH, TBSO) | 39 |

TABLE 1-continued

Compound Structures

| Compound structure | Number |
|---|---|
| (structure) | 41 |
| (structure) | 42 |
| (structure) | 43 |
| (structure) | 46 |
| (structure) | 47 |
| (structure) | 48 |
| (structure) | 56 |

TABLE 1-continued

Compound Structures

| Compound structure | Number |
|---|---|
| (structure) | 57 |
| (structure) | 58α |
| (structure) | 58β |
| (structure) | 59 |
| (structure) | 60 |
| (structure) | 61 |
| (structure) | 62 |
| (structure) | 52 |

TABLE 1-continued

Compound Structures

| Compound structure | Number |
|---|---|
| (cycloheptene with PhO₂S, OMe, OTBS, TBSO, and two methyl substituents) | 53 |
| (acyclic chain with TBSO, OTBS, CHO, CO₂Me, OMe and methyl substituents) | 51 |

TABLE 2

NMR Data

| Number | $^1$H NMR | $^{13}$C NMR | LRMS | HRMS Calculated. Or EA | HRMS Found Or EA | MP (° C.) | $[a]_D°$ | Misc (x-ray, etc) |
|---|---|---|---|---|---|---|---|---|
| 13 | Y | Y | | | | 61.9-63.8 | | |
| 21 | Y | Y | Y | 375.1089 | 375.1088 | | | |
| 23 | Y | Y | Y | 446.1406 | 446.1390 | 114.5-116.5 | +29.4 | |
| 23 | Y | Y | Y | 446.1406 | 446.1398 | | −36.8 | |
| 22 | Y | Y | Y | 489.1953 | 489.1951 | | | |
| 29 | Y | Y | Y | 233.1000 | 233.0991 | | +200.5 | |
| 27 | Y | Y | Y | 347.1865 | 347.1861 | | | |
| 31 | Y | Y | | C: 73.13; H: 7.36 | C: 72.42; H: 7.22 | 81.5-83.5 | +407.8 | X-ray |
| 32 | Y | Y | | C: 64.72; H: 6.52 | C: 64.63; H: 6.47 | 100.0-101.5 | +272.3 | |
| 33 | Y | Y | Y | 392.1841 | 392.1840 | | +126.7 | |
| 34 | Y | Y | | | | | | |
| 35 | Y | Y | | | | | | unstable |
| α36 | Y | Y | | C: 61.20; H: 6.16 | C: 60.95; H: 6.07 | 137.0-139.0 | +59.3 | |
| β36 | Y | Y | | C: 61.20; H: 6.16 | C: 61.30; H: 6.06 | 118.0-119.5 | +89.4 | |
| α37 | Y | Y | | C: 61.72; H: 7.89 | C: 61.39; H: 7.59 | 89.0-90.0 | −30.5 | |
| β37 | Y | Y | Y | 408.1791 | 408.1782 | | +94.8 | |
| 38 | Y | Y | Y | 313.1110 | 313.1102 | 143-145 | −40.3 | |
| 39 | Y | Y | | C: 59.12; H: 8.03 | C: 59.07; H: 7.89 | 117.0-119.0 | −72.7 | |
| 41 | Y | Y | Y | — | — | | | |
| 42 | Y | Y | Y | 410.3036 | 410.3023 | | | |
| 43 | Y | Y | Y | 442.2935 | 442.2925 | | | |
| 46 | Y | Y | Y | 461.3119 | 461.3112 | | | |
| 47 | Y | Y | Y | 475.3275 | 475.3268 | | | |
| 48 | Y | Y | Y | 505.3381 | 505.3388 | | | |
| 56 | Y | Y | Y | 411.2025 | 411.2021 | | −3.2 | |
| 57 | Y | Y | | | | | | |
| 58α | Y | Y | | | | | +116.5 | |
| 58β | Y | Y | | | | | +14.3 | |
| 59 | Y | Y | Y | 411.2025 | 411.2025 | | −77.7 | |
| 60 | Y | Y | Y | 411.2025 | 411.2022 | | −32.9 | |
| 61 | Y | Y | | | | | | |
| 62 | Y | Y | Y | 331.1941 | 331.1931 | | | |
| 52 | Y | Y | Y | 541.2839 | 541.2834 | 81.0-83.0 | +38.8 | |
| 53 | Y | Y | Y | 555.2996 | 555.2998 | | −39.7 | |
| 51 | Y | Y | Y | 477.3068 | 477.3063 | | | |

TABLE 3

| Polametric Data or HPLC (% ee) | | | |
|---|---|---|---|
| Compound structure | Number in paper | Concentration g/100 mL | $[a]_D^o$ |
| (structure with SO₂Ph, TMSO, SPh) | 23 | 0.77 | +29.4 (CH₂Cl₂) |
| (structure with SO₂Ph, TMSO, SPh) | 23 | 0.93 | −36.8 (CH₂Cl₂) |
| (structure with PhS, OH) | 29 | 0.60 | +200.5 (CH₂Cl₂) |
| (structure with PhS, HO) | 31 | 0.55 | +407.8 (CH₂Cl₂) |
| (structure with PhO₂S, HO) | 32 | 0.51 | +272.3 (CH₂Cl₂) |
| (structure with PhO₂S, TBSO) | 33 | 0.80 | +126.7 (CH₂Cl₂) |
| (structure with PhO₂S, epoxide, HO) | α36 | 0.51 | +59.3 (CH₂Cl₂) |
| (structure with PhO₂S, epoxide, HO) | β36 | 0.60 | +89.4 (CH₂Cl₂) |

TABLE 3-continued

Polametric Data or HPLC (% ee)

| Compound structure | Number in paper | Concentration g/100 mL | $[a]_D^o$ |
|---|---|---|---|
| (PhO₂S, epoxide, TBSO, Me) | α37 | 0.61 | −30.5 (CH₂Cl₂) |
| (PhO₂S, epoxide, TBSO, Me) | β37 | 1.18 | +94.8 (CH₂Cl₂) |
| (PhO₂S, triol, HO) | 38 | 0.64 | −40.3 (CH₂Cl₂) |
| (PhO₂S, diol, TBSO) | 39 | 1.09 | −72.7 (CH₂Cl₂) |
| (PhO₂S, OH, TBSO) | 56 | 0.75 | −3.2 (CH₂Cl₂) |
| (MeO, pyran, CO₂Me, OTBS) | 58α | 0.40 | +116.5 (CH₂Cl₂) |
| (MeO, pyran, CO₂Me, OTBS) | 58β | 0.60 | +14.3 (CHCl₃) |

TABLE 3-continued

| Polametric Data or HPLC (% ee) | | | |
|---|---|---|---|
| Compound structure | Number in paper | Concentration g/100 mL | $[\alpha]_D^o$ |
| PhO$_2$S, cycloheptene with OH, TBSO, methyl substituents | 59 | 0.65 | −77.7 (CHCl$_3$) |
| PhO$_2$S, cycloheptene with OH, TBSO, methyl substituents | 60 | 0.75 | −32.9 ((CH$_2$Cl$_2$)) |
| PhO$_2$S, cycloheptene with OH, OH, TBSO, methyl substituents | 52 | 1.27 | +38.8 (CHCl$_3$) |
| PhO$_2$S, cycloheptene with OMe, OTBS, TBSO, methyl substituents | 53 | 0.65 | −39.7 (CHCl$_3$) |

The invention is described further in the following examples, which are illustrative and in no way limiting.

EXAMPLES

Experimental Procedures and Spectral Assignment

General Procedures

All purchased reagents were used as received. Tetrahydrofuran (THF) and diethyl ether (Et$_2$O) were distilled from sodium benzophenone ketyl. Benzene, toluene, dichloromethane (CH$_2$Cl$_2$), anhydrous methanol, dimethyl sulfoxide (DMSO), were distilled from calcium hydride. Acetonitrile (CH$_3$CN), chloroform (CHCl$_3$), and methanol were spectra-grade. n-BuLi and t-BuLi were titrated prior to use by dropwise addition to a solution of N-benzylbenzamide in THF at −78° C. to 0° C. Sodium sulfate (Na$_2$SO$_4$) and magnesium sulfate (MgSO$_4$) were used as received. Powdered 4 Å molecular sieves (Aldrich) were oven and/or flame activated under vacuum prior to use.

Glassware was oven dried and/or flame dried. All reactions were carried out under a positive pressure of argon in anhydrous solvents (unless otherwise indicated), and the reaction flasks were fitted with rubber septa for the introduction of substrates and reagents via syringe. Unless otherwise noted all reaction were worked up using standard conditions. Standard workup conditions are the addition of an equal volume of the stated organic solvent followed by two equal volumes of water or aqueous solution. All subsequent washes were preformed with volumes equal to the organic solution being washed. The progress of reactions was monitored by thin layer chromatography (TLC) in comparison with the starting material(s). TLC was performed on glass-backed silica gel 60 F 254 plates (EM reagents, 0.25 mm) and eluted with (v/v) Ethyl Acetate (EA) in hexanes (Hex) or the specified solvent solutions. The TLC plates were visualized with a UV lamp (254 nm) and/or with TLC visualizing solutions activated with heat. The two commonly employed TLC visualizing solutions were: (i) p-anisaldehyde solution (1350 mL absolute ethanol, 50 mL concentrated H$_2$SO$_4$, 15 mL glacial acetic acid, 37 mL p-anisaldehyde), and (ii) permanganate solution (weight percents of 1% KMnO$_4$ and 2% Na$_2$CO$_3$ in H$_2$O). All organic extracts were dried with MgSO$_4$ unless otherwise noted. Analytical samples were obtained from flash silica gel chromatography (SGC), using silica gel of 230-400 mesh, or from recrystalization of the crude products. Silica gel was washed with Et$_3$N and acetone to render it deactivated. Melting points were obtained on a MEL-TEMP capillary melting point apparatus and uncorrected. Optical rotations were taken on a Rudolph Research Autopol III instrument at 25° C. $^1$H-NMR spectra were recorded on Varian IONVA-300 (300 MHz) and Varian VXR (500 MHz) spectrometers. $^{13}$C-NMR spectra were recorded on Varian INOVA-300 (75 MHz) and Varian VXR (125 MHz) spectrometers. NMR spectra were determined in chloroform-d1 (CDCl$_3$) solution and are reported in parts per million (ppm) from the residual chloroform (7.26 ppm and 77.00 ppm). Peak multiplicities in $^1$H-NMR spectra, when reported, are abbreviated as s (singlet), d (doublet), t (triplet), m (multiplet), and b (broad). Mass spectra were run by the Purdue University campus wide mass spectrometry facility. The low resolution EI and CI (isobutane) spectra were obtained on a Finnigan 4000 mass spectrometer with a Nova 4 data system with the molecular ion designated as "M$^+$." The high resolution mass spectra were obtained on a Kratos MS-50 instrument.

General Procedure for the Addition of Mixed Alkyl Cuprates to Epoxyvinyl Sulfone To 530 mg (5.9 mmol) dry CuCN in 25 mL THF cooled to −78° C. was added 1.15 eq (4.86 mmol) of the desired alkyl lithium or Grignard reagent. The stirred mixture was allowed to warm to −20° C. for 15 min. The reaction temperature was returned to −78° C. and 1.0 g (4.23 mmol) epoxyvinyl sulfone in 10 mL THF was added via cannula. The reaction was then allowed to stir for 4-6 h without further cooling. When complete by TLC, the reaction was quenched with sat'd NH$_4$Cl and extracted with ether. The organic layer was then washed again with 5% HCl. After drying and removing the solvent in vacuo the resulting material can typically be used without purification and was 95% pure by NMR.

General Procedure for the Etherification of γ-Hydroxy Vinyl Sulfones

Crude γ-hydroxy vinyl sulfone (4.0 mmol), was dissolved and rapidly stirred in 30 mL anhydrous DMSO and cooled in a 25° C. water bath. 20-30 equiv. of MeI were added. Powdered KOH was added slowly, approximately 1 pellet every 3 min for a total of 5 pellets. When complete by TLC, the dark mixture was poured into ice water. The mixture was extracted with ether 3 times and the solvent removed in vacuo. SGC, 6:4 Hex/EA, provided the desired methyl ethers in nearly quant. yield.

General Procedure for the Conversion of γ-Methoxy Vinyl Sulfones to Enones 1.2 equiv. of t-BuLi (0.61 mmol) were added to the γ-methoxy vinyl sulfone (0.51 mmol) in 20 mL THF at −78° C. over 2 min. The resulting bright orange reaction was stirred at this temperature for 25 min. 10 mL sat'd solution of NaHCO$_3$ was added and the reaction allowed to warm to room temperature. The mixture was extracted into 40 mL ether and concentrated. 15 mL THF was added followed by water until the two solvents begin to separate. More THF was added just until the solution becomes homogeneous. 0.5 mL Et$_3$N was then added and the reaction was stirred for 15 h. Monitoring the reaction was best accomplished by NMR. When complete, ether and water was added and the organic layer separated and the solvent was removed in vacuo. SGC, 8:2 Hex/EA, provided the desired enones in good yield.

Example 1

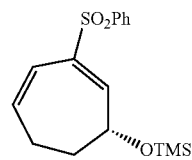

(1R)-(3-Benzenesulfonylcyclohepta-2,4-dienyloxy)-trimethylsilane (13): A solution of alcohol 4 (1.56 g, 6.23 mmol) and imidazole (0.85 g, 12.48 mmol) in methylene chloride (20 mL) was cooled to 0° C., and 0.87 mL (6.85 mmol) of TMSCl was added dropwise. The resulting suspension was stirred at 0° C. for 1 h. The mixture was then filtered through a short silica gel pad and washed with a mixture of ethyl acetate and hexanes (1:2). The filtrate was concentrated via rotary evaporation, and further dried under vacuum to give 13 (1.86 g, 93%) as a white solid. m.p=61.9-63.8° C.; $^1$H NMR (CDCl$_3$, 300 MHz) δ 7.85-7.88 (m, 2H), 7.50-7.63 (m, 3H), 7.16 (d, J=3.3 Hz, 1H), 6.03-6.14 (m, 2H), 4.48-4.53 (m, 1H), 2.26-2.32 (m, 2H), 1.90-2.08 (m, 2H), 0.17 (s, 9H); $^{13}$C NMR (CDCl$_3$, 75 MHz) δ 144.4, 139.6, 139.0, 136.8, 133.1, 129.0, 127.8, 118.8, 70.0, 35.3, 26.2, −0.04.

Example 2

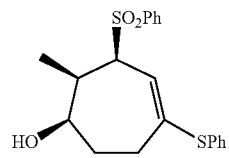

(1R, 2R, 3R)-3-Benzenesulfonyl-2-methyl-5-phenylsulfanylcyclohept-4-enol (21): To a solution of dienyl sulfone 4 (822 mg, 3.29 mmol) in THF (30 mL) at −78° C. was slowly added MeLi in Et$_2$O (1.4M, 5.9 mL, 8.22 mmol) over a period of 30 minutes using a syringe pump. The resulting orange solution was left stirring for 30 minutes to ensure complete reaction. After 30 minutes phenyl disulfide (1.8 g, 8.22 mmol) dissolved in THF (4 mL) was rapidly added via cannula. The temperature was allowed to rise to 25° C. and the reaction mixture was left stirring for 6 h. Saturated NH$_4$Cl (50 mL) was added to the mixture followed by Et$_2$O (100 mL). The aqueous phase was extracted with Et$_2$O (2×100 mL) and the combined organic extracts dried over MgSO$_4$ and concentrated. The product was purified via column chromatography using silica gel to give 835 mg of pure 21 in a 68% yield. Further product may be obtained by heating the higher Rf mixture, diastereomers at the sulfone carbon, at reflux (~435 mg) in CH$_2$Cl$_2$ (10 mL) with a catalytic amount of DBU (0.05 mL) for 24 h. The mixture was washed with 5% HCl (1×5 mL) and the organic layer is dried over Na$_2$SO$_4$ and concentrated. The product was purified via column chromatography using silica gel to give an additional 165 mg of 21, giving a combined yield of 81%. When the reaction was run on 12.1 g (48.4 mmol) the syringe pump was replaced by a pressure equalizing addition funnel, the final yield was 79% (14.2 g) after isomerization. $^1$HNMR (300 MHz, CDCl$_3$) δ 7.62-7.72 (m, 2H), 7.49-7.52 (m, 2H), 7.30-7.40 (m, 6H), 5.37 (d, J=6.0 Hz, 1H), 3.65-3.75 (m, 2H), 2.82-2.91 (m, 1H), 2.14-2.18 (m, 2H), 1.65-1.72 (m, 1H), 1.45-1.60 (m, 1H), 1.00 (d, J=6.85 Hz, 3H). $^{13}$CNMR (75 MHz, CDCl$_3$) δ 141.7, 138.5, 134.0, 133.7, 131.5, 129.4, 129.2, 128.7, 128.5, 115.8, 76.4, 65.8, 35.2, 29.8, 27.8, 7.8. LRMS (EI) m/z: 374 (M$^+$); HRMS (CI) calculated for, C$_{20}$H$_{22}$O$_3$S$_2$, 375.1089; found 375.1088.

Example 3

(1R, 2R)-(3-Benzenesulfonyl-2-methyl-5-phenylsulfanyl-cyclohept-4-enyloxy)-trimethylsilane (23): A solution of dienyl sulfone 13 (1.70 g, 5.27 mmol) in THF (60 mL) was cooled to −78° C., and 4.2 mL (5.88 mmol) of MeLi (1.4M in diethyl ether) was added dropwise over 30 min via syringe pump. The resulting orange solution was stirred at −78° C. for 15 min followed by addition of a solution of PhSSPh (1.80 g, 8.24 mmol) and THF (10 mL). The resulting mixture was slowly warmed up to room temperature over 6 h, and quenched with H$_2$O and diluted with EtOAc (30 mL). The layers were separated, and the aqueous phase was extracted with EtOAc (2×30 mL). The combined organic layers were washed with brine, then dried (Na$_2$SO$_4$) and concentrated via rotary evaporation. Column chromatography (EtOAc-hexane; 1:7) of the crude residue afforded 2.15 g (91%) of 23 as a 1:1 diastereomeric mixture. The two diastereomers can be separated by flash column chromatography (EtOAc-hexane; 1:10) for characterization, but were used as a mixture for the next reaction. Characterization data of two isomers:

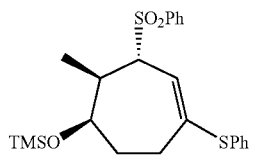

23 α white solid, mp 114.5-116.5° C.; [α]$^{20}_D$=+29.4° (c=0.77, CH$_2$Cl$_2$); $^1$H NMR (CDCl$_3$, 300 MHz) δ 7.34-7.78 (m, 10H), 5.51 (d, J=6.0 Hz, 1H), 3.69 (d, J=6.0 Hz, 1H), 3.58 (m, 1H), 2.64 (m, 1H), 2.08-2.22 (m, 2H), 1.54 (m, 2H), 0.98 (d, J=6.9 Hz, 3H), 0.063 (s, 9H); $^{13}$C NMR (CDCl$_3$, 75 MHz) δ 141.5, 138.9, 134.1, 133.9, 132.0, 129.7, 129.4, 128.9, 116.6, 77.3, 66.2, 36.1, 30.3, 29.0, 7.9, 0.26; LRMS (CI): m/z 447 [M+H]$^+$; HRMS (CI) calculated for C$_{23}$H$_{30}$O$_3$S$_2$Si, 446.1406; found, 446.1390.

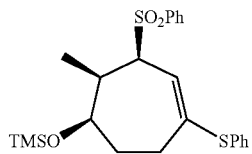

23 β light yellow oil; [α]$^{20}_D$=−36.8° (c=0.93, CH$_2$Cl$_2$); $^1$H NMR (CDCl$_3$, 300 MHz) δ 7.29-7.86 (m, 10H), 4.83 (d, J=8.7 Hz, 1H), 4.61 (dt, J=10.8, 3.9 Hz, 1H), 3.64 (dd, J=8.7, 3.9 Hz, 1H), 2.94-3.04 (m, 2H), 2.17-2.25 (m, 1H), 1.63-1.83 (m 2H), 1.05 (d, J=7.2 Hz, 3H), 0.22 (s, 9H); $^{13}$C NMR (CDCl$_3$, 75 MHz) δ 148.2, 140.1, 133.9, 133.6, 132.4, 129.5, 129.3, 128.7, 113.6, 72.0, 69.3, 36.1, 30.4, 29.6, 12.6, 0.41; LRMS (CI): m/z 447 [M+H]$^+$; HRMS (CI) calculated for C$_{23}$H$_{30}$O$_3$S$_2$Si, 446.1406; found, 446.1398.

Example 4

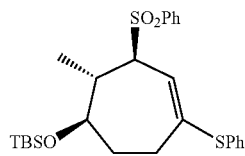

(1R, 2S)-3-Benzenesulfonyl-2-methyl-5-phenylsulfanylcyclohept-4-enyloxy)-tert-butyldimethylsilane (22): A solution of dienyl sulfone 5 (437 mg, 1.20 mmol) in THF (15 mL) was cooled to −78° C., and MeLi (1.4 M in diethyl ether, 2.21 mL, 3.08 mmol) was slowly added. The resulting orange solution was stirred at −78° C. for 30 min followed by addition (via cannula) of a solution of (PhS)$_2$ (537 mg, 2.46 mmol) in THF (5 mL). The resulting mixture was slowly warmed up to room temperature over 12 h, then quenched with H$_2$O and diluted with EtOAc (30 mL). The layers were separated, and the aqueous phase was extracted with EtOAc (2×30 mL). The combined organic layers were washed with brine, then dried (Na$_2$SO$_4$) and concentrated. Flash column chromatography (EtOAc-hexanes; 1:10) of the crude residue afforded 453 mg (77%) of a 2:1 diastereomeric mixture at the sulfone position, of 22 as a yellow oil. $^1$H NMR (CDCl$_3$, 300 MHz) δ 7.29-7.73 (m, 10H), 5.36 (m, 1H), 4.55 (d, J=6.1 Hz, 1H), 3.84 (br t, J=7.8 Hz, 1H), 2.48-2.86 (m, 2H), 1.67-1.78 (m, 2H), 1.43 (m, 1H), 1.06 (d, J=7.0 Hz, 3H), 0.87 (s, 9H), −0.013 (s, 6H); $^{13}$C NMR (CDCl$_3$, 75 MHz) δ 133.7, 133.4, 129.3, 129.1, 128.5, 117.4, 117.3, 73.1, 62.8, 36.1, 27.4, 26.4, 25.8, 17.9, 12.6, −5.00, −5.04.; LRMS(CD): m/z 489 [M+H]$^+$, 143 m/z [Base]; HRMS(CI) calculated for C$_{26}$H$_{36}$O$_3$S$_2$Si 489.1953; found 489.1951.

Example 5

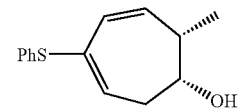

(1R, 2S)-2-Methyl-5-phenylsulfanylcyclohepta-3,5-dienol (29): 22 or 23 (2.15 g, 4.81 mmol) was dissolved in dry methylene chloride (20 mL), and 4.0 mL of Et$_3$N (28.7 mmol) was added at room temperature, followed by addition of 3.0 mL (16.6 mmol) of TMSOTf. This mixture was brought to reflux under N$_2$, and stirred for 8 h until the starting material was consumed (monitored by TLC using 30% ethyl acetate in hexanes). The reaction mixture was cooled to 0° C., and the excess TMSOTf was quenched by adding MeOH (1.0 mL, 24.7 mmol), diluted with EtOAc (20 mL), separated, and the aqueous layer was extracted with EtOAc (2×20 mL). The combined organic layers were concentrated via rotary evaporation, dissolved in a mixture of THF (30 mL) and H$_2$O (10 mL). 10 mL of AcOH were added to the mixture and left stirring at room temperature for 3 h. It was then transferred to a 1 L beaker and saturated aqueous NaHCO$_3$ was carefully added until the solution became slightly basic, copious CO$_2$ evolved during this process. The organic layer was separated, and the aqueous layer was extracted with EtOAc (3×50 mL). The combined organic layers were washed by saturated NaHCO$_3$, followed by brine, and dried over Na$_2$SO$_4$. Flash column chromatography (EtOAc-hexane; 1:4) afforded 0.97 g (86%) of 29 as an oil. Care must be taken during purification that the mixture not be exposed to silica for extended time since this will cause some decomposition. The product slowly decomposes at 25° C., but stores well at −10° C. $[\alpha]^{20}_D$=+ 200.5 (c=0.55, CH$_2$Cl$_2$); $^1$H NMR (CDCl$_3$, 300 MHz) δ 7.20-7.33 (m, 5H), 6.27 (t, J=5.4 Hz, 1H), 5.92 (d, J=11.4 Hz, 1H), 5.69 (dd, J=4.8, 11.4 Hz, 1H), 4.17 (br s, 1H), 2.59-2.68 (m, 2H), 2.42-2.52 (m, 1H), 1.97 (br s, 1H), 1.22 (d, J=7.2 Hz, 3H); $^3$C NMR (CDCl$_3$, 75 MHz) δ 137.2, 136.1, 133.9, 131.5, 129.9, 129.5, 129.2, 126.7, 76.4, 40.8, 38.3, 16.7; LRMS (CI): m/z 233 [M+H]$^+$; HRMS (CI) calculated for C$_{14}$H$_{17}$OS, 233.1000; found, 233.0991.

Example 6

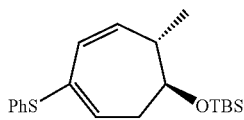

(1R,2R)-tert-Butyldimethyl-(2-methyl-5-phenylsulfanylcyclohepta-3,5-dienyloxy)-silane (27): To vinyl sulfide 22 (400 mg, 0.819 mmol) in CH$_2$Cl$_2$ (10 mL) was added Et$_3$N (0.67 mL, 4.92 mmol) followed by TMSOTf (0.74 mL, 4.10 mmol). The stirred mixture was heated to reflux for 8 h at which point all starting material has been consumed. The solution was allowed to cool to 25° C. and isopropyl alcohol was added (3 mL). The reaction was then concentrated the residue was purified by filtering through a 1 inch silica plug, eluting with 30% ethyl acetate in hexanes and collecting in separate fractions giving 269 mg of sulfide 27 (5:1 mixture) in 95% yield. Care must be taken during purification that the mixture not be exposed to silica for extended time since this will cause some decomposition. The product slowly decomposes at 25° C., but stores well at −10° C. $^1$H NMR (CDCl$_3$, 300 MHz) δ 7.15-7.27 (m, 5H), 6.38 (t, J=6.4 Hz, 1H), 5.73 (m, 2H), 3.85 (dt, J=4.6 Hz, 8.1 Hz, 1H), 2.37 (m, 3H), 1.10 (d, J=7.0 Hz), 0.91 (s, 9H), 0.083 (s, 3H), 0.071(s, 3H); $^{13}$C NMR (CDCl$_3$, 75 MHz) δ 138.7, 138.6, 136.4, 135.2, 132.1, 129.3, 129.2, 128.8, 128.6, 126.0, 81.1, 43.7, 38.0, 25.8, 18.8, 18.0, −4.4, −4.7. LRMS (CI): m/z 347 [M+H]$^+$; HRMS (CI) calculated for C$_{20}$H$_{30}$OSSi, 346.1865; found, 346.1861.

Example 7

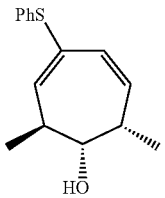

(1S, 2S, 7S)-2,7-Dimethyl-4-phenylsulfanylcyclohepta-3,5-dienol (31): A solution of alcohol 29 (887 mg, 3.82 mmol) in THF (50 mL) was cooled to −78° C., and 3.20 mL of n-BuLi (2.5 M in hexanes, 8.00 mmol) was added dropwise. The mixture was slowly brought to −7° C. over 1 h, and stirred at this temperature for 10 min. It was then cooled to −100° C. in a THF-liquid N$_2$ bath. To this cold dark orange solution was slowly added a solution of MeI (0.72 mL, 11.56 mmol) in THF (5 mL) over 30 min via syringe pump. The resulting light yellow solution was warmed to −60° C. prior to quenching with saturated aqueous NH$_4$Cl. After warming to room temperature, the two layers were separated, and the aqueous layer was extracted with EtOAc (3×30 mL). The combined organic layers were washed with brine, and dried over Na$_2$SO$_4$. Flash column chromatography (EtOAc/hexanes; 1:4) afforded 660 mg (70% yield) of 31 as a white solid. mp 81.5-83.5° C.; $[\alpha]^{20}_D$=+407.8 (c=0.55CH$_2$Cl$_2$); $^1$H NMR (CDCl$_3$, 300 MHz) δ 7.20-7.35 (m, 5H), 6.27 (d, J=5.4 Hz, 1H), 5.98 (br d, J=10.8 Hz, 1H), 5.75 (dd, J=4.5 Hz, 10.8 Hz), 3.79 (dd, J=2.7 Hz, 6.0 Hz, 1H), 2.55 (m, 1H), 2.45 (m, 1H), 1.65 (br s, 1H), 1.25 (d, J=7.5 Hz, 3H), 1.20 (d, J=6.9 Hz, 3H); $^{13}$C NMR (CDCl$_3$, 75 MHz) δ 140.9, 138.7, 136.1, 130.5, 130.2, 129.9, 129.2, 126.7, 84.7, 43.5, 38.1, 19.4, 17.6; Analytical. Calculated for C$_{15}$H$_{18}$OS: C, 73.13; H, 7.36. Found: C, 72.42; H, 7.22.

Example 8

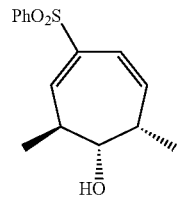

(1S, 2S, 7S)-4-Benzenesulfonyl-2,7-dimethylcyclohepta-3,5-dienol (32): A solution of dienyl sulfide 31 (600 mg, 2.43 mmol) in CH$_2$Cl$_2$ (25 mL) was cooled to 0° C., and 1.3 g of m-CPBA (5.34 mmol based on 70% content) was added in 2 portions. The mixture was stirred at 0° C. for 1 h, and at room temperature for 10 min. The excess m-CPBA was quenched with aqueous NaHSO$_3$. The resulting two layers were separated, and the aqueous phase was extracted with CH$_2$Cl$_2$ (3×20 mL). The combined organic extracts were washed with saturated aqueous Na$_2$CO$_3$, dried over Na$_2$SO$_4$ and concentrated. The residue was purified by flash column chromatography (EtOAc/hexanes; 50:50) to afford 630 mg (93%) of sulfone 32 as a white solid. mp 100.0-101.5° C.; $[\alpha]^{20}_D$=+ 272.3 (c=0.51, CH$_2$Cl$_2$); $^1$H NMR (CDCl$_3$, 300 MHz) δ 7.76-7.90 (m, 2H), 7.53-7.70 (m, 3H), 7.19 (d, J=5.4 Hz, 1H), 6.23 (br d, J=11.4 Hz, 1H), 5.86 (dd, J=4.5 Hz, 11.4 Hz, 1H) 3.73 (d, J=5.4 Hz, 1H), 2.70 (m, 1H), 2.38 (m, 1H), 1.56 (br s, 1H)1.24 (d, J=7.2 Hz, 3H), 1.19 (d, J=7.5 Hz, 3H); $^{13}$C NMR (CDCl$_3$, 75 MHz) δ 144.1, 141.8, 140.0, 138.5, 133.6, 129.5, 127.9, 120.2, 81.7, 42.2, 38.1, 19.0, 16.9; Analytical. Calculated for $C_{15}H_{18}O_3S$: C, 64.72; H, 6.52. Found: C, 64.63; H, 6.47.

Example 9

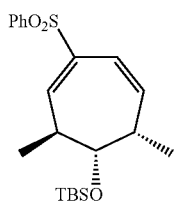

(1S, 2S, 7S)-(4-Benzenesulfonyl-2,7-dimethylcyclohepta-3,5-dienyloxy)-tert-butyldimethylsilane (33): A solution of alcohol 32 (550 mg, 1.98 mmol) and 2,6-lutidine (0.34 mL, 2.97 mmol) in $CH_2Cl_2$ (20 mL) was cooled to −78° C., and 0.55 mL (2.39 mmol) of TBSOTf was added. The cold solution was stirred and allowed to warm to 0° C. over a 1 h. MeOH (40 μL, 1 mmol) was then added and the resulting mixture was concentrated via rotary evaporation. The crude residue was purified with flash column chromatography (EtOAc/hexanes; 1:5) to afford 760 mg (98%) of 33 as colorless oil. $[\alpha]^{20}_D$=+126.7 (c=0.80, $CH_2Cl_2$); $^1H$ NMR ($CDCl_3$, 300 MHz) δ 7.86-7.90 (m, 2H), 7.50-7.64 (m, 3H), 7.09 (d, J=5.4 Hz, 1H), 6.06 (dt, J=11.7 Hz, 1.5 Hz, 1H), 5.80 (dd, J=11.7 Hz, 5.1 Hz, 1H), 3.66 (dd, J=6.3 Hz, 2.1 Hz, 1H), 2.70 (m, 1H), 2.47 (m, 1H), 1.18 (d, J=7.2 Hz, 3H), 1.06 (d, J=7.2 Hz, 3H), 0.81 (s, 9H), 0.038 (s, 3H), 0.032 (s, 3H); $^{13}C$ NMR ($CDCl_3$, 75 MHz) δ 142.8, 140.4, 140.2, 137.8, 133.2, 129.3, 128.0, 118.4, 76.8, 41.4, 38.8, 26.0, 19.1, 18.2, 16.7, −4.1, −4.4; LRMS (CI): m/z 393 [M+H]$^+$; HRMS (CI) calculated for $C_{21}H_{32}O_3SSi$, 392.1841; found, 392.1840.

Example 10

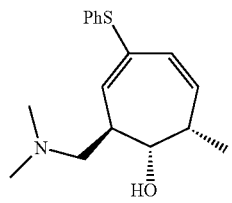

(1S, 2R, 7S)-2-Dimethylaminomethyl-7-methyl-4 phenylsulfanylcyclohepta-3,5-dienol (34): A solution of alcohol 29 (80 mg, 0.34 mmol) in THF (4 mL) was cooled to −78° C., and 0.30 mL of n-BuLi (2.5M in hexanes, 0.75 mmol) was added dropwise via syringe. This mixture was brought to −7° C. over 1 h, and stirred at −7° C. for 10 min, then cooled to −78° C., and transferred to a flask containing N,N-dimethylmethyleneammonium iodide (Eschenmoser's salt, 160 mg, 0.86 mmol) in THF (4 mL) via cannula. The resulting suspension was warmed to room temperature over 2 h, then saturated aqueous $NaHCO_3$ (5 mL) was added, the organic layer was separated, and the aqueous layer was extracted with EtOAc (3×5 mL). The combined organic layers were washed with brine, and dried ($Na_2SO_4$). Flash column chromatography ($CH_2Cl_2$/MeOH; 10:1) afforded 58 mg (58% yield) of 34 as a light yellow oil. $^1H$ NMR ($CDCl_3$, 300 MHz) δ 7.20-7.38 (m, 5H), 6.11 (dd, J=10.5 Hz, 6.3 Hz, 1H), 5.89-5.96 (m, 2H), 4.20 (dd, J=8.4 Hz, 4.2 Hz, 1H), 2.79 (t, J=12.6 Hz, 1H), 2.45-2.55 (m, 3H), 2.31 (s, 6H), 2.24-2.28 (m, 1H), 1.19 (d, J=7.2 Hz, 3H); $^{13}C$ NMR ($CDCl_3$, 75 MHz) δ 142.0, 135.6, 134.5, 133.7, 130.3, 129.5, 129.1, 126.9, 89.3, 64.9, 45.9, 43.5, 39.4, 23.9, 14.6.

Example 11

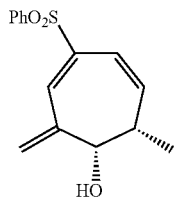

(1S, 7S)-4-Benzenesulfonyl-7-methyl-2-methylenecyclohepta-3,5-dienol (35): To a solution of amine 34 (42 mg, 0.14 mmol) in $CH_2Cl_2$ (2 mL) was added 140 mg of m-CPBA (0.57 mmol based on 70% content). The mixture was stirred at room temperature for 30 min, then aqueous $NaHSO_3$ was added, the resulting two layers were separated, and the aqueous phase was extracted with $CH_2Cl_2$ (3×3 mL). The combined organic layers were washed with saturated aqueous $Na_2CO_3$, dried with $Na_2SO_4$, and concentrated. The residue was purified by flash column chromatography (EtOAc/hexanes; 1:2) to afford 36 mg (91%) of trienyl sulfone 35. $^1H$ NMR ($CDCl_3$, 300 MHz) δ 7.88-7.92 (m, 2H), 7.54-7.67 (m, 3H), 7.51 (s, 1H), 6.24 (dt, J=11.4 Hz, 1.2 Hz, 1H), 5.90 (dd, J=11.4 Hz, 5.4 Hz, 1H), 5.78 (s, 1H), 5.72 (s, 1H), 4.36 (s, 1H), 2.64 (m, 1H), 1.81 (br s, 1H), 1.11 (d, J=7.5 Hz, 3H); $^{13}C$ NMR ($CDCl_3$, 75 MHz) δ 145.6, 140.2, 139.3, 137.0, 136.1, 133.6, 129.5, 128.1, 128.0, 120.2, 75.1, 39.3, 16.4.

Example 12

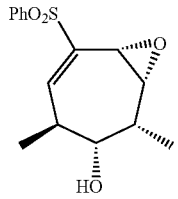

(1R, 2R, 3R, 4S, 7R)-6-Benzenesulfonyl-2,4-dimethyl-8-oxabicyclo[5.1.0]oct-5-en-3-ol (α36): A suspension of dienyl sulfone 32 (67 mg, 0.24 mmol), molybdenum hexacarbonyl (3 mg, 0.01 mmol), and tert-butylhydroperoxide (74 μL of 5M solution in decane) in benzene (3 mL) was heated at 80° C. for 10 h. The reaction mixture was concentrated via rotary evaporation, purified by flash column chromatography (ethyl acetate/hexanes; 50:50) to afford 62 mg (88% yield) of epoxide α36 as a light yellow solid. mp 137.0-139.0° C.; $[\alpha]^{20}_D$=+59.3 (c=0.51, $CH_2Cl_2$); $^1H$ NMR ($CDCl_3$, 300 MHz) δ 7.93-7.96 (m, 2H), 7.58-7.70 (m, 3H), 7.39 (d, J=7.2 Hz, 1H), 3.90 (dd, J=4.5 Hz, 1.5 Hz, 1H), 3.64 (br s, 1H), 3.42 (m, 1H), 3.05-3.15 (m, 2H), 2.55 (tq, J=2.1 Hz, 7.2 Hz, 1H), 1.39 (d J=7.2 Hz, 3H), 1.18 (d, J=7.5 Hz, 3H); $^{13}C$ NMR ($CDCl_3$, 75 MHz) δ 147.9, 139.7, 136.5, 133.9, 129.7, 128.2, 78.3, 65.5, 52.5, 41.5, 32.2, 17.4, 17.2; Analytical. Calculated for $C_{15}H_{18}O_4S$: C, 61.20; H, 6.16. Found: C, 60.95; H, 6.07.

Example 13

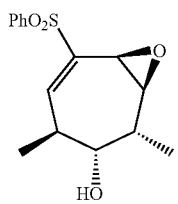

(1S, 2R, 3R, 4S, 7S)-6-Benzenesulfonyl-2,4-dimethyl-8oxabicyclo[5.1.0]oct-5-en-3-ol (β36): To a mixture of dienyl sulfone 31 (126 mg, 0.453 mmol), (R,R)-(−)-N,N'-Bis(3,5-di-tert-butylsalicylidene)-1,2-cyclohexanediamino-manganese(III) chloride (29 mg, 0.0456 mmol) and ammonium acetate (90 mg, 1.17 mmol) in methylene chloride (2.0 mL) and methanol (2.0 mL) at 0° C. was added 0.5 mL of 30% $H_2O_2$ in portions and is stirred using a mechanical stirrer (550 rpm). After stirring at 0° C. for 17 h, aqueous $NaHSO_3$ was added, and the mixture was extracted with methylene chloride (3×10 mL). The combined organic layers were washed with brine, dried over $Na_2SO_4$, concentrated via rotary evaporation, and purified via flash column chromatography (ethyl acetate/hexanes; 1:2) to afford 110 mg (83%) of β36 as a white solid. mp 118.0-119.5° C.; $[\alpha]^{20}_D$=+89.4 (c=0.60, $CH_2Cl_2$); $^1H$ NMR ($CDCl_3$, 300 MHz) δ 7.94-7.97 (m, 2H), 7.56-7.70 (m, 3H), 6.94 (d, J=4.8 Hz, 1H), 3.74 (d, J=4.2 Hz, 1H), 3.57 (m, 1H), 3.13 (dd, J=6.6 Hz, 4.2 Hz, 1H), 2.75 (m, 1H), 1.80 (m, 1H), 1.31 (d, J=7.2 Hz, 3H), 1.17 (d, J=6.9 Hz, 3H); $^{13}C$ NMR ($CDCl_3$, 75 MHz) δ 146.2, 139.9, 138.2, 133.9, 129.5, 128.4, 75.3, 58.5, 49.7, 40.2, 38.6, 18.7, 14.3; Analytical. Calculated for $C_{15}H_{18}O_4S$: C, 61.20; H, 6.16. Found: C, 61.30; H, 6.06.

Example 14

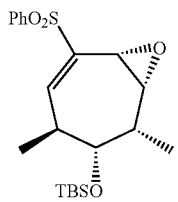

(1R, 2S, 3R, 4S, 7R)-(6-Benzenesulfonyl-2,4-dimethyl-8-oxabicyclo[5.1.0]oct-5-en-3-yloxy)-tert-butyldimethylsilane (α37): A mixture of alcohol α36 (62 mg, 0.21 mmol) and 2,6-lutidine (50 μL, 0.43 mmol) in $CH_2Cl_2$ (2 mL) was cooled to −78° C., and 63 μL (0.27 mmol) of TBSOTf was added. The stirred cold solution was warmed to 0° C. over 5 h. MeOH (40 μL, 1 mmol) was then added to quench the excess TBSOTf. The resulting mixture was concentrated via rotary evaporation, and the crude residue was purified by flash column chromatography (EtOAc/hexanes; 1:5) to afford 82 mg (95%) of α37 as a white solid. mp 89.0-90.0° C.; $[\alpha]^{20}_D$=−30.5 (c=0.61, $CH_2Cl_2$); $^1H$ NMR ($CDCl_3$, 300 MHz) δ 7.93-7.97 (m, 2H), 7.55-7.70 (m, 3H), 7.09 (d, J=5.1 Hz, 1H), 3.70 (dd, J=8.4 Hz, 2.1 Hz, 1H), 3.67 (d, J=4.8 Hz, 1H), 3.37 (dd, J=7.2 Hz, 4.2 Hz, 1H), 2.60 (m, 1H), 2.49 (m, 1H), 1.26 (d, J=7.2 Hz, 3H), 0.90 (s, 9H), 0.74 (d, J=7.2 Hz, 3H), 0.10 (s, 3H), 0.09 (s, 3H); $^{13}C$ NMR ($CDCl_3$, 75 MHz) δ 146.0, 140.2, 136.1, 133.7, 129.3, 128.4, 74.5, 56.8, 48.7, 40.9, 36.9, 25.9, 18.4, 18.1, 9.7, −4.3, −4.4; Analytical. Calculated for $C_{21}H_{32}O_4S$: C, 61.72; H, 7.89. Found: C, 61.39; H, 7.59.

Example 15

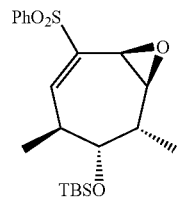

(1S, 2S, 3R, 4S, 7S)-(6-Benzenesulfonyl-2,4-dimethyl-8-oxabicyclo[5.1.0]oct-5-en-3-yloxy)-tert-butyldimethylsilane (β37): Procedure same as for preparation of β36, (R,R)-Jacobsen catalyst and diene 33 were used. A single diastereomer β37 was isolated as light yellow oil in 80% yield. $[\alpha]^{20}_D$=+94.8 (c=1.18, $CH_2Cl_2$); $^1H$ NMR ($CDCl_3$, 300 MHz) δ 7.89-7.93 (m, 2H), 7.50-7.65 (m, 3H), 6.97 (d, J=3.9 Hz, 1H), 3.66 (d, J=4.2 Hz, 1H), 3.57 (dd, J=5.4 Hz, 1.5 Hz, 1H), 3.02 (pseudo t, J=4.5 Hz, 1H), 2.66 (m, 1H), 1.98 (m, 1H), 1.14 (d, J=7.2 Hz, 3H), 1.12 (d, J=7.2 Hz, 3H), 0.86 (s, 9H), 0.063 (s, 3H), 0.045 (s, 3H); $^{13}C$ NMR ($CDCl_3$, 75 MHz) δ 145.0, 140.1, 137.2, 133.7, 129.4, 128.3, 76.0, 60.1, 49.4, 41.7, 37.3, 26.0, 18.5, 18.2, 16.0, −4.2, −4.3; LRMS (CI): m/z 409 [M+H]$^+$; HRMS (CI) calculated for $C_{21}H_{32}O_4SSi$, 408.1791; found, 408.1782.

Example 16

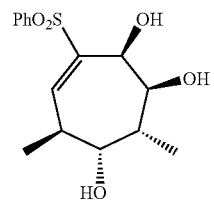

(1S, 2S, 3R, 4R, 5S)-7-Benzenesulfonyl-3,5-dimethylcyclohept-6-ene-1,2,4-triol (38): A mixture of dienyl sulfone 32 (300 mg, 1.08 mmol), $OsO_4$ (14 mg, 0.054 mmol), 4-methylmorpholine N-oxide (250 mg, 2.14 mmol) in acetone (3 mL) and $H_2O$ (3 mL) was stirred at room temperature for 36 h, then saturated aqueous $Na_2S_2O_3$ (5 mL) was added, and stirred for 30 min. The reaction mixture was diluted with ethyl acetate (10 mL) and separated, the aqueous layer was extracted with ethyl acetate (5×10 mL). The combined organic layers were dried over $Na_2SO_4$ and concentrated. The residue was purified with flash column chromatography (ethyl acetate/hexanes; 2:1) to afford 285 mg (85%) of triol 38 as a colorless solid. mp 143.0-145.0° C.; $[\alpha]^{20}_D$=−40.3 (c=0.64, $CH_2Cl_2$); $^1H$ NMR ($CDCl_3$, 300 MHz) δ 7.88-7.91 (m, 2H), 7.56-7.68 (m, 3H), 7.29 (d, J=7.2 Hz, 1H), 4.61 (br s, 1H), 3.89 (dd, J=5.7, 2.1 Hz, 1H), 3.48 (br d, J=7.5 Hz, 1H), 2.85 (m, 2H), 2.34 (m, 1H), 2.12 (br s, 1H), 1.68 (br s, 1H), 1.32 (d, J=7.5 Hz, 3H), 1.19 (d, J=6.9 Hz, 3H); $^{13}C$ NMR (CDCl$_3$, 75 MHz) δ 148.7, 140.5, 139.3, 133.8, 129.6, 128.1, 75.5, 72.9, 69.9, 38.9, 37.7, 17.7, 15.5; LRMS (CI): m/z 313 [M+H]$^+$; HRMS (CI) calculated for C$_{15}$H$_{21}$O$_5$S, 313.1110; found, 313.1102.

Example 17

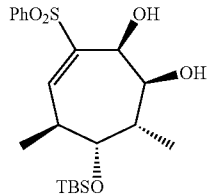

(1S, 2S, 5S, 6R, 7S)-3-Benzenesulfonyl-6-(tert-butyldimethylsilanyloxy)-5,7-dimethylcyclohept-3-ene-1,2-diol (39): A mixture of dienyl sulfone 33 (45 mg, 0.11 mmol), OsO$_4$ (2 mg, 0.0078 mmol), 4-methylmorpholine N-oxide (27 mg, 0.23 mmol) in acetone (0.5 mL) and H$_2$O (0.5 mL) as co-solvent was stirred at room temperature for 36 h, then saturated aqueous Na$_2$S$_2$O$_3$ (5 mL) was added, and stirred for 30 min. The reaction mixture was diluted with ethyl acetate (10 mL), separated, and the aqueous layer was extracted with ethyl acetate (3×5 mL). The combined organic layers were dried over Na$_2$SO$_4$ and concentrated. The residue was purified by flash column chromatography (ethyl acetate/hexanes; 1:1) to afford 40 mg (83%) of diol 39 as a colorless solid. mp 117.0-119.0° C.; [α]$^{20}_D$=−72.7 (c=1.09, CH$_2$Cl$_2$); $^1$H NMR (CDCl$_3$, 300 MHz) δ 7.86-7.90 (m, 2H), 7.52-7.67 (m, 3H), 7.31 (d, J=7.5 Hz, 1H), 4.55 (d, J=2.7 Hz, 1H), 3.79 (dd, J=5.4 Hz, 1.5 Hz, 1H), 3.47 (dd, J=9.9 Hz, 2.4 Hz, 1H), 2.82 (m, 2H), 2.35 (m, 1H), 2.06 (br s, 1H), 1.26 (d J=7.5 Hz, 3H), 1.13 (d, J=6.9 Hz, 3H), 0.88 (s, 9H), 0.10 (s, 3H), 0.08 (s, 3H); $^{13}$C NMR (CDCl$_3$, 75 MHz) δ 147.9, 140.1, 138.9, 133.4, 129.2, 127.7, 77.5, 71.8, 69.8, 40.1, 35.9, 25.8, 18.0, 17.4, 16.8, −4.5, −4.8; Analytical. Calculated for C$_{21}$H$_{34}$O$_5$SSi: C, 59.12; H, 8.03. Found: C, 59.07; H, 7.89.

Example 18

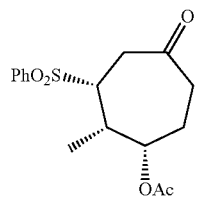

(1S, 2S, 3R)-Acetic acid 3-benzenesulfonyl-2-methyl-5-oxo-cycloheptylester (41): To a solution of 21 (4.63 g, 12.38 mmol) in dichloromethane (62 mL) was added acetic anhydride (1.40 mL, 14.9 mmol), triethylamine (2.61 mL, 18.6 mmol), and a catalytic amount of N,N-dimethylaminopyridine. The solution was stirred for 30 minutes at room temperature, diluted with dichloromethane (60 mL), washed with water (100 mL) and 5% HCl solution (100 mL). The organic layer was washed with a saturated NaHCO$_3$ solution (100 mL), dried over MgSO$_4$, and concentrated to give a light yellow oil. To a heterogeneous mixture of HgCl$_2$(6.72 g, 24.8 mmol) and sodium iodide (5.53 g, 37.1 mmol) in acetonitrile (180 mL) was added chlorotrimethylsilane (4.71 mL, 37.1 mmol) at room temperature, followed by the addition of water (0.67 mL, 37.1 mmol). After 5 min, a solution of acetylated compound of 21 in acetonitrile (120 mL) was added. The reaction was allowed to stir at room temperature for 16 h. The contents of the reaction were filtered through a pad of celite. The filtrate was treated with water (500 mL) and the product extracted with diethyl ether. The combined organic extracts were washed with brine, dried over MgSO$_4$, and concentrated. The product was purified via flash column chromatography using silica gel to give 41 (3.41 g, 85%). $^1$H NMR (300 MHz, CDCl$_3$) δ 7.89 (d, J=7.2 Hz, 2H), 7.69 (t, J=7.5 Hz, 1H), 7.59 (t, J=7.2 Hz, 2H), 4.84 (m, 1H), 3.51 (dd, J=12.9 Hz, 4.2 Hz, 1H), 3.00 (m, 1H), 2.88 (dd, J=17.7 Hz, 12.9 Hz, 1H), 2.67 (dd, J=17.7, 4.5 Hz, 1H), 2.41 (m, 2H), 2.02 (s, 3H), 1.90 (m, 1H), 1.71 (m, 1H), 1.00 (d, J=7.2 Hz, 3H); $^{13}$C NMR (75 MHz, CDCl$_3$) δ 207.0, 169.6, 137.0, 134.2, 129.5, 128.7, 75.8, 60.8, 38.9, 33.9, 24.6, 21.0, 7.3; LRMS (CI) m/z 325 (M+H), 265 (M+H-AcOH).

Example 19

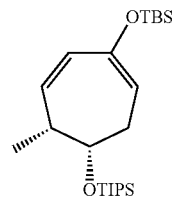

(1E, 3Z, 5R, 6S)-2-(tert-Butyldimethylsilanyloxy)-5-methyl-6-triisopropylsilanyloxycyclobepta-1,3-diene (42): To a solution of 41 (3.10 g, 9.57 mmol) in toluene (64 mL) was added DBU (1.60 g, 10.53 mmol) at room temperature. The solution was stirred for 2 h and then washed with water (10 mL) and brine (10 mL). The organic layer was dried over MgSO$_4$ and concentrated. The resulting oil was dissolved in methylene chloride (32 mL) and diisopropylethylamine (1.48 g, 11.48 mmol) and tert-butyldimethylsilyl trifluoromethanesulfonate (2.78 g, 10.5 mmol) were added at 0° C. The solution was stirred for 1 h at room temperature. The reaction mixture was concentrated and then treated with 1M KOH in methanol (50 mL) for 10 min at room temperature followed by treatment with saturated ammonium chloride solution. The product was extracted with diethyl ether and the combined organic extracts were washed with brine, dried over MgSO$_4$, and concentrated. The colorless crude oil was dissolved in dichloromethane (50 mL) and triethylamine (1.45 g, 14.4 mmol) and triisopropylsilyl trifluoromethanesulfonate (3.23 g, 10.5 mmol) were added at 0° C. The solution was stirred for 1 h at room temperature and then washed with water (2×50 mL), dried over MgSO$_4$, and concentrated. The product was purified via column chromatography using silica gel column to give 42 (2.67 g, 68%) as an oil. $^1$H NMR (300 MHz, CDCl$_3$) δ 5.75 (dd, J=12.3 Hz, 6.6 Hz, 1H), 5.63 (dd, J=12.3 Hz, 1.8 Hz, 1H), 5.04 (m, 1H), 4.16 (m, 1H), 2.60 (m, 1H), 2.41 (m, 1H), 2.29 (m, 1H), 1.09 (br s, 24H), 0.96 (s, 9H), 0.15 (s, 3H), 0.14 (s, 3H); $^{13}$C NMR (75 MHz, CDCl$_3$) δ 148.4, 135.0, 126.8, 107.2, 73.9, 42.0, 32.0, 25.8, 18.2, 18.1, 13.8, 12.5, −4.4, −4.5; LRMS (CI) m/z 411 (M+H); HRMS (EI) m/z 410.3023 (410.3036 calculated for $C_{23}H_{46}O_2Si_2$, $M^+$).

Example 20

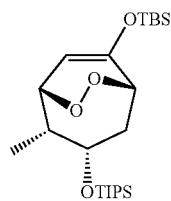

(1R, 2R, 3S, 5S, 8E)-9-(tert-Butyldimethylsilanyloxy)-2-methyl-3-triisopropylsilanyloxy-6,7-dioxabicyclo[3.2.2]-non-8-ene (43): Diene 42 (1.15 g, 2.80 mmol) was dissolved in dichloromethane (28 mL). A catalytic amount (17 mg) of 5,10,15,20-tetraphenyl-21H,23H-porphine (TPP) was added. The reaction mixture was cooled to −78° C. and was irradiated with a tungsten 75W broad-band lamp while bubbling $O_2$ through the reaction mixture. When the reaction was completed (TLC, Rf=0.72 EA/Hexanes 1:9, ca. 30 min), solvent was removed to give 43 (1.24 g), which was used in the next step without purification. $^1$H NMR (300 MHz, CDCl$_3$) δ 5.22 (dd, J=7.8 Hz, 2.1 Hz, 1H), 4.62 (dd, J=7.8 Hz, 5.1 Hz, 1H), 4.36 (d, J=6.0 Hz, 1H), 4.09 (m, 1H), 2.20 (m, 1H), 2.13 (m, 2H), 1.14 (d, J=7.2 Hz, 1H), 1.08 (br s, 21H), 0.96 (s, 9H), 0.26 (s, 3H), 0.24 (s, 3H); $^{13}$C NMR (75 MHz, CDCl$_3$) δ 151.5, 98.2, 78.1, 77.4, 68.8, 41.6, 36.3, 26.1, 25.4, 18.1, 12.3, 9.1, −4.5, −5.0; LRMS (CI) m/z 443 (M+H); HRMS (EI) m/z 442.2925 (442.2935 calculated for $C_{23}H_{46}O_4Si_2$, $M^+$).

Example 21

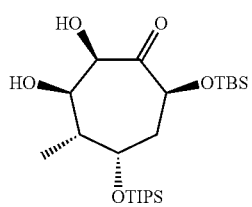

(1R, 2R, 3R, 4S, 6S)-7-(tert-Butyldimethylsilanyloxy)-2,3-dihydroxy-4-methyl-5-triisopropylsilanyloxycyclo-heptanone (46): To a solution of crude 43 (1.24 g, 2.80 mmol) in dichloromethane (5 mL) was added freshly prepared dimethyldioxirane solution in dichloromethane (ca. 0.1M, 60 mL) at 0° C. After the reaction mixture was stirred for 2 h at 0° C., it was concentrated and then dissolved in methanol (28 mL). 5% Pd on carbon (1.20 g, 0.56 mmol) and sodium bicarbonate (0.47 g, 5.60 mmol) were added. The reaction mixture was stirred under hydrogen (1 atm) for 20 min at room temperature. After the reaction mixture was diluted with dichloromethane (28 mL), it was filtered through a pad of celite, which was then washed with dichoromethane (50 mL). The combined filtrate was concentrated and the crude was purified by using a 1" pad of silica gel to give 46 (0.68 g, 53% overall from diene 42). $^1$H NMR (300 MHz, CDCl$_3$) δ 4.39 (t, J=6.9 Hz, 1H), 4.28 (m, 2H), 4.03 (br s, 1H), 2.24 (t, J=6.9 Hz, 2H), 2.12 (m, 1H), 1.11 (br s, 24H), 0.93 (s, 9H), 0.15 (s, 3H), 0.06 (s, 3H); $^{13}$C NMR (75MHz, CDCl$_3$) δ 208.1, 77.2, 74.0, 73.0, 72.6, 42.7, 40.9, 25.8, 18.5, 18.2, 18.1, 12.6, 12.5, −4.5, −5.4; LRMS (CI) m/z 461 (M+H); HRMS (CI) m/z 461.3112 (461.3119 calculated for $C_{23}H_{48}O_5Si_2$, M+H).

Example 22

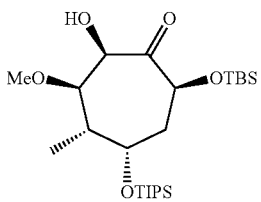

(1R, 2R, 3R, 4S, 6S)-7-(tert-Butyldimethylsilanyloxy)-2-hydroxy-3-methoxy-4-methyl-5-triisopropylsilanyloxycyclo-heptanone (47): To a solution of 46 (0.62 g, 1.35 mmol) in freshly distilled dichloromethane (13 mL) was added a catalytic amount of dimethyltin dichloride (15 mg), followed by addition of potassium carbonate (0.93 g, 6.75 mmol). After stirring for 5 min at room temperature, the solution was cooled to 0° C. Methyl trifluoromethanesulfonate (0.15 mL, 1.35 mmol) was added and the bath temperature was set to 17° C. to 20° C. Additional stoichiometric amount of methyl trifluoromethanesulfonate was added every 1 h (up to total 5 equivalents). When all the starting material was consumed (TLC, ca. 8 h), saturated sodium bicarbonate solution was added. The product was extracted with dichloromethane (3×10 mL) and the organic layers were washed with water, dried over MgSO$_4$, and concentrated. The product was purified by filtering through a 2 inch pad of silica gel to give 47 (0.56 g, 88%). $^1$H NMR (300 MHz, CDCl$_3$) δ 4.41 (d, J=2.4 Hz, 1H), 4.23 (m, 2H), 3.64 (t, J=3.0 Hz, 1H), 3.49 (s, 3H), 2.42 (m, 1H), 2.33 (m, 1H), 1.98 (m, 1H), 1.11 (br s, 21H), 1.01 (d, J=7.2 Hz, 3H), 0.94 (s, 9H), 0.16 (s, 3H), 0.07 (s, 3H); $^{13}$C NMR (75 MHz, CDCl$_3$) δ 208.2, 83.6, 76.2, 74.3, 69.8, 60.2, 41.9, 39.7, 25.8, 18.4, 18.1, 12.4, 8.8, −4.4, −5.2; LRMS (CI) m/z 475 (M+H); HRMS (CI) m/z 475.3268 (475.3275 calculated for $C_{24}H_{50}O_5Si_2$, M+H).

Example 23

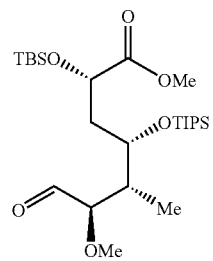

(2S, 4S, 5R, 6R)-2-(tert-Butyldimethylsilanyloxy)-6-methoxy-5-methyl-7-oxo-4-triiso-propylsilanyloxyheptanoic acid methyl ester (48): To a solution of 47 (0.51 g, 1.08 mmol) in 1:1 ratio of dry MeOH-benzene (10 mL) were added pyridine (0.44 mL, 5.40 mmol) and Pb(OAc)$_4$ (0.72 g, 1.62 mmol) at 0° C. After the mixture was stirred for 1.5 h at 0° C., saturated sodium bicarbonate solution (5 mL) was added. The mixture was extracted with diethyl ether (3×10 mL) and the organic layers were washed with water, dried over MgSO$_4$, and concentrated. The product was purified by flash column chromatography to give 48 (0.46 g, 85%). $^1$H NMR (300 MHz, CDCl$_3$) δ 9.64 (d, J=3.0 Hz, 1H), 4.41 (dd, J=7.8 Hz, 6.0 Hz, 1H), 4.21 (m, 1H), 3.76 (s, 3H), 3.57 (dd, J=7.8 Hz, 3.3 Hz, 1H), 3.37 (s, 3H), 2.19 (m, 1H), 2.14 (m, 1H), 1.89 (m, 1H), 1.11 (br s, 21H), 1.00 (d, J=7.2 Hz, 3H), 0.93 (s, 9H), 0.11 (s, 3H), 0.09 (s, 3H); $^{13}$C NMR (75 MHz, CDCl$_3$) δ 202.6, 173.9, 86.4, 70.5, 70.0, 58.1, 51.8, 39.3, 38.9, 25.7, 18.3, 17.7, 13.0, 11.7, −4.9, −5.2; LRMS (CI) m/z 505 (M+H); HRMS (CI) m/z 505.3388 (505.3381 calculated for C$_{25}$H$_{52}$O$_6$Si$_2$, M+H).

Example 24

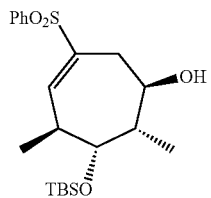

(1R, 5S, 6R, 7S)-3-Benzenesulfonyl-6-(tert-butyldimethylsilanyloxy)-5,7-dimethylcyclohept-3-enol (56): Compound β37 (294 mg, 0.719 mmol) was dissolved in dry toluene (7.0 mL), and the temperature is lowered to −78° C., to this solution was added DIBAL-H (0.72 mL of 1.55 M in toluene) under nitrogen, stirred magnetically at −78° C. for 3 h. The reaction was quenched with 5% HCl aqueous solution, the mixture was extracted with ethyl acetate (3×5 mL). The organic layers were combined and washed with brine and dried over anhydrous Na$_2$SO$_4$. The crude reaction mixture was purified by flash column chromatography (ethyl acetate/hexanes 1:3) to afford 39 mg (13%) of 1,4-reduction compound 59 followed by 197 mg (67%) of compound 56 as a light yellow oil. $[α]^{20}_D$=−32.9 (c=0.75, CH$_2$Cl$_2$); $^1$H NMR (CDCl$_3$, 300 MHz) δ 7.88-7.92 (m, 2H), 7.55-7.68 (m, 3H), 7.05 (d, J=5.4 Hz, 1H), 3.75 (dd, J=6.9 Hz, 2.4 Hz, 1H), 3.61 (m, 1H), 2.72-2.82 (m, 2H), 2.52 (dd, J=15.6 Hz, 7.2 Hz, 1H), 2.05 (dt, J=2.4 Hz, 6.9 Hz, 1H), 1.77 (br s, 1H), 1.20 (d, J=7.2 Hz, 3H), 1.07 (d, J=6.9 Hz, 3H), 0.91 (s, 9H), 0.10 (s, 3H), 0.09 (s, 3H); $^{13}$C NMR (CDCl$_3$, 75 MHz) δ 145.2, 138.8, 137.8, 133.3, 129.2, 128.2, 73.9, 70.7, 43.7, 37.9, 31.7, 25.8, 18.0, 17.4, 14.8, −4.5, −4.8; LRMS (CI): m/z 411 [M+H]$^+$; HRMS (CI) calculated for C$_{21}$H$_{35}$O$_4$SSi, 411.2025; found, 411.2022.

Example 25

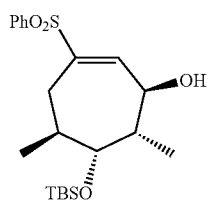

(1S, 5S, 6R, 7S)-3-Benzenesulfonyl-6-(tert-butyldimethylsilanyloxy)-5,7-dimethylcyclohept-2-enol (59): $[α]^{20}_D$=−3.2 (c=0.75, CH$_2$Cl$_2$); $^1$H NMR (CDCl$_3$, 300 MHz) δ 7.88-7.92 (m, 2H), 7.54-7.68 (m, 3H), 7.16 (s, 1H), 4.63 (d, J=10.5 Hz, 1H), 3.64 (d, J=4.8 Hz, 1H), 2.82 (dd, J=15.6 Hz, 2.1 Hz, 1H), 2.22 (dd, J=15.6 Hz, 5.7 Hz, 1H), 1.97 (m, 1H), 1.88 (m, 2H), 1.08 (d, J=6.9 Hz, 3H), 0.91 (s, 9H), 0.59 (d, J=7.2 Hz, 3H), 0.08 (s, 3H), 0.04 (s, 3H); $^{13}$C NMR (C$_6$D$_6$, 75 MHz) δ 148.4, 140.1, 139.1, 132.7, 128.9, 128.7, 79.0, 68.9, 37.1, 36.1, 26.5, 26.0, 18.2, 16.5, 15.3, −4.3, −4.8; LRMS (CI): m/z 411 [M+H]$^+$; HRMS (CI) calculated for C$_{21}$H$_{35}$O$_4$SSi, 411.2025; found, 411.2021.

Example 26

4-(tert-Butyldimethylsilanyloxy)-6-methoxy-3,5-dimethyltetrahydropyran-2-yl]-acetic acid methyl ester (58): To a solution of compound 56 (108 mg, 0.263 mmol), NaHCO$_3$ (40 mg, 0.47 mmol) in methyl alcohol (3.0 mL) and methylene chloride (1.5 mL) at −78° C. was bubbled O$_3$ for 15 minutes, followed by O$_2$ for 5 minutes untill the blue solution became colorless. Me$_2$S (0.5 mL) was added, the mixture warmed up to 25° C. for 5 h. Solvent was removed via rotary evaporation, and the residue purified via flash column chromatography (ethyl acetate/hexane, 1:5) to afford 64 mg (73%) of 57 as an inseparable anomeric mixture (α/β; 1:1). To the lactol mixture 57 (160 mg, 0.481 mmol) was added Ag$_2$O (236 mg, 1.02 mmol), MeI (0.5 mL), and CH$_3$CN (5 mL). This mixture was brought to reflux and left stirring for 1 h. The solvent was removed via rotary evaporation, the residue was purified by flash column chromatography (ethyl acetate/hexanes; 1:10) to afford 28 mg (17% yield) of 58β followed by 108 mg (65% yield) of 58α.

Example 27

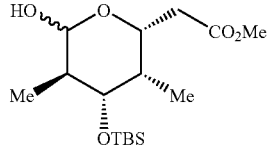

(2R, 3S, 4S, 5R)-[4-(tert-Butyldimethylsilanyloxy)-6-hydroxy-3,5-dimethyltetrahydropyran-2-yl]-acetic acid methyl ester (57): $^1$H NMR (300 MHz, CDCl$_3$) δ 5.11 (d, J=3.6 Hz, 1H), 4.62 (ddd, J=9.6 Hz, 3.6 Hz, 2.1 Hz, 1H), 4.40 (dd, J=8.4 Hz, 5.7 Hz, 1H), 4.00 (ddd, J=8.7 Hz, 4.5 Hz, 2.1 Hz, 1H), 3.93 (dd, J=10.8 Hz, 4.8 Hz, 1H), 3.74 (s, 6H), 3.49 (dd, J=10.5 Hz, 4.8 Hz, 1H), 2.88 (br d, J=6.0 Hz, 1H), 2.71 (dd, J=15.9 Hz, 8.7 Hz, 1H), 2.63 (dd, J=15.6 Hz, 9.6 Hz, 1H), 2.44 (dd, J=15.9 Hz, 4.5 Hz, 1H), 2.38 (dd, J=15.6 Hz, 3.9 Hz, 1H), 1.83 (m, 3H), 1.56 (m, 2H), 1.03 (d, J=6.6 Hz, 3H), 0.99 (d, J=6.9 Hz, 3H), 0.98 (d, J=6.9 Hz, 3H), 0.95 (d, J=6.9 Hz, 3H), 0.94 (s, 9H), 0.93 (s, 9H), 0.11 (s, 6H), 0.08 (s, 6H). $^{13}$C NMR (75MHz, CDCl$_3$) δ 172.5, 172.2, 99.8, 96.0, 75.9, 71.9, 71.3, 67.3, 52.0, 51.9, 40.1, 39.4, 38.9, 37.9, 37.8, 36.3, 26.1, 26.0, 18.3, 13.5, 13.3, 6.2, 5.4, −4.0, −4.1, −4.5, −4.6.

Example 28

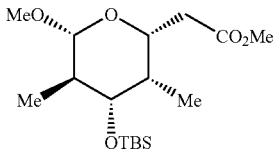

(2R, 3S, 4S, 5R, 6R)-[4-(tert-Butyldimethylsilanyloxy)-6-methoxy-3,5-dimethyltetrahydropyran-2-yl]-acetic acid methyl ester (58α): Major isomer: $[\alpha]^{20}{}_D$=+14.3 (c=0.60, CHCl$_3$); $^1$H NMR (CDCl$_3$, 300 MHz) δ 3.92 (d, J=8.7 Hz, 1H), 3.88-3.92 (m, 1H), 3.79 (s, 3H), 3.46 (s, 3H), 2.63 (dd, J=15.0 Hz, 9.9 Hz, 1H), 3.41-3.45 (m, 1H), 2.71 (dd, J=15.6 Hz, 9.0 Hz, 1H), 2.42 (dd, J=15.6 Hz, 4.5 Hz, 1H), 1.78 (m, 1H), 1.60 (m, 1H), 0.95 (d, J=7.2 Hz, 6H), 0.92 (s, 9H), 0.08 (s, 3H), 0.06 (s, 3H); $^{13}$C NMR (CDCl$_3$, 75 MHz) δ 172.1, 106.9, 76.2, 71.3, 57.0, 51.9, 39.0, 38.5, 37.8, 26.0, 18.3, 13.0, 6.2, −4.0, −4.6.

Example 29

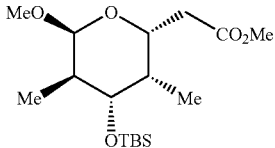

(2R, 3S, 4S, 5R, 6S)-[4-(tert-Butyldimethylsilanyloxy)-6-methoxy-3,5-dimethyltetrahydropyran-2-yl]-acetic acid methyl ester (58β): Minor isomer:$[\alpha]^{20}{}_D$=+116.5 (c=0.40, CH$_2$Cl$_2$); $^1$H NMR (CDCl$_3$, 300 MHz) δ 4.51 (d, J=3.6 Hz, 1H), 4.36 (dt, J=9.6, 3.0 Hz, 1H), 3.84 (dd, J=10.8 Hz, 5.1 Hz, 1H), 3.72 (s, 3H), 3.33 (s, 3H), 2.63 (dd, J=15.0 Hz, 9.9 Hz, 1H), 2.35 (dd, J=15.0 Hz, 3.6 Hz, 1H), 1.81 (m, 2H), 0.92-0.96 (m, 15H), 0.09 (s, 3H), 0.07 (s, 3H); $^{13}$C NMR (CDCl$_3$, 75 MHz) δ 172.1, 102.5, 72.0, 66.9, 54.9, 51.7, 39.2, 37.9, 36.0, 25.8, 18.1, 13.1, 5.2, −4.3, −4.8.

Example 30

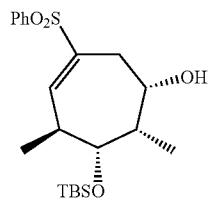

(1S, 5S, 6R, 7S)-3-Benzenesulfonyl-6-(tert-butyl-dimethyl-silanyloxy)-5,7-dimethylcyclohept-3-enol (60): Compound α37 (39 mg, 0.095 mmol) was dissolved in dry toluene (1.0 mL), and the temperature lowered to −78° C. To this cold solution was added THF (10 μL, 0.12 mmol), followed by DIBAL-H solution (0.20 mL of 1.55M in toluene) under nitrogen, and the reaction stirred magnetically at −78° C. for 3 hours. Upon completion, the reaction was quenched by 5% HCl aqueous solution, and extracted with ethyl acetate (3×5 mL). The organic layers were combined and washed with brine, and dried over anhydrous Na$_2$SO$_4$. The crude reaction mixture was purified by flash column chromatography (ethyl acetate/hexanes; 1:3) to afford 34 mg (85%) of a mixture (1,2 vs 1,4-reduction; 4.5:1). 13 mg (35%) of pure 60 was obtained via flash column chromatography eluting with CH$_2$Cl$_2$: CH$_3$CN (25:1). $[\alpha]^{20}{}_D$=−77.7 (c=0.65, CHCl$_3$); $^1$H NMR (CDCl$_3$, 300 MHz) δ 7.87-7.91 (m, 2H), 7.49-7.63 (m, 3H), 7.31 (br d, J=8.4 Hz, 1H), 3.80 (d, J=5.1 Hz, 1H), 3.66 (m, 1H), 3.32 (d, J=9.3 Hz, 1H), 2.94 (m, 2H), 2.57 (dt, J=16.5 Hz, 2.1 Hz, 1H), 1.98 (m, 1H), 1.18 (d, J=7.2 Hz, 3H), 1.13 (d, J=7.2 Hz, 3H), 0.88 (s, 9H), 0.14 (s, 3H), 0.10 (s, 3H); $^{13}$C NMR (C$_6$D$_6$, 75 MHz) δ 143.1, 140.4, 138.9, 133.5, 129.1, 128.8, 79.6, 71.0, 39.6, 38.0, 34.4, 25.9, 18.2, 18.0, 15.0, −4.4, −4.8; LRMS (CI): m/z 411 [M+H]$^+$; HRMS (CI) calculated for C$_{21}$H$_{35}$O$_4$SSi, 411.2025; found, 411.2025

Example 31

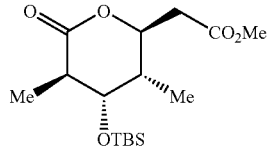

(2S, 3S, 4S, 5R)-[4-(tert-Butyldimethylsilanyloxy)-3,5-dimethyl-6-oxotetrahydropyran-2-yl]-acetic acid methyl ester (62): To a suspension of 60 (35 mg, 0.085 mmol), NaHCO$_3$ (20 mg, 0.23) in a mixture of methyl alcohol (2.0 mL) and methylene chloride (1.5 mL) at −78° C. was bubbled O$_3$ for 15 minutes, followed by O$_2$ for 5 minutes until the blue solution became colorless. Me$_2$S (0.5 mL) of was added, the mixture was warmed to room temperature and stirred for 5 h. Solvent was removed via rotary evaporation and the residue purified with flash column chromatography (ethyl acetate/hexane, 1:5) to afford 25 mg (88%) of lactol 61 as an inseparable anomeric mixture (α/β; 1:1). Lactol mixture 61 (20 mg as a 1:1 mixture, 0.06 mmol) and pyridinium dichromate (110 mg, 0.28 mmol) in CH$_2$Cl$_2$ (0.5 mL) were stirred at room temperature for 15 h. The reaction mixture was quenched with saturated aqueous NaHSO$_3$ (1 mL), and extracted with CH$_2$Cl$_2$ (3×3 mL). The combined organic layers were dried over Na$_2$SO$_4$, concentrated, and purified by flash column chromatography (ethyl acetate/hexanes; 1:5) to afforded 15 mg (75%) of lactone 62 as an oil. $^1$H NMR (CDCl$_3$, 300 MHz) δ 4.70-4.76 (m, 1H), 3.71 (s, 3H), 3.67 (t, J=2.7 Hz, 1H), 2.55-2.77 (m, 3H), 2.12-2.23 (m, 1H), 1.29 (d, J=7.2 Hz, 3H), 1.01 (d, J=6.6 Hz, 3H), 0.89 (s, 9H), 0.08 (s, 3H), 0.07 (s, 3H); $^{13}$C NMR (CDCl$_3$, 75 MHz) δ 173.3, 170.5, 77.4, 74.3, 51.9, 44.0, 37.9, 33.1, 25.7, 18.0, 16.2, 13.8, −4.5, −4.8. LRMS (CI) m/z 331 [M+H]; HRMS (CI), calculated for $C_{16}H_{31}O_5Si$, 331.1941, found 331.1931

Example 32

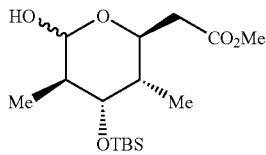

(2S, 3S, 4S, 5R)-[4-(tert-Butyldimethylsilanyloxy)-6-hydroxy-3,5-dimethyltetrahydropyran-2-yl]-acetic acid methyl ester (61): $^1$H NMR (300 MHz, CDCl$_3$) δ 5.42 (d, J=11.8 Hz, 1H), 5.22 (s, 1H), 4.87 (d, J=10.2 Hz, 1H), 4.28 (m 1H), 4.04 (dd, J=9.9 Hz, 3.3 Hz, 1H), 3.75 (br s, 1H), 3.73 (s, 3H), 3.71 (s, 3H), 3.68 (m, 1H), 2.93 (br s, 1H), 2.42-2.68 (m, 4H), 1.95 (m, 2H), 1.74 (m, 2H), 1.04 (d, J=7.2 Hz, 3H), 0.97 (d, J=7.2 Hz, 3H), 0.96 (s, 9H), 0.93 (s, 9H), 0.91 (d, J=6.9 Hz, 3H), 0.85 (d, J=6.6 Hz, 3H), 0.16 (s, 3H), 0.13 (s, 3H), 0.08 (s, 3H), 0.06 (s, 3H). $^{13}$C NMR (75 MHz, CDCl$_3$) δ 172.1, 96.9, 94.0, 76.6, 76.5, 73.2, 66.2, 52,0, 51.9, 41.4, 40.4, 38.8, 38.6, 34.6, 33.8, 26.3, 26.1, 18.2, 15.1, 14.7, 13.9, 9.2, −4.3, −4.6.

Example 33

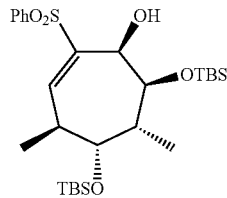

(1S, 4S, 5R, 6R, 7S)-2-Benzenesulfonyl-5,7-bis-(tert-butyldimethylsilanyloxy)-4,6-dimethylcyclohept-2-enol (52): Compound 39 (77 mg, 0.18 mmol) was dissolved in dry methylene chloride (2.0 mL), and cooled to −78° C. To this cold solution were added 2,6-lutidine (32 μL, 0.27 mmol), followed by TBSOTf (50 μL, 0.22 mmol) under nitrogen. After stirring for 2 h at −78° C. (the reaction was monitored by TLC until completion using a mixture of 1:1 EA/hexanes), 0.2 mL of methyl alcohol was then added to quench the excess of TBSOTf. The resulting solution was concentrated via rotary evaporation and the residue was purified by flash column chromatography (ethyl acetate/hexane, 1:5) to afford 97 mg (99% yield) of 52 as a white solid. mp 81.0-83.0° C.; $[\alpha]^{20}_D$=+38.8 (c=1.3, CHCl$_3$); $^1$H NMR (CDCl$_3$, 300 MHz) δ 7.83-7.86 (m, 2H), 7.50-7.71 (m, 3H), 7.37 (d, J=7.8 Hz, 1H), 4.29 (br s, 1H), 3.81 (d, J=4.5 Hz, 1H), 3.56 (dd, J=2.1 Hz, 8.7 Hz, 1H), 2.79 (m, 1H), 2.53 (br s, 1H), 2.45 (m, 1H), 1.22 (d, J=7.2 Hz, 3H), 0.99 (d, J=7.2 Hz, 3H), 0.88 (s, 9H), 0.81 (s, 9H), 0.077 (s, 3H), 0.052 (s, 3H), −0.14 (s, 3H), −0.35 (s, 3H). $^{13}$C NMR (CDCl$_3$, 75 MHz) δ 148.8, 139.6, 139.5, 133.5, 129.4, 128.1, 77.7, 73.3, 70.6, 40.3, 36.3, 26.1, 18.3, 18.1, 17.6, 17.5, −4.11, −4.54, −4.61, −4.90. LRMS (CI): m/z 541 [M+H]$^+$; HRMS (CI) calculated for $C_{27}H_{48}O_5SSi_2$, 541.2839; found, 541.2834.

Example 34

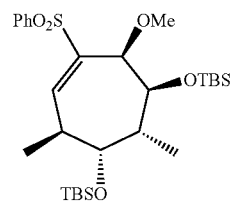

(3S, 4R, 5R, 6S, 7S)-1-Benzenesulfonyl-4,6-bis-(tert-butyldimethylsilanyloxy)-7-methoxy-3,5-dimethylcycloheptene (53): To a solution of compound 52 (75 mg, 0.14 mmol) and MeI (86 μL, 1.4 mmol) in DMSO (2.0 mL) was added powdered KOH (23 mg, 0.42 mmol) and the resulting mixture was stirred for 5 min (until no starting material was present by TLC, developed in 1:3 EA/hexanes) at room temperature. 5 mL of H$_2$O was added, and extracted with diethyl ether (3×5 mL). The organic layers were combined washed with brine, dried over anhydrous Na$_2$SO$_4$ and concentrated. Flash chromatography (ethyl acetate/hexane, 1:10) afforded 72 mg (yield 94%) of compound 53 as a colorless oil which slowly solidified when left standing. m.p.=94.0° C.-96.0° C.; $[\alpha]^{20}_D$=−39.7 (c=0.65, CHCl$_3$); $^1$H NMR (CDCl$_3$, 300 MHz) δ 7.86-7.89 (m, 2H), 7.51-7.61 (m, 3H), 7.35 (d, J=7.8 Hz, 1H), 3.98 (s, 1H), 3.83 (d, J=3.9 Hz, 1H), 3.57 (d, J=9.3 Hz, 1H), 3.35 (s, 3H), 2.77 (m, 1H), 2.54 (m, 1H), 1.23 (d, J=7.2 Hz, 3H), 1.01 (d, J=7.2 Hz, 3H), 0.91 (s, 9H), 0.84 (s, 9H), 0.09 (s, 3H), 0.07 (s, 3H), −0.14 (s, 3H), −0.31 (s, 3H). $^{13}$C NMR (CDCl$_3$, 75 MHz) δ 149.4, 140.3, 139.9, 133.4, 129.4, 128.3, 79.8, 78.7, 73.7, 59.4, 40.2, 36.6, 26.1, 28.3, 18.2, 17.7, 16.9, −4.1, −4.5, −4.6, −4.7; LRMS (CI) m/z 555 [M+H]$^+$; HRMS (CI) calculated for $C_{28}H_{50}O_5SSi_2$, 555.2996; found, 555.2998.

Example 35

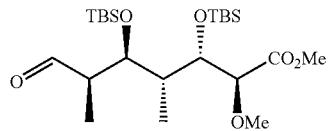

(2S, 3S, 4R, 5S, 6R)-3,5-Bis-(tert-butyldimethylsilanyloxy)-2-methoxy-4,6-dimethyl-7-oxoheptanoic acid methyl ester (51): To a suspension of compound 53 (57 mg, 0.103 mmol) and NaHCO$_3$ (20 mg, 0.23 mmol) in methyl alcohol (3.0 mL) and methylene chloride (1.5 mL) at −78° C. was bubbled O$_3$ for 15 minutes, followed by O$_2$ for 5 minutes until the blue solution became colorless. Me$_2$S (0.5 mL) of was added and the mixture warmed to room temperature for 5 h. The solvent was removed via rotary evaporation and the residue was purified with flash column chromatography (ethyl acetate/hexane, 1:10) to afford 45 mg (92%) of aldehyde 51. $^1$H NMR (CDCl$_3$, 300 MHz) δ 9.69 (s, 1H), 4.31 (dd, J=6.3 Hz, 2.1 Hz, 1H), 3.99 (dd, J=5.1 Hz, 3.0 Hz, 1H), 3.89 (d, J=3.3 Hz, 1H), 3.77 (s, 3H), 3.40 (s, 3H), 2.43 (m, 1H), 2.14 (m, 1H), 1.19 (d, J=7.2 Hz, 3H), 0.98 (d, J=6.9 Hz, 3H), 0.92 (s, 9H), 0.90 (s, 9H), 0.15 (s, 3H), 0.14 (s, 3H), 0.12 (s, 3H), 0.03 (3H); $^{13}$C NMR (CDCl$_3$, 75 MHz) δ 205.0, 170.1, 84.4, 74.4, 71.3, 58.3, 51.7, 49.3, 41.1, 25.9, 25.8, 18.3, 18.2, 11.9, 8.2, −4.0, −4.1, −4.2, −4.5. LRMS (CI): m/z 477 [M+H]$^+$; HRMS (CI) calculated for C$_{23}$H$_{49}$O$_6$Si$_2$, 477.3068; found, 477.3063.

Example 36

(3S, 6S)-(3-Methoxy-6-methylcyclohex-1-enesulfonyl)-benzene (13t-Mea). Quant. yield. clear oil. $^1$H NMR (CDCl$_3$): δ 7.85 (d, J=9.5 Hz, 2H), 7.60 (m, 3H), 7.03 (d, J=2.6 Hz, 1H), 3.86 (m, 1H), 3.40 (s, 3H), 2.45 (m, 1H), 1.93-1.60 (m, 3H), 1.38 (m, 1H), 1.17 (d, J=7 Hz, 3H). $^{13}$C NMR (CDCl$_3$): δ 147.17, 139.71, 136.63, 133.27, 129.13, 128.02, 73.04, 56.74, 28.68, 27.26, 23.90, 19.02. LRMS: (EI) 266 (highest mass) 125 (base peak). (CI) 129 (M+H). HRMS: calculated for C$_{14}$H$_{18}$O$_3$S 267.1055, found 267.1053. [α]$_D$ (c 2.28, CHCl$_3$)=−132°

Example 37

(S)-4-Methylcyclohex-2-enone (14Mea). 93% yield. Clear colorless oil. $^1$H NMR (CDCl$_3$): δ 6.80 (ddd, J=10.2, 4.8, 2.2 Hz, 1H), 5.94 (dd, J=10.2, 4.8 Hz, 1H), 2.60-2.30 (m, 3H), 2.10 (m, 1H), 1.67 (m, 1H), 1.16 (d, J=7 Hz, 3H). [α]$_D$ (c 0.56, CHCl$_3$)=−116°

Example 38

(1S, 4S)-3-Benzenesulfonyl-4-ethylcyclohex-2-enol (12ta-Et). 92% yield. Clear colorless oil. $^1$H NMR (CDCl$_3$): δ 7.85 (d, J=9.5 Hz, 2H), 7.60 (m, 3H), 6.98 (d, J=3.4 Hz, 1H), 4.32 (m, 1H), 3.16 (d, J=6 Hz, 1H), 2.29 (m, 1H), 2.00-1.40 (m, 5H), 1.22 (m, 1H), 0.78 (t, J=7.3 Hz, 3H). $^{13}$C NMR (CDCl$_3$): δ 145.61, 139.89, 139.61, 133.24, 129.06, 127.74, 64.03, 34.80, 26.93, 24.07, 21.55, 11.28. LRMS: (EI) 266 (highest mass) 125 (base peak). (CI) 267 (M+H). HRMS: calculated for C$_{14}$H$_{18}$O$_3$S 266.0977, found 266.0975. [α]$_D$ (c 9.07, CHCl$_3$)=−87°

Example 39

(3S, 6S)-(6-Ethyl-3-methoxycyclohex-1-enesulfonyl)-benzene (13ta-Et). 97% yield. Clear colorless oil. $^1$H NMR (CDCl$_3$): δ 7.85 (d, J=9.5 Hz, 2H), 7.60 (m, 3H), 7.05 (d, J=3.2 Hz, 1H), 3.86 (m, 1H), 3.42 (s, 3H), 2.29 (m, 1H), 2.00-1.40 (m, 5H), 1.32 (m, 1H), 0.85 (t, J=7.2 Hz, 3H). $^{13}$C NMR (CDCl$_3$): δ 146.52, 139.75, 137.28, 133.20, 129.07, 127.92, 72.91, 56.64, 35.05, 24.21, 23.76, 21.92, 11.39. LRMS: (EI) 280 (highest mass) 139 (base peak). (CI) 281 (M+H). HRMS: calculated for C$_{15}$H$_{20}$O$_3$S 280.1133, found 280.1132. [α]$_D$ (c 2.30, CHCl$_3$)=−150°

Example 40

(S)-4-Ethyleyclohex-2-enone (14aEt). 93% yield. Clear colorless oil. $^1$H NMR (CDCl$_3$): δ 6.90 (ddd, J=10.2, 2.6, 1.4 Hz, 1H), 6.01 (ddd, J=10.2, 2.4, 0.8 Hz, 1H), 2.54 (dt, J=16.8, 5.3 Hz, 1H), 2.40 (m, 2H), 2.16 (m, 1H), 1.60 (m, 3H), 1.04 (t, J=7.3 Hz, 3H). 93.7% ee HPLC Chiralcel AD 0.75 mL/min 99.5:0.5 Hex:2-propanol. 15.57 min minor enantiomer, 16.59 min major enantiomer.

Example 41

(1S, 4R)-3-Benzenesulfonyl-4-isopropylcyclohex-2-enol (12ta-Pr). 94% yield. White solid. m.p=105° C. $^1$H NMR (CDCl$_3$): δ 7.85 (d, J=9.5 Hz, 2H), 7.60 (m, 3H), 7.10 (m, 1H), 4.32 (m, 1H), 2.94 (d, J=5.8 Hz, 1H), 2.50 (m, 2H), 2.1 (m, 1H), 1.80 (m, 1H), 1.4 (m, 2H), 0.87 (d, J=6.8 Hz, 3H), 0.50 (d, J=6.8 Hz, 3H). $^3$C NMR (CDCl$_3$): δ 144.77, 143.97, 140.00, 133.19, 129.04, 127.91, 66.57, 39.73, 30.33, 27.98, 20.19, 19.07, 15.80. LRMS: (EI) 262 (highest mass) 77 (base peak). (CI) 281 (M+H). HRMS: calculated for C$_{15}$H$_{20}$O$_3$S 280.1133, found 280.1129. MP 105° C., [α]$_D$ (c 5.22, CHCl$_3$)=−24°

Example 42

(3S, 6R)-(6-Isopropyl-3-methoxycyclohex-1-enesulfonyl)-benzene (13ta-Pr). Quant. yield. White solid, m.p. 113° C. $^1$H NMR (CDCl$_3$): δ 7.95 (m, 2H), 7.60 (m, 3H), 7.13 (m, 1H), 3.87 (m, 1H), 3.44 (s, 3H), 2.50 (m, 2H), 2.1 (m, 1H), 1.80 (m, 1H), 1.4 (m, 2H), 0.92 (d, J=6.8 Hz, 3H), 0.64 (d, J=6.8 Hz, 3H). $^{13}$C NMR (CDCl$_3$): δ 144.58, 141.72, 133.16, 129.03, 128.04, 75.29, 56.35, 39.93, 28.13, 27.10, 20.21, 15.95. LRMS: (EI) 294 (highest mass) 110 (base peak). (CI) 295 (M+H). HRMS: calculated for C$_{16}$H$_{22}$O$_3$S 294.1290, found 294.1282. MP=113° C. [α]$_D$ (c 1.44, CHCl$_3$)=−87°.

Example 43

(R)-4-Isopropylcyclohex-2-enone (14iaPr). 94% yield. Clear colorless oil. $^1$H NMR (CDCl$_3$): δ 6.94 (dt, J=10.4, 2.1 Hz, 1H), 6.04 (dd, J=10.4, 2.6 Hz, 1H), 2.56 (dt, J=16.6, 4.3 Hz, 1H), 2.40 (m, 2H), 2.10 (m, 1H), 1.80 (m, 2H), 1.01 (d, J=6.8 Hz, 3H), 1.00 (d, J=6.8 Hz, 3H). 94.7% ee HPLC Chiralcel AD 0.75 mL/min 99.5:0.5 Hex:2-propanol. 21.20 min. minor enantiomer, 24.70 min. major enantiomer.

Example 44

(1S,4R)-3-Benzenesulfonyl-4-tert-butylcyclohex-2-enol (12ta-tBu). 93% yield. Sticky clear, colorless film. $^1$H NMR (CDCl$_3$): δ 7.85 (d, J=9.5 Hz, 2H), 7.60 (m, 3H), 6.86 (d, J=2.1 Hz, 1H), 4.32 (m, 1H), 2.56 (m, 2H), 2.17 (m, 1H), 1.84 (m, 1H), 1.53 (m, 1H), 1.37 (m, 1H), 1.03 (s, 9H). $^{13}$C NMR (CDCl$_3$): δ 145.92, 144.25, 140.19, 133.16, 129.06, 128.03, 64.20, 42.10, 34.92, 29.88, 29.12, 22.40. LRMS: (EI) 261 (highest mass) 220 (base peak). (CI) 295 (M+H). HRMS: calculated for C$_{16}$H$_{22}$O$_3$S 294.1290, found 294.1277. [α]$_D$ (c 7.35, CHCl$_3$)=−107°.

Example 45

(3S, 6R)-(6-tert-Butyl-3-methoxycyclohex-1-enesulfonyl)-benzene (13ta-tBu). 98% yield. White oily solid. $^1$H NMR (CDCl$_3$): δ7.85 (d, J=9.5 Hz, 2H), 7.60 (m, 3H), 6.91 (d, J=2.6 Hz, 1H), 3.85 (m, 1H), 3.32 (s, 3H), 2.59 (dd, J=6.1, 3.1 Hz, 1H), 2.14 (m, 1H), 1.84 (m, 1H), 1.54 (m, 1H), 1.31 (m, 1H), 1.05 (s, 9H). $^{13}$C NMR (CDCl$_3$): □146.54, 142.28, 140.53, 133.14, 129.09, 128.11, 73.09, 56.42, 42.56, 35.22, 29.88, 26.12, 22.71, 10.22. LRMS: (EI) 293 (highest mass) 220 (base peak). (CI) 309 (M+H). HRMS: calculated for C$_{17}$H$_{24}$O$_3$S 308.1446, found 308.1436. [α]$_D$ (c 4.47, CHCl$_3$)=−142°.

Example 46

(S)-4-tert-Butylcyclohex-2-enone (14taBu). 89% yield. $^1$H NMR (CDCl$_3$): δ 7.05 (dt, J=10.5, 2.0 Hz, 1H), 6.07 (ddd, J=10.5, 2.9, 1.2 Hz, 1H), 2.56 (dt, J=16.5, 3.4 Hz, 1H), 2.40 (m, 1H), 2.23 (m, 1H), 2.18 (m, 1H), 1.8 (m, 1H), 1.01 (s, 9H).

91% ee HPLC Chiralcel AD 1.0 mL/min 99:1 Hex:2-propanol. 10.60 min. minor enantiomer, 13.86 min. major enantiomer.

Example 47

(1S,4S)-3-Benzenesulfonyl-4-(dimethylphenylsilanyl)cyclohex-2-enol(12ta-PhMe$_2$Si). 87% yield. Clear colorless oil. $^1$H NMR (CDCl$_3$): δ 7.76-7.33 (m, 10H), 6.80 (d, J=3.7 Hz, 1H), 4.20 (m, 1H), 2.06 (m, 2H), 1.60 (m, 4H), 0.55 (s, 3H), 0.48 (s, 3H). $^{13}$C NMR (CDCl$_3$): δ 146.48, 138.72, 137.96, 134.81, 134.08, 133.25, 129.04, 128.11, 127.64, 62.97, 29.41, 24.90, 21.39, 13.65, 10.35, −1.83, −1.94. LRMS: (EI) 372 (highest mass) 135 (base peak). (CI) 372 (M+). HRMS: calculated for C$_{20}$H$_{24}$O$_3$SSi 372.1215, found 372.1197. [α]$_D$ (c 3.49, CHCl$_3$)=−174°.

Example 48

(1S,4S)-(2-Benzenesulfonyl-4-methoxycyclohex-2-enyl)-1-dimethylphenylsilane (13ta-PhMe$_2$Si). 93% yield. Clear colorless oil. $^1$H NMR (CDCl$_3$): δ 7.76-7.35 (m, 10H), 6.92 (m, 1H), 3.66 (m, 1H), 3.36 (s, 3H), 2.01 (m, 1H), 1.60 (m, 4H), 1.40 (m, 1H), 0.56 (s, 3H), 0.49 (s, 3H). $^{13}$C NMR (CDCl$_3$): δ 146.63, 138.94, 138.06, 134.10, 133.24, 133.15, 129.03, 129.00, 128.09, 127.63, 71.83, 56.61, 26.07, 25.00, 21.86, −1.86, −1.95. LRMS: (EI) 386 (highest mass) 135 (base peak). HRMS: calculated for C$_{21}$H$_{26}$O$_3$SSi 386.1372, found 386.1355. [α]$_D$ (c 3.00, CHCl$_3$)=−186°.

Example 49

(1S, 4S)-3-Benzenesulfonyl-4-methylcyclohept-2-enol (25a). 93% yield. Clear colorless oil. $^1$H NMR (CDCl$_3$): δ 7.85 (m, 2H), 7.55 (m, 3H), 7.20 (m, 1H), 4.63 (m, 1H), 3.40 (d, J=4.9 Hz, 1H), 2.78 (m, 1H), 2.00-1.40 (m, 5H), 1.20 (m, 1H), 0.95 (d, J=6.2 Hz, 3H).

$^{13}$C NMR (CDCl$_3$): δ 148.27, 143.80, 138.76, 133.17, 129.03, 127.95, 70.71, 35.83, 31.94, 31.71, 20.52, 16.10. LRMS: (EI) 237 (highest mass) 125 (base peak). (CI) 267 (M+H). HRMS: calculated for C$_{14}$H$_{18}$O$_3$S 266.0977, found 266.0964. [α]$_D$ (c 2.26, CHCl$_3$)=−21°.

Example 50

(3S, 7S)-1-Benzenesulfonyl-3-metboxy-7-methylcyclobeptene (26a). 88% yield. Clear colorless oil. $^1$H NMR (CDCl$_3$): δ 7.85 (m, 2H), 7.55 (m, 3H), 7.20 (m, 1H), 4.63 (dt, J=11.4, 2.1 Hz, 1H), 2.80 (m, 1H), 2.00-1.20 (m, 6H), 1.00 (d, J=7.2 Hz, 3H). $^{13}$C NMR (CDCl$_3$): δ 145.45, 145.08, 138.95, 133.11, 129.00, 128.02, 79.80, 56.60, 32.23, 31.93, 31.79, 20.72, 16.24. LRMS: (EI) 280 (highest mass) 239 (base peak). (CI) 281 (M+H). HRMS: calculated for C$_{15}$H$_{20}$O$_3$S 280.1133, found 280.1126. [α]$_D$ (c 8.06, CHCl$_3$)=−74°.

Example 51

(S)-4-Methylcyclohept-2-enone (27a). 90% yield. Conversion to enone required 3 days. Clear colorless oil. $^1$H NMR (CDCl$_3$): δ 6.36 (ddd, J=12.2, 3.6, 0.8 Hz, 1H), 5.96 (dd, J=12.2, 2.4 Hz, 1H), 2.63 (m, 3H), 1.96 (m, 1H), 1.83 (m, 2H), 1.55 (m, 1H), 1.20 (d, J=7.2 Hz, 3H). $^{13}$C NMR (CDCl$_3$): δ 204.42, 151.68, 130.61, 43.60, 35.65, 34.27, 21.88, 20.63. [α]$_D$ (c 2.03, CHCl$_3$)=−94°.

General Procedure for Generation of β-Substituted Enones Via Electrophile Capture.

Following the general procedure for the conversion of β-methoxy vinyl sulfones to enones the orange anionic solution was quenched with 1.1 equivalents of the desired electrophile. The reaction decolorizes at −78° C. after 15 min. A sat'd solution of NaHCO$_3$ was added followed by ether. The organic layer was dried over MgSO$_4$ and concentrated in vacuo. The residue was dissolved in CHCl$_3$ mL/mmol and SiO$_2$ 250 mg/mmol added. After 2 h the solution was filtered and the solvent removed in vacuo. The enones are typically 90-95% pure. Silica gel chromatography can be used if necessary.

HMPA Modified Procedure for Generation of β-Substituted Enones Via Electrophile Capture.

1.2 equiv. of t-BuLi (0.61 mmol) were added to the mixture of β-methoxy vinyl sulfone (0.51 mmol) and HMPA (2.5 mmol) in 20 mL THF at −78° C. over 2 min. The resulting dark orange reaction was stirred at this temperature for 10 min. The solution was quenched with 3.1 equivalents of the desired electrophile. The reaction decolorizes at −78° C. after 15 min. A sat'd solution of NaHCO$_3$ was added followed by ether. The organic layer was dried over MgSO$_4$ and concentrated in vacuo. The residue was dissolved in CHCl$_3$ mL/mmol and SiO$_2$ 250 mg/mmol added. After 3 h the solution was filtered and the solvent removed in vacuo. The enones are typically 90-95% pure. Silica gel chromatography can be used if necessary General Procedure for the Oxidation of γ-Hydroxy Vinyl Sulfones.

2 mmol of γ-hydroxy vinyl sulfone was dissolved in 100 mL ether. Activated MnO$_2$ was added portionwise with rapid stirring until the reaction was complete as determined by TLC. The reaction was filtered through a 1:1 mixture of celite and SiO$_2$. The resulting enones did not require purification and were routinely used crude.

General Procedure for Generation of β-Substituted Enones Via Addition/Elimination.

Alkyl cuprates, prepared as above, were added to δ-sulfonyl-enones at −78° C. in THF. The reactions were allowed to warm slowly to room temperature overnight. Ether and water were added to the reactions. The organic layer was dried and concentrated in vacuo. SGC, 8:2, Hex:EA, provided the desired enones in the yields indicated with the remaining mass recovered as unreacted starting material.

(S)-3-Benzenesulfonyl-4-methylcyclohex-2-enone (17aa). 92% yield. Clear colorless oil. $^1$H NMR (CDCl$_3$): δ7.95 (m, 2H), 7.69 (m, 3H), 6.57 (s, 1H), 2.93 (m, 1H), 2.63 (ddd, J=18.7, 13.6, 5.2 Hz, 1H), 2.44 (dt, J=17.9, 3.8 Hz, 1H), 2.09 (m, 1H), 1.94 (m, 1H), 1.33 (d, J=6.4 Hz, 3H). $^{13}$C NMR (CDCl$_3$): δ197.78, 163.83, 137.82, 134.35, 130.00, 129.54, 128.66, 32.86, 30.13, 28.50, 18.19. LRMS: (EI) 250 (highest mass) 81 (base peak). (CI) 251 (M+H). HRMS: calculated for C$_{13}$H$_{14}$O$_3$S 250.0664, found 250.0660. [α]$_D$ (c 5.19, CHCl$_3$)=−11°.

(R)-3-Benzenesulfonyl-4-isopropylcyclohex-2-enone (17ba). 91% yield. Clear colorless oil. $^1$H NMR (CDCl$_3$): δ7.95 (m, 2H), 7.68 (m 3H), 6.61 (m, 1H), 2.82 (m, 1H), 2.65-2.30 (m, 3H), 2.20 (m, 1H), 1.92 (m, 1H), 1.12 (d, J=6.9 Hz, 3H), 0.89 (d, J=6.9 Hz, 3H). $^{13}$C NMR (CDCl$_3$): δ198.14, 162.75, 138.33, 134.25, 131.89, 129.50, 128.60, 39.38, 34.81, 30.29, 22.92, 21.55, 18.79. LRMS: (EI) 278 (highest mass) 236 (base peak). (CI) 279 (M+H). HRMS: calculated for C$_{15}$H$_{18}$O$_3$S 278.0977, found 278.0968. [α]$_D$ (c 1.71, CHCl$_3$)=−75°.

(S)-3,4-Dimethylcyclohex-2-enone (14aa). 92% yield. Clear colorless oil. $^1$H NMR (CDCl$_3$): δ 5.80 (t, J=1.2 Hz, 1H), 2.50-2.20 (m, 3H), 2.10 (m, 1H), 1.75 (m, 1H), 1.18 (d, J=7.1 Hz, 3H). $^{13}$C NMR (CDCl$_3$): δ 199.60, 166.59, 126.26, 34.48, 34.29, 30.24, 22.66, 17.66. [α]$_D$ (c 0.51, CHCl$_3$)=+106'.

(S)-3-Allyl-4-methylcyclohex-2-enone (14ba). 96% allyl bromide capture. Clear, light yellow oil. $^1$H NMR (CDCl$_3$): δ 5.86 (s, 1H), 5.83 (m, 1H), 5.19 (m, 2H), 3.00 (d, J=7.0 Hz, 2H), 2.53 (m, 2H), 2.36 (m, 1H), 2.16 (m, 1H), 1.83 (m, 1H), 1.24 (d, J=7.2 Hz, 3H). $^{13}$C NMR (CDCl$_3$): δ 199.41, 167.93, 133.52, 125.68, 118.11, 39.80, 34.12, 32.84, 30.10, 17.53. LRMS: (EI) 150 (highest mass) 79 (base peak). (CI) 151 (M+H). HRMS: calculated for C$_{10}$H$_{14}$O 150.1045, found 150.1043. [α]$_D$ (c 1.40, CHCl$_3$)=−153°.

(S)-3-Isopropyl-4-methylcyclohex-2-enone (14ca). 45% yield, i-PrCu(CN)Li addition. Clear colorless oil. $^1$H NMR (CDCl$_3$): δ 5.87 (m, 1H), 2.53 (m, 2H), 2.34 (dt, J=17.4, 5.1 Hz, 1H), 2.12 (m, 1H), 1.84 (m, 1H), 1.24 (d, J=6.9 Hz, 3H), 1.15 (d, J=6.6 Hz, 3H), 1.13 (d, J=6.6 Hz, 3H). $^{13}$C NMR (CDCl$_3$): δ 200.09, 176.52, 122.43, 33.64, 32.93, 32.38, 30.26, 22.30, 20.68, 17.89. LRMS: (EI) 152 (highest mass) 109 (base peak). (CI) 153 (M+H). HRMS: calculated for C$_{10}$H$_{16}$O 152.1201, found 152.1199. [α]$_D$ (c 0.43, CHCl$_3$)=+119°.

(R)-4-Isopropyl-3-methylcyclohex-2-enone (14da). 90% yield MeI capture, 60% yield MeCu(CN)Li addition. Clear colorless oil. $^1$H NMR (CDCl$_3$): □05.95 (m, 1H), 2.48 (ddd, J=17.1, 7.2, 5.1 Hz, 1H), 2.27 (m, 2H), 2.00 (m, 1H), 1.99 (m, 3H), 1.93 (m, 2H), 1.06 (d, J=6.9 Hz, 3H), 0.86 (d, J=6.9 Hz, 3H). $^{13}$C NMR (CDCl$_3$): δ200.32, 165.75, 128.86, 45.94, 36.51, 29.18, 23.82, 22.61, 21.92, 18.38.93% ee HPLC Chiralcel AD 1.0 mL/min 97.5:2.5 Hex:2-propanol. 7.68 min. minor enantiomer, 8.36 min. major enantiomer.

(4S)-3-Allyl-4-isopropylcyclohex-2-enone (14ea). Using HMPA, 92% yield allyl bromide capture. Clear colorless oil. $^1$H NMR (CDCl$_3$): δ5.92 (m, 1H), 5.77 (m 1H), 2.98 (d, J=6.9 Hz, 2H), 2.47 (m, 1H), 2.22 (m, 3H), 1.94 (m, 2H), 1.03 (d, J=6.7 Hz, 3H), 0.87 (d, J=6.9 Hz, 3H). $^{13}$C NMR (CDCl$_3$): δ 199.75, 166.74, 133.85, 127.47, 43.83, 40.49, 35.46, 28.83, 22.43, 21.47, 18.39. LRMS: (EI) 178 (highest mass) 135 (base peak). HRMS: calculated for C$_{12}$H$_{18}$O 178.1358, found 178.1354. [α]$_D$ (c 6.80, CHCl$_3$)=−69'.

(4R)-3-Butyl-4-isopropylcyclohex-2-enone (14ga). Using HMPA, 84% yield butyl iodide capture. Clear colorless oil. $^1$H NMR (CDCl$_3$): δ5.91 (m, 1H), 2.46 (m, 1H), 2.20 (m, 5H), 1.93 (m, 2H), 1.42 (m, 4H), 1.03 (d, J=6.7 Hz, 3H), 0.92 (t, J=7.2 Hz, 3H), 0.86 (d, J=6.7 Hz, 3H). $^{13}$C NMR (CDCl$_3$): δ199.93, 169,32, 126.64, 43.90, 36.70, 35.47, 29.85, 28.98, 22.48, 21.51, 18.46, 13.85. LRMS: (EI) 194 (highest mass) 110 (base peak). HRMS: calculated for C$_{13}$H$_{22}$O 194.1671, found 1941675. [α]$_D$ (c 5.8, CHCl$_3$)=−12°.

(R)-4-Isopropyl-2-methylcyclohex-2-enone (19a). 3 equivalents of MeLi (1.5 mmol) were added to 140 mg (0.5 mmol) 12t-iPr in 20 mL THF at −78° C. After 1 h, ether and water were added to the reaction. The organic layer was dried over MgSO$_4$ and concentrated in vacuo. The residue was dissolved in 20 mL of acetone and cooled to 0° C. Jones reagent was added until an orange color persisted. Several drops of 2-propanol were added to bring the reaction back to green. The entire contents of the flask were filtered through a plug of fluorosil and the solvent was removed in vacuo. The residue was dissolved in 20 mL of CHCl$_3$ and 0.76 g (0.5 mmol) of DBU was added and the reaction heated to reflux for 2 h. The solvent was removed in vacuo. The crude material was loaded directly onto silica. SGC, 8:2, Hex:EA, provided 19 as a clear colorless liquid. 57 mg 75% yield. $^1$H NMR (CDCl$_3$): δ 6.68 (m, 1H), 2.56 (dt, J=16.6, 4.3 Hz, 1H), 2.33 (m, 2H), 2.00 (m, 1H), 1.81 (dd, J=2.4, 1.4 Hz, 3H), 1.76 (m, 2H), 0.99 (d, J=6.7 Hz, 3H), 0.97 (d, J=6.7 Hz, 3H). $^{13}$C NMR (CDCl$_3$): δ 200.35, 149.45, 135.45, 42.82, 37.61, 31.70, 25.62, 19.64, 19.40, 16.10. 91.2% ee HPLC Chiralcel AD 1.0 mL/min 99:1 Hex:2-propanol. 5.79 min. minor enantiomer, 6.49 min. major enantiomer.

(4R)-4-Isopropyl-2,3-dimethylcyclohex-2-enone (21a). 3 equivalents of MeLi (1.65 mmol) were added to a mixture of 157 mg (0.55 mmol) of 12t-iPr and HMPA (0.48 mL, 2.75 mmol) in 6 mL THF at −78° C. After 30 min, methyl iodide (0.17 mL, 2.75 mmol) was added and the temperature is allowed to rise to −30° C. Ether (10 mL) and water (5 mL) were added to the reaction and the mixture was then extracted. The organic layer was dried over MgSO$_4$ and concentrated in vacuo. The residue was dissolved in 10 mL of acetone and cooled to 0° C. Jones reagent was added until an orange color persisted. Several drops of 2-propanol were added to bring the reaction back to green. The entire contents of the flask were filtered through a plug of fluorosil and the solvent was removed in vacuo. The residue was dissolved in 20 mL of CHCl$_3$ and 0.123 mL (0.83 mmol) of DBU were added and the reaction heated to reflux for 2 h. The solvent was removed in vacuo. The crude material was loaded directly onto silica. SGC, 8:2, hexane:ethyl acetate, provided 21 as a clear colorless liquid. 83.7 mg 92% yield. $^1$H NMR (CDCl$_3$): δ 2.50 (m, 1H), 2.29 (m, 1H), 2.14 (m, 2H), 1.90 (m, 9H), 1.02 (d, J=6.6 Hz, 3H), 0.85 (d, J+6.6 Hz, 3H). $^{13}$C NMR (CDCl$_3$): δ 199.01, 158.04, 132.11, 46.86, 35.24, 29.44, 22.15, 21.51, 20.67, 18.68, 11.32. LRMS: (EI) 166 (highest mass), 124 (base peak). HRMS: calculated for C$_{11}$H$_{18}$O 166.1358, found 166.1355. [α]$_D$ (c 1.40, CHCl$_3$)=+10°.

Procedure for Nucleophilic Addition to γ-Hydroxy Dienyl Sulfones:

(1S, 5S, 6S)-5-Benzenesulfonyl-6-methylcyclohex-3-enol (22aMe). To a solution of epoxy-dienyl sulfone SS-9a (0.377 g, 1.6 mmol) in THF (10 mL) at −78° C. was slowly added LiHMDS (1.8 mL, 1.8 mmol). The solution was stirred for 30 min, followed by addition of sat'd solution of NH$_4$Cl (5 mL). Et$_2$O (5 mL) was added to the mixture and separated. The aqueous layer was extracted with Et$_2$O (2×5 mL) and the organic layers are combined, dried over MgSO$_4$ and concentrated. The resulting solid was dissolved in THF (10 mL) at −78° C. was added MeLi (3.4 mL, 4.8 mmol) in Et$_2$O over a period of 15 min, addition must be done slowly to minimize aromatization. The orange solution was stirred for 20 min and then quenched by slowly adding a solution of sat'd NH$_4$Cl (5 mL). The temperature was allowed to rise to 25° C. and diethyl ether was added (10 mL). The organic layer was separated and the aqueous layer was extracted with diethyl ether (2×10 mL). The organic layers were combined, dried over MgSO$_4$, and concentrated. The resultant mixture was filtered through a one inch silica gel plug eluting with a 3:1 mixture of ethyl acetate/hexanes to give 0.370 g of the desired sulfone as an oil in 92% yield and a 9:1 ratio of diastereomers. $^1$H NMR (CDCl$_3$): δ 7.88 (m, 2H), 7.61 (m, 3H), 5.97 (m, 1H), 5.54 (m, 1H), 4.17 (m, 1H), 3.62 (m, 1H), 2.47 (m, 1H), 2.28 (m, 1H), 2.05 (m,1H), 1.77 (m, 1H), 1.07 (d, J=6.9 Hz, 3H). $^{13}$C NMR (CDCl$_3$): δ137.9 133.7, 132.3, 129.1, 128.9, 117.5, 68.6, 66.2, 32.7, 30.3, 15.5. LRMS: (CI) highest mass 253 (M+H), base peak 143. HRMS: (CI) calculated for C$_{13}$H$_{16}$O$_3$S 253.0898, found 253.0905

(1S, 5S, 6S)-5-Benzenesulfonyl-6-isopropylcyclohex-3-enol (22aPr). To a solution of epoxy-dienyl sulfone SS-9a (0.350 g, 1.5 mmol) in THF (10 mL) at −78° C. was slowly added LiHMDS (1.6 mL, 1.6 mmol). The solution was stirred for 30 min, followed by addition of a sat'd solution of $NH_4Cl$ (5 mL). $Et_2O$ (5 mL) was added to the mixture and separated. The aqueous layer was extracted with $Et_2O$ (2×5 mL) and the organic layers are combined, dried over $MgSO_4$ and concentrated. To the resulting solid in THF (10 mL) at −78° C. was slowly added iPrMgCl (3.7 mL, 7.4 mmol) over a period of 15 min, addition must be done slowly to minimize aromatization. The orange solution was stirred for 20 min and the temperature allowed to slowly rise to −10° C. over a period of 1 h. The solution was quenched by slowly adding a solution of sat'd $NH_4Cl$ (10 mL). The temperature was allowed to rise to 25° C. and diethyl ether was added (10 mL). The organic layer was separated and the aqueous layer was extracted with diethyl ether (2×10 mL). The organic layers were combined, dried over $MgSO_4$, and concentrated. The resultant mixture was filtered through a one inch silica gel plug eluting with a 3:1 mixture of ethyl acetate:hexanes to give 0.375 g of the desired sulfone as an oil in 89% yield and a 30:1 ratio of diastereomers. $^1$H NMR ($CDCl_3$): δ 7.88 (m, 2H), 7.59 (m, 3H), 5.99 (m, 1H), 5.66 (m, 1H), 4.31 (m, 1H), 3.77 (m, 1H), 2.17 (m, 4H), 0.81 (d, J=6.9 Hz, 3H), 0.76 (d, J=6.9 Hz, 3H). $^{13}$C NMR ($CDCl_3$): δ 137.6, 133.7, 133.2, 129.1, 129.0, 118.5, 65.6, 63.9, 42.6, 31.5, 24.8, 22.1, 19.7. LRMS: (CI) highest mass 281 (M+H), base peak 143. HRMS: (CI) calculated for $C_{15}H_{20}O_3S$ 281.1211, found 281.1199.

(2R, 3S, 4S)-(3-Benzenesulfonyl-2-methylcyclohept-4-enyloxy)-tert-butyldimethylsilane (30). To a solution of dienyl sulfone 2 (FIG. 1) (0.322 g, 0.89 mmol) in THF (9 mL) at −78° C. was slowly added MeLi (1.8 mL, 1.95 mmol) in $Et_2O$ over a period of 10 min. The orange solution was stirred for 20 min and was then quenched by slowly adding a solution of sat'd $NH_4Cl$ (10 mL). The temperature was allowed to rise to 25° C. and diethyl ether was added (10 mL). The organic layer was separated and the aqueous layer was extracted with diethyl ether (2×10 mL). The organic layers were combined, dried over $MgSO_4$, and concentrated. The resultant mixture was filtered through a one inch silica gel plug eluting with a 3:1 mixture of ethyl acetate:hexanes to give 0.317 g of the desired sulfone as an oil in 94% yield and a 20:1 ratio of diastereomers. $^1$H NMR ($CDCl_3$): δ7.87 (m, 2H), 7.58 (m, 3H), 6.03 (m, 1H), 5.87 (m, 1H), 4.60 (m, 1H), 3.83 (m, 1H), 2.42 (m, 4H), 1.77 (m, 1H), 1.63 (m, 1H), 1.41 (m, 1H), 1.09 (d, J=7.0 Hz, 3H), 0.85 (s, 9H), −0.02 (s, 3H), −0.08 (s, 3H). $^{13}$C NMR ($CDCl_3$): δ 139.0, 134.9, 133.4, 129.1, 128.5, 123.2, 73.6, 62.3, 35.9, 27.1, 25.7, 20.0, 17.9, 12.3, −5.1. LRMS: (CI) highest mass 381 (M+H), base peak 249. HRMS: (CI) calculated for $C_{20}H_{32}O_3SSi$ 381.1920, found 381.1917.

General Procedure for Molybdenum Catalyzed Epoxidations:

To a solution of hydroxy allyl sulfone (0.98 mmol) in benzene (10 mL) was added solid molybdenum hexacarbonyl (0.005 g, 0.021 mmol, 5 mol %). The solution was heated to reflux and tert-butyl hydrogen peroxide (0.312 mL, 1.56 mmol) in decanes was slowly added over a period of 5 min. The solution was heated at reflux for 1.5 h. The reaction was allowed to cool to 25° C. and diethyl ether (10 mL) was added to the reaction mixture. The mixture was washed with a saturated solution of sodium bisulfite (5 mL), and the organic layer was concentrated. The resultant mixture was filtered through a one inch silica gel plug eluting with a 1:1 mixture of ethyl acetate/hexanes; which upon concentration affords epoxy sulfone as a crystalline solid in a high yields and the same ratio as that of the corresponding starting material. The crystalline product can be further recrystalized from chloroform and hexanes to separate the diastereomers.

(1R, 3S, 4S, 5R, 6R)-5-Benzenesulfonyl-4-methyl-7-oxabicyclo[4.1.0]heptan-3-ol (23aMe). 99% yield 6:1 ratio, after recrystalization 83% yield 30:1 ratio. $^1$H NMR ($CDCl_3$): δ 7.96 (m, 2H), 7.67 (m, 3H), 3.64 (m, 1H), 3.58 (d, J=3.8 Hz, 1H), 3.51 (d, J=9.3 Hz, 1H), 3.40 (m, 1H), 2.68 (d, J=10.8 Hz, 1H, (OH)), 2.40 (ddd, J=15.7 Hz, 5.6 Hz, 2.7 Hz, 1H), 2.03 (m, 1H), 1.90 (dddd,15.7 Hz, 5.0 Hz, 3,8 Hz, 1.2 Hz, 1H), 1.25 (d, J=6.9 Hz, 3H). $^{13}$C NMR ($CDCl_3$): δ 137.9, 134.3, 129.6, 128.7, 69.2, 64.0, 53.4, 51.2, 32.4, 29.8, 18.8. LRMS: (CI) highest mass 269 (M+H), base peak 233. HRMS: (CI) calculated for $C_{13}H_{16}O_4S$ 269.0848, found 269.0852. m.p.=133.5° C.-134.0° C. $[\alpha]_D$ (c 2.90, $CHCl_3$)=+27°.

(1R, 3S, 4S, 5R, 6R)-5-Benzenesulfonyl-4-isopropyl-7-oxabicyclo[4.1.0]heptan-3-ol (23aPra). 95%>50:1 ratio. $^1$H NMR ($CDCl_3$): δ 7.94 (m, 2H), 7.67 (m, 3H), 4.05 (m, 1H), 3.89 (d, J=8.4 Hz, 1H), 3.61 (d, J=3.7 Hz, 1H), 3.38 (m, 1H), 2.28 (m, 2H), 1.88 (m, 1H), 1.74 (m, 1H), 1.06 (d, J=7.5 Hz, 3H), 1.03 (d, J=7.5 Hz, 3H). $^{13}$C NMR ($CDCl_3$): δ138.0 134.2, 129.5, 128.7, 64.8, 60.7, 53.4, 51.7, 30.2, 29.5, 20.6, 18.3. LRMS: (CI) highest mass 269 (M+H), base peak 233. HRMS: (CI) calculated for $C_{15}H_{20}O_4S$ 297.1161, found 297.1173. m.p.=147.5° C.-148.0° C.>99% ee HPLC Chiralcel OD 1.0 mL/min 90:10 Hex:2-propanol. 16.04 min. minor enantiomer, 14.60 min. major enantiomer. $[\alpha]_D$ (c 3.1, $CHCl_3$)=+63°.

(1R, 2R, 3R, 4S, 7R)-(2-Benzenesulfonyl-3-methyl-8-oxabicyclo[5.1.0]oct-4-yloxy)-tert-butyldimethylsilane (31). To a stirring solution of allyl sulfone 30 (0.884 g, 2.33 mmol) in $CH_2Cl_2$ (23 mL) at room temperature was added m-CPBA (1.56 g, 6.33 mmol). The mixture was stirred for 18 h at which point diethyl ether (20 mL) was added followed by saturated solution of sodium bisulfite (20 mL). The organic phase was separated and washed with 10% NaOH (2×20 mL) then dried over $MgSO_4$ and concentrated to give 0.848 g of the desired epoxy sulfone as a single diastereomer in 92% yield. $^1$H NMR ($CDCl_3$): δ7.92 (m, 2H), 7.61 (m, 3H), 3.86 (m, 1H), 3.42 (m, 2H), 3.06 (m, 1H), 2.68 (m, 1H), 1.91 (m, 1H), 1.75 (m, 1H), 1.53 (m, 2H), 1.25 (d, J=7.5 Hz, 3H), 0.84 (s, 9H), 0.00 (s, 3H), −0.01 (s, 3H). $^{13}$CNMR ($CDCl_3$): δ 139.4, 133.7, 129.2, 128.5, 72.2, 63.6, 53.2, 51.6, 37.6, 26.3, 25.6, 22.1, 17.8, 13.0, −5.1, −5.2. LRMS: (EI) highest mass 359 (M−$C_4H_9$), base peak 73. HRMS: (EI) calculated for $C_{20}H_{32}O_4SSi$ 396.1791, found 396.1782.

General Procedure for Silyl Protection of the Epoxy Alcohols:

To a stirring solution of the epoxy sulfone (0.42 mmol) and triethylamine (0.63 mmol) in $CH_2Cl_2$ (4.0 mL) at room temperature was added tert-butyldimethylsilyl triflouromethylsulfonate (0.50 mmol). The solution was stirred for 30 min. Diethyl ether (10 mL) was added and the crude mixture concentrated. The mixture was then filtered through a one inch silica plug eluting with a 1:3 solution of ethyl acetate/hexanes to give, after concentration, the desired protected alcohol in quantitative yield.

(1R, 3S, 4S, 5R, 6R)-(5-Benzenesulfonyl-4-methyl-7-oxabicyclo[4.1.0]hept-3-yloxy)-tert-butyldimethylsilane 23bMe Quantitative yield. $^1$H NMR ($CDCl_3$): δ 7.91 (m, 2H), 7.62 (m, 3H), 4.15 (ddd, J=10.4 Hz, 6.3 Hz, 4.4 Hz, 1H), 3.59 (d, J=2.4 Hz, 1H), 3.35 (d, J=3.5 Hz, 1H), 3.25 (dd, J=5.0 Hz, 4.3 Hz, 1H), 2.32 (m, 1H), 1.98 (m, 2H), 1.01 (d, J=7.2 Hz, 3H), 0.86 (s, 9H), 0.05 (s, 6H). $^{13}$C NMR ($CDCl_3$): □138.3 134.0, 129.4, 128.4, 65.7, 65.3, 52.1, 49.4, 31.8, 28.5, 14.1, −4.8, −4.9. LRMS: (CI) highest mass 383 (M+H), base peak 383. HRMS: (CI) calculated for $C_{19}H_{30}O_4SSi$ 383.1712, found 383.1700. $[\alpha]_D$ (c 5.0, CHCl$_3$)=+16°.

(1R, 3S, 4S, 5R, 6R)-(5-Benzenesulfonyl-4-isopropyl-7-oxabicyclo[4.1.0]hept-3-yloxy)-tert-butyldimethylsilane 23b Pr Quantitative yield. $^1$H NMR (CDCl$_3$): δ7.93 (m, 2H), 7.64 (m, 3H), 4.41 (ddd, J=11.1 Hz, 6.9 Hz, 4.3 Hz, 1H), 3.84 (m, 1H), 3.42 (m, 1H), 3.31 (m, 1H), 1.98 (m, 4H), 0.91 (d, J=6.6 Hz, 3H), 0.88 (s, 9H), 0.66 (d, J=6.4 Hz, 3H), 0.11 (s, 3H), 0.10 (s, 3H). $^{13}$C NMR (CDCl$_3$): δ138.3, 134.0, 129.4, 128.5, 67.0, 62.6, 52.5, 48.8, 42.6, 29.0, 26.9, 25.8, 23.5, 22.0, 17.9, −4.7, −5.0. LRMS: (CI) highest mass 411 (M+H), base peak 137 HRMS: (CI) calculated for $C_{21}H_{34}O_4SSi$ 411.2025, found 411.2005. $[\alpha]_D$ (c 38.0, CHCl$_3$)=−1°.

General Procedure for Base Induced Epoxide Opening Followed by Etherification of β-Hydroxy Vinyl Sulfones:

To a solution of the silylated epoxy sulfone (0.25 mmol) in THF (2.5 mL) was added DBU (0.30 mmol). The stirring solution was heated to reflux for 1 h. The temperature was lowered to room temperature and diethyl ether (5 mL) was added to the mixture followed by water (5 mL). The organic phase was separated and concentrated. The resulting mixture was filtered through a one inch silica gel plug eluting with a 1:1 solution of ethyl acetate/hexanes, which upon concentration gives the vinyl sulfone in high yield. Etherification is performed as explained previously.

(1R, 4S, 5S)-3-Benzenesulfonyl-5-(tert-butyldimethylsilanyloxy)-4-methylcycloex-2-enol (24Me a). 96% yield. $^1$H NMR (CDCl$_3$): δ7.88 (m, 2H), 7.58 (m, 3H), 6.92 (d, J=3.2 Hz, 1H), 4.43 (m, 1H), 3.75 (m, 1H), 2.60 (m, 1H), 1.98 (m, 1H), 1.83 (m, 1H), 1.02 (d, J=6.9 Hz, 3H), 0.82 (s, 9H), 0.01 (s, 3H), −0.04 (s, 3H). $^{13}$C NMR (CDCl$_3$): δ 145.1, 139.9, 138.7, 133.4, 129.2, 128.0, 69.0, 66.0, 35.3, 35.2, 25.7 18.0, 13.7, −4.8, −5.0. LRMS: (CI) highest mass 383 (M+H), base peak 365. HRMS: (CI) calculated for $C_{19}H_{30}O_4SSi$ (M+H−H$_2$O) 365.1607, found 365.1595. $[\alpha]_D$ (c 88.0, CHCl$_3$)=−2°.

(2S, 3S, 5R)-(3-Benzenesulfonyl-5-methoxy-2-methylcyclohex-3-enyloxy)-tert-butyldimethylsilane (24aMe). Reaction time: 10 min, 98% yield. $^1$H NMR (CDCl$_3$): □7.87 (m, 2H), 7.57 (m, 3H), 6.92 (d, J=2.4 Hz, 1H), 4.03 (m, 1H), 3.65 (m, 1H), 3.40 (s, 3H), 2.59 (m, 1H), 1.97 (m, 1H), 1.70 (m, 1H), 0.95 (d, J=6.9 Hz, 3H), 0.83 (s, 9H), −0.03 (s,3H), −0.04 (s, 3H). $^{13}$CNMR (CDCl$_3$): δ146.4, 139.8, 136.0, 133.4, 129.2, 128.1, 68.4, 56.3, 35.0, 31.6, 25.6, 18.0, 13.1, −4.9. LRS: (CI) highest mass 397 (M+H), base peak 263. HRMS: (CI) calculated for $C_{20}H_{32}O_4SSi$ 396.1791, found 396.1787. $[\alpha]_D$ (c 27.0, CHCl$_3$)=−0.5°.

(1R, 4S, 5S)-3-Benzenesulfonyl-5-(tert-butyldimethylsilanyloxy)-4-isopropylcyclohex-2-enol (24a Pr). 99% yield. $^1$H NMR (CDCl$_3$): δ 7.85 (m, 2H), 7.58 (m, 3H), 6.88 (d, J=3.4 Hz, 1H), 4.45 (m, 1H), 3.40 (dt, J=12.7 Hz, 4.0 Hz, 1H), 2.27 (m, 1H), 2.01 (m, 2H), 1.74 (m, 1H), 1.14 (d, J=7.0 Hz, 3H), 0.97 (d, J=7.3 Hz, 3H), 0.80 (s, 9H), −0.13 (s, 3H), −0.16 (s, 3H). $^{13}$C NMR (CDCl$_3$): δ144.1, 139.1, 133.4, 129.2, 128.4, 70.4, 66.2, 46.0, 35.8, 25.7, 25.2, 24.4, 21.8, 18.0, −5.1, −5.2. LRMS: (CI) highest mass 411 (M+H), base peak 137. HRMS: (CI) calculated for $C_{21}H_{34}O_4SSi$ 411.2025, found 411.2012. m.p.=133.5° C.-134.5° C. $[\alpha]_D$ (c 5.0, CHCl$_3$)=−60°.

(1S, 2S, 5R)-(3-Benzenesulfonyl-2-isopropyl-5-methoxycyclohex-3-enyloxy)-tert-butyldimethylsilane (24b Pr). Reaction time: 10 min 98% yield. m.p.=133.5-134.5° C. $^1$H NMR (CDCl$_3$): δ 7.85 (m, 2H), 7.57 (m, 3H), 6.97 (d, J=3.5 Hz, 1H), 4.01 (m, 1H), 3.41 (s, 3H), 3.38 (m, 1H), 2.24 (m, 2H), 1.97 (m, 1H), 1.74 (m, 1H), 1.13 (d, J=6.9 Hz, 3H), 0.94 (d, J=6.9 Hz, 3H), 0.80 (s, 9H), −0.13 (s, 3H), −0.16 (s, 3H). $^{13}$C NMR (CDCl$_3$): δ144.7, 139.2, 136.6, 133.3, 129.1, 128.4, 74.6, 70.5, 56.6, 49.1, 32.8, 25.7, 25.3, 24.5, 21.6, 18.0, −5.1, −5.2. LRMS: (CI) highest mass 424 (M+H), base peak 133. HRMS: (CI) calculated for $C_{21}H_{34}O_4SSi$ 425.2182, found 425.2176. $[^6]D$ (c 3.0, CHCl$_3$)=−39°.

(1R, 4R, 5S)-3-Benzenesulfonyl-5-(tert-butyldimethylsilanyloxy)-4-methylcyclohept-2-enol Reaction time 5 h, 97% yield. $^1$H NMR (CDCl$_3$): δ 7.87 (m, 2H), 7.55 (m, 3H), 7.19 (d, J=3.5 Hz, 1H) 4.51 (m, 1H), 3.80 (ddd, J=7.2 Hz, 4.6 Hz, 2.3 Hz, 1H), 2.86 (dq, J=7.3 Hz, 2.1 Hz, 1H), 2.65 (d, J=6.6 Hz, 1H, (OH)), 2.14 (m, 1H), 1.92 (m, 1H), 1.80 (m, 1H), 1.69 (m, 1H), 0.97 (d, J=7.3 Hz, 3H), 0.75 (s, 9H), −0.07 (s, 3H), −0.19 (s, 3H). $^{13}$C NMR (CDCl$_3$): δ145.5, 142.5, 139.5, 133.1, 129.1, 128.5, 71.0, 70.0, 40.0, 28.6, 28.0, 25.8, 18.0, 16.3, −5.0, −5.5. LRMS: (EI) highest mass 339 (M−C$_4$H$_9$), base peak 75. (CI) highest mass 397 (M+H), base peak 379. HRMS: (EI) calculated for $C_{20}H_{32}O_4SSi$ 396.1791, found 396.1772.

(1S, 2R, 5R)-(3-Benzenesulfonyl-5-methoxy-2-methylcyclohept-3-enyloxy)-tert-butyldimethylsilane Reaction time 10 min, 98% yield. White solid m.p.=116.0° C.-117.5° C. $^1$H NMR (CDCl$_3$): δ 7.84 (m, 2H), 7.52 (m, 3H), 7.19 (m, 1H), 3.95 (dt, J=11.4 Hz, 2.9 Hz, 1H), 3.74 (m, 1H), 3.38 (s, 3H), 2.82 (dq, J=12.1 Hz, 7.3 Hz, 1H), 1.78(m, 4H) 0.93 (d, J=7.5 Hz, 3H), 0.72 (s, 9H), −0.10 (s, 3H), −0.21 (s, 3H). $^{13}$C NMR (CDCl$_3$): δ145.5, 142.5, 139.5, 133.1, 129.1, 128.5, 71.0, 70.0, 40.0, 28.6, 28.0, 25.8, 18.0, 16.3, −5.0, −5.5. LRMS: (CI) highest mass 411 (M+H), base peak 411. HRMS: (CI) calculated for $C_{21}H_{34}O_4SSi$ 411.2025, found 411.2030.

Enone Formation:

(4R, 5S)-5-(tert-Butyldimethylsilanyloxy)-3,4-dimethylcyclohex-2-enone (25aMe). t-BuLi (0.32 mL, 0.38 mmol) was slowly added to a mixture of HMPA (0.17 mL, 0.95 mmol) and β-methoxy vinyl sulfone 24aMe (0.08g, 0.19 mmol) in 2 mL THF at −78° C. The resulting bright orange mixture was stirred at −78° C. for 5 min. Iodomethane (0.06 mL, 0.95 mmol) was added and was stirred for 15 min. 1 mL of sat'd solution of NaHCO$_3$ was added and the reaction allowed to warm to room temperature. The mixture was extracted into diethyl ether (4 mL) and concentrated in vacuo. CHCl$_3$ (1 mL) was added followed by SiO$_2$ (0.500 g) and the reaction was stirred for 2 h. Monitoring the reaction was best accomplished by $^1$HNMR. When complete, the silica was filtered and the solution was concentrated. Silica gel column purification eluting with 1:4 ethyl acetate/hexanes provided the desired enone in 0.044 g, 93% yield. $^1$H NMR (CDCl$_3$): δ5.83 (s, 1H), 4.17 (dt J=10.7 Hz, 5.2 Hz, 1H), 2.32 (m, 3H), 1.99 (s, 3H), 1.16 (d, J=7.2 Hz 3H), 0.89 (s, 9H), 0.06 (s, 6H). $^{13}$C NMR (CDCl$_3$): δ198.4, 165.5, 126.1, 69.2, 42.2, 41.8, 25.7, 23.1, 18.0, 11.7, −4.4, −4.9. LRMS: (CI) highest mass 255 (M+H), base peak 255. HRMS: (CT) calculated for $C_{14}H_{26}O_2Si$ 255.1780, found 255.1779. 98.7% ee HPLC Chiralcel OD 1.0 mL/min 90.0:10.0 Hex:2-propanol. 5.25 min. minor enantiomer, 4.46 min. major enantiomer. $[\alpha]_D$ (c 9.9, CHCl$_3$)=−41°.

(4R, 5S)-5-(tert-Butyldimethylsilanyloxy)-4-isopropyl-3-methylcyclohex-2-enone (25aPr). t-BuLi (0.15 mL, 0.18 mmol) was slowly added to a mixture of HMPA (0.08 ml, 0.45 mmol) and β-methoxy vinyl sulfone 24aPr (0.0382 g, 0.09 mmol) in 2 mL THF at −78° C. The resulting bright orange mixture was stirred at −78° C. for 5 min. Iodomethane (0.03 mL, 0.45 mmol) was added and was stirred for 15 min. Sat.

NaHCO$_3$ (2 mL) was added and the reaction allowed to warm to room temperature. The mixture was extracted into diethyl ether (5 mL) and concentrated in vacuo. CHCl$_3$ (1 mL) was added followed by SiO$_2$ (0.500 g) and the reaction was stirred for 3 h. Monitoring the reaction was best accomplished by $^1$HNMR. When complete, the silica was filtered and the solution was concentrated. Silica gel column purification eluting with 1:4 ethyl acetate/hexanes provided the desired enone in 0.023 g, 91% yield. $^1$H NMR (CDCl$_3$): δ 5.92 (s, 1H), 4.21 (dt, J=11.4 Hz, 5.8 Hz, 1H), 2.46 (m, 3H), 2.25 (m, 1H), 2.01 (d, J=1.4 Hz, 1H), 1.14 (d, J=7.0 Hz, 3H), 0.90 (s, 9H), 0.88 (d, J=7.2 Hz, 3H), 0.070 (s, 3H), 0.065 (s, 3H). $^3$C NMR (CDCl$_3$): δ 199.0, 163.9, 127.8, 69.9, 53.1, 42.9, 26.0, 25.7, 25.4, 24.5, 21.0, −4.7, −4.8. LRMS: (CI) highest mass 283 (M+H), base peak 283. HRMS: (CI) calculated for C$_{16}$H$_{30}$O$_2$Si 283.2093, found 283.2094. 97.7% ee HPLC Chiralcel OD 1.0 mL/min 90.0:10.0 Hex:2-propanol. 4.67 min. minor enantiomer, 4.13 min. major enantiomer. [α]$_D$ (c 4.0, CHCl$_3$)=−68°.

(4S, 5S)-5-(tert-Butyldimethylsilanyloxy)-3,4-dimethylcyclohept-2-enone. t-BuLi (0.06 mL, 0.07 mmol) was added to the β-methoxy vinyl sulfone 33 (0.02 g, 0.05 mmol) in 1 mL THF at −78° C. over 2 min. The resulting bright orange solution was stirred at −78° C. for 5 min. Iodomethane (0.02 mL, 0.25 mmol) was added and was stirred for 15 min. Sat. NaHCO$_3$ (1 mL) was added and the reaction allowed to warm to room temperature. The mixture was extracted into diethyl ether (5 mL) and concentrated in vacuo. CHCl$_3$ (1 mL) was added followed by SiO$_2$ (0.500 g) and the reaction was stirred for 4 h. Monitoring the reaction was best accomplished by NMR. When complete, the silica was filtered and the solution was concentrated. Silica gel chromatography eluting with 1:4 ethyl acetate/hexanes provided the desired enone in 0.011 g, 84% yield. $^1$H NMR (CDCl$_3$): δ 5.85 (s, 1H), 3.87 (ddd, J=8.1 Hz, 5.6 Hz, 2.4 Hz, 1H), 2.84 (dq, J=16.3 Hz, 10.8 Hz, 1H), 2.49 (m, 2H), 2.04 (m, 1H), 1.92 (d, J=1.2 Hz, 3H), 1.82 (m, 1H), 1.14 (d, J=7.3 Hz, 3H), 0.88 (s, 9H), 0.06 (s, 6H). $^{13}$C NMR (CDCl$_3$): δ204.2, 155.4, 128.5, 72.7, 47.6, 37.8, 27.5, 26.4, 18.1, 18.0, −4.7, −4.9. LRMS: (EI) highest mass 211 (M+H−C$_4$H$_9$), base peak 75. HRMS: (EI) calculated for C$_{15}$H$_{28}$O$_2$Si 268.1859, found 268.1848. 99.2% ee HPLC Chiralcel AD 1.0 mL/min 99.0:1.0 Hex:2-propanol. 11.18 min. minor enantiomer, 9.27 min. major enantiomer. [α]$_D$ (c 0.4, CHCl$_3$)=+50°.

(4S, 5S)-5-(tert-Butyldimethylsilanyloxy)-2,4-dimethylcyclohept-2-enone. To a solution of a methyl substituted hydroxy dienyl sulfone (0.132 g, 0.33 mmol) in THF (3.3 mL) at −78° C. was slowly added MeLi (0.83 mL, 0.99 mmol) in Et$_2$O over a period of 10 min. The temperature was allowed to slowly rise to −10° C. and was then quenched by slow addition of a solution of sat'd NH$_4$Cl (5 mL). The temperature was allowed to rise to 25° C. and diethyl ether was added (10 mL). The organic layer was separated and the aqueous layer was extracted with diethyl ether (2×10 mL). The organic layers were combined, dried over MgSO$_4$, and concentrated. CH$_2$Cl$_2$ (6 mL) was added to the mixture followed by PCC (0.310 g, 1.44 mmol). The mixture was allowed to stir for 2 h. THF (5 mL) was added followed by 10% NaOH (2 mL), and the mixture was allowed to stir for 10 h. At this point H$_2$O (5 mL) was added followed by diethyl ether (10 mL) and the mixture separated, the aqueous layer was extracted with diethyl ether (2×10 mL). The combined organic layer were dried over MgSO$_4$ and concentrated. Purification was done by silica gel chromatography eluting with a 1:9 solution of ethyl acetate/hexanes to give 0.84 g of the desired enone as an oil in 88% yield. $^1$H NMR (CDCl$_3$): δ 6.06 (m, 1H), 3.65 (dt, J=8.2 Hz, 3.8 Hz, 1H), 2.75 (m, 1H), 2.59 (m, 1H), 2.48 (m, 1H), 1.95 (m, 1H), 1.80 (s, 3H), 1.79 (m, 1H), 1.17 (d, J=6.9 Hz, 3H), 0.89 (s, 9H), 0.06 (s, 6H). $^{13}$C NMR (CDCl$_3$): δ205.4, 144.1, 137.3, 73.8, 40.2, 37.9, 30.8, 25.8, 19.3, 18.0, −4.3, −4.8. LRMS: (EI) highest mass 268 (M+H), base peak 73. (CI) highest mass 269 (M+H), base peak 269. HRMS: (CI) calculated for C$_{15}$H$_{28}$O$_2$Si 269.1937, found 269.1930. 99.7% ee HPLC Chiralcel AD 1.0 mL/min 99.0:1.0 Hex:2-propanol. 3.70 min. minor enantiomer, 4.08 min. major enantiomer. [α]$_D$ (c 11.0, CHCl$_3$)=+139°.

Further Examples

Synthesis of Termini-Differentiated 6-Carbon Stereotetrads: An Alkylative Oxidation Strategy for Preparation of the C21-C26 Segment of Apoptolidin

| Compounds | Numbers in Experimental Below |
|---|---|
| (structure) | 22z |
| (structure) | 23z |
| (structure) | 24z |
| (structure) | 28z |
| (structure) | 29z |
| (structure) | 30z |
| (structure) | 31z |

-continued
| Compounds | Numbers in Experimental Below |
|---|---|
| 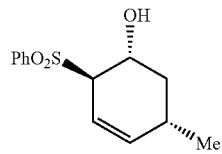 | 32z |
| 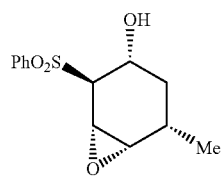 | 33z |
| 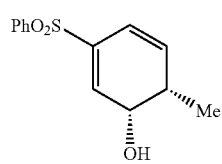 | 35z |
| 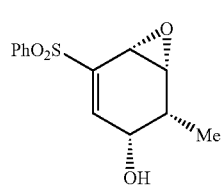 | 36z |
-continued
| Compounds | Numbers in Experimental Below |
|---|---|
| 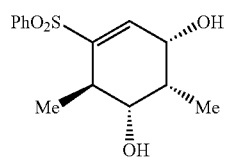 | 37z |
| 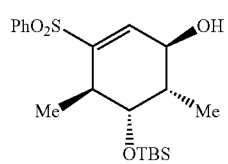 | 38z |
| 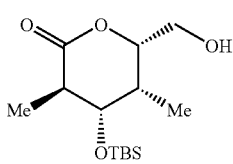 | 39z |
| 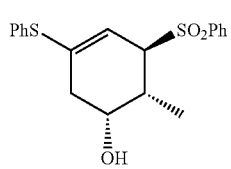 | 43β |
| Number in Experiment | $^1$H NMR | $^{13}$C NMR | LRMS | HRMS Or Microanalysis Calcd | HRMS Or Microanalysis Found | ee (%) | MP (° C.) | Misc (x-ray, etc) |
|---|---|---|---|---|---|---|---|---|
| 22z | Y | Y | | | | | | |
| 23z | Y | Y | Y | 283.1004 | 283.0998 | | | |
| 24z | Y | Y | | C: 61.88 H: 6.39 | C: 61.73 H: 6.25 | | 79.0-81.0 | |
| 28z | Y | Y | Y | 218.0765 | 218.0765 | | | |
| 29z | Y | Y | Y | 233.0636 | 233.0632 | 99% | 54.0-56.0 | |
| 30z | Y | Y | | C: 62.38 H: 5.64 | C: 62.12 H: 5.68 | | 63.0-65.0 | microanalysis |
| 31z | Y | Y | Y | 250.0664 | 250.0664 | | | |
| 32z | Y | Y | Y | 253.0898 | 253.0898 | | 72.0-74.0 | X-ray |
| 33z | Y | Y | Y | C: 58.19 H: 6.01 | C: 58.34 H: 5.84 | | 81.6-83.6 | X-ray |
| 35z | Y | Y | | C: 62.38 H: 5.64 | C: 62.57 5.67 | | 80.8-84.0 | |
| 36z | Y | Y | | C: 58.63 H: 5.30 | C: 58.34 H: 5.30 | | 73.2-75.2 | |
| 37z | Y | Y | Y | 283.1004 | 283.0999 | 98% | 112.0-114.0 | |
| 38z | Y | Y | | C: 60.57 H: 8.13 | C: 60.82 H: 8.07 | | 106.6-108.5 | |
| 39z | Y | Y | Y | 289.1835 | 289.1825 | | 85.0-87.8 | |
| 43β | Y | Y | Y | 361.0932 | 361.0926 | | | |

General Synthetic Procedures

All common reagents and solvents were purchased from commercial suppliers and used as received. Solvents were dried by standard methods: tetrahydrofuran (THF) and diethyl ether were distilled from sodium benzophenone ketyl. Benzene, toluene, dichloromethane ($CH_2Cl_2$), and acetonitrile ($CH_3CN$) were distilled from calcium hydride. Powdered 4 Å molecular sieves (Aldrich) were oven and/or flame activated under vacuum prior to use.

All glassware was oven dried and/or flame dried, evacuated, and purged with nitrogen. All reactions involving air and moisture-sensitive compounds were carried out under a nitrogen atmosphere, and the reaction flasks were fitted with rubber septa for the introduction of substrates and reagents via syringe. The progress of reactions was monitored by thin layer chromatography (TLC) in comparison with the starting material(s). TLC was performed on glass-backed silica gel 60 F 254 plates (EM reagents, 0.25 mm) and eluted with a mixture of ethyl acetate (EA) and hexanes (Hex) or the specified solvent solutions. Analytically pure samples were obtained from flash silica gel chromatography (SGC), using silica gel 60, 230-400 mesh, or from recrystalization of the crude products. Melting points were obtained on a MEL-TEMP capillary melting point apparatus and uncorrected. $^1$H-NMR spectra were recorded on Varian IONVA-300 (300 MHz) and Varian VXR (500 MHz) spectrometers. C-NMR spectra were recorded on Varian INOVA-300 (75 MHz) and Varian VXR (125 MHz) spectrometers. NMR spectra were determined in chloroform-$d_1$ ($CDCl_3$) solution and are reported in parts per million (ppm) from the residual chloroform (7.26 ppm and 77.00 ppm). Peak multiplicities in $^1$H-NMR spectra, when reported, are abbreviated as s (singlet), d (doublet), t (triplet), m (multiplet), and br (broad). Mass spectra were run by the Purdue University campus wide mass spectrometry facility. Low resolution EI and CI (isobutane) spectra were obtained on a Finnigan 4000 mass spectrometer with a Nova 4 data system with the molecular ion designated as "M$^+$". High resolution mass spectra were obtained on a Kratos MS-50 instrument.

Experimental Section

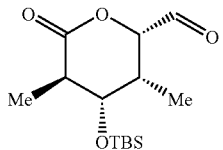

22z (2S, 3S, 4S, 5R)-4-(tert-Butyl-dimethyl-silanyloxy)-3,5-dimethyl-6-oxo-tetrahydro-pyran-2-carbaldehyde (22z). To a cold (−300° C.) mixture of 38 (165 mg, 0.416 mmol) and $NaHCO_3$ (35 mg, 0.42 mmol) in methylene chloride was bubbled $O_3$ for 1 h, then switched to $O_2$ for 5 min to expell excess ozone, followed by addition of methyl sulfide (0.5 mL). The resulting mixture was warmed to room temperature, and stirred for 5 h. The solvent was removed via rotary evaporation, dissolved in diethyl ether (20 mL), washed with $H_2O$, brine, and dried over $Na_2SO_4$. The ether was removed via rotary evaporation, and further dried in vacuo to afford 140 mg crude oily residue. Fairly pure aldehyde 22 (90% purity by $^1$H NMR) can be obtained with florisil column chromatography (ethyl acetate/hexanes; 1:3), but in a poor yield due to decomposition during column chromatography. $^1$H NMR ($CDCl_3$, 300 MHz): s, 1H), δ9.68 (s, 1H), 4.58 (dd, J=1.5, 4.5 Hz, 1H), 3.76 (dd, J=2.4, 4.5 Hz, 1H), 2.74 (m, 1H), 2.61 (m, 1H), 1.38 (d, J=7.5 Hz, 3H), 1.13 (d, J=6.9 Hz, 3H), 0.92 (s, 9H), 0.13 (s, 3H), 0.11 (s, 3H); $^{13}$C NMR ($CDCl_3$, 75 MHz): δ198.4, 172.0, 83.3, 73.8, 43.2, 34.9, 25.6, 17.9, 16.2, 10.2, −4.7, −4.8.

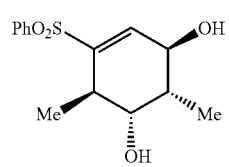

23z (1S, 2R, 3S, 4R)-5-Benzenesulfonyl-2,6-dimethyl-cyclohex-4-ene-1,3-diol (23z). To a mixture of 37z (1.06 g, 3.75 mmol), $PPh_3$ (2.95 g, 11.2 mmol), and $HCO_2H$ (0.90 mL, 5.62 mmol) in THF (37 mL) was added diethyl azodicarboxylate (1.87 mL, 11.2 mmol) dropwise via syringe at room temperature. After being stirred at room temperature for 2 h, the solution was concentrated via rotary evaporation. The residue was dissolved in methanol (40 mL), and excess $NaHCO_3$ was added. After being stirred at room temperature for 30 min, the solvent was removed via rotary evaporation, the residue was loaded onto silica gel, and eluted with ethyl acetate and hexanes mixture (1:1) to afford 1.0 g (95%) of 23 as a light yellow oil. $^1$H NMR ($CDCl_3$, 300 MHz): δ 7.88 (d, J=7.2 Hz, 2H), 7.51-7.65 (m, 3H), 6.93 (d, J=2.4 Hz, 1H), 4.21 (d, J=9 Hz, 1H), 3.66 (s, 1H), 2.49 (q, J=6.6 Hz, 1H), 1.94 (br s, 1H), 1.82 (m, 1H), 1.60 (br s, 1H), 1.18 (d, J=6.9 Hz, 3H), 1.15 (d, J=7.2 Hz, 3H); $^{13}$C NMR ($CDCl_3$, 75 MHz): δ 143.0, 139.7, 139.3, 133.5, 129.2, 128.0, 77.2, 70.4, 37.6, 35.7, 18.04, 14.6. MS(CI) m/z 283 [M+H]$^+$; HRMS (EI) calcd for $C_{14}H_{19}O_4S$, 283.1004; found, 283.0998.

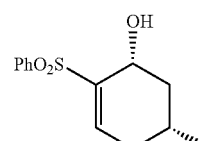

24z (1R, 5R)-2-Benzenesulfonyl-5-methyl-cyclohex-2-enol (24z). A solution of ketone 28z (45 g, 206 mmol) and $CeCl_3 \cdot 7H_2O$ (106 g, 284 mmol) in MeOH (500 ml) was cooled to 0° C. Under mechanical stirring, 10.6 g (279 mmol) of $NaBH_4$ was added in small portions. When the reaction was complete by TLC, $H_2O$ was slowly added until no further bubbling was observed, then a total of 500 ml of $H_2O$ was added. The solution was then extracted with $CH_2Cl_2$ (3×300 mL). If the solution forms an emulsion, 10-20 mL of aqueous 5% HCl can be added which will clear the solution and break any emulsion. The combined organic layers were dried over $Na_2SO_4$, and concentrated via rotary evaporation to afford 43 g analytically pure compound, which was used directly for next oxidation step. It was dissolved in MeOH (800 mL) and THF (200 mL), and cooled to 0° C., under mechanical stirring, a solution of 380 g (600 mmol) of Oxone in $H_2O$ (800 mL) was added in portions. The cooling bath was removed after half of the Oxone solution was added, and the reaction was stirred for further 24 h at room temperature, then 300 mL of $CH_2Cl_2$ was added, the layers were separated, and the aqueous layer was further extracted with $CH_2Cl_2$ (4×300 mL). The combined organic layers were dried over $Na_2SO_4$, and concentrated via rotary evaporation to give 46.9 g (95%) of an analytically pure white solid. Mp 79.0-81.0° C.; $^1$H NMR (CDCl$_3$, 300 MHz): 67.91-7.95 (m, 2H), 7.53-7.68 (m, 3H), 7.14 (dd, J=5.7, 2.7 Hz, 1H), 4.54 (m, 1H), 3.38 (br s, 1H), 2.38 (dm, J=18.9 Hz, 1H), 2.11 (m, 1H), 1.94 (ddt, J=18.9, 9.8, 2.7 Hz, 1H), 1.76 (m, 1H), 1.41 (td, J=12.4, 8.9 Hz, 1H), 1.00 (d, J=6.6 Hz, 3H). $^{13}$C NMR (CDCl$_3$, 75 MHz): δ142.9, 142.3, 140.9, 133.6, 129.4, 127.9, 65.6, 40.1, 34.6, 27.5, 21.3. Anal. Calcd for C$_{13}$H$_{16}$O$_3$S: C, 61.88; H, 6.39. Found: C, 61.73; H, 6.25.

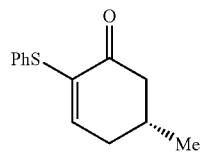

28z (5R)-5-Methyl-2-phenylsulfanyl-cyclohex-2-enone (28z). To a solution of sulfoxide 27z (56.0 g, 0.237 mol) and Ac$_2$O (27.0 mL, 0.284 mol) in CH$_2$Cl$_2$ (800 mL) was added 0.5 mL (7.7 mmol) of methylsulfonic acid. After being stirred at room temperature for 14 h, saturated aqueous NaHCO$_3$ was added in small portions until no more CO$_2$ was generated. The organic layer was separated, and the aqueous layer extracted with CH$_2$Cl$_2$ (2×100 mL). The combined organic layers were washed with brine and dried over Na$_2$SO$_4$. The solvent was removed via rotary evaporation to give 48.6 g (94%) of analytically pure 28 as a light yellow oil. Compound 28 was used for next step without further purification. If necessary, it can be purified with flash column chromatography (ethyl acetatelhexanes; 1:10). $^1$H NMR (CDCl$_3$, 300 MHz) δ 7.30-7.42 (m, 5H), 6.46 (dd, J=3.0, 6.0 Hz, 1H), 2.56-2.67 (m, 1H), 2.37-2.46 (m, 1H), 2.18-2.28 (m, 2H), 2.00-2.11 (m, 1H), 1.05 (d, J=6.0 Hz, 3H); $^{13}$C NMR (CDCl$_3$, 75 MHz) δ 195.0, 144.4, 136.8, 133.4, 131.8, 129.2, 127.9, 46.3, 35.0, 30.1, 20.6. MS(EI) m/z 218 [M]$^+$; HRMS (ED) calcd for C$_{13}$H$_{14}$OS, 218.0765; found, 218.0765.

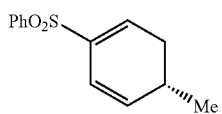

29z (4S)-4-Methyl-cyclohexa-1,5-dienesulfonyl)-benzene (29z). To a solution of 24z (355 mg, 1.40 mmol) and Et$_3$N (0.19 mL, 1.40 mmol) in THF (10 mL) at 0° C. was added 0.11 mL (1.40 m-mol) of MsCl dropwise. After stirring at 0° C. for 1 h, the reaction mixture was cooled to −78° C., and freshly prepared LiHMDS (2.8 mL, 1.0 M in THF, 2.8 mmol) was added dropwise over 20 min. After stirring at −78° C. for 15 min, the reaction was quenched with saturated aqueous NH$_4$Cl, diluted with ether, separated, further extracted with ether. The organic layers were washed with brine, dried over Na$_2$SO$_4$, and concentrated via rotary evaporation. The crude residue was purified with flash column chromatography (ethyl acetate/hexanes; 1:3) to provide 303 mg (92% yield) of 29 as a white solid with 99% ee by HPLC (Chiralpak AD 1.0 ml/min; 95:5 Hex:2-propanol, 19.57 min for minor enantiomer, 20.51 min for major enantiomer). Mp 54.0-56.0° C.; $^1$H NMR (CDCl$_3$, 300 MHz): δ 7.85 (m, 2H), 7.48-7.61 (m, 3H), 6.91 (t, J=4.2 Hz, 1H), 6.01 (d, J=10.3 Hz, 1H), 5.81 (dd, J=10.3, 3.9 Hz, 1H), 2.38-2.57 (m, 2H), 2.15 (ddd, J=17.1, 11.1, 4.5 Hz, 1H), 0.98 (d, J=6.6 Hz, 3H); $^{13}$C NMR (CDCl$_3$, 75 MHz): δ139.9, 138.2, 136.4, 134.5, 133.2, 129.1, 127.6, 117.4, 30.6, 26.9, 19.4. MS(EI) m/z 233 [M−H]$^+$; HRMS (EI) calcd for C$_{13}$H$_{13}$O$_2$S, 233.0636; found, 233.0632.

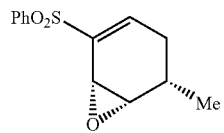

30z (3S, 4S, 5S)-2-Benzenesulfonyl-5-methyl-7-oxa-bicyclo[4.1.0]-hept-2-ene (30z). mCPBA oxidation: To a solution of dienyl sulfone 29z (108 mg, 0.461 mmol) in methylene chloride (5 mL) was added 151 mg (70-75% purity) of mCPBA in one portion. After stirring at room temperature for 4 h, aqueous NaHSO$_3$ solution was added, and the organic layer was separated. The aqueous layer was extracted with methylene chloride (2×5 mL), the combined organic layers were washed with saturated aqueous sodium carbonate, brine, dried over anhydrous sodium sulfate, concentrated via rotary evaporation. The crude residue was purified with flash column chromatography (ethyl acetate/hexanes; 1:4) to give 97 mg (84%) of a mixture of two diastereomers (30:31; 3:2) verified by $^1$H NMR.

Jacobsen epoxidation: The mixture of dienyl sulfone 29z (106 mg, 0.453 mmol), (R,R)-(−)-N,N'-Bis(3,5-di-tert-butylsalicylidene-1,2-cyclohexanediamino-manganese(III) chloride (14 mg, 0.0226 mmol), ammonia acetate (35 mg, 0.453 mmol) in methylene chloride (2.0 mL) and methanol (2.0 mL) was cooled to 0° C., and 0.4 mL of 30% H$_2$O$_2$ was added in portions under mechanically stirring (550 rps). After being stirred at 0° C. for 5 h, aqueous NaHSO$_3$ was added, extracted with methylene chloride (3×10 mL). The combined organic layers were washed with brine, dried over Na$_2$SO$_4$, concentrated via rotary evaporation, and purified with flash column chromatography (ethyl acetate/hexanes; 1:2) to afford 62 mg (55%) of a mixture of two diastereomers (30:31; 6:1) verified by $^1$H NMR.

From 33z. To a solution of 33z (1.59 g, 5.92 mmol) and Et$_3$N (2.1 mL, 14.8 mmol) in CH$_2$Cl$_2$ (50 mL) at 0° C. was slowly added 0.60 mL (7.75 mmol) of MsCl via syringe over 10 min. After stirring at 0° C. for further 5 min, the reaction mixture was quenched with saturated aqueous NH$_4$Cl, and extracted with CH$_2$Cl$_2$ (3×30 mL). The organic layers were washed with brine, dried over Na$_2$SO$_4$, and concentrated via rotary evaporation. The crude residue was purified with flash column chromatography (ethyl acetate/hexanes; 1:4) to afford 1.41 g (95%) of 30 as a white solid. Mp 63.0-65.0° C.; $^1$H NMR (CDCl$_3$, 300 MHz): δ7.90-7.93 (m, 2H), 7.53-7.68 (m, 3H), 7.15 (dt, J=7.2, 2.4 Hz, 1H), 3.71 (dd, J=4.2, 2.4 Hz, 1H), 3.39 (ddd, J=4.2, 2.1, 1.2 Hz, 1H), 2.33 (m, 1H), 1.90 (m, 2H), 1.26 (d, J=6.6 Hz, 3H); $^{13}$C NMR (CDCl$_3$, 75 MHz): δ 142.3, 140.1, 138.40 133.8, 129.7, 128.0, 59.5, 47.2, 29.5, 26.5, 18.7. Anal. Calcd for C$_{13}$H$_{14}$O$_3$S: C, 62.38; H, 5.64. Found: C, 62.12; H, 5.68.

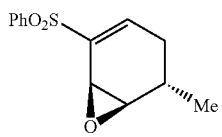

(2R, 3R, 4S)-2-Benzenesulfonyl-5-methyl-7-oxa-bicyclo [4.1.0]-hept-2-ene (31z). $^1$H NMR (CDCl$_3$, 300 MHz): δ 7.90-7.92 (m, 2H), 7.53-7.68 (m, 3H), 7.08 (dt, J=7.2, 2.4 Hz, 1H), 3.64 (dd, J=4.2, 2.4 Hz, 1H), 3.33 (ddd, J=4.2, 2.1, 1.8 Hz, 1H), 2.50 (m, 1H), 2.38 (ddd, J=18.0, 7.8, 2.1 Hz, 1H), 2.13 (dd, J=18.0, 7.2 Hz, 1H), 0.89 (d, J=7.2 Hz, 3H); $^{13}$C NMR (CDCl3, 75 MHz): 140.0, 139.6, 137.5, 133.4, 129.3, 127.5, 58.4, 44.9, 28.2, 24.5, 15.5; MS(EI) m/z 250 [M]+; HRMS (EI) calcd for C13H14O3S, 250.0664; found, 250.0664.

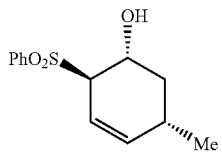

(1R, 2R, SS)-2-Benzenesulfonyl-5-methyl-cyclohex-3-enol (32z). To a solution of compound 24z (6.62 g, 26.2 mmol) in CH$_2$Cl$_2$ (40 mL) was added 10 drops of DBU, and the resulting mixture was stirred at room temperature for 24 h. The solution was concentrated via rotary evaporation, the crude residue was separated with flash column chromatography (CH$_2$Cl$_2$/CH$_3$CN; 10:1) to provide 4.37 g (66%) of compound 32 as a white solid, and 1.61 g (24%) of starting material 24, which can be re-submitted to isomerization. Mp 72.0-74.0° C.; $^1$H NMR (CDCl$_3$, 300 MHz): □7.94 (m, 2H), 7.58-7.78 (m, 3H), 5.76 (d, J=9.9 Hz, 1H), 5.5 (dt, J=9.9, 2.4 Hz, 1H) 4.09 (m 1H), 3.84 (m, 2H), 2.11 (m, 2H), 1.30 (m, 1H), 1.01 (d, J=6.9 Hz, 3H); $^{13}$C NMR (CDCl$_3$, 75 MHz): □ 140.4, 136.2, 134.4, 129.6, 129.3, 116.8, 70.7, 66.6, 38.4, 30.2, 20.9. MS(CI) m/z 253 [M+H]$^+$; HRMS (CI) calcd for C$_{13}$H$_{17}$O$_3$S, 253.0898; found, 253.0898.

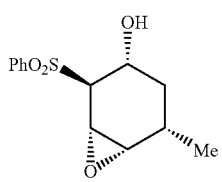

(1R, 2S, 3S, 4S, 5S)-2-Benzenesulfonyl-5-methyl-7-oxa-bi-cyclo-[4.1.0]-heptan-3-ol (33z). To a solution of 32 (2.29 g, 9.07 mmol) in CH$_2$Cl$_2$ (90 mL) was added mCPBA (13.5 g, 70-75% purity) in portions. After stirring at room temperature for 3 days, the excess mCPBA was quenched with saturated aqueous NaHSO$_3$, the organic layer was separated, and the aqueous layer was extracted with ethyl acetate (3×100 mL). The combined organic layers were washed with saturated aqueous Na$_2$CO$_3$ twice, brine, and dried over Na$_2$SO$_4$. The solvent was removed via rotary evaporation, and the crude residue was purified with flash column chromatography (ethyl acetate/hexanes; 1:2) to afford 2.09 g (86%) of 33 as a white solid. Mp 81.6-83.6° C.; $^1$H NMR (CDCl$_3$, 300 MHz): δ 8.02 (m, 2H), 7.64-7.80 (m, 3H), 4.17 (ddd, J=12.6, 9.6, 3.9 Hz, 1H), 3.72 (s, 1H), 3.48 (d, J=9.0 Hz, 1H), 3.26 (d, J=3.6 Hz, 1H), 3.07 (d, J=3.3 Hz, 1H), 2.07 (m, 1H), 1.75 (dt, J=12.6, 4.8 Hz, 1H), 1.35 (m, 1H), 1.15 (d, J=6.9 Hz, 3H); $^{13}$C NMR (CDCl$_3$, 75 MHz): δ137.5, 134.9, 129.5, 129.0, 67.3, 65.8, 57.0, 50.5, 32.4, 28.8, 18.4. Anal. Calcd for C$_{13}$H$_{16}$O$_4$S: C, 58.19; H, 6.01. Found: C, 58.34; H, 5.84.

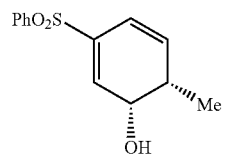

(1S, 6S)-3-Benzenesulfonyl-6-methylcyclohexa-2,4-dienol (35z). Procedure 1: A solution of 30 (2.77 g, 11.1 mmol) in THF (100 mL) was cooled at −78° C., and a freshly prepared LiHMDS solution (12.0 mL, 1.0 M in THF, 12.0 mmol) was added dropwise. After stirring at −78° C. for 15 min, the saturated aqueous NH$_4$Cl was added, the resulting solution was extracted with ethyl acetate (3×50 mL). The combined organic layers were dried over Na$_2$SO$_4$ and concentrated via rotary evaporation. The crude residue was purified with flash column chromatography (ethyl acetate/hexanes; 1:3) to provide 2.68 g (97%) of 35 as a white solid. $^1$H NMR (CDCl$_3$, 300 MHz): δ7.87 (m, 2H), 7.63 (m, 1H), 7.55 (m, 2H), 6.99 (dd, J=5.1, 1.2 Hz, 1H), 6.16 (dt, J=9.6, 1.8 Hz, 1H), 5.89 (dd, J=9.6, 3.6 Hz, 1H), 4.36 (dd, J=6.9, 5.1 Hz, 1H), 2.49 (m, 1H), 1.8 (bs, 1H), 1.14 (d, J=7.5 Hz, 3H); $^{13}$C NMR (CDCl$_3$, 75 MHz): δ 139.6, 139.4, 137.1, 134.3, 133.9, 129.6, 128.2, 117.6, 67.2, 34.6, 12.5. Anal. Calcd for C$_{13}$H$_{14}$O$_3$S: C, 62.38; H, 5.64. Found: C, 62.57; H, 5.67.

Procedure 2: Compound 43β (34.9 mg, 0.097 mmol) was dissolved in dry methylene chloride (5 mL), and 81 µL of Et$_3$N (0.58 mmol) was added at room temperature, followed by addition of 88 µL (0.485 mmol) of TMSOTf. This mixture was brought to reflux under N$_2$, and stirred for 4 h until the starting material was consumed (monitored by TLC). The reaction mixture was cooled to 0° C., and the excess of TMSOTf was quenched by adding MeOH (1.0 mL, 24.7 mmol), diluted with EtOAc (5 mL), separated, and the aqueous layer was extracted with EtOAc (2×5 mL). The combined organic layers were dried over MgSO$_4$ and concentrated. The residual mixture was dissolved in methylene chloride (5 mL), and solid m-CPBA (41 mg, ~90% purity, 0.21 mmol) was added in portions. The purity of the m-CPBA is crucial for good yields. The reaction mixture was left stirring for 6 h. 2 mL of saturated solution of NaHSO$_3$ was added to the mixture, followed by 5 mL of EtOAc. The organic layer was separated, and the aqueous layer was extracted with EtOAc (3×5 mL). The combined organic layers were washed with saturated NaHCO$_3$ (3×10 mL), followed by brine (5 mL), and dried over Na$_2$SO$_4$. Flash column chromatography (EtOAc-hexane; 1:3) afforded 21.7 mg (89%) of 35.

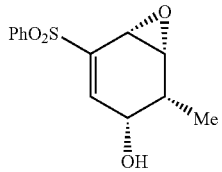

36z

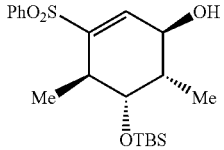

38z (1S, 2R, 3R, 4R)-5-Benzenesulfonyl-2-methyl-7-oxa-bicyclo-[4.1.0]hept-4-en-3-ol (36z). To a mixture of 35 (330 mg, 1.32 mmol) and Mo(CO)$_6$ (7 mg, 0.026 mmol) in benzene (13 mL) was added 0.40 mL of tert-butyl hydroperoxide (~2 mmol, 5.0-6.0M in decane) via syringe, the resulting mixture was brought to reflux under nitrogen. After stirring at reflux for 1.5 h, the reaction mixture was cooled to room temperature, and the solution was loaded to silica gel directly, eluted with CH$_2$Cl$_2$—CH$_3$CN (10:1) mixture. The organic was removed via rotary evaporation to afford 330 mg (94%) of 36 as a white solid. Mp 73.2-75.2° C.; $^1$H NMR (CDCl$_3$, 300 MHz): □ 7.98 (m, 2H), 7.59-7.74 (m, 3H), 7.38 (dd, J=6.6, 2.4 Hz, 1H), 4.15 (br s, 1H), 3.90 (dd, J=4.5, 2.7 Hz, 1H), 3.57 (dd, J=4.5, 2.4 Hz, 1H), 2.03 (m, 1H), 1.82 (br s, 1H), 1.43 (d, J=7.2 Hz, 3H); $^{13}$C NMR (CDCl$_3$, 75 MHz): δ141.6, 141.5, 139.1, 134.3, 129.9, 128.3, 66.3, 60.8, 48.5, 31.9, 13.3; Anal. Calcd for C$_{13}$H$_{14}$O$_4$S: C, 58.63; H, 5.30. Found: C, 58.34; H, 5.30.

(1S, 4R, 5S, 6S)-3-Benzenesulfonyl-5-(tert-butyl-dimethyl-silanyloxy)-4,6-dimethyl-cyclohex-2-enol (38). The mixture of diol 23 (585 mg, 2.07 mmol), TBSCl (1.0 g, 6.63 mmol), and imidazole (564 mg, 8.28 mmol) in DMF (5.0 mL) was stirred at 70° C. for 20 h under nitrogen. After being quenched by aqueous NH$_4$Cl, the reaction mixture was extracted with diethyl ether (3×20 mL). The organic layers were washed with brine, dried over Na$_2$SO$_4$, concentrated via rotary evaporation, and further dried in vacuo. The crude residue was dissolved in THF (20 mL), and a THF solution (2.3 mL, 2.3 mmol, 1M) of TBAF was added at room temperature. After being stirred at room temperature for 30 min, the solution was quenched with aqueous NH$_4$Cl solution, and the product was extracted with ethyl acetate (3×10 mL). The organic layers were dried over Na$_2$SO$_4$ and concentrated via rotary evaporation. The crude product was purified by flash column chromatography (ethyl acetate/hexanes; 1:4) to afford 690 mg (84%) of 38 as a white solid. Mp 106.6-108.5° C.; $^1$H NMR (CDCl$_3$, 300 MHz): δ 7.86 (d, J=7.5 Hz, 2H), 7.48-7.62 (m, 3H), 7.00 (d, J=2.1 Hz, 1H), 4.13 (d, J=9.3 Hz, 1H), 3.54 (s, 1H), 2.27 (q, J=6.9 Hz, 1H), 2.01 (s, 1H), 1.78 (m, 1H), 1.24 (d, J=7.2 Hz, 3H), 1.09 (d, J=6.3 Hz, 3H), 0.64 (s, 9H), −0.06 (s, 3H), −0.35 (s, 3H); $^{13}$C NMR (CDCl$_3$, 75 MHz): δ 142.8, 140.4, 139.4, 133.3, 129.2, 128.2, 77.9, 70.7, 37.7, 36.3, 25.6, 18.5, 17.7, 14.9, −4.7, −5.3. Anal. Calcd for C$_{20}$H$_{32}$O$_4$SSi: C, 60.57; H, 8.13. Found: C, 60.82; H, 8.07.

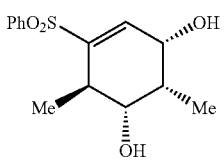

37z (1R, 2R, 3S, 4R)-5-Benzenesulfonyl-2,6-dimethylcyclohex-4-ene-1,3-diol (37z). To a suspension of CuI (27 mg, 0.14 mmol) in THF (12 mL) was added methyllithium solution (100 μL, 0.14 mmol, 1.4M in ether) at −30° C. After stirring at −30° C. for 15 min, a solution of trimethylaluminum (1.57 mL, 3.14 mmol, 2.0M in toluene) was added, and the resulting turbid mixture slowly warmed to 0° C. over 30 min. After the mixture was re-cooled to −78° C., a solution of epoxide 36 (379 mg, 1.42 mmol) in THF (2 mL) was added. The resultant solution was slowly warmed to 10° C. over 10 h under magnetic stirring, quenched with 5% HCl aqueous solution, and extracted by ethyl acetate (3×30 mL). The combined organic layers were washed with saturated aqueous NH$_4$Cl, dried over Na$_2$SO$_4$, and concentrated via rotary evaporation. The crude residue was purified with flash column chromatography (ethyl acetate/hexanes; 1:1) to afford 370 mg (92%) of 37 as a white solid with >98% ee by HPLC (ChiralPak AD, 5 cm, 1.0 ml/min, hexane/2-propanol: 90/10, 6.10 min for major enantiomer, 7.65 min for minor enantiomer). Mp 112.0-114.0° C.; $^1$H NMR (CDCl$_3$, 300 MHz): δ7.95 (m, 2H), 7.56-7.67 (m, 3H), 7.14 (d, J=4.8 Hz, 1H), 4.12 (t, J=4.8 Hz, 1H), 3.78 (s, 1H), 2.61 (dq, J=2.4, 7.2 Hz, 1H), 2.11 (br s, 2H), 1.98 (m, 1H), 1.28 (d, J=7.2 Hz, 3H), 1.16 (d, J=7.2 Hz, 3H); $^{13}$C NMR (CDCl$_3$, 75 MHz): δ 142.8, 138.9, 137.9, 133.4, 129.1, 127.9, 75.8, 66.7, 37.7, 31.0, 17.4, 13.3. MS(CI) m/z 283 [M+H]$^+$; HRMS (CI) calcd for C$_{14}$H$_{19}$O$_4$S, 283.1004; found, 283.0999.

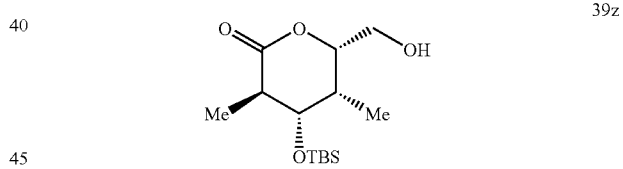

39z (3R, 4S, 5S, 6S)-4-(tert-Butyl-dimethyl-silanyloxy)-6-hydroxymethyl-3,5-dimethyl-tetrahydro-pyran-2-one (39). The crude aldehyde 22 (140 mg) obtained from the previous ozonolysis was dissolved in methylene chloride (4 mL), cooled to −78° C., then 0.65 mL of LiAlH(t-Bu)$_3$ solution (0.65 mmol, 1M in THF) was added. After being stirred at −78° C. for 1 h, the solution was quenched with 5% aqueous HCl, extracted with ethyl acetate (3×10 mL). The combined organic layers were washed with aqueous NaHCO$_3$, dried over Na$_2$SO$_4$, and concentrated via rotary evaporation. The crude residue was purified with silica gel column chromatography (ethyl acetate/hexanes; 1:1) to afford 60 mg (50% 2 steps) of alcohol 39 as a white solid. $^1$H NMR (CDCl$_3$, 300 MHz): δ 4.39 (m 1H), 3.93 (dd, J=7.5, 12.3 Hz, 1H), 3.79 (dd, J=4.2, 9.0 Hz, 1H), 3.69 (dd, J=4.2, 12.3 Hz, 1H), 2.56 (m, 1H), 2.20 (m, 1H), 1.38 (d, J=7.2 Hz, 3H), 1.01 (d, J=7.2 Hz, 3H), 0.95 (s, 9H), 0.14 (s, 3H), 0.13 (s, 3H); $^{13}$C NMR (CDCl$_3$, 75 MHz): δ 173.3, 80.5, 74.1, 63.1, 40.9, 35.2, 25.6, 17.9, 14.9, 6.1, −4.4, −4.9. MS(CI) m/z 289 [M+H]$^+$; HRMS (CI) calcd for C$_{14}$H$_{29}$O$_4$Si, 289.1835; found, 289.1825.

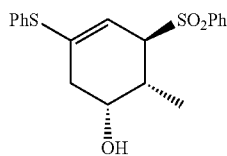

43β

(1R, 6R)-5-Benzenesulfonyl-6-methyl-3-phenylsulfanyl-cyclohex-3-enol (43β): To a solution of dienyl sulfone 40 (1.03 g, 4.30 mmol) in THF (50 mL) at −78° C. was slowly added MeLi Et$_2$O solution (1.4M, 9.3 mL, 13.0 mmol). The resulting orange solution was left stirring for 15 minutes to ensure complete alkylation. After 15 minutes a solution of phenyl disulfide (2.84 g, 13.0 mmol) in THF (5 mL) was added via cannula. The temperature was allowed to rise to 25° C. and the reaction mixture was left stirring for 8 h. A solution of saturated NH$_4$Cl (50 mL) was added to the mixture followed by Et$_2$O (100 mL). The aqueous phase was extracted with Et$_2$O (2×100 mL) and the combined organic extracts dried over MgSO$_4$ and concentrated. The product was purified via column chromatography using silica gel to give 1.26 g (82%) of pure 43β (one diastereomer). $^1$HNMR (300 MHz, CDCl$_3$) δ 7.77 (m, 2H), 7.63 (m, 1H), 7.51 (m, 2H), 7.35 (m, 5H), 5.29 (dt, J=1.4, 4.3 Hz, 1H), 4.19 (m, 1H), 3.62 (m, 1H), 2.47 (m, 1H), 2.31 (m, 1H), 2.15 (m, 1H), 1.12 (d, J=6.9 Hz, 3H). $^{13}$C NMR (75 MHz, CDCl$_3$) δ 140.1, 137.7, 133.7, 133.5, 131.4, 129.3, 129.1, 128.9, 128.4, 113.9, 69.1, 67.3, 34.7, 32.3, 14.1; LRMS (CI): m/z 361 (M+H)$^+$, 219 (Base peak); HRMS (CI): Calculated for C$_{19}$H$_{21}$O$_3$S$_2$ 361.0932, found 361.0926.

It is to be understood by those skilled in the art that the foregoing description and examples are illustrative of practicing the present invention, but are in no way limiting. Variations of the detail presented herein may be made without departing from the spirit and scope of the present invention as defined by the following claims.

What is claimed is:
1. The compound
   (1R)-(3-Benzenesulfonylcyclohepta-2,4-dienyloxy)-trimethylsilane;
   (1R, 2R, 3R)-3-Benzenesulfonyl-2-methyl-5-phenylsulfanylcyclohept-4-enol;
   (1R,2R)-(3-Benzenesulfonyl-2-methyl-5-phenylsulfanyl-cyclohept-4-enyloxy)-trimethylsilane;
   (1R,2S)-3-Benzenesulfonyl-2-methyl-5-phenylsulfanyl-cyclohept-4-enyloxy)-tert-butyldimethylsilane;
   (1R, 2S)-2-Methyl-5-phenylsulfanylcyclohepta-3,5-dienol;
   (1R,2R)-tert-Butyldimethyl-(2-methyl-5-phenylsulfanyl-cyclohepta-3,5-dienyloxy)-silane;
   (1S, 2S, 7S)-2,7-Dimethyl-4-phenylsulfanylcyclohepta-3,5-dienol;
   (1S, 2S, 7S)-4-Benzenesulfonyl-2,7-dimethylcyclohepta-3,5-dienol;
   (1S,2S,7S)-(4-Benzenesulfonyl-2,7-dimethylcyclohepta-3,5-dienyloxy)-tert-butyldimethylsilane;
   (1S,2R,7S)-2-Dimethylaminomethyl-7-methyl-4-phenyl-sulfanylcyclohepta-3,5-dienol;
   (1S, 2S, 3R, 4R, 5S)-7-Benzenesulfonyl-3,5-dimethylcyclohept-6-ene-1,2,4-triol;
   (1S,2S,5S,6R,7S)-3-Benzenesulfonyl-6-(tert-butyldimethylsilanyloxy)-5,7-dimethylcyclohept-3-ene-1,2-diol;
   (1S, 2S, 3R)-Acetic acid 3-benzenesulfonyl-2-methyl-5-oxocycloheptylester;
   (1E,3Z,5R,6S)-2-(tert-Butyldimethylsilanyloxy)-5-methyl-6-triisopropylsilanyloxycyclohepta-1,3-diene;
   1R,2R,3R,4S,6S)-7-(tert-Butyldimethylsilanyloxy)-2,3-dihydroxy-4-methyl-5-triisopropylsilanyloxycycloheptanone;
   (1R,2R, 3R, 4S, 6S)-7-(tert-Butyldimethylsilanyloxy)-2-hydroxy-3-methoxy-4-methyl-5-triisopropylsilanyloxycycloheptanone;
   (2S, 4S, 5R, 6R)-2-(tert-Butyldimethylsilanyloxy)-6-methoxy-5-methyl-7-oxo-4-triisopropylsilanyloxyheptanoic acid methyl ester;
   (1R,5S,6R,7S)-3-Benzenesulfonyl-6-(tert-butyldimethylsilanyloxy)-5,7-dimethylcyclohept-3-enol;
   (1S,5S,6R,7S)-3-Benzenesulfonyl-6-(tert-butyldimethylsilanyloxy)-5,7-dimethylcyclohept-2-enol;
   (1S,5S,6R,7S)-3-Benzenesulfonyl-6-(tert-butyl-dimethylsilanyloxy)-5,7-dimethylcyclohept-3-enol;
   (1S,4S,5R,6R,7S)-2-Benzenesulfonyl-5,7-bis-(tert-butyldimethylsilanyloxy)-4,6-dimethylcyclohept-2-enol;
   (3S,4R,5R,6S,7S)-1-Benzenesulfonyl-4,6-bis-(tert-butyldimethylsilanyloxy)-7-methoxy-3,5-dimethylcycloheptene;
   (2S, 3S, 4R, 5S, 6R)-3,5-Bis-(tert-butyldimethylsilanyloxy)-2-methoxy-4,6-dimethyl-7-oxoheptanoic acid methyl ester;
   (3S, 7S)-1-Benzenesulfonyl-3-methoxy-7-methylcycloheptene; or
   (S)-4-Methylcyclohept-2-enone.
2. A compound selected from compounds of the formulae:

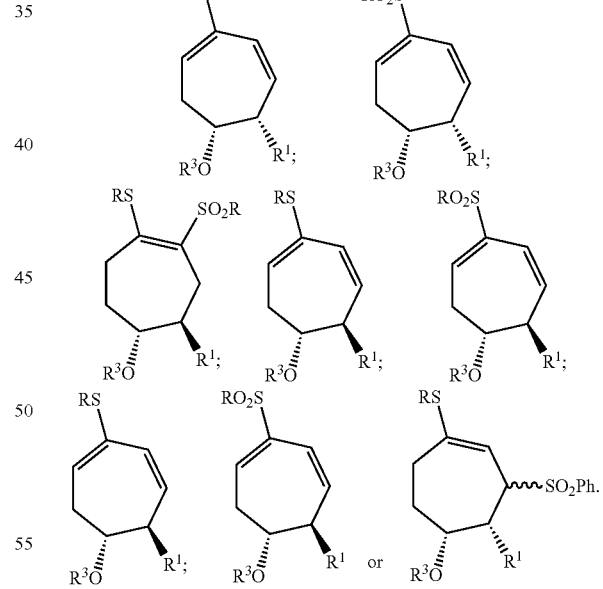

wherein:
   $R^1$ is a C$_1$-C$_5$ alkyl group;
   $R^2$ and $R^3$ are independently selected from the group consisting of H, a C$_1$-C$_4$ alkyl group, a trimethyl silyl group and a tertiarybutyl dimethyl silyl group; and
   R is a phenyl or substituted phenyl group wherein the substituted phenyl group is substituted in one instance at the ortho, meta or para position of the phenyl group with a C$_1$-C$_4$ alkyl group, a halogen (F, Cl, Br, I) a nitro group, an amine, hydroxyl, a $C_1$-$C_4$ alkyl ester, a $C_1$-$C_4$ alkylether or acyl group, and stereoisomers thereof.

3. A compound of claim 2, wherein the compound is produced by oxidation of dienylsulfides through addition of an oxidizing agent.

4. A compound of claim 2, wherein the compound is made by a process in which reaction of allyl sulfones with TMS triflate and an amine in a solvent at reflux effects regiospecific elimination to yield dienylsulfides; the dienylsulfides are oxidized through addition of an oxidizing agent; and wherein the entire process optionally can be preformed in a single pot.

5. A compound of claim 2, wherein the compound is made by:

(a) reacting allyl sulfones of the formula

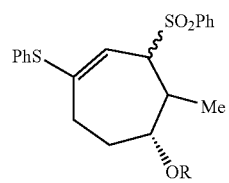

with TMS triflate and an amine in a solvent, at reflux to yield a dienylsulfide of the formula

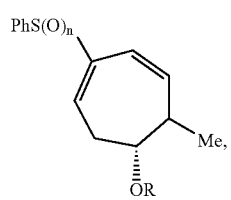

and oxidizing the dienylsulfide with an oxidizing agent where R is $C_1$-$C_5$ alkyl, phenyl, substituted phenyl wherein the substituted phenyl group is substituted in one instance at the ortho, meta or para position of the phenyl group with the $C_1$-$C_4$ alkyl group, a halogen (F, Cl, Br, I), a nitro group, an amine, hydroxyl, a $C_1$-$C_4$ alkyl ester, a $C_1$-$C_4$ alkylether or acyl group, vinyl, alkynyl, trimethylsilyl or t-butyldimethylsilyl and n=0 or 2.

6. A compound of claim 2, wherein the compound is made by alkylating an epoxyvinylsulfone of the formula

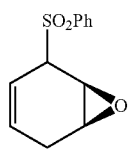

in a reaction medium comprising $(R)_2CuLi$ and a solvent, where R is a $C_1$ to $C_5$ alkyl and wherein the reaction optionally can be performed in a single pot.

7. A compound of claim 2, wherein the compound is made by oxidizing an allylic alcohol of the formula

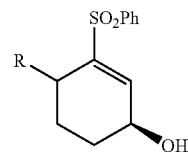

where R is a $C_1$ to $C_5$ alkyl, phenyl, substituted phenyl wherein the substituted phenyl group is substituted in one instance at the ortho, meta or para position of the phenyl group with a $C_1$-$C_4$ alkyl group, a halogen (F, Cl, Br, I) a nitro group, an amine, hydroxyl, a $C_1$-$C_4$ alkyl ester, a $C_1$-$C_4$ alkylester or acyl group, vinyl, alkynyl, trimethylsilyl or t-butyldimethylsilyl to yield a β-sulfonyl enone of the formula

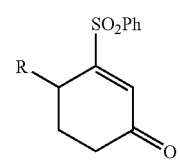

wherein the β-sulfonyl enone is subjected to Michael addition of heterocuprates and subsequent β-elimination of sulfinate, and wherein the reactions optionally are performed in a single pot.

8. A compound of claim 2, wherein the compound is made by reacting a sulfone of the formula

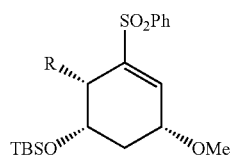

where R is a $C_1$ to $C_5$ alkyl, phenyl, substituted phenyl wherein the substituted phenyl group is substituted in one instance at the ortho, meta or para position of the phenyl group with a $C_1$-$C_4$ alkyl group, a halogen (F, Cl, Br, I), a nitro group, an amine, hydroxyl, a $C_1$-$C_4$ alkyl ester, a $C_1$-$C_4$ alkylether or acyl group, vinyl, alkynyl, trimethylsilyl or t-butyldimethylsilyl with one or more alkyl halides.

9. A compound of claim 2, wherein the compound is selected from compounds of the formulae:

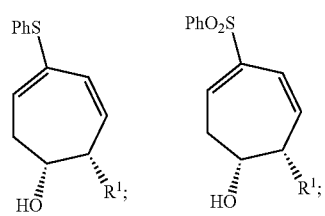

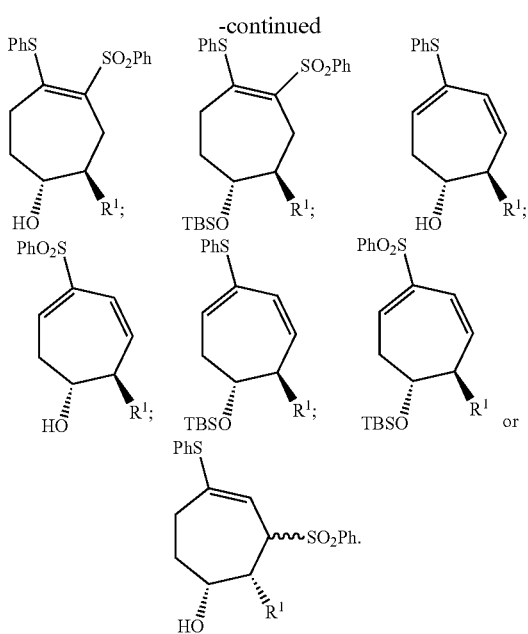

and stereoisomers thereof.

10. A compound according to claim 4 wherein said amine is an organic amine.

11. The compound according to claim 4 wherein said amine is triethylainine and said solvent is methylene chloride.

12. The compound according to claim 4 wherein said oxidizing agent is a peroxide oxidizing agent.

13. The compound according to claim 12 wherein said oxidizing agent is meta-chloroperbenzoic acid (mCPBA).

14. The compound according to claim 5 wherein said amine is triethylamine and said solvent is methylene chloride.

15. The compound according to claim 5 wherein said oxidizing agent is meta-chloroperbenzoic acid (mCPBA).

16. The compound according to claim 14 wherein said oxidizing agent is meta-chloroperbenzoic acid (mCPBA).

17. The compound according to claim 6 wherein said solvent is an ether solvent selected from the group consisting of tetrahydrofuran (THF), diethylether ($ET_2O$) and mixtures thereof.

18. The compound according to claim 2 wherein $R^2$ and $R^3$ are each independently a trimethyl silyl group or a tertiary-butyl dimethyl silyl group.

19. The compound according to claim 18 wherein $R^2$ and $R^3$ are each a trimethyl silyl group.

20. The compound according to claim 18 wherein $R^2$ and $R^3$ are each a tertiarybutyl dimethyl silyl group.

* * * * *